US 12,152,019 B2

(12) United States Patent
Clausen et al.

(10) Patent No.: US 12,152,019 B2
(45) Date of Patent: Nov. 26, 2024

(54) ARYLALKYL PYRAZOLE COMPOUNDS AS INDOLEAMINE 2,3-DIOXYGENASE INHIBITORS

(71) Applicant: Merck Sharp & Dohme LLC, Rahway, NJ (US)

(72) Inventors: Dane Clausen, Rahway, NJ (US); Ping Chen, Edison, NJ (US); Xavier Fradera, Brookline, MA (US); Liangqin Guo, Monroe, NJ (US); Yongxin Han, Needham, MA (US); Shuwen He, Fanwood, NJ (US); Jongwon Lim, Lexington, MA (US); Theodore A. Martinot, Southborough, MA (US); Alexander Pasternak, Jamaica Plain, MA (US); Li Xiao, Cranbury, NJ (US); Wensheng Yu, Edison, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 773 days.

(21) Appl. No.: 17/282,821

(22) PCT Filed: Oct. 11, 2019

(86) PCT No.: PCT/US2019/055761
§ 371 (c)(1),
(2) Date: Apr. 5, 2021

(87) PCT Pub. No.: WO2020/081381
PCT Pub. Date: Apr. 23, 2020

(65) Prior Publication Data
US 2021/0380572 A1 Dec. 9, 2021

Related U.S. Application Data

(60) Provisional application No. 62/746,764, filed on Oct. 17, 2018.

(51) Int. Cl.
| *C07D 413/14* | (2006.01) |
| *C07D 401/06* | (2006.01) |
| *C07D 401/14* | (2006.01) |
| *C07D 413/06* | (2006.01) |
| *A61P 35/00* | (2006.01) |
| *C07D 231/54* | (2006.01) |
| *C07D 401/12* | (2006.01) |
| *C07D 403/06* | (2006.01) |
| *C07D 405/14* | (2006.01) |

(52) U.S. Cl.
CPC ......... *C07D 413/14* (2013.01); *C07D 401/06* (2013.01); *C07D 401/14* (2013.01); *C07D 413/06* (2013.01)

(58) Field of Classification Search
CPC .. C07D 413/14; C07D 401/06; C07D 401/14; C07D 413/06
See application file for complete search history.

(56) References Cited

U.S. PATENT DOCUMENTS

| 7,488,802 B2 | 2/2009 | Collins et al. |
| 7,521,051 B2 | 4/2009 | Collins et al. |
| 8,008,449 B2 | 8/2011 | Korman et al. |
| 8,168,757 B2 | 5/2012 | Finnefroch et al. |

(Continued)

FOREIGN PATENT DOCUMENTS

| WO | 2004004771 A1 | 1/2004 |
| WO | 2004056875 A1 | 7/2004 |

(Continued)

OTHER PUBLICATIONS

PubChem CID: 134573220, create date Jun. 23, 2018 (Jun. 23, 2018) p. 1.

(Continued)

*Primary Examiner* — Deepak R Rao
*Assistant Examiner* — Kevin S Martin
(74) *Attorney, Agent, or Firm* — Kristi K. Harman; Catherine D. Fitch

(57) ABSTRACT

Disclosed herein are compounds of formula (I) which are inhibitors of an IDO enzyme: Also disclosed herein are uses of the compounds in the potential treatment or prevention of an IDO-associated disease or disorder. Also disclosed herein are compositions comprising these compounds. Further disclosed herein are uses of the compositions in the potential treatment or prevention of an IDO-associated disease or disorder.

20 Claims, No Drawings

(56) References Cited

U.S. PATENT DOCUMENTS

| | | | |
|---|---|---|---|
| 8,354,509 | B2 | 1/2013 | Carven et al. |
| 8,383,796 | B2 | 2/2013 | Korman et al. |
| 8,507,541 | B2 | 8/2013 | Combs et al. |
| 9,439,962 | B2 | 9/2016 | Honjo et al. |
| 2008/0025979 | A1 | 1/2008 | Honjo et al. |
| 2011/0271358 | A1 | 11/2011 | Freeman et al. |
| 2021/0330676 | A1* | 10/2021 | Clausen .................. A61P 31/12 |

FOREIGN PATENT DOCUMENTS

| | | |
|---|---|---|
| WO | 2004072286 A1 | 8/2004 |
| WO | 2010027827 A2 | 3/2010 |
| WO | 2010077634 A1 | 7/2010 |
| WO | 2011066342 A2 | 6/2011 |
| WO | 2013019906 A1 | 2/2013 |
| WO | 2020041100 A1 | 2/2020 |

OTHER PUBLICATIONS

PubChem CID: 5048985, create date: Sep. 18, 2005 (Sep. 18, 2005) p. 1.

Cheong, Jae Eun et al., A patent review of IDO1 inhibitors for cancer, Expert Opinion on Therapeutic Patents, 2018, 317-330, 28.

Brown, R.R. et al., Implications of Interferon-Induced Tryptophan Catabolismin Cancer, Autoimmune Diseases and Aids, Adv. Exp. Med. Biol., 1991, 425-435, 294.

Daubener, Walter et al., IFN-γ Activated Indoleamine 2,3-Dioxygenase Activity in Human Cells is an Antiparasitic and an Antibacterial Effector Mechanism, Adv. Exp. Med. Biol., 1999, 517-524, 467.

Grohmann, Ursula et al., Tolerance, DCs and tryptophan: much ado about IDO, Trends in Immunology, 2003, 242-248, 24.

Logan, Grant J. et al., HeLa cells cocultured with peripheral blood lymphocytes acquire an immuno-inhibitory phenotype through up-regulation of indoleamine 2,3-dioxygenase activity, Immunology, 2002, 478-487, 105.

Medawar, P. B., Some Immunological and Endocrinological Problems Raised by the Evolution of Viviparity in Vertebrates, Symposia of the Society for Experimental Biology, 1953, 320-338, 7.

Muller, Alexander J et al., Inhibition of indoleamine 2,3-dioxygenase, an immunoregulatory target of the cancer suppression gene Bin1, potentiates cancer chemotherapy, Nature Medicine, 2005, 312-319, 11.

Munn, David H. et al., Expression of indoleamine 2,3-dioxygenase by plasmacytoid dendritic cells in tumor-draining lymph nodes, J. Clin. Invest., 2004, 280-290, 114(2).

Munn, David H. et al., Potential Regulatory Function of Human Dendritic Cells Expressing Indoleamine 2,3-Dioxygenase, Science, 2002, 1867-1870, 297.

Munn, David H. et al., Prevention of Allogeneic Fetal Rejection by Tryptophan Catabolismscience, 1998, 1191-1193, 281.

Potula, Raghava et al., Inhibition of indoleamine 2,3-dioxygenase (IDO) enhances elimination of virus-infected macrophages in an animal model of HIV-1 encephalitis, Blood, 2005, 2382-2390, 106(7).

Taylor, Milton W. et al., Relationship between interferon-γ, indoleamine 2,3-dioxygenase, and tryptophan catabolism, FASEB, 1991, 2516-2522, 5.

Uyttenhove, Catherine et al., Evidence for a tumoral immune resistance mechanism based on tryptophan degradation by indoleamine 2,3-dioxygenase, Nature Medicine, 2003, 1269-1274, 9.

Wirleitner, B. et al., Interferon-γ-Induced Conversion of Tryptophan: Immunologic and Neuropsychiatric Aspects, Current Medicinal Chemistry, 2003, 1581-1591, 10.

\* cited by examiner

ARYLALKYL PYRAZOLE COMPOUNDS AS INDOLEAMINE 2,3-DIOXYGENASE INHIBITORS

CROSS REFERENCE TO RELATED APPLICATIONS

The present application is the 371 national phase application of International Application No. PCT/US2019/055761, filed Oct. 11, 2019, which claims the benefit of U.S. Provisional Application No. 62/746,764, filed Oct. 17, 2018, hereby incorporated by reference in their entirety.

BACKGROUND OF THE INVENTION

Tryptophan (Trp) is an essential amino acid required for the biosynthesis of proteins, niacin and the neurotransmitter 5-hydroxytryptamine (serotonin). The enzyme indoleamine 2,3-dioxygenase (IDO) catalyzes the first and rate limiting step in the degradation of L-tryptophan to N-formyl-kynurenine. In human cells, a depletion of Trp resulting from IDO activity is a prominent gamma interferon (IFN-γ)-inducible antimicrobial effector mechanism. IFN-γ stimulation induces activation of IDO, which leads to a depletion of Trp, thereby arresting the growth of Trp-dependent intracellular pathogens such as *Toxoplasma gondii* and *Chlamydia trachomatis*. IDO activity also has an antiproliferative effect on many tumor cells, and IDO induction has been observed in vivo during rejection of allogeneic tumors, indicating a possible role for this enzyme in the tumor rejection process (Daubener, et al, 1999, Adv. Exp. Med. Biol, 467: 517-24; Taylor, et al, 1991, FASEB J., 5: 2516-22).

It has been observed that HeLa cells co-cultured with peripheral blood lymphocytes (PBLs) acquire an immuno-inhibitory phenotype through up-regulation of IDO activity. A reduction in PBL proliferation upon treatment with interleukin-2 (IL2) was believed to result from IDO released by the tumor cells in response to IFN-γ secretion by the PBLs. This effect was reversed by treatment with 1-methyl-tryptophan (1-MT), a specific IDO inhibitor. It was proposed that IDO activity in tumor cells may serve to impair anti-tumor responses (Logan, et al, 2002, Immunology, 105: 478-87).

Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. For example, increased levels of IFNs and elevated levels of urinary Trp metabolites have been observed in autoimmune diseases; it has been postulated that systemic or local depletion of Trp occurring in autoimmune diseases may relate to the degeneration and wasting symptoms of these diseases. In support of this hypothesis, high levels of IDO were observed in cells isolated from the synovia of arthritic joints. IFNs are also elevated in human immunodeficiency virus (HIV) patients, and increasing IFN levels are associated with a worsening prognosis. Thus, it was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, Adv. Exp. Med. Biol, 294: 425-35). To this end, it has recently been shown that IDO inhibition can enhance the levels of virus-specific T cells and, concomitantly, reduce the number of virally-infected macrophages in a mouse model of HIV (Portula et al., 2005, Blood, 106: 2382-90).

IDO is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, Symp. Soc. Exp. Biol. 7: 320-38). Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to 1-MT, and a rapid, T cell-induced rejection of all allogeneic conception was observed. Thus, by catabolizing tryptophan, the mammalian conceptus appears to suppress T-cell activity and defends itself against rejection, and blocking tryptophan catabolism during murine pregnancy allows maternal T cells to provoke fetal allograft rejection (Moan, et al., 1998, Science, 281: 1191-3).

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003, Nature Med., 9: 1269-74). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Müller et al, 2005, Nature Med., 11: 312-9).

One mechanism contributing to immunologic unresponsiveness toward tumors may be presentation of tumor antigens by tolerogenic host APCs. A subset of human IDO-expressing antigen-presenting cells (APCs) that coexpressed CD 123 (IL3RA) and CCR6 and inhibited T-cell proliferation have also been described. Both mature and immature CD123-positive dendritic cells suppressed T-cell activity, and this IDO suppressive activity was blocked by 1-MT (Munn, et al, 2002, Science, 297: 1867-70). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs.

Within the population of pDCs, the majority of the functional IDO-mediated suppressor activity segregated with a novel subset of pDCs coexpressing the B-lineage marker CD19. Thus, it was hypothesized that IDO-mediated suppression by pDCs in TDLNs creates a local microenvironment that is potently suppressive of host antitumor T cell responses (Munn, et al., 2004, J. Clin. Invest, 114(2): 280-90).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival. IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al, 2003, Trends Immunol, 24: 242-8). In states of persistent immune activation, availability of free serum Trp is diminished and, as a consequence of reduced serotonin production, serotonergic functions may also be affected (Wirleitner, et al., 2003, Curr. Med. Chem., 10: 1581-91).

In light of the experimental data indicating a role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression. [1.1.1] Bicyclo compounds disclosed herein are useful in the potential treatment or prevention of IDO-related diseases.

SUMMARY OF THE INVENTION

Disclosed herein are novel compounds of formula (I) which are inhibitors of the IDO enzyme. Also disclosed herein are uses of these compounds in the potential treatment or prevention of an IDO-associated disease or disorder. Also disclosed herein are compositions comprising one or more of the compounds. Further disclosed herein are uses of these compositions in the potential prevention or treatment of an IDO-associated disease or disorder.

DETAILED DESCRIPTION OF THE INVENTION

Disclosed herein are compounds of formula (I), or a pharmaceutically acceptable salt thereof:

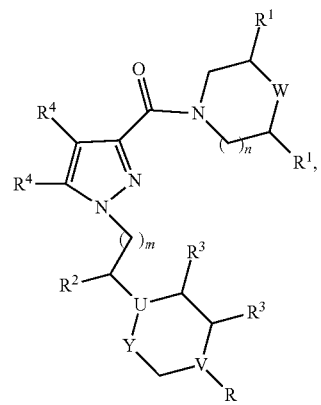

wherein:
m is 0 or 1; n is 0 or 1;
U is selected from (1) N and (2) $CR^a$, wherein Ra is selected from: (a) H and (b) —OH;
V is selected from (1) N and (2) $CR^b$, wherein $R^b$ is selected from: (1) H and (2) $C_{1-6}$ alkyl;
W is selected from (1) —O—, (2) —$NR^c$—, and (3) —$CR^d R^d$—;
  wherein $R^c$ is selected from:
    (a) H,
    (b) —OH, and
    (c) —C(O)—$C_{1-6}$ alkyl, optionally substituted with —OH;
  each occurrence of $R^d$ is independently selected from:
    (a) H,
    (b) halogen,
    (c) —OH,
    (d) —$NH_2$,
    (e) —NH—C(O)—$C_{1-6}$ alkyl, optionally substituted with —OH,
    (f) —NH—C(O)—O—$C_{1-6}$ alkyl,
    (g) $C_{1-6}$ alkyl, optionally substituted 1-3 substituents independently selected from with —OH and halogen, and
    (h) —O—$C_{1-6}$ alkyl, optionally substituted with —OH;
Y is selected from (1) —O— and (2) —$CH_2$—;
R is selected from:
  (1) H,
  (2) aryl,
  (3) —O-aryl,
  (4) —C(O)-aryl,
  (5) heteroaryl, and
  (6) —O-heteroaryl,
  wherein each of the aryl of (2), (3), and (4) and each of the heteroaryl of (5) and (6) is optionally substituted with 1-3 substituents independently selected from:
    (a) —OH,
    (b) halogen,
    (c) —CN, and
    (d) $C_{1-6}$ alkyl, optionally substituted with 1-3 halogens;
each occurrence of $R^1$ is independently selected from: (1) H, (2) halogen, and (3) $C_{1-6}$ alkyl, optionally substituted with —OH;
$R^2$ is selected from: (1) H, (2) halogen, (3) —OH, (4) —O—$C_{1-6}$ alkyl, and (5) $C_{1-6}$ alkyl, optionally substituted with —OH;

each occurrence of $R^3$ is independently selected from: (1) H, (2) halogen, (3) —OH, (4) $C_{1-6}$ alkyl, optionally substituted with —OH, and (5) —O-heteroaryl, optionally substituted with 1-3 halogens; and each occurrence of $R^4$ is independently selected from: (1) H, (2) halogen, (3) $C_{1-6}$ alkyl, optionally substituted with 1-3 halogens, and (4) $C_{3-6}$ cycloalkyl;

or alternatively, the two $R^4$ groups together with the two carbon atoms to which they are attached form a 5-7 membered monocyclic or bicyclic carbocyclyl, optionally substituted with 1-3 substituents independently selected from (a) halogen and (b) $C_{1-6}$ alkyl.

In one embodiment of the compound of formula (I), or a pharmaceutically acceptable salt thereof, at least one of the R and $R^3$ groups is not hydrogen.

In one embodiment of the compound of formula (I), or a pharmaceutically acceptable salt thereof, when both $R^3$ groups are hydrogen, then R is not hydrogen.

In one embodiment of the compound of formula (I), or a pharmaceutically acceptable salt thereof, when one $R^3$ group is hydrogen, then R is not hydrogen.

In one embodiment of the compound of formula (I), or a pharmaceutically acceptable salt thereof, U is selected from (1) N, (2) CH, and (3) C(OH).

In one embodiment of the compound of formula (I), or a pharmaceutically acceptable salt thereof, V is selected from (1) N and (2) CH.

In one embodiment of the compound of formula (I), or a pharmaceutically acceptable salt thereof, W is selected from:
(1) —O—,
(2) —N(C(O)—$C_{1-4}$ alkyl)-, optionally substituted with —OH—, and
(3) —$CR^dR^d$—, wherein each occurrence of $R^d$ is independently selected from:
(a) H,
(b) halogen,
(c) —OH,
(d) —$NH_2$,
(e) —NH—C(O)—$CH_3$, optionally substituted with —OH,
(f) —NH—C(O)—O—$C_{1-4}$ alkyl,
(g) $C_{1-4}$ alkyl, optionally substituted with 1-3 substituents independently selected from —OH and halogen, and
(h) —O—$C_{1-4}$ alkyl, optionally substituted with —OH.

In one embodiment of the compound of formula (I), or a pharmaceutically acceptable salt thereof, W is selected from:
(1) —O—,
(2) —N(C(O)—$CH_2$—OH)—,
(3) —$CR^dR^d$—, wherein each occurrence of $R^d$ is independently selected from:
(a) H,
(b) halogen,
(c) —OH,
(d) —$NH_2$,
(e) —NH—C(O)—$CH_3$, optionally substituted with —OH,
(f) —NH—C(O)—O—$CH_3$,
(g) $C_{1-4}$ alkyl, optionally substituted with 1-3 substituents independently selected from —OH and halogen, and
(h) —O—$C_{1-4}$ alkyl, optionally substituted with —OH.

In one embodiment of the compound of formula (I), or a pharmaceutically acceptable salt thereof, R is selected from:
(1) H,
(2) phenyl,
(3) —O-phenyl,
(4) —C(O)-phenyl,
(5) a 5-6 membered monocyclic heteroaryl,
(6) a 9-12 membered bicyclic fused heteroaryl, and
(7) —O-heteroaryl, wherein the heteroaryl is a 5-6 membered monocyclic heteroaryl, wherein each of the phenyl of (2), (3), and (4) and each of the heteroaryl of (5), (6), and (7) is optionally substituted with 1-3 substituents independently selected from:
(a) —OH,
(b) halogen,
(c) —CN, and
(d) $C_{1-4}$ alkyl, optionally substituted with 1-3 halogens.

In one embodiment of the compound of formula (I), or a pharmaceutically acceptable salt thereof, R is selected from:
(1) H,
(2) phenyl,
(3) —O-phenyl,
(4) —C(O)-phenyl,
(5) a heteroaryl selected from quinolinyl, pyrazinyl, pyrazolyl, pyridazinyl, pyridinyl, and pyrimidinyl, and
(6) —O-heteroaryl, wherein the heteroaryl is selected from pyrazinyl, pyrazolyl, pyridazinyl, pyridinyl, and pyrimidinyl, wherein each of the phenyl of (2), (3), and (4) and each of the heteroaryl of (5) and (6) is optionally substituted with 1-3 substituents independently selected from:
(a) —OH,
(b) halogen,
(c) —CN, and
(d) $C_{1-4}$ alkyl, optionally substituted with 1-3 halogens.

In one embodiment of the compound of formula (I), or a pharmaceutically acceptable salt thereof, each occurrence of $R^1$ is independently selected from: (1) H, (2) halogen, and (3) methyl.

In one embodiment of the compound of formula (I), or a pharmaceutically acceptable salt thereof, $R^2$ is selected from: (1) H, (2) halogen, (3) —OH, and (4) —O—$C_{1-4}$ alkyl.

In one embodiment of the compound of formula (I), or a pharmaceutically acceptable salt thereof, each occurrence of $R^3$ is independently selected from: (1) H and (2) —O-pyridinyl, optionally substituted with halogen.

In one embodiment of the compound of formula (I), or a pharmaceutically acceptable salt thereof:
each occurrence of $R^4$ is independently selected from: (1) H, (2) halogen, (3) $C_{1-4}$ alkyl, optionally substituted with 1-3 halogens, and (4) cyclopropyl;

or alternatively, the two $R^4$ groups together with the two carbon atoms to which they are attached form a 5-6 membered carbocyclyl selected from:
(1) monocyclic saturated or partially unsaturated carbocyclyl,
(2) bicyclic fused saturated or partially unsaturated carbocyclyl, and
(3) monocyclic aromatic carbocyclyl;
wherein each of the carbocyclyl of (1), (2), and (3) is optionally substituted with 1-3 substituents independently selected from (a) halogen and (b) $C_{1-6}$ alkyl, optionally substituted with halogen.

In one embodiment of the compound of formula (I), or a pharmaceutically acceptable salt thereof, the compound is of formula (Ia):

(Ia)

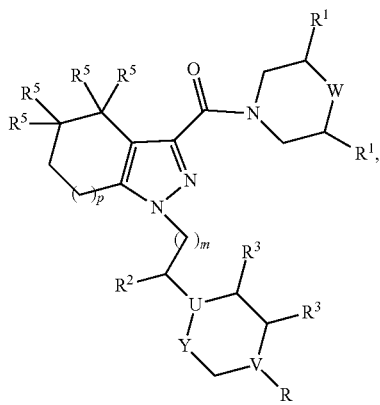

wherein:
m is 0 or 1; p is 0 or 1;
U is selected from (1) N, (2) CH, and (3) C(OH);
V is selected from (1) N and (2) CH;
W is selected from:
  (1) —O—,
  (2) —N(C(O)—CH$_2$—OH)—,
  (3) —CR$^d$R$^d$—, wherein each occurrence of R$^d$ is independently selected from:
    (a) H,
    (b) halogen,
    (c) —OH,
    (d) —NH$_2$,
    (e) —NH—C(O)—CH$_3$, optionally substituted with —OH,
    (f) —NH—C(O)—O—CH$_3$,
    (g) C$_{1-4}$ alkyl, optionally substituted with 1-3 substituents independently selected from —OH and halogen, and
    (h) —O—C$_{1-4}$ alkyl, optionally substituted with —OH;
Y is selected from (1) —O— and (2) —CH$_2$—;
R is selected from:
  (1) H,
  (2) aryl,
  (3) —O-aryl,
  (4) —C(O)-aryl,
  (5) heteroaryl, and
  (6) —O-heteroaryl,
  wherein each of the aryl of (2), (3) and (4) and each of the heteroaryl of (5) and (6) is optionally substituted with 1-3 substituents independently selected from:
    (a) —OH,
    (b) halogen,
    (c) —CN, and
    (d) C$_{1-6}$ alkyl, optionally substituted with 1-3 halogens;
each occurrence of R$^1$ is independently selected from: (1) H, (2) halogen, and (3) C$_{1-6}$ alkyl, optionally substituted with —OH;
R$^2$ is selected from: (1) H, (2) halogen, (3) —OH, (4) —O—C$_{1-6}$ alkyl, and (5) C$_{1-6}$ alkyl, optionally substituted with —OH;
each occurrence of R$^3$ is independently selected from: (1) H, (2) halogen, (3) —OH, (4) C$_{1-6}$ alkyl, optionally substituted with —OH, and (5) —O-heteroaryl, optionally substituted with 1-3 halogens; and each occurrence of R$^5$ is independently selected from: (1) H, (2) halogen, and (3) C$_{1-4}$ alkyl, optionally substituted with 1-3 halogens;
or alternatively, two R$^5$ groups on two adjacent ring carbons together with the two ring carbons form a 3-4 membered new carbocyclic ring.

In one embodiment of the compound of formula (Ia), or a pharmaceutically acceptable salt thereof:
R is selected from:
  (1) phenyl,
  (2) —O-phenyl,
  (3) —C(O)-phenyl,
  (4) a heteroaryl selected from quinolinyl, pyrazinyl, pyrazolyl, pyridazinyl, pyridinyl, and pyrimidinyl, and
  (5) —O-heteroaryl, wherein the heteroaryl is selected from pyrazinyl, pyrazolyl, pyridazinyl, pyridinyl, and pyrimidinyl,
  wherein each of the phenyl of (1), (2), and (3) and each of the heteroaryl of (4) and (5) is optionally substituted with 1-3 substituents independently selected from:
    (a) —OH,
    (b) halogen,
    (c) —CN, and
    (d) C$_{1-4}$ alkyl, optionally substituted with 1-3 halogens;
each occurrence of R$^1$ is independently selected from: (1) H, (2) halogen, and (3) methyl;
R$^2$ is selected from: (1) H, (2) halogen, (3) —OH, and (4) —O—C$_{1-4}$ alkyl;
each occurrence of R$^3$ is H; and
each occurrence of R$^5$ is independently selected from: (1) H, (2) halogen, and (3) C$_{1-4}$ alkyl, optionally substituted with 1-3 halogens.

In one embodiment of the compound of formula (I), or a pharmaceutically acceptable salt thereof, the compound is of formula (Ib):

(Ib)

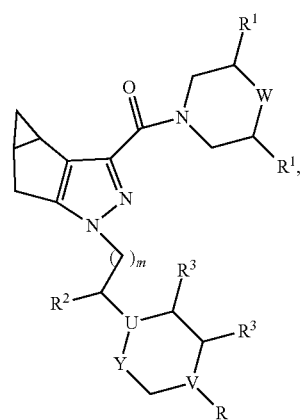

wherein:
m is 0 or 1;
U is selected from (1) N, (2) CH, and (3) C(OH);
V is selected from (1) N and (2) CH;
W is selected from:
  (1) —O—,
  (2) —N(C(O)—CH$_2$—OH)—,
  (3) —CR$^d$R$^d$—, wherein each occurrence of R$^d$ is independently selected from:

(a) H,
(b) halogen,
(c) —OH,
(d) —NH$_2$,
(e) —NH—C(O)—CH$_3$, optionally substituted with —OH,
(f) —NH—C(O)—O—CH$_3$,
(g) C$_{1-4}$ alkyl, optionally substituted with 1-3 substituents independently selected from —OH and halogen, and
(h) —O—C$_{1-4}$ alkyl, optionally substituted with —OH;

Y is selected from (1) —O— and (2) —CH$_2$—;
R is selected from:
(1) H,
(2) aryl,
(3) —O-aryl,
(4) —C(O)-aryl,
(5) heteroaryl, and
(6) —O-heteroaryl,
wherein each of the aryl of (2), (3) and (4) and each of the heteroaryl of (5) and (6) is optionally substituted with 1-3 substituents independently selected from:
(a) —OH,
(b) halogen,
(c) —CN, and
(d) C$_{1-6}$ alkyl, optionally substituted with 1-3 halogens;

each occurrence of R$^1$ is independently selected from: (1) H, (2) halogen, and (3) C$_{1-6}$ alkyl, optionally substituted with —OH;
R$^2$ is selected from: (1) H, (2) halogen, (3) —OH, (4) —O—C$_{1-6}$ alkyl, and (5) C$_{1-6}$ alkyl, optionally substituted with —OH; and
each occurrence of R$^3$ is independently selected from: (1) H, (2) halogen, (3) —OH, (4) C$_{1-6}$ alkyl, optionally substituted with —OH, and (5) —O-heteroaryl, optionally substituted with 1-3 halogens.

In one embodiment of the compound of formula (Ib), or a pharmaceutically acceptable salt thereof:
R is selected from:
(1) phenyl,
(2) —O-phenyl,
(3) —C(O)-phenyl,
(4) a heteroaryl selected from quinolinyl, pyrazinyl, pyrazolyl, pyridazinyl, pyridinyl, and pyrimidinyl, and
(5) —O-heteroaryl, wherein the heteroaryl is selected from pyrazinyl, pyrazolyl, pyridazinyl, pyridinyl, and pyrimidinyl,
wherein each of the phenyl of (1), (2), and (3) and each of the heteroaryl of (4) and (5) is optionally substituted with 1-3 substituents independently selected from:
(a) —OH,
(b) halogen,
(c) —CN, and
(d) C$_{1-4}$ alkyl, optionally substituted with 1-3 halogens;

each occurrence of R$^1$ is independently selected from: (1) H, (2) halogen, and (3) methyl;
R$^2$ is selected from: (1) H, (2) halogen, (3) —OH, and (4) —O—C$_{1-4}$ alkyl; and
each occurrence of R$^3$ is H.

In one embodiment of the compound of formula (I), or a pharmaceutically acceptable salt thereof, the compound is of formula (Ic):

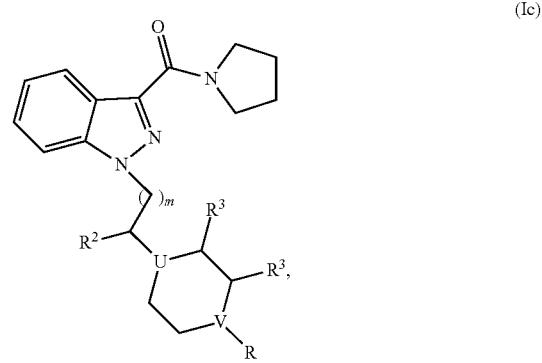

wherein:
m is 0 or 1;
U is selected from (1) N, (2) CH, and (3) C(OH);
V is selected from (1) N and (2) CH;
R is selected from:
(1) aryl,
(2) —O-aryl,
(3) —C(O)-aryl,
(4) heteroaryl, and
(5) —O-heteroaryl,
wherein each of the aryl of (1), (2) and (3) and each of the heteroaryl of (4) and (5) is optionally substituted with 1-3 substituents independently selected from:
(a) —OH,
(b) halogen,
(c) —CN, and
(d) C$_{1-6}$ alkyl, optionally substituted with 1-3 halogens;

R$^2$ is selected from: (1) H, (2) halogen, (3) —OH, (4) —O—C$_{1-6}$ alkyl, and (5) C$_{1-6}$ alkyl, optionally substituted with —OH; and
each occurrence of R$^3$ is independently selected from: (1) H, (2) halogen, (3) —OH, and (4) C$_{1-6}$ alkyl, optionally substituted with —OH.

In one embodiment of the compound of formula (Ic), or a pharmaceutically acceptable salt thereof:
m is 1;
R is phenyl, optionally substituted with 1-3 substituents independently selected from:
(a) —OH,
(b) halogen, and
(c) C$_{1-4}$ alkyl, optionally substituted with 1-3 halogens;
R$^2$ is H; and
each occurrence of R$^3$ is H.

In one embodiment of the compound of formula (I), or a pharmaceutically acceptable salt thereof, the compound is of formula (Id):

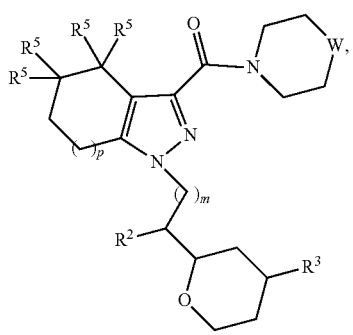

(Id)

wherein:
m is 0 or 1; p is 0 or 1;
W is —CR$^d$R$^d$—, wherein each occurrence of R$^d$ is independently selected from:
(a) H,
(b) —OH,
(c) —NH—C(O)—CH$_3$, optionally substituted with —OH, and
(d) —O—C$_{1-4}$ alkyl, optionally substituted with —OH;
R$^3$ is —O-heteroaryl, optionally substituted with 1-3 halogens; and
each occurrence of R$^5$ is independently selected from: (1) H, (2) halogen, and (3) C$_{1-4}$ alkyl, optionally substituted with 1-3 halogens;
or alternatively, two R$^5$ groups on two adjacent ring carbons together with the two ring carbons form a 3-4 membered new carbocyclic ring.

In one embodiment of the compound of formula (Id), or a pharmaceutically acceptable salt thereof:
m is 0 or 1; p is 0 or 1;
W is —CR$^d$R$^d$—, wherein each occurrence of R$^d$ is independently selected from:
(a) H,
(b) —OH,
(c) —NH—C(O)—CH$_3$, and
(d) —O—C$_{1-4}$ alkyl, optionally substituted with —OH;
R$^3$ is —O-pyridinyl, optionally substituted with halogen; and
each occurrence of R$^5$ is independently selected from: (1) H and (2) halogen;
or alternatively, two R$^5$ groups on two adjacent ring carbons together with the two ring carbons form a new cyclopropyl ring.

In one embodiment, the compound disclosed herein is selected from the group consisting of the compounds exemplified herein, for example, in Examples 1-104, or a pharmaceutically acceptable salt thereof.

Also disclosed herein is a pharmaceutical composition comprising a compound disclosed herein, or a pharmaceutically acceptable salt thereof, and at least one pharmaceutically acceptable carrier.

Also disclosed herein is a method of inhibiting activity of indoleamine 2,3-dioxygenase (IDO) comprising contacting IDO with a compound disclosed herein, or a pharmaceutically acceptable salt thereof.

Also disclosed herein is a method of inhibiting immunosuppression in a patient comprising administering to said patient an effective amount of a compound disclosed herein, or a pharmaceutically acceptable salt thereof.

Also disclosed herein is a method of treating cancer, viral infection, depression, a neurodegenerative disorder, trauma, age-related cataracts, organ transplant rejection, or an autoimmune disease in a patient comprising administering to said patient an effective amount of a compound disclosed herein, or a pharmaceutically acceptable salt thereof.

Also disclosed herein is a method of treating melanoma in a patient comprising administering to said patient an effective amount of a compound disclosed herein, or a pharmaceutically acceptable salt thereof.

Further disclosed herein is a compound disclosed herein, or a pharmaceutically acceptable salt thereof, for use in therapy. In one embodiment, disclosed herein is the use of a compound disclosed herein, or a pharmaceutically acceptable salt thereof, for the preparation of a medicament for use in therapy.

As used herein, "alkyl" refers to both branched- and straight-chain saturated aliphatic hydrocarbon groups of 1 to 18 carbon atoms, or more specifically, 1 to 12 carbon atoms. Examples of such groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), sec-butyl (s-Bu), tert-butyl (t-Bu), isopentyl, and isohexyl. Alkyl groups may be optionally substituted with one or more substituents as defined herein. "C$_{1-6}$alkyl" refers to an alkyl group as defined herein having 1 to 6 carbon atoms.

"Aryl" refers to an aromatic monocyclic or multicyclic ring moiety comprising 6 to 14 ring carbon atoms, or more specifically, 6 to 10 ring carbon atoms. Monocyclic aryl rings include, but are not limited to, phenyl and naphthyl. Multicyclic rings include, but are not limited to, naphthyl and bicyclic rings wherein phenyl is fused to a C$_{5-7}$cycloalkyl or C$_{5-7}$cycloalkenyl ring. Aryl groups may be optionally substituted with one or more substituents as defined herein. Bonding can be through any of the carbon atoms of any ring. In one embodiment, the aryl is phenyl.

"Carbocyclyl" or "carbocyclic ring" refers to a saturated, partially unsaturated or aromatic ring moiety having only ring carbon atoms. Carbocyclyl moieties include both monocyclic and multicyclic (e.g., bicyclic) ring moieties. Bicyclic carbocyclyl moieties include fused, spirocyclic and bridged bicyclic rings. Examples of carbocyclyl moieties include, but are not limited to, cyclopentyl, cyclohexyl, cycloheptyl, cyclooctyl, cyclopentenyl, cyclohexenyl, cyclohexadienyl, bicyclo[3.1.0]hexanyl, phenyl, naphthyl and 2,3-dihydro-1H-indenyl. Carbocyclic rings may be optionally substituted with one or more substituents as defined herein. "C$_{5-9}$ carbocycle" refers to a carbocycle group as defined herein having 5 to 9 ring carbon atoms.

In one embodiment, the carbocyclyl is an aryl. In another embodiment, the carbocyclyl is selected from phenyl and naphthyl. In another embodiment, the carbocyclyl is a bicyclic fused ring wherein one 6-membered aromatic ring is fused to a 5-membered partially unsaturated ring. In one embodiment, the bicyclic fused ring is 2,3-dihydro-1H-indenyl. In one embodiment, the bicyclic fused ring is bicyclo[3.1.0]hexanyl or bicyclo[4.1.0]heptanyl.

"Cycloalkyl" refers to a monocyclic saturated carbocyclic ring having the specified number of carbon atoms. For example, C$_{3-6}$ cycloalkyl refers to a cycloalkyl group as defined herein having 3 to 6 carbon atoms. Examples of cycloalkyl include, but are not limited to, cyclopropyl, cyclobutyl, cyclopentyl, and cyclohexyl. Cycloalkyl groups may be optionally substituted with one or more substituents as defined herein.

"Halo" or "halogen" refers to fluoro, chloro, bromo or iodo, unless otherwise noted.

"Heterocycle" or "heterocyclyl" refers to a saturated, partially unsaturated or aromatic ring moiety having at least one ring heteroatom and at least one ring carbon atom. In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocyclic and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or aromatic. The heterocycle may be attached to the rest of the molecule via a ring carbon atom, a ring oxygen atom or a ring nitrogen atom. Non-limiting examples of heterocycles are described below.

In one embodiment, the heterocyclyl is a 5-7 membered monocyclic heteroaryl.

In one embodiment, the heterocyclyl is a 5-6 membered monocyclic heteroaryl.

In one embodiment, the heterocyclyl is a 9-12 membered bicyclic fused heteroaryl. Such fused ring may be attached to the rest of the molecule via a carbon atom or a nitrogen atom on either ring. A heterocycle of this type includes a bicyclic ring comprising only one nitrogen as the sole heteroatom when the nitrogen is located at the bridgehead.

In one embodiment, the heterocyclyl is selected from quinolinyl, pyrazinyl, pyrazolyl, pyridazinyl, pyridinyl, and pyrimidinyl.

In one embodiment, the heterocyclyl is selected from pyrazinyl, pyrazolyl, pyridazinyl, pyridinyl, and pyrimidinyl.

Heterocyclic groups may be optionally substituted with one or more substituents as defined herein.

"Optionally substituted" refers to "unsubstituted or substituted," and therefore, the generic structural formulas described herein encompass compounds containing the specified optional substituent(s) as well as compounds that do not contain the optional substituent(s). Each substituent is independently defined each time it occurs within the generic structural formula definitions.

Polymorphism

A compound disclosed herein, including a salt or solvate thereof, may exist in crystalline form, non-crystalline form, or a mixture thereof. A compound or a salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound disclosed herein.

Optical Isomers—Diastereomers—Geometric Isomers—Tautomers

Included herein are various isomers of the compounds disclosed herein. The term "isomers" refers to compounds that have the same composition and molecular weight but differ in physical and/or chemical properties. The structural difference may be in constitution (geometric isomers) or in the ability to rotate the plane of polarized light (stereosiomers).

With regard to stereoisomers, a compound disclosed herein may have one or more asymmetric carbon atom and may occur as a racemic mixture or as individual enantiomers or diastereomers. All such isomeric forms are included herein, including mixtures thereof. If a compound disclosed herein contains a double bond, the substituent may be in the E or Z configuration. If a compound disclosed herein contains a disubstituted cycloalkyl, the cycloalkyl substituent may have a cis- or trans-configuration. All tautomeric forms are also intended to be included.

Any asymmetric atom (e.g., carbon) of a compound disclosed herein can be present in racemic mixture or enantiomerically enriched, for example the ©-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the ©- or (S)-configuration. Substituents at atoms with unsaturated double bonds may, if possible, be present in cis-(Z)- or trans-©-form.

A compound disclosed herein can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of the final compounds of the examples or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds can also be resolved by chiral chromatography, e.g., high pressure liquid chromatography (HPLC) using a chiral adsorbent.

Some of the compounds described herein may exist with different points of attachment of hydrogen, referred to as tautomers. For example, compounds including carbonyl —$CH_2C(O)$— groups (keto forms) may undergo tautomerism to form hydroxyl —$CH{=}C(OH)$— groups (enol forms). Both keto and enol forms, individually as well as mixtures thereof, are included within the scope of the present invention.

Isotopic Variations

Compounds disclosed herein include unlabeled forms, as well as isotopically labeled forms. Isotopically labeled compounds have structures depicted by the formulas given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, sulfur, fluorine, iodine and chlorine, such as $^{2}H$ (i.e., Deuterium or "D"), $^{3}H$, $^{11}C$, $^{13}C$, $^{14}C$, $^{13}N$, $^{15}N$, $^{15}O$, $^{17}O$, $^{18}O$, $^{32}P$, $^{35}S$, $^{18}F$, $^{123}I$, $^{125}I$ and $^{36}$Cl. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, substitution with positron emitting isotopes, such as $^{11}$C, $^{18}$F, $^{15}$O and $^{13}$N, may be particularly desirable for PET or SPECT studies.

Isotopically-labeled compounds disclosed herein can generally be prepared by conventional techniques known to those skilled in the art. Furthermore, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index.

Pharmaceutically Acceptable Salts

The term "pharmaceutically acceptable salt" refers to a salt prepared from a pharmaceutically acceptable non-toxic base or acid, including inorganic or organic base and inorganic or organic acid. Salts derived from inorganic bases include aluminum, ammonium, calcium, copper, ferric, ferrous, lithium, magnesium, manganic salts, manganous, potassium, sodium, zinc, and the like. Particular embodiments include ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound disclosed herein is basic, a salt may be prepared from a pharmaceutically acceptable non-toxic acid, including an inorganic and organic acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, trifluoroacetic acid (TFA) and the like. Particular embodiments include the citric, hydrobromic, hydrochloric, maleic, phosphoric, sulfuric, fumaric, tartaric and trifluoroacetic acids. It will be understood that, as used herein, references to the compounds disclosed herein are meant to also include pharmaceutically acceptable salts thereof.

Methods of Use

Compounds disclosed herein can inhibit activity of the enzyme indoleamine-2,3-dioxygenase (IDO). For example, the compounds disclosed herein can potentially be used to inhibit activity of IDO in cell or in an individual in need of modulation of the enzyme by administering an effective amount of a compound. Further disclosed herein are methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound or composition provided herein. Methods of measuring tryptophan levels and tryptophan degradation are routine in the art.

Also disclosed herein are methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, viral replication, etc.

Also disclosed herein are methods of treating diseases associated with activity or expression, including abnormal activity and/or overexpression, of IDO in an individual (e.g., patient) by administering to the individual in need of such treatment an effective amount or dose of a compound disclosed herein or a pharmaceutical composition thereof. Example diseases can include any disease, disorder or condition that may be directly or indirectly linked to expression or activity of the IDO enzyme, such as over expression or abnormal activity. An IDO-associated disease can also include any disease, disorder or condition that may be prevented, ameliorated, or cured by modulating enzyme activity. Examples of IDO-associated diseases include cancer, viral infection such as HIV and HCV, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosusor. Example cancers potentially treatable by the methods herein include cancer of the colon, pancreas, breast, prostate, lung, brain, ovary, cervix, testes, renal, head and neck, lymphoma, leukemia, melanoma, and the like. The compounds of the invention may also be useful in the treatment of obesity and ischemia. As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound disclosed herein includes the administration of a compound of the present invention to an individual or patient, such as a human, as well as, for example, introducing a compound of the invention into a sample containing a cellular or purified preparation containing the IDO enzyme.

A subject administered with a compound disclosed herein, or a pharmaceutically acceptable salt thereof, is generally a mammal, such as a human being, male or female. A subject also refers to cows, sheep, goats, horses, dogs, cats, rabbits, rats, mice, fish, and birds. In one embodiment, the subject is a human.

As used herein, the terms "treatment" and "treating" refer to all processes wherein there may be a slowing, interrupting, arresting, controlling, or stopping of the progression of a disease or disorder that may be associated with IDO enzyme activity. The terms do not necessarily indicate a total elimination of all disease or disorder symptoms. The terms also include the potential prophylactic therapy of the mentioned conditions, particularly in a subject that is predisposed to such disease or disorder.

The terms "administration of" and or "administering a" compound should be understood to include providing a compound described herein, or a pharmaceutically acceptable salt thereof, and compositions of the foregoing to a subject.

The amount of a compound administered to a subject is an amount sufficient to inhibit IDO enzyme activity in the subject. In an embodiment, the amount of a compound can be an "effective amount", wherein the subject compound is administered in an amount that will elicit a biological or medical response of a tissue, system, animal or human that is being sought by a researcher, veterinarian, medical doctor or other clinician. An effective amount does not necessarily include considerations of toxicity and safety related to the administration of a compound. It is recognized that one skilled in the art may affect physiological disorders associated with an IDO enzyme activity by treating a subject presently afflicted with the disorders, or by prophylactically treating a subject likely to be afflicted with the disorders, with an effective amount of a compound disclosed herein, or a pharmaceutically acceptable salt thereof.

An effective amount of a compound will vary with the particular compound chosen (e.g. considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen. Typical daily dosages for oral administration, to a human weighing approximately 70 kg would range from about 0.1 mg to about 2 grams, or more specifically, 0.1 mg to 500 mg, or even more specifically, 0.2 mg to 100 mg, of a compound disclosed herein.

One embodiment of the present invention provides for a method of treating a disease or disorder associated with IDO enzyme activity comprising administration of an effective amount of a compound disclosed herein to a subject in need of treatment thereof. In one embodiment, the disease or disorder associated with an IDO enzyme is a cell proliferation disorder.

In one embodiment, disclosed herein is the use of a compound disclosed herein in a therapy. The compound may be useful in a method of inhibiting IDO enzyme activity in a subject, such as a mammal in need of such inhibition, comprising administering an effective amount of the compound to the subject.

In one embodiment, disclosed herein is a pharmaceutical composition comprising a compound disclosed herein, or a pharmaceutically acceptable salt thereof, for use in potential treatment of a disorder or disease related to IDO enzyme activity.

Compositions

The term "composition" as used herein is intended to encompass a dosage form comprising a specified compound in a specified amount, as well as any dosage form which results, directly or indirectly, from combination of a specified compound in a specified amount. Such term is intended to encompass a dosage form comprising a compound disclosed herein, or a pharmaceutically acceptable salt thereof, and one or more pharmaceutically acceptable carriers or excipients. Accordingly, the compositions of the present invention encompass any composition made by admixing a compound of the present invention and one or more pharmaceutically acceptable carrier or excipients. By "pharmaceutically acceptable" it is meant the carriers or excipients are compatible with the compound disclosed herein and with other ingredients of the composition.

In one embodiment, disclosed herein is a composition comprising a compound disclosed herein, or a pharmaceutically acceptable salt thereof, and one or more pharmaceutically acceptable carriers or excipients. The composition may be prepared and packaged in bulk form wherein an effective amount of a compound of the invention can be extracted and then given to a subject, such as with powders or syrups. Alternatively, the composition may be prepared and packaged in unit dosage form wherein each physically discrete unit contains an effective amount of a compound disclosed herein. When prepared in unit dosage form, the composition of the invention typically contains from about 0.1 mg to 2 grams, or more specifically, 0.1 mg to 500 mg, or even more specifically, 0.2 mg to 100 mg, of a compound disclosed herein, or a pharmaceutically acceptable salt thereof.

A compound disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the invention are prepared using techniques and methods known to those skilled in the art. Some methods commonly used in the art are described in Remington's Pharmaceutical Sciences (Mack Publishing Company).

In one embodiment, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example polylactic acid, polepsilon caprolactone, polyhydroxy butyric acid, polyorthoesters, polyacetals, polydihydropyrans, polycyanacrylates and cross-linked or amphipathic block copolymers of hydrogels.

In one embodiment, the invention is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the invention in a suitably flavored aqueous solution; while elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the invention is directed to compositions for parenteral administration. Compositions adapted for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

A compound disclosed herein may be used in combination with one or more other active agents, including but not limited to, other anti-cancer agents, that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

When a compound disclosed herein is used contemporaneously with one or more other active agents, a composition containing such other active agents in addition to the compound disclosed herein is contemplated. Accordingly, the compositions of the present invention include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as a combined preparation include a composition comprising a compound disclosed herein and one or more other active agent(s) together in the same pharmaceutical composition, or a compound disclosed herein and one or more other therapeutic agent(s) in separate form, e.g. in the form of a kit.

The weight ratio of a compound disclosed herein to a second active agent may be varied and will depend upon the effective dose of each agent. Generally, an effective dose of each will be used. Thus, for example, when a compound disclosed herein is combined with another agent, the weight ratio of the compound disclosed herein to the other agent will generally range from about 1000:1 to about 1:1000, such as about 200:1 to about 1:200. Combinations of a compound disclosed herein and other active agents will generally also be within the aforementioned range, but in each case, an effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, the invention provides a composition comprising a compound disclosed herein and at least one other therapeutic agent as a combined preparation for simultaneous, separate or sequential use in therapy. In one embodiment, the therapy is the treatment of a disease or disorder associated with IDO enzyme activity.

In one embodiment, the invention provides a kit comprising two or more separate pharmaceutical compositions, at least one of which contains a compound disclosed herein. In one embodiment, the kit comprises means for separately retaining said compositions, such as a container, divided bottle, or divided foil packet. An example of such a kit is a blister pack, as typically used for the packaging of tablets, capsules and the like.

A kit disclosed herein may be used for administering different dosage forms, for example, oral and parenteral, for administering the separate compositions at different dosage intervals, or for titrating the separate compositions against one another. To assist with compliance, a kit of the invention typically comprises directions for administration.

Disclosed herein is a use of a compound disclosed herein for treating a disease or disorder associated with IDO enzyme activity, wherein the medicament is prepared for administration with another active agent. The invention also provides the use of another active agent for treating a disease or disorder associated with an IDO enzyme, wherein the medicament is administered with a compound disclosed herein.

The invention also provides the use of a compound disclosed herein for treating a disease or disorder associated with IDO enzyme activity, wherein the patient has previously (e.g. within 24 hours) been treated with another active agent. The invention also provides the use of another therapeutic agent for treating a disease or disorder associated with IDO enzyme activity, wherein the patient has previously (e.g. within 24 hours) been treated with a compound disclosed herein. The second agent may be applied a week, several weeks, a month, or several months after the administration of a compound disclosed herein.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)-(©-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indoi-6-yl)-2-[(4-pyridinyimethyj)amino]-3-pyfidinecarboxamide. And described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX and MYLERAN), carboplatin (sold under the tradename PARAPLATIN), lomustine (also known as CCNU, sold under the tradename CeeNU), cisplatin (also known as CDDP, sold under the tradenames PLATINOL and PLATINOL-AQ), chlorambucil (sold under the tradename LEUKERAN), cyclophosphamide (sold under the tradenames CYTOXAN and NEOSAR), dacarbazine (also known as DTIC, DIC and imidazole carboxamide, sold under the tradename DTIC-DOME), altretamine (also known as hexamethylmelamine (HMM) sold under the tradename HEXALEN), ifosfamide (sold under the tradename IFEX), procarbazine (sold under the tradename MATULANE), mechlorethamine (also known as nitrogen mustard, mustine and mechloroethamine hydrochloride, sold under the tradename MUSTARGEN), streptozocin (sold under the tradename ZANOSAR), thiotepa (also known as thiophosphoamide, TESPA and TSPA, and sold under the tradename THIOPLEX).

Examples of anti-tumor antibiotics include, but are not limited to, doxorubicin (sold under the tradenames ADRIAMYCIN and RUBEX), bleomycin (sold under the tradename LENOXANE), daunorubicin (also known as dauorubicin hydrochloride, daunomycin, and rubidomycin hydrochloride, sold under the tradename CERUBIDINE), daunorubicin liposomal (daunorubicin citrate liposome, sold under the tradename DAUNOXOME), mitoxantrone (also known as DHAD, sold under the tradename NOVANTRONE), epirubicin (sold under the tradename ELLENCE), idarubicin (sold under the tradenames IDAMYCIN, IDAMYCIN PFS), and mitomycin C (sold under the tradename MUTAMYCIN).

Examples of anti-metabolites include, but are not limited to, claribine (2-chlorodeoxyadenosine, sold under the tradename LEUSTATIN), 5-fluorouracil (sold under the tradename ADRUCIL), 6-thioguanine (sold under the tradename PURINETHOL), pemetrexed (sold under the tradename ALIMTA), cytarabine (also known as arabinosylcytosine (Ara-C), sold under the tradename CYTOSAR-U), cytarabine liposomal (also known as Liposomal Ara-C, sold under the tradename DEPOCYT), decitabine (sold under the tradename DACOGEN), hydroxyurea (sold under the tradenames HYDREA, DROXIA and MYLOCEL), fludarabine (sold under the tradename FLUDARA), floxuridine (sold under the tradename FUDR), cladribine (also known as 2-chlorodeoxyadenosine (2-CdA) sold under the tradename LEUSTATIN), methotrexate (also known as amethopterin, methotrexate sodium (MTX), sold under the tradenames RHEUMATREX and TREXALL), and pentostatin (sold under the tradename NIPENT).

Examples of retinoids include, but are not limited to, alitretinoin (sold under the tradename PANRETIN), tretinoin (all-trans retinoic acid, also known as ATRA, sold under the tradename VESANOID), Isotretinoin (13-c/s-retinoic acid, sold under the tradenames ACCUTANE, AMNESTEEM, CLARAVIS, CLARUS, DECUTAN, ISOTANE, IZOTECH, ORATANE, ISOTRET, and SOTRET), and bexarotene (sold under the tradename TARGRETIN).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments. Examples of PD-1 antagonists include, but are not limited to, pembrolizumab (sold under the tradename KEYTRUDA) and nivolumab (sold under the tradename OPDIVO).

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename TRISENOX), asparaginase (also known as L-asparaginase, and *Erwinia* L-asparaginase, sold under the tradenames ELSPAR and KIDROLASE).

EXPERIMENTAL

The following examples are intended to be illustrative only and not limiting in any way. Abbreviations used are those conventional in the art or the following.

ACN or MeCN acetonitrile
Boc tert-butyloxycarbonyl
° C. degree Celsius
Celite diatomaceous earth used as a filtration medium
$Cs_2CO_3$ cesium carbonate
DAST (dimethylamino)sulfur trifluoride
DCM dichloromethane
DEAD diethyl azodicarboxylate
DIAD diisopropyl azodicarboxylate
DIEA diisopropylethylamine
DIPEA N,N-diisopropylethylamine
DMF N,N-dimethylformamide
DMAP 4-dimethylaminopyridine
DMSO dimethylsulfoxide
dppf or DPPF 1,1'-bis(diphenylphosphino)ferrocene
DTBPF 1,1'-bis(di-t-butylphosphino)ferrocene
EDC N-(3-Dimethylaminopropyl)-N'-ethylcarbodiimide hydrochloride
EMEM Eagle's minimal essential medium
$Et_3N$ triethylamine
EtOAc ethyl acetate
EtOH ethanol
g gram
h hour(s)
HATU (1-[Bis(dimethylamino)methylene]-1H-1,2,3-triazolo[4,5-b]pyridinium 3-oxide hexafluorophosphate)
Hex or hex hexane
HOAt 1-hydroxy-7-azabenzotriazole
HPLC high pressure liquid chromatography
kg kilogram
KHMDS potassium bis(trimethylsilyl)amide
KOtBu potassium t-butoxide
L liter
LAH lithium aluminum hydride
LC liquid chromatography
LCMS liquid chromatography and mass spectrometry LiHMDS lithium bis(trimethylsilyl)amide
MeI methyl iodide
MeOH methanol
MS mass spectrometry
MTBE methyl tert-butyl ether
min minutes
mL or ml milliliter(s)
MsCl methanesulfonyl chloride (mesyl chloride)
m/z mass to charge ratio
$NaBH_4$ sodium borohydride
nm nanometer
nM nanomolar
NMP N-methyl-2-pyrrolidone
N normal
OTBDPS tert-butyldiphenylsilyl
PPH3 triphenylphosphine
RPMI Roswell Park Memorial Institute
RuPhos Pd G2 Chloro(2-dicyclohexylphosphino-2',6'-di-isopropoxy-1,1'-biphenyl)[2-(2'-amino-1,1'-biphenyl)]palladium(II)
RT or r.t. room temperature
sat. saturated
SFC supercritical fluid chromatography
SPhos G3 (2-dicyclohexylphosphino-2',6'-dimethoxybiphenyl) [2-(2'-amino-1,1'-biphenyl)]palladium(II) methanesulfonate
TBAF tetrabutylammonium fluoride
TBDPSCl tert-butyldiphenylchlorosilane
TBTU 2-(1H-benzotriazole-1-yl)-1,1,3,3-tetramethylaminium tetrafluoroborate
TEA triethylamine
TFA trifluoroacetic acid
THF tetrahydrofuran
TsCl or Ts-Cl toluenesulfonyl chloride
Xphos Pd G2 chloro(2-dicyclohexylphosphino-2',4',6'-tri-isopropyl-1,1'-biphenyl)[2-(2' amino-1,1'-biphenyl)]palladium(II)
XanPhos G2 chloro[(4,5-bis(diphenylphosphino)-9,9-dimethylxanthene)-2-(2'-amino-1,1'-biphenyl)]palladium(II)

The compounds disclosed herein may be prepared by methods known in the art of organic synthesis as set forth in part by the following synthetic schemes and synthetic procedures and conditions for the illustrative intermediates and examples.

In the synthetic procedures described below, it is well understood that protecting groups for sensitive or reactive groups are employed where necessary in accordance with general principles of chemistry. Protecting groups are manipulated according to standard methods of organic synthesis (T. W. Greene and P. G. M. Wuts, "Protective Groups in Organic Synthesis", 3$^{rd}$ edition, Wiley, NY 1999). These groups are removed at a convenient stage of the compound synthesis using methods that are readily apparent to those skilled in the art.

Intermediate A: (4-((Tert-butyldiphenylsilyl)oxy)piperidin-1-yl)(1-(2-(piperidin-4-yl)ethyl)-1,4,5,6-tetrahydrocyclopenta[c]pyrazol-3-yl)methanone

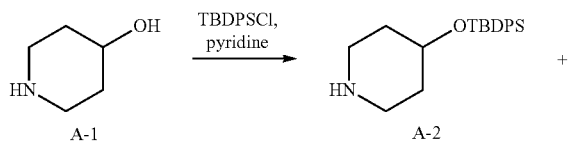

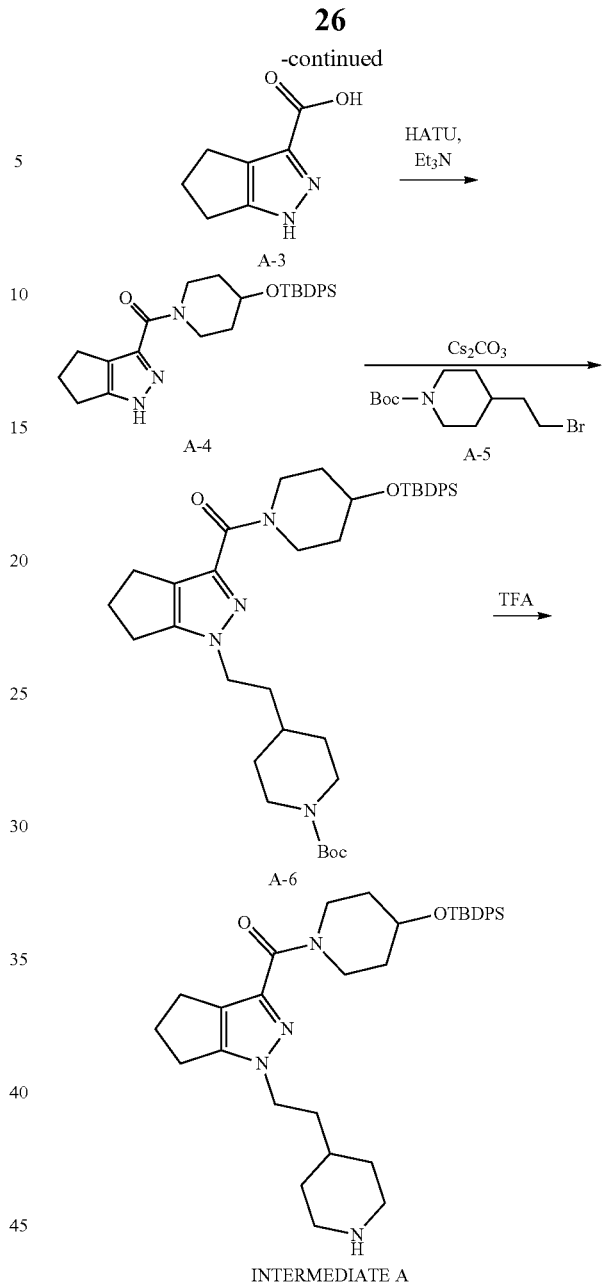

INTERMEDIATE A

Step 1: 4-((Tert-butyldiphenylsilyl)oxy)piperidine (A-2)

To a mixture of piperidin-4-ol (A-1) (3.00 g, 29.7 mmol) in DCM (29.7 ml) at ambient temperature were added pyridine (4.80 ml, 59.3 mmol) and TBDPS-Cl (8.38 ml, 32.6 mmol). The mixture was stirred for 3 h to afford a solution containing the title compound which was used directly in the next step. MS: 340.3 (M+1).

Step 2: (4-((tert-butyldiphenylsilyl)oxy)piperidin-1-yl)(1,4,5,6-tetrahydrocyclopenta[c]pyrazol-3-yl)methanone (A-4)

To a mixture of 1,4,5,6-tetrahydrocyclopenta[c]pyrazole-3-carboxylic acid (A-3) (3.50 g, 23.00 mmol) in DMF (92 ml) at ambient temperature were added HATU (10.50 g, 27.6 mmol) and TEA (3.85 ml, 27.6 mmol). The mixture was stirred for 10 min before adding a solution of 4-((tert-butyldiphenylsilyl)oxy)piperidine (A-2) (29.9 ml, 29.9 mmol) in DCM. The mixture was stirred for 3 h before quenching with water (100 mL) and taking up in EtOAc (250 mL). The mixture was washed with a sat. solution of NaHCO$_3$ (200 mL×2), water (200 mL), and brine (200 mL). The organic layer was dried over Na$_2$SO$_4$ and concentrated. The residue was purified by column chromatography on silica (2-60% 3:1 EtOAc:EtOH/hexane) to afford the title compound. MS: 474.4 (M+1).

Step 3: tert-butyl 4-(2-(3-(4-((tert-butyldiphenylsilyl)oxy)piperidine-1-carbonyl)-5,6-dihydrocyclopenta[c]pyrazol-1(4H)-yl)ethyl)piperidine-1-carboxylate (A-6)

To a mixture of (4-((tert-butyldiphenylsilyl)oxy)piperidin-1-yl)(1,4,5,6-tetrahydrocyclopenta[c]pyrazol-3-yl)methanone (A-4) (1.10 g, 2.322 mmol) in DMF (11.61 ml) at ambient temperature were added Cs$_2$CO$_3$ (0.908 g, 2.79 mmol) and tert-butyl 4-(2-bromoethyl)piperidine-1-carboxylate (A-5) (0.814 g, 2.79 mmol). The mixture was warmed to 65° C. and stirred overnight. The mixture was quenched with water (50 mL) and taken up in EtOAc (100 mL). The mixture was washed with water (50 mL×3) and brine (50 mL), dried over Na$_2$SO$_4$, and concentrated to afford the title compound. MS: 685.6 (M+1).

Step 4: (4-((tert-butyldiphenylsilyl)oxy)piperidin-1-yl)(1-(2-(piperidin-4-yl)ethyl)-1,4,5,6-tetrahydrocyclopenta[c]pyrazol-3-yl)methanone To a mixture of tert-butyl 4-(2-(3-(4-((tert-butyldiphenylsilyl)oxy)piperidine-1-carbonyl)-5,6-dihydrocyclopenta[c]pyrazol-1(4H)-yl)ethyl)piperidine-1-carboxylate (A-6) (1.59 g, 2.321 mmol) in dioxane (3.52 ml) at ambient temperature was added TFA (0.537 ml, 6.96 mmol). After 3 h, HCl (1.741 ml, 6.96 mmol) in dioxane was added and the mixture stirred for 4 h. The mixture was purified directly by column chromatography on C18 (5-95% ACN/water with 0.05% TFA modifier) to afford the title compound. MS: 585.5 (M+1).

Intermediate B: ((2R,6S)-2,6-dimethylmorpholino)(1-(2-(1-(2,3-dimethylphenyl)piperidin-4-yl)-2-hydroxyethyl)-1,4,5,6-tetrahydrocyclopenta[c]pyrazol-3-yl)methanone

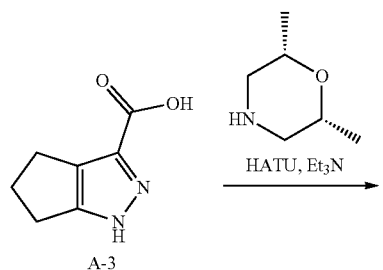

A-3

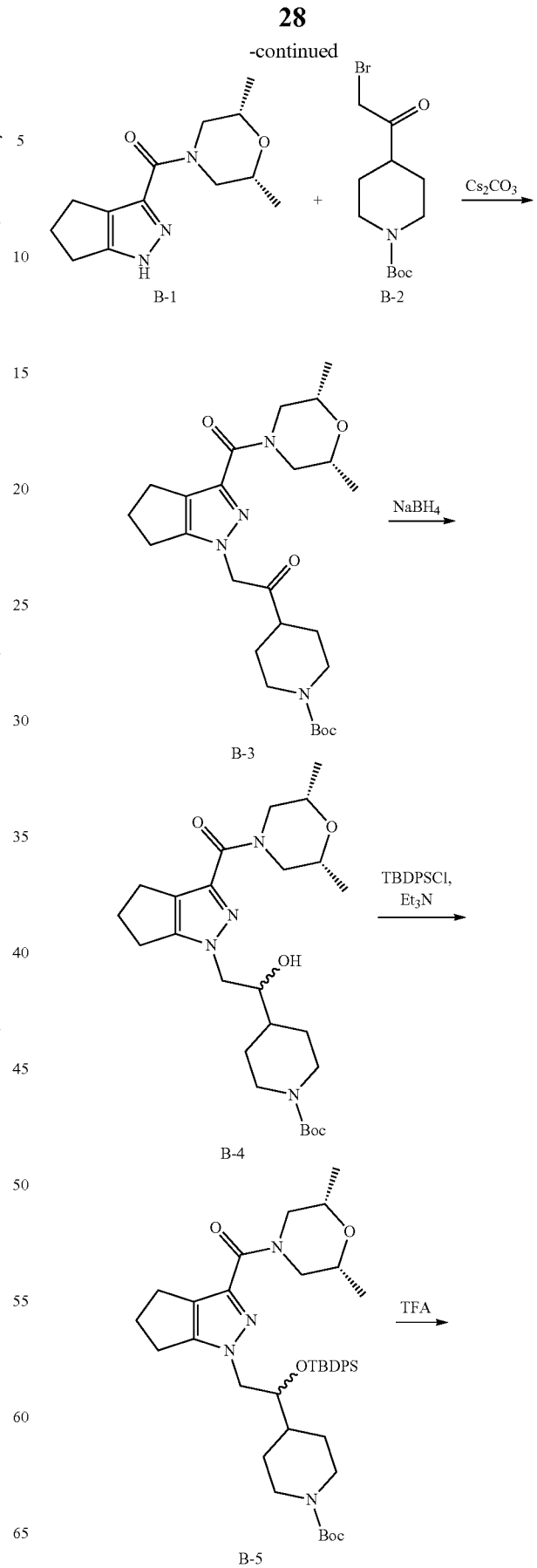

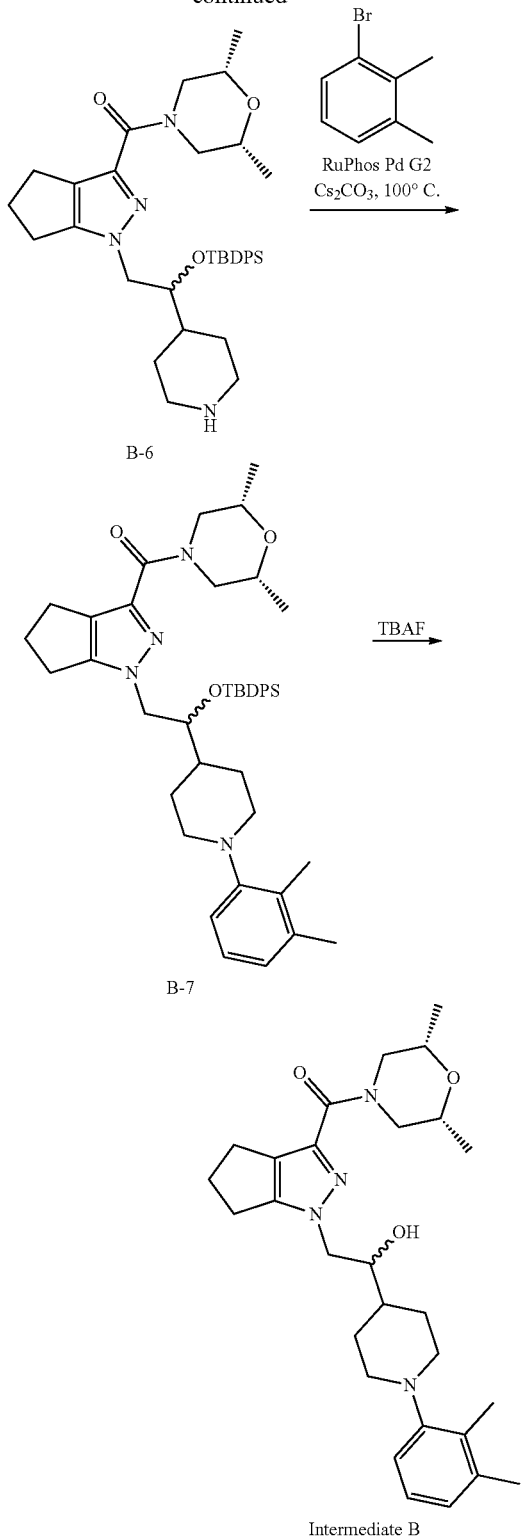

(16.43 ml) at ambient temperature were added TEA (2.75 ml, 19.72 mmol), HATU (7.50 g, 19.72 mmol), and (2R,6S)-2,6-dimethylmorpholine (2.84 g, 24.65 mmol). The mixture stirred for 3 h before acidifying with AcOH (5 mL). The mixture was purified directly by column chromatography on C18 column (5-95% ACN/water with 0.05% TFA modifier) to afford the title compound. MS: 250.3 (M+1).

Step 2: tert-butyl 4-(2-(3-((2R,6S)-2,6-dimethylmorpholine-4-carbonyl)-5,6-dihydrocyclopenta[c]pyrazol-1(4H)-yl)acetyl)piperidine-1-carboxylate (B-3)

To a mixture of ((2R,6S)-2,6-dimethylmorpholino)(1,4,5,6-tetrahydrocyclopenta[c]pyrazol-3-yl)methanone (B-1) (3.00 g, 12.03 mmol) in DMF (12.03 ml) at ambient temperature were added $Cs_2CO_3$ (9.80 g, 30.1 mmol) and tert-butyl 4-(2-bromoacetyl)piperidine-1-carboxylate (B-2) (5.53 g, 18.05 mmol). The mixture was stirred for 3 h before quenching with water (100 mL) and EtOAc (100 mL). The organic layer was separated and the aq. layer was extracted with EtOAc (100 mL×2), dried over $Na_2SO_4$, and concentrated. The residue was purified by column chromatography on silica (10-80% 3:1 EtOAc:EtOH/hexanes) to afford the title compound. MS: 475.5 (M+1).

Step 3: tert-butyl 4-(2-(3-((2R,6S)-2,6-dimethylmorpholine-4-carbonyl)-5,6-dihydrocyclopenta[c]pyrazol-1(4H)-yl)-1-hydroxyethyl)piperidine-1-carboxylate (B-4)

To a mixture of tert-butyl 4-(2-(3-((2R,6S)-2,6-dimethylmorpholine-4-carbonyl)-5,6-dihydrocyclopenta[c]pyrazol-1(4H)-yl)acetyl)piperidine-1-carboxylate (B-3) (5.20 g, 10.96 mmol) in MeOH (21.91 ml) at 0° C. was added $NaBH_4$ (0.415 g, 10.96 mmol). The mixture was stirred for 1 h before adding a sat. solution of $NH_4Cl$ (150 mL). The mixture was extracted with EtOAc (150 mL×3), dried over $Na_2SO_4$, and concentrated. The residue was purified by column chromatography on silica (10-80% 3:1 EtOAc:EtOH/hexanes) to afford the title compound. MS: 477.5 (M+1).

Step 4: tert-butyl 4-(1-((tert-butyldiphenylsilyl)oxy)-2-(3-((2R,6S)-2,6-dimethylmorpholine-4-carbonyl)-5,6-dihydrocyclopenta[c]pyrazol-1(4H)-yl)ethyl)piperidine-1-carboxylate (B-5)

To a mixture of tert-butyl 4-(2-(3-((2R,6S)-2,6-dimethylmorpholine-4-carbonyl)-5,6-dihydrocyclopenta[c]pyrazol-1(4H)-yl)-1-hydroxyethyl)piperidine-1-carboxylate (B-4) (4.67 g, 9.80 mmol) in DMF (9.80 ml) at ambient temperature were added imidazole (0.800 g, 11.76 mmol) and TBDPS-Cl (2.77 ml, 10.78 mmol). The mixture was stirred overnight before quenching with water (100 mL) and EtOAc (100 mL). The organic layer was separated, dried over $Na_2SO_4$, and concentrated. The residue was purified by column chromatography on silica (2-60% 3:1 EtOAc:EtOH/hexane) to afford the title compound. MS: 715.7 (M+1).

Step 5: (1-(2-((tert-butyldiphenylsilyl)oxy)-2-(piperidin-4-yl)ethyl)-1,4,5,6-tetrahydrocyclopenta[c]pyrazol-3-yl)((2R,6S)-2,6-dimethylmorpholino)methanone (B-6)

To a mixture of tert-butyl 4-(1-((tert-butyldiphenylsilyl)oxy)-2-(3-((2R,6S)-2,6-dimethylmorpholine-4-carbonyl)-5,6-dihydrocyclopenta[c]pyrazol-1(4H)-yl)ethyl)piperidine- Step 1: ((2R,6S)-2,6-dimethylmorpholino)(1,4,5,6-tetrahydrocyclopenta[c]pyrazol-3-yl)methanone (B-1)

To a mixture of 1,4,5,6-tetrahydrocyclopenta[c]pyrazole-3-carboxylic acid (A-3) (2.50 g, 16.43 mmol) in DMF 1-carboxylate (B-5) (6.20 g, 8.67 mmol) in DCM (17.34 ml) at ambient temperature was added TFA (2.67 ml, 34.7 mmol). The mixture was stirred for 3 h before concentration and taken up in EtOAc (100 mL), washed with a sat. solution of NaHCO₃ (100 mL×2), dried over Na₂SO₄, and concentrated to afford the title compound. MS: 615.6 (M+1).

Step 6: (1-(2-((tert-butyldiphenylsilyl)oxy)-2-(1-(2,3-dimethylphenyl)piperidin-4-yl)ethyl)-1,4,5,6-tetrahydrocyclopenta[c]pyrazol-3-yl)((2R,6S)-2,6-dimethylmorpholino)methanone (B-7)

To a mixture of (1-(2-((tert-butyldiphenylsilyl)oxy)-2-(piperidin-4-yl)ethyl)-1,4,5,6-tetrahydrocyclopenta[c]pyrazol-3-yl)((2R,6S)-2,6-dimethylmorpholino)methanone (B-6) (2.50 g, 4.07 mmol) in dioxane (8.13 ml) at ambient temperature were added 1-bromo-2,3-dimethylbenzene (1.102 ml, 8.13 mmol), Cs₂CO₃ (3.97 g, 12.20 mmol), and RuPhos Pd G2 (0.316 g, 0.407 mmol). The mixture was heated to 100° C. and stirred overnight. The mixture was cooled, quenched with water (25 mL), extracted with EtOAc (25 mL×3), dried over Na₂SO₄, and concentrated. The residue was purified by column chromatography on silica (2-90% 3:1 EtOAc:EtOH/hexane) to afford the title compound. MS: 719.7 (M+1).

Step 7: ((2R,6S)-2,6-dimethylmorpholino)(1-(2-(1-(2,3-dimethylphenyl)piperidin-4-yl)-2-hydroxyethyl)-1,4,5,6-tetrahydrocyclopenta[c]pyrazol-3-yl)methanone To a mixture of (1-(2-((tert-butyldiphenylsilyl)oxy)-2-(1-(2,3-dimethylphenyl)piperidin-4-yl)ethyl)-1,4,5,6-tetrahydrocyclopenta[c]pyrazol-3-yl)((2R,6S)-2,6-dimethylmorpholino)methanone (B-7) (2.10 g, 2.92 mmol) in THF (2.92 ml) at ambient temperature was added 1.0 M TBAF (8.76 ml, 8.76 mmol) in THF. The mixture was stirred for 2 h before concentration. The residue was purified by column chromatography on silica (2-90% 3:1 EtOAc:EtOH/hexanes) to afford the title compound. MS: 481.5 (M+1).

Intermediate C: ethyl 1-(2-(4-oxocyclohexyl)ethyl)-1,4,5,6-tetrahydrocyclopenta[c]pyrazole-3-carboxylate

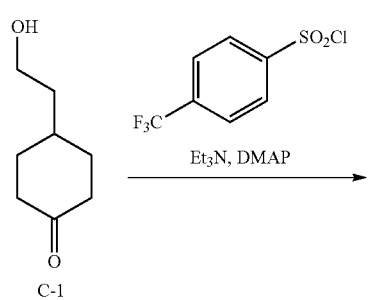

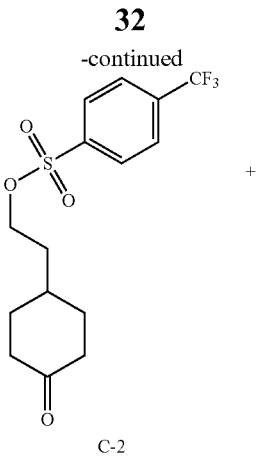

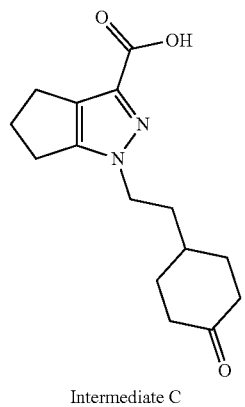

Step 1: 2-(4-oxocyclohexyl)ethyl 4-(trifluoromethyl)benzenesulfonate (C-2)

To a mixture of 4-(2-hydroxyethyl)cyclohexanone (C-1) (4.00 g, 28.1 mmol) in DCM (56.3 ml) at RT were added 4-(trifluoromethyl)benzene-1-sulfonyl chloride (8.26 g, 33.8 mmol), TEA (4.70 ml, 33.8 mmol), and DMAP (0.172 g, 1.407 mmol). The mixture was stirred for 2 h before quenching with water (100 mL), extracting with DCM (100 mL×3), drying over Na₂SO₄, and concentrating. The residue was purified by column chromatography on silica (2-60% 3:1 EtOAc:EtOH/hexane) to afford the title compound. MS: 351.0 (M+1).

Step 2: ethyl 1-(2-(4-oxocyclohexyl)ethyl)-1,4,5,6-tetrahydrocyclopenta[c]pyrazole-3-carboxylate To a mixture of 2-(4-oxocyclohexyl)ethyl 4-(trifluoromethyl)benzenesulfonate (C-2) (6.25 g, 17.84 mmol) in NMP (54.1 ml) at ambient temperature were added ethyl 1,4,5,6-tetrahydrocyclopenta[c]pyrazole-3-carboxylate (A-3) (4.18 g, 23.19 mmol), Cs₂CO₃ (11.62 g, 35.7 mmol), sodium iodide (2.67 g, 17.84 mmol), and lithium chloride (1.513 g, 35.7 mmol). The mixture was warmed to 80° C. and stirred for 24 h. The mixture was cooled, quenched with water (100 mL), extracted with EtOAc (100 mL×3), dried over Na₂SO₄, and concentrated. The residue was purified by column chromatography on silica (2-80% 3:1 EtOAc:EtOH/hexane) to afford the title compound. MS: 305.1 (M+1).

Intermediates D and E: ethyl 1-(2-((1r,4r)-4-hydroxycyclohexyl)ethyl)-1,4,5,6-tetrahydrocyclopenta[c]pyrazole-3-carboxylate and ethyl 1-(2-((1s,4s)-4-hydroxycyclohexyl)ethyl)-1,4,5,6-tetrahydrocyclopenta[c]pyrazole-3-carboxylate

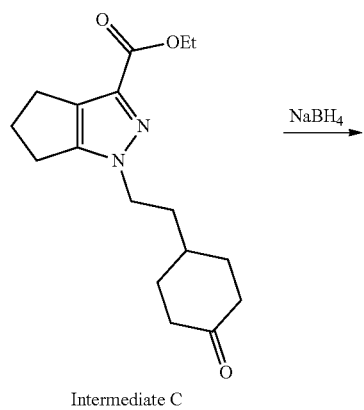

Intermediate C

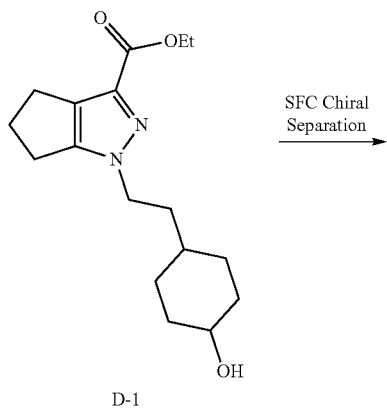

D-1

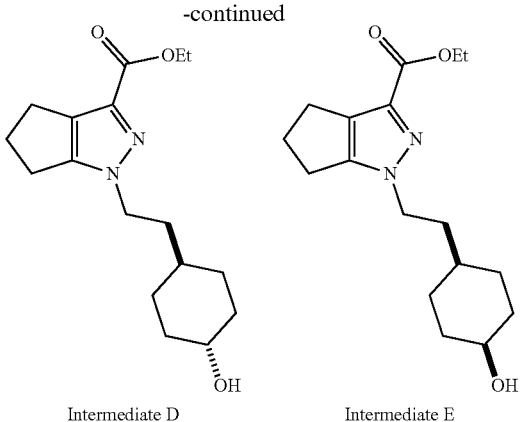

Intermediate D           Intermediate E

Step 1: ethyl 1-(2-(4-hydroxycyclohexyl)ethyl)-1,4,5,6-tetrahydrocyclopenta[c]pyrazole-3-carboxylate (D-1)

To a mixture of ethyl 1-(2-(4-oxocyclohexyl)ethyl)-1,4,5,6-tetrahydrocyclopenta[c]pyrazole-3-carboxylate (Intermediate C) (750 mg, 2.464 mmol) in MeOH (1.23E+04 µl) at 0° C. was added NaBH$_4$ (93 mg, 2.464 mmol). The mixture was stirred for 2 h before adding a sat. NH$_4$Cl (30 mL), extracting with EtOAc (30 mL×3), drying over Na$_2$SO$_4$, and concentrating. The mixture was purified directly by column chromatography on a C18 column (5-95% ACN/water with 0.05% TFA modifier) to afford the title compound. MS: 307.1 (M+1).

Step 2: ethyl 1-(2-((1r,4r)-4-hydroxycyclohexyl)ethyl)-1,4,5,6-tetrahydrocyclopenta[c]pyrazole-3-carboxylate (Intermediate D) and ethyl 1-(2-((1s,4s)-4-hydroxycyclohexyl)ethyl)-1,4,5,6-tetrahydrocyclopenta[c]pyrazole-3-carboxylate (Intermediate E)

The diastereomeric ethyl 1-(2-(4-hydroxycyclohexyl)ethyl)-1,4,5,6-tetrahydrocyclopenta[c]pyrazole-3-carboxylate (Intermediate C) was submitted for SFC purification to obtain two chiral isomers.

Intermediate D (peak 1, trans): MS: 307.1 (M+1).
Intermediate E (peak 2, cis): MS: 307.1 (M+1).

Intermediate F: ethyl 5,5-difluoro-4,5,6,7-tetrahydro-1H-indazole-3-carboxylate

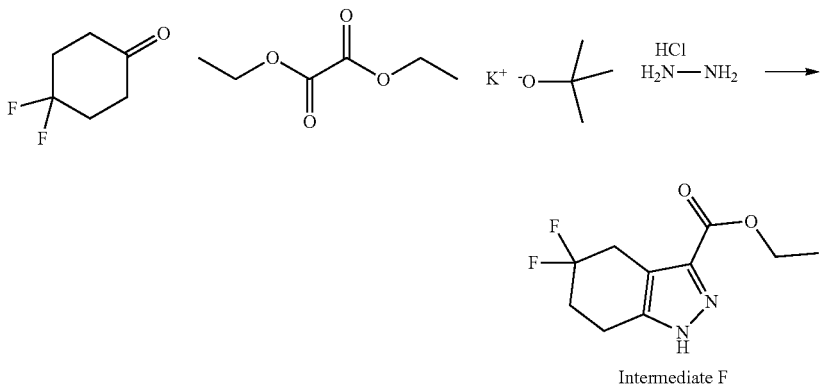

Intermediate F

To a solution of 4,4-difluorocyclohexanone (10 g, 74.6 mmol) and diethyl oxalate (11.99 g, 82 mmol) in ethanol (80 ml) was added potassium 2-methylpropan-2-olate (82 ml, 82 mmol) at 0° C. The mixture was warmed up to RT upon completion of the KOtBu addition. The mixture was stirred at RT for 1.5 h. The mixture was cooled back to 0° C., hydrazine hydrochloride (6.13 g, 89 mmol) in water (5 mL) was added, and the mixture was then allowed to stir at RT overnight. Most solvent was removed on rotovap, the residue was then partitioned between EtOAc (100 ml) and water (100 ml), and the combined organics were dried and concentrated. The residue was purified on normal phase chromatography, eluted with EtOAc/hex (5% to 100%) to afford the title compound as an oil. MS: 231.18 (M+1). 1H NMR (500 MHz, Methanol-d4) δ 4.37 (q, J=7.0 Hz, 2H), 3.39-3.30 (m, 1H), 3.24 (t, J=14.1 Hz, 2H), 2.91 (t, J=6.6 Hz, 2H), 2.30 (tt, J=13.3, 6.7 Hz, 2H), 1.40 (t, J=7.1 Hz, 3H).

Intermediate G: ((2R,4S)-4-((tert-butyldimethylsilyl)oxy)tetrahydro-2H-pyran-2-yl)methyl 4-methylbenzenesulfonate

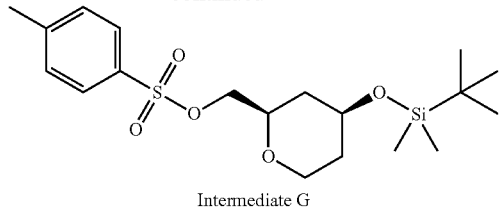

Intermediate G

The mixture of 2((2R,4S)-4-((tert-butyldimethylsilyl)oxy)tetrahydro-2H-pyran-2-yl)methanol (5.42 g, 22.00 mmol) and 4-methylbenzene-1-sulfonyl chloride (5.03 g, 26.4 mmol) in pyridine (15 ml)) was stirred at RT for 2 h before pyridine was removed from rotovap. The residue was then diluted with EtOAc (50 ml) and water (50 ml), the organic layer was concentrated, purified on normal phase chromatography with 0 to 100% EtOAc in hexane. The title compound was isolated as an oil. MS: 400.0 (M+1).

Intermediate H: 1-(((2S,4S)-4-((5-chloropyridin-2-yl)oxy)tetrahydro-2H-pyran-2-yl)methyl)-5,5-difluoro-4,5,6,7-tetrahydro-1H-indazole-3-carboxylic Acid

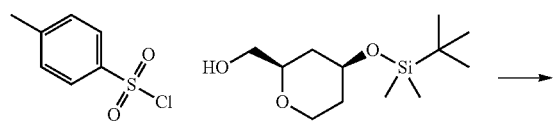

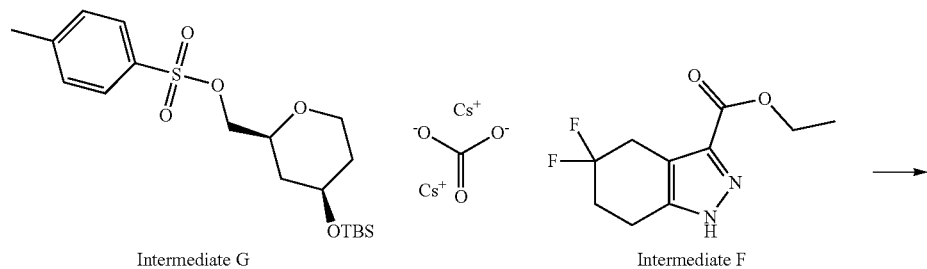

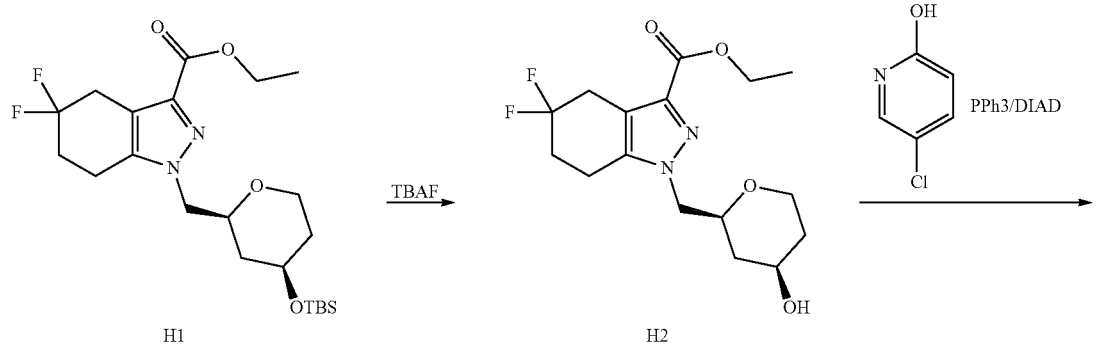

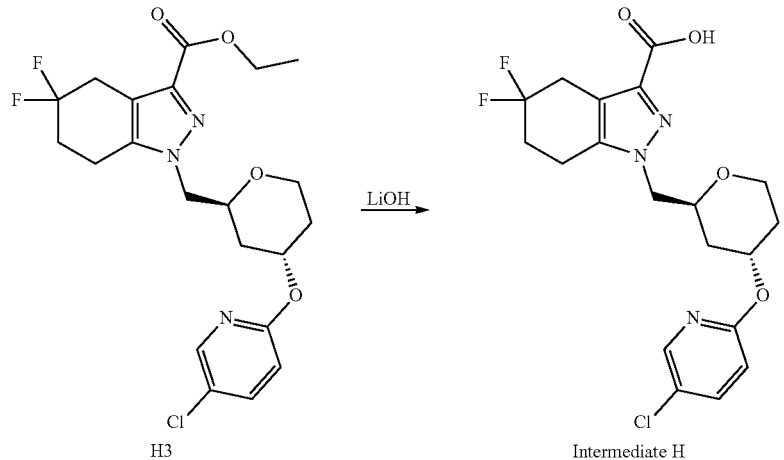

Step 1: ethyl 1-(((2S,4R)-4-((tert-butyldimethylsilyl)oxy)tetrahydro-2H-pyran-2-yl)methyl)-5,5-difluoro-4,5,6,7-tetrahydro-1H-indazole-3-carboxylate (H1)

To a solution of ((2S,4R)-4-((tert-butyldimethylsilyl)oxy)tetrahydro-2H-pyran-2-yl)methyl 4-methylbenzenesulfonate (1.740 g, 4.34 mmol) in 1,4-dioxane (15 ml) were added cesium carbonate (2.123 g, 6.52 mmol) and ethyl 5,5-difluoro-4,5,6,7-tetrahydro-1H-indazole-3-carboxylate (1 g, 4.34 mmol). The mixture was stirred at 50° C. for 3 h before quenching with water at 0° C., and diluting with EtOAc (50 ml) and water (50 ml). The organic layer was concentrated, and purified on normal phase chromatography with 0 to 100% EtOAc in hexane. The title compound was isolated and concentrated as an oil. MS: 459.38 (M+1).

Step 2: ethyl 5,5-difluoro-1-(((2S,4R)-4-hydroxytetrahydro-2H-pyran-2-yl)methyl)-4,5,6,7-tetrahydro-1H-indazole-3-carboxylate (H2)

To a solution of ethyl 1-(((2S,4R)-4-((tert-butyldimethylsilyl)oxy)tetrahydro-2H-pyran-2-yl)methyl)-5,5-difluoro-4,5,6,7-tetrahydro-1H-indazole-3-carboxylate (1 g, 2.180 mmol) in THF (10 ml) was added TBAF (8.72 ml, 8.72 mmol) at RT. The mixture was then stirred at RT before quenching with water, and diluting with EtOAc (50 ml) and water (50 ml). The organic layer was concentrated, purified on normal phase chromatography with 0 to 100% EtOAc:EtOH/hexane to afford the title compound as an oil. MS: 345.2 (M+1).

Step 3. Ethyl 1-(((2S,4S)-4-((5-chloropyridin-2-yl)oxy)tetrahydro-2H-pyran-2-yl)methyl)-5,5-difluoro-4,5,6,7-tetrahydro-1H-indazole-3-carboxylate (H3)

To a mixture of triphenylphosphine (152 mg, 0.581 mmol) and 5-chloropyridin-2-ol (52.7 mg, 0.407 mmol) were added ethyl 5,5-difluoro-1-(((2S,4R)-4-hydroxytetrahydro-2H-pyran-2-yl)methyl)-4,5,6,7-tetrahydro-1H-indazole-3-carboxylate (100 mg, 0.290 mmol) and THF (0.1 ml). The mixture was sealed and stirred at 0° C., followed by the addition of DIAD (0.113 ml, 0.581 mmol). The mixture was placed in sonicator for 1 h. LCMS showed the desired product was obtained. The mixture was diluted with EtOAc (20 ml) and water (20 ml), and the organics were concentrated and purified on normal phase chromatography. Eluting with 0 to 100% EtOAc in hexane and isolation resulted in the title compound as an oil. MS: 455.10 (M+1).

Step 4. 1-(((2S,4S)-4-((5-chloropyridin-2-yl)oxy)tetrahydro-2H-pyran-2-yl)methyl)-5,5-difluoro-4,5,6,7-tetrahydro-1H-indazole-3-carboxylic acid To a solution of ethyl 1-(((2S,4S)-4-((5-chloropyridin-2-yl)oxy)tetrahydro-2H-pyran-2-yl)methyl)-5,5-difluoro-4,5,6,7-tetrahydro-1H-indazole-3-carboxylate (110 mg, 0.241 mmol in MeOH (1 ml) was added LiOH (0.643 ml, 0.965 mmol). The mixture was stirred at 50° C. for 1 h, the reaction was then cooled down, quenched with water and 1 N HCl, and diluted with 20 ml EtOAc. The organics were concentrated, purified on C18 reversed phase chromatography with 0 to 100% ACN in water with 0.05% TFA. The title compound was collected and concentrated as a solid. MS: 428.17 (M+1).

Intermediate I: methyl 5,5-difluoro-1-(((2S,4S)-4-hydroxytetrahydro-2H-pyran-2-yl)methyl)-4,5,6,7-tetrahydro-1H-indazole-3-carboxylate

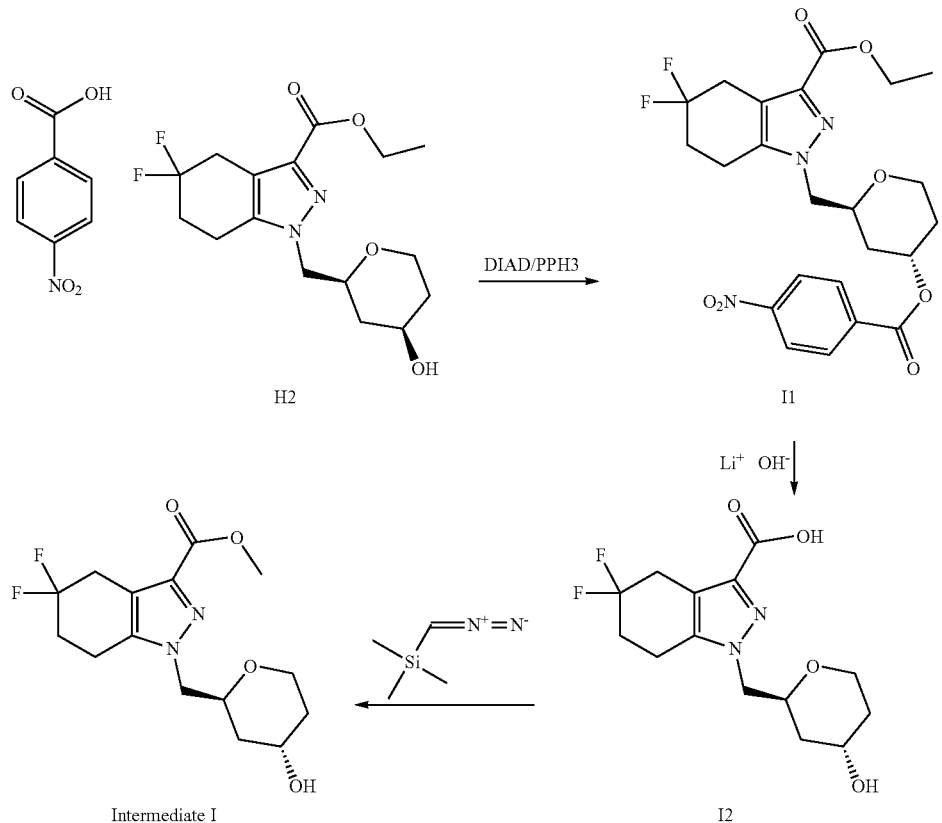

Step 1: ethyl 5,5-difluoro-1-(((2S,4S)-4-((4-nitrobenzoyl)oxy)tetrahydro-2H-pyran-2-yl)methyl)-4,5,6,7-tetrahydro-1H-indazole-3-carboxylate (I1)

To a mixture of triphenylphosphine (254 mg, 0.970 mmol), 4-nitrobenzoic acid (113 mg, 0.679 mmol) and ethyl 5,5-difluoro-1-(((2S,4R)-4-hydroxytetrahydro-2H-pyran-2-yl)methyl)-4,5,6,7-tetrahydro-1H-indazole-3-carboxylate (167 mg, 0.485 mmol) in THF (1 ml), sealed and stirred at 0° C., was added DIAD (0.189 ml, 0.970 mmol). The mixture was stirred at RT for 3 h before diluting with EtOAc (20 ml) and water (20 ml). The organics were concentrated, purified on normal phase chromatography, and eluted with 0 to 100% EtOAc in hexane. The title compound was isolated as an oil. MS: 494.27 (M+1).

Step 2: 5,5-difluoro-1-(((2S,4S)-4-hydroxytetrahydro-2H-pyran-2-yl)methyl)-4,5,6,7-tetrahydro-1H-indazole-3-carboxylic Acid (I2)

To a solution of ethyl 5,5-difluoro-1-(((2S,4S)-4-((4-nitrobenzoyl)oxy)tetrahydro-2H-pyran-2-yl)methyl)-4,5,6,7-tetrahydro-1H-indazole-3-carboxylate (203 mg, 0.411 mmol) in MeOH (1 ml) was added LiOH (1.097 ml, 1.646 mmol) and stirred at RT overnight. The reaction was then quenched with drops of 1 N HCl diluted with 1 ml MeOH, and purified on C18 reversed phase chromatography with 0 to 100% ACN in water with 0.05% TFA. The title compound was isolated and lyophilized as a solid. MS: 317.17 (M+1).

Step 3: methyl 5,5-difluoro-1-(((2S,4S)-4-hydroxytetrahydro-2H-pyran-2-yl)methyl)-4,5,6,7-tetrahydro-1H-indazole-3-carboxylate To a stirred solution of 5,5-difluoro-1-(((2S,4S)-4-hydroxytetrahydro-2H-pyran-2-yl)methyl)-4,5,6,7-tetrahydro-1H-indazole-3-carboxylic acid (50 mg, 0.158 mmol) in MeOH (1 ml) was added TMS-Diazomethane (0.158 ml, 0.316 mmol) in THF solution dropwise until the solution was turned yellow. The resulting solution was stirred at RT for 2 h. The mixture was carefully quenched with acetic acid. The reaction mixture was concentrated and partitioned between EtOAc (10 ml) and water (10 ml). The combined organic layers were concentrated, purified on normal phase chromatography with 0 to 100% 3:1 EtOAc/EtOH and hexane. The title compound was collected as an oil. MS: 331.16 (M+1).

Intermediate J: ethyl (3bR,4aR)-3b,4,4a,5-tetrahydro-2H-cyclopropa[3,4]cyclopenta[1,2-c]pyrazole-3-carboxylate

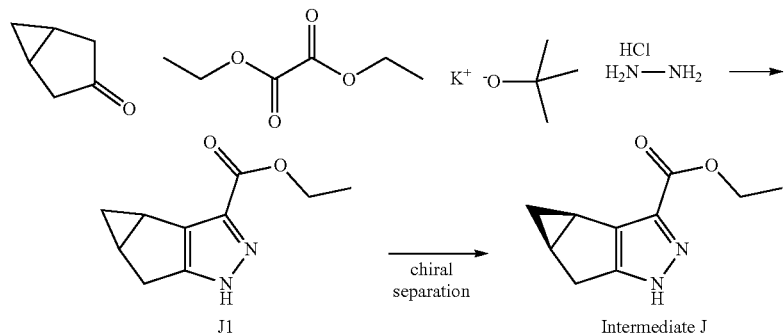

Step 1: ethyl 3b,4,4a,5-tetrahydro-1H-cyclopropa[3,4]cyclopenta[1,2-c]pyrazole-3-carboxylate (J1)

To a solution of bicyclo[3.1.0]hexan-3-one (3.1 g, 32.2 mmol) and diethyl oxalate (4.40 ml, 32.2 mmol) in EtOH (64.5 ml) was added KOtBu (32.2 ml, 32.2 mmol) at 0° C. The mixture was warmed up to RT upon completion of the KOtBu addition, and stirred at RT for 2.5 h. The reaction was then cooled to 0° C., hydrazine monohydrochloride (2.65 g, 38.7 mmol) in water (15 mL) was added. The resulting mixture was stirred overnight before being treated with water, and extracted with EtOAc (2×50 mL). The combined organics were dried over $Na_2SO_4$. The resulting mixture was concentrated, purified on HPLC silica gel, and eluted with EtOAc/hexane (5% to 100%) to afford the title compound. MS: 193.16 (M+1).

Step 2: ethyl (3bR,4aR)-3b,4,4a,5-tetrahydro-2H-cyclopropa[3,4]cyclopenta[1,2-c]pyrazole-3-carboxylate The first peak from chiral separation using a chiral column: AD-H, co-solvent: EtOH is Intermediate J.

Intermediate K: (3bR,4aR)-1-(2-((1s,4S)-4-((3-methylpyridin-2-yl)oxy)cyclohexyl)ethyl)-3b,4,4a,5-tetrahydro-1H-cyclopropa[3,4]cyclopenta[1,2-c]pyrazole-3-carboxylic Acid

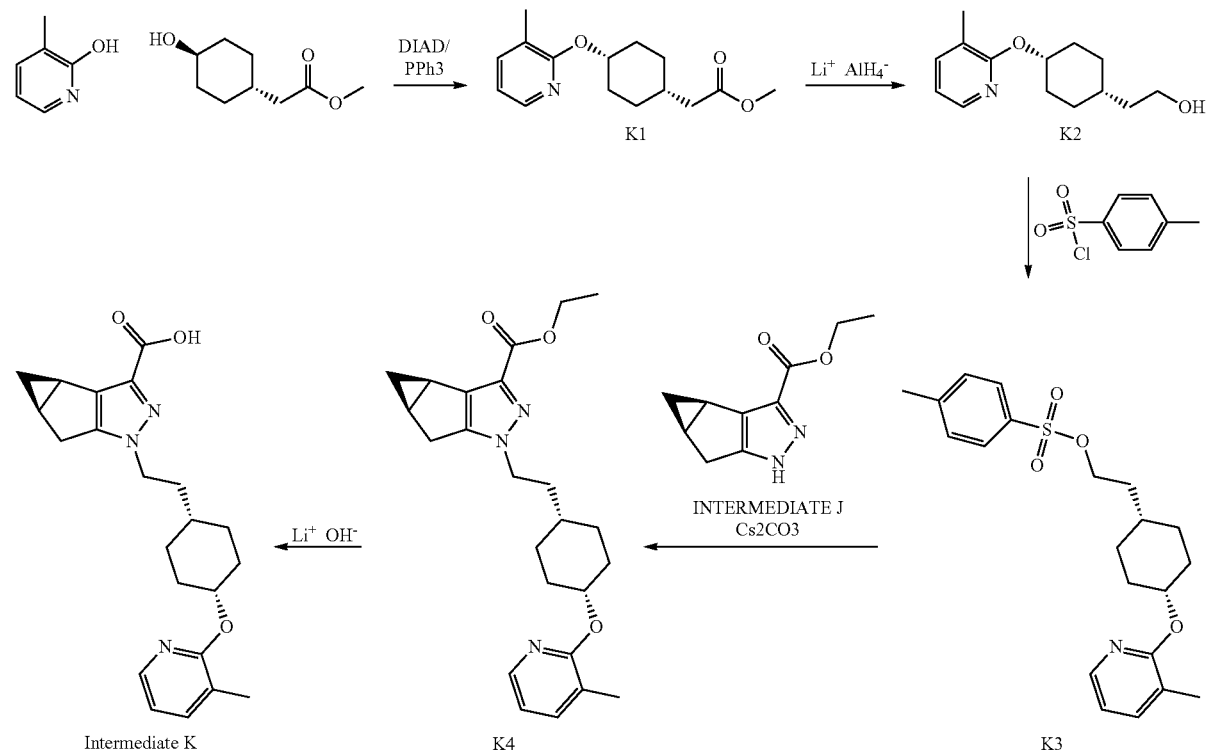

Step 1: methyl 2-((1s,4s)-4-((3-methylpyridin-2-yl)oxy)cyclohexyl)acetate (K1)

To a stirring solution of methyl 2-((1r,4r)-4-hydroxycyclohexyl)acetate (500 mg, 2.90 mmol), 3-methylpyridin-2-ol (380 mg, 3.48 mmol) and triphenylphosphine (1523 mg, 5.81 mmol) in THE (1 ml) at 0° C. was added DIAD (1.129 ml, 5.81 mmol). The mixture was stirred at 50° C. overnight before cooled down and diluted with EtOAc (50 ml) and water (50 ml). The organic layer was concentrated, purified on normal phase chromatography with 0 to 100% EtOAc in hexane. The title compound was isolated as an oil. MS: 265.21 (M+1).

Step 2: 2-((1s,4s)-4-((3-methylpyridin-2-yl)oxy)cyclohexyl)ethan-1-ol (K2)

To a stirring solution of methyl 2-((1s,4s)-4-((3-methylpyridin-2-yl)oxy)cyclohexyl)acetate (325 mg, 1.234 mmol) in THE (1 ml) at 0° C. was added LiAlH$_4$ (0.617 ml, 1.234 mmol). The mixture was stirred at RT for 4 h before quenched with water at 0° C. The mixture was then diluted with 10 ml of EtOAc, and washed with 2×5 ml of water and 1 ml of 1N HCl. The organic layer was dried over Na$_2$SO$_4$, concentrated, and purified on normal phase chromatography with 0 to 100% EtOAc in hexane. The title compound was isolated as an oil. MS: 237.18 (M+1).

Step 3: 2-((1s,4s)-4-((3-methylpyridin-2-yl)oxy)cyclohexyl)ethyl 4-methylbenzenesulfonate (K3)

To a solution of 2-((1s,4s)-4-((3-methylpyridin-2-yl)oxy)cyclohexyl)ethanol (575 mg, 2.443 mmol) in pyridine (2 ml) was added Ts-Cl (559 mg, 2.93 mmol). The mixture was stirred at RT for 2 h before pyridine was removed from rotovap. The residue was diluted with EtOAc (20 ml) and water (20 ml). The organic layer was concentrated, purified on normal phase chromatography with 0 to 100% EtOAc in hexane. The title compound was isolated as an oil. MS: 391.25 (M+1).

Step 4: ethyl (3bR,4aR)-1-(2-((1s,4S)-4-((3-methylpyridin-2-yl)oxy)cyclohexyl)ethyl)-3b,4,4a,5-tetrahydro-1H-cyclopropa[3,4]cyclopenta[1,2-c]pyrazole-3-carboxylate (K4)

To a solution of (3bS,4aS)-ethyl 3b,4,4a,5-tetrahydro-1H-cyclopropa[3,4]cyclopenta[1,2-c]pyrazole-3-carboxylate (420 mg, 2.187 mmol) in 1,4-dioxane (5 ml) were added Cs$_2$CO$_3$ (1188 mg, 3.65 mmol) and 2-((1s,4S)-4-((3-methylpyridin-2-yl)oxy)cyclohexyl)ethyl 4-methylbenzenesulfonate (710 mg, 1.823 mmol). The mixture was stirred at 50° C. overnight, quenched with water at RT, and diluted with EtOAc (20 ml) and water (20 ml). The organic layer was concentrated, purified on normal phase chromatography with 0 to 100% EtOAc in hexane. The title compound was isolated and concentrated as an oil. MS: 410.17 (M+1).

Step 5. (3bR,4aR)-1-(2-((1s,4S)-4-((3-methylpyridin-2-yl)oxy)cyclohexyl)ethyl)-3b,4,4a,5-tetrahydro-1H-cyclopropa[3,4]cyclopenta[1,2-c]pyrazole-3-carboxylic acid To a stirring solution of (3bR,4aR)-ethyl 1-(2-((1s,4R)-4-((3-methylpyridin-2-yl)oxy)cyclohexyl)ethyl)-3b,4,4a,5-tetrahydro-1H-cyclopropa[3,4]cyclopenta[1,2-c]pyrazole-3-carboxylate (723 mg, 1.765 mmol) in MeOH (3 ml) and water (3 ml) was added LiOH (254 mg, 10.59 mmol). The mixture was stirred at RT for 2 h, then heated to 40° C. for 1 h. The solvent was removed under rotovap. The residue was partitioned between EtOAc (50 ml) and water (50 ml). The pH was adjusted to 4.5 to afford the title compound. MS: 382.22 (M+1).

Intermediate L: ethyl 6-(trifluoromethyl)-4,5,6,7-tetrahydro-1H-indazole-3-carboxylate

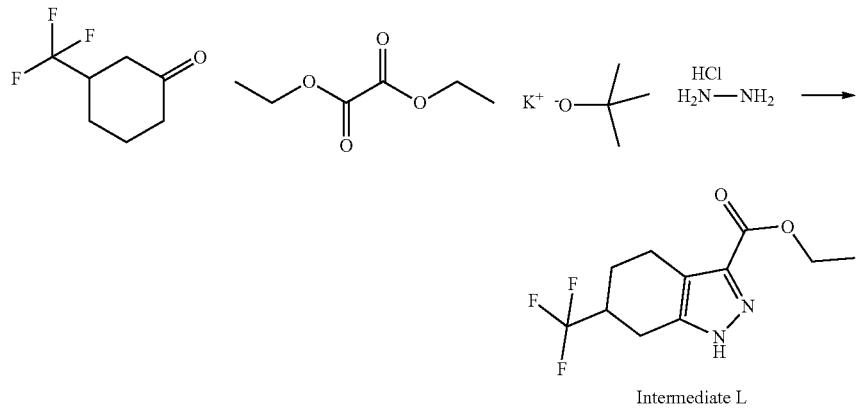

Intermediate L

To a solution of 3-(trifluoromethyl)cyclohexanone (3.3 g, 19.86 mmol) and diethyl oxalate (2.90 g, 19.86 mmol) in EtOH (20 ml) was added potassium tert-butoxide (19.86 ml, 19.86 mmol) at 0° C. The mixture was warmed up to RT upon completion of the KOtBu addition. The mixture was stirred at RT for 1.5 h. The mixture was then cooled back to 0° C., and hydrazine monohydrochloride (1.633 g, 23.84 mmol) in water (5 mL) was added. The mixture was stirred at RT overnight before the solvent was removed on rotovap. The residue was then partitioned between EtOAc (50 ml) and water (50 ml), and the combined organics were dried over Na$_2$SO$_4$ and concentrated. The resulting mixture was purified by normal phase chromatography with EtOAc/hexane (5% to 100%) to afford the title compound as an oil. MS: 263.25 (M+1).

Intermediate M: ethyl 6-(difluoromethyl)-4,5,6,7-tetrahydro-1H-indazole-3-carboxylate

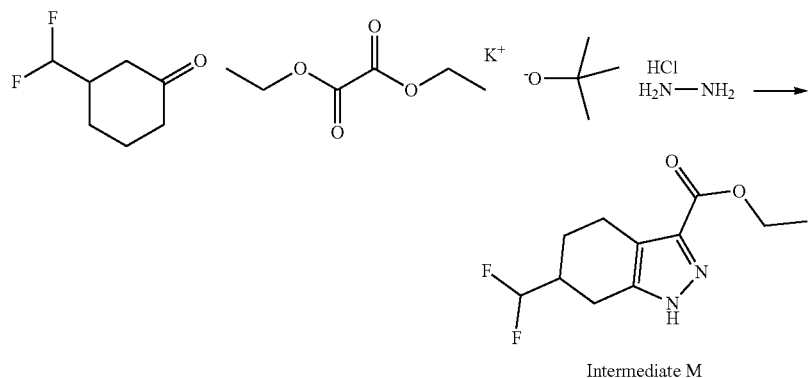

Intermediate M

To a solution of 3-(difluoromethyl)cyclohexanone (1 g, 6.75 mmol) and diethyl oxalate (0.986 g, 6.75 mmol) in EtOH (20 ml) was added potassium tert-butoxide (6.75 ml, 6.75 mmol) at 0° C. The mixture was warmed up to RT upon completion of the KOtBu addition. The mixture was stirred at RT for 1.5 h. The mixture was then cooled back to 0° C., and hydrazine monohydrochloride (0.555 g, 8.10 mmol) in water (5 mL) was added. The resulting mixture was stirred at RT overnight before the solvent was removed on rotovap. The residue was partitioned between EtOAc (50 ml) and water (50 ml), and the combined organics were dried over Na₂SO₄ and concentrated. The resulting mixture was purified by normal phase chromatography with EtOAc/hexane (5% to 100%) to afford the title compound as an oil. MS: 245.26 (M+1).

EXAMPLES

Example 1: (1-(2-(1-(2,3-dimethylphenyl)piperidin-4-yl)ethyl)-1,4,5,6-tetrahydrocyclopenta[c]pyrazol-3-yl)(4-hydroxypiperidin-1-yl)methanone

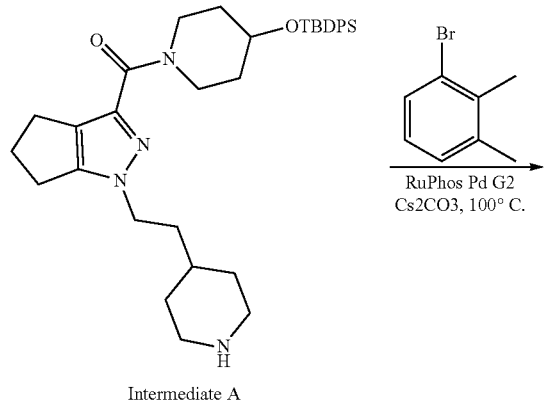

Intermediate A

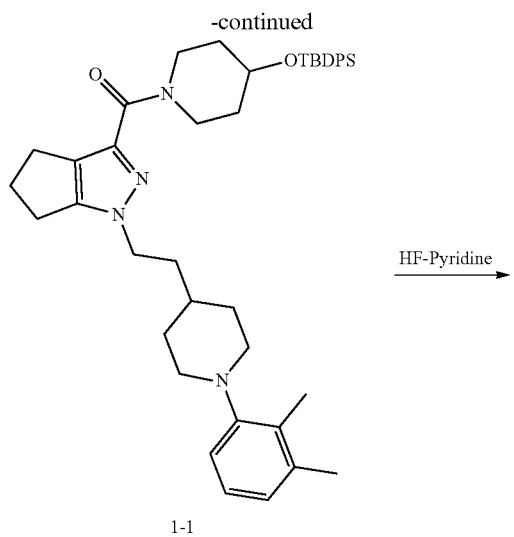

1-1

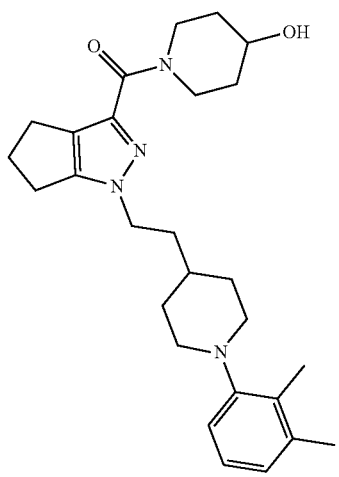

Step 1: (4-((tert-butyldiphenylsilyl)oxy)piperidin-1-yl)(1-(2-(1-(2,3-dimethylphenyl)piperidin-4-yl)ethyl)-1,4,5,6-tetrahydrocyclopenta[c]pyrazol-3-yl)methanone (1-1)

To a mixture of (4-((tert-butyldiphenylsilyl)oxy)piperidin-1-yl)(1-(2-(piperidin-4-yl)ethyl)-1,4,5,6-tetrahydrocyclopenta[c]pyrazol-3-yl)methanone (Intermediate A) (50 mg, 0.085 mmol) in dioxane (427 μl) at ambient temperature were added 1-bromo-2,3-dimethylbenzene (100 mg, 0.540 mmol), $Cs_2CO_3$ (84 mg, 0.256 mmol), and RuPhos Pd G2 (6.64 mg, 8.55 μmol). The mixture was heated to 100° C. and stirred overnight. The mixture was purified by column chromatography on silica (2-60% 3:1 EtOAc:EtOH/hexane) to afford the title compound. MS: 689.8 (M+1).

Step 2: (1-(2-(1-(2,3-dimethylphenyl)piperidin-4-yl)ethyl)-1,4,5,6-tetrahydrocyclopenta[c]pyrazol-3-yl)(4-hydroxypiperidin-1-yl)methanone (Example 1)

To a mixture of (4-((tert-butyldiphenylsilyl)oxy)piperidin-1-yl)(1-(2-(1-(2,3-dimethylphenyl)piperidin-4-yl)ethyl)-1,4,5,6-tetrahydrocyclopenta[c]pyrazol-3-yl)methanone (1-1) (26.8 mg, 0.039 mmol) in THF (156 μl)/water (38.9 μl) at ambient temperature was added HF-pyridine (38.5 mg, 0.389 mmol). The mixture was stirred overnight and purified by reversed phase HPLC (5-95% ACN/water with 0.05% TFA modifier) to afford the title compound. MS: 451.5 (M+1). $^1$H NMR (500 MHz, DMSO-d6) δ 7.23-6.80 (m, 3H), 4.34-4.26 (s, 2H), 4.07 (t, J=6.9 Hz, 2H), 4.03-3.97 (m, 2H), 3.70 (tt, J=8.3, 3.9 Hz, 2H), 3.47-3.38 (m, 2H), 3.13-3.05 (m, 2H), 2.71 (t, J=7.1 Hz, 2H), 2.59 (t, J=7.1 Hz, 2H), 2.50-2.44 (m, 2H), 2.22 (s, 3H), 2.18 (s, 3H), 1.90-1.78 (m, 2H), 1.77-1.69 (m, 4H), 1.52-1.37 (m, 2H), 1.36-1.21 (m, 3H).

The examples in the following table were prepared in an analogous manner to Example 1 using appropriate starting materials described previously or commercially available.

| Ex. # | Structure | Chemical Name | Mass [M + H]⁺ |
|---|---|---|---|
| 2 | 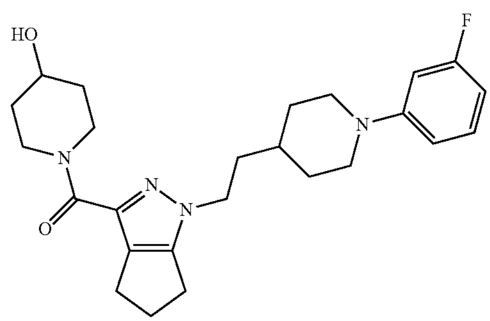 [SMILES: O=C(c1nn(CCC2CCN(c3cccc(F)c3)CC2)c2c1CCC2)N1CCC(O)CC1] | [1-[2-[1-(3-fluorophenyl)piperidin-1-ium-4-yl]ethyl]-5,6-dihydro-4H-cyclopenta[c]pyrazol-3-yl]-(4-hydroxy-1-piperidyl)methanone | 441.5 |
| 3 | 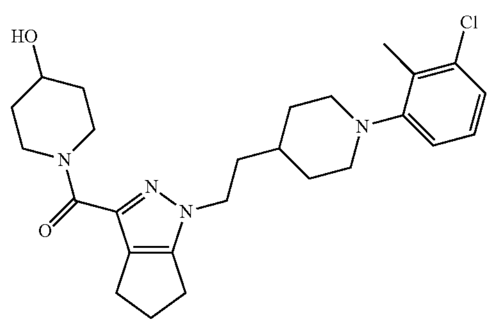 [SMILES: Cc1c(Cl)cccc1N1CCC(CCn2nc(C(=O)N3CCC(O)CC3)c3c2CCC3)CC1] | [1-[2-[1-(3-chloro-2-methylphenyl)piperidin-1-ium-4-yl]ethyl]-5,6-dihydro-4H-cyclopenta[c]pyrazol-3-yl]-(4-hydroxy-1-piperidyl)methanone | 471.3 |
| 4 | 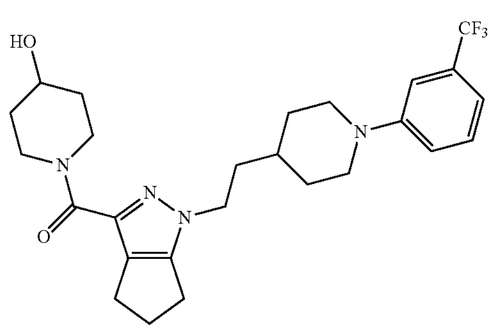 [SMILES: O=C(c1nn(CCC2CCN(c3cccc(C(F)(F)F)c3)CC2)c2c1CCC2)N1CCC(O)CC1] | (4-hydroxy-1-piperidyl)-[1-[2-[1-[3-(trifluoromethyl)phenyl]-4-piperidyl]ethyl]-5,6-dihydro-4H-cyclopenta[c]pyrazol-3-yl]methanone | 491.2 |

-continued

| Ex. # | Structure | Chemical Name | Mass [M + H]+ |
|---|---|---|---|
| 5 | 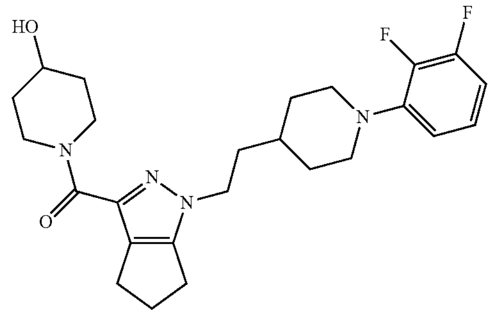 [SMILES: O=C(c1nn(CCC2CCN(c3cccc(F)c3F)CC2)c2c1CCC2)N1CCC(O)CC1] | [1-[2-[1-(2,3-difluorophenyl)piperidin-1-ium-4-yl]ethyl]-5,6-dihydro-4H-cyclopenta[c]pyrazol-3-yl]-(4-hydroxy-1-piperidyl)methanone | 459.4 |
| 6 | 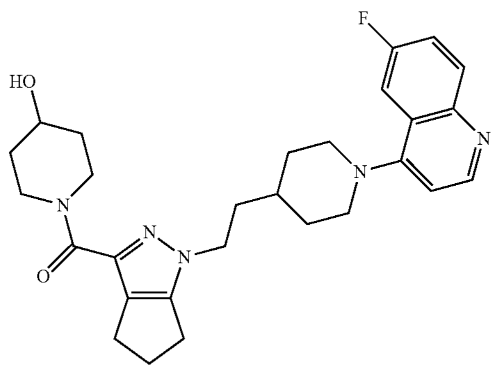 [SMILES: O=C(c1nn(CCC2CCN(c3ccnc4ccc(F)cc34)CC2)c2c1CCC2)N1CCC(O)CC1] | [1-[2-[1-(6-fluoroquinolin-1-ium-4-yl)-4-piperidyl]ethyl]-5,6-dihydro-4H-cyclopenta[c]pyrazol-3-yl]-(4-hydroxy-1-piperidyl)methanone | 492.4 |
| 7 | 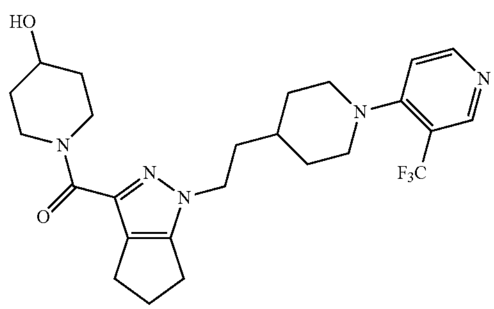 [SMILES: O=C(c1nn(CCC2CCN(c3ccncc3C(F)(F)F)CC2)c2c1CCC2)N1CCC(O)CC1] | (4-hydroxy-1-piperidyl)-[1-[2-[1-[3-(trifluoromethyl)pyridin-1-ium-4-yl]-4-piperidyl]ethyl]-5,6-dihydro-4H-cyclopenta[c]pyrazol-3-yl]methanone | 492.4 |

Example 8: (1-(2-(1-(4-fluoro-2,3-dimethylphenyl)piperidin-4-yl)ethyl)-1,4,5,6-tetrahydrocyclopenta[c]pyrazol-3-yl)(4-fluoro-4-(hydroxymethyl)piperidin-1-yl)methanone

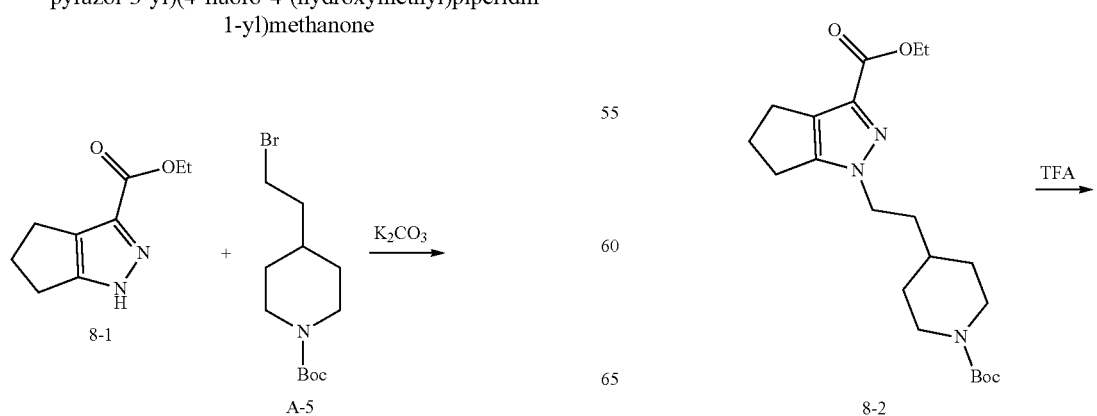

-continued

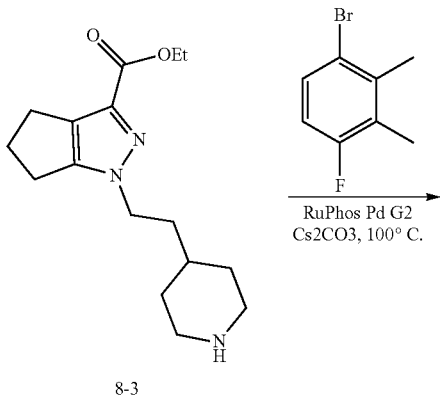

8-3

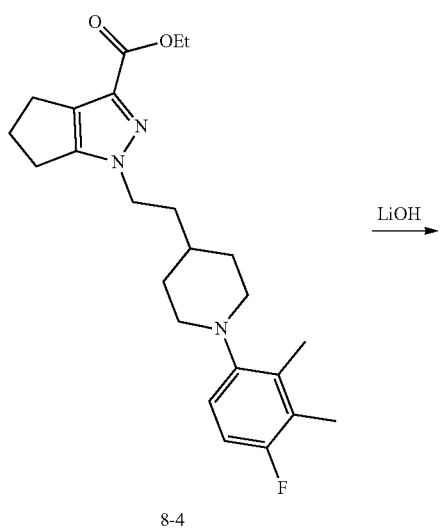

8-4

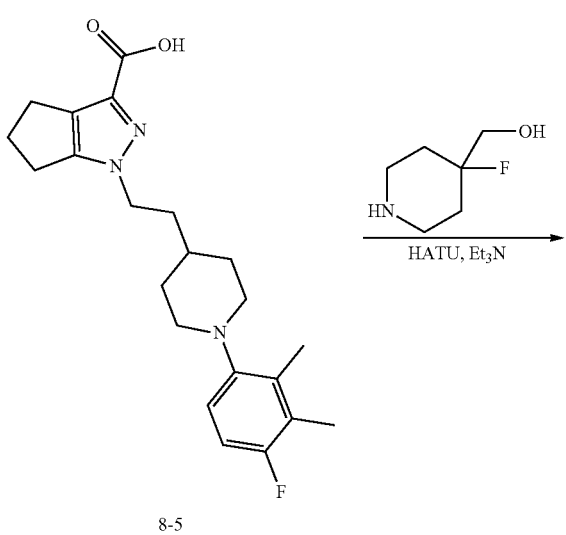

8-5

-continued

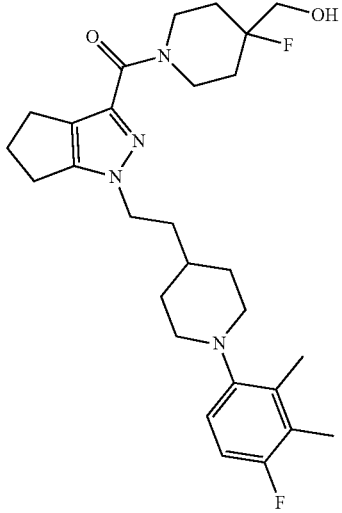

Example 8

Step 1: ethyl 1-(2-(1-(tert-butoxycarbonyl)piperidin-4-yl)ethyl)-1,4,5,6-tetrahydrocyclopenta[c]pyrazole-3-carboxylate (8-2)

To a mixture of ethyl 1,4,5,6-tetrahydrocyclopenta[c]pyrazole-3-carboxylate (8-1) (2.50 g, 13.87 mmol) in DMF (13.87 ml) at ambient temperature were added tert-butyl 4-(2-bromoethyl)piperidine-1-carboxylate (A-5) (4.86 g, 16.65 mmol) and $K_2CO_3$ (3.83 g, 27.7 mmol). The mixture was allowed to stir overnight before quenching with water (50 mL), extracting with EtOAc (50 mL×3), drying over $Na_2SO_4$, and concentrating. The residue was purified by column chromatography on silica (2-80% 3:1 EtOAc:EtOH/hexane) to afford the title compound. MS: 392.2 (M+1).

Step 2: ethyl 1-(2-(piperidin-4-yl)ethyl)-1,4,5,6-tetrahydrocyclopenta[c]pyrazole-3-carboxylate (8-3

To a mixture of ethyl 1-(2-(1-(tert-butoxycarbonyl)piperidin-4-yl)ethyl)-1,4,5,6-tetrahydrocyclopenta[c]pyrazole-3-carboxylate (8-2) (1000 mg, 2.55 mmol) in DCM (6386 µl) at ambient temperature was added TFA (1968 µl, 25.5 mmol). The mixture was stirred for 2 h before concentrating, taking up in toluene, and reconcentrating. The resulting residue was taken up in 10 mL water/10 mL ACN and was lyophilized to afford the title compound. MS: 292.2 (M+1).

Step 3: ethyl 1-(2-(1-(4-fluoro-2,3-dimethylphenyl)piperidin-4-yl)ethyl)-1,4,5,6-tetrahydrocyclopenta[c]pyrazole-3-carboxylate (8-4)

To a mixture of ethyl 1-(2-(piperidin-4-yl)ethyl)-1,4,5,6-tetrahydrocyclopenta[c]pyrazole-3-carboxylate (8-3) (250 mg, 0.858 mmol) in dioxane (2600 µl) at ambient temperature were added 1-bromo-4-fluoro-2,3-dimethylbenzene (523 mg, 2.57 mmol), $Cs_2CO_3$ (839 mg, 2.57 mmol), and RuPhos Pd G2 (66.6 mg, 0.086 mmol). The mixture was heated to 100° C. and stirred overnight. The mixture was purified directly by column chromatography on silica (2-60% 3:1 EtOAc:EtOH/hexane) to afford the title compound. MS: 414.2 (M+1).

Step 4: 1-(2-(1-(4-fluoro-2,3-dimethylphenyl)piperidin-4-yl)ethyl)-1,4,5,6-tetrahydrocyclopenta[c]pyrazole-3-carboxylic Acid (8-5)

To a mixture of ethyl 1-(2-(1-(4-fluoro-2,3-dimethylphenyl)piperidin-4-yl)ethyl)-1,4,5,6-tetrahydrocyclopenta[c]pyrazole-3-carboxylate (8-4) (200 mg, 0.484 mmol) in THF (806 µl)/MeOH (806 µl)/acetonitrile (806 µl) at ambient temperature was added 2.0 M LiOH (484 µl, 0.967 mmol). The mixture stirred for 5 h before acidifying with TFA. The mixture was purified directly by column chromatography on a C18 column (5-95% ACN/water with 0.05% TFA modifier) to afford the title compound. MS: 386.2 (M+1).

Step 5: (1-(2-(1-(4-fluoro-2,3-dimethylphenyl)piperidin-4-yl)ethyl)-1,4,5,6-tetrahydrocyclopenta[c]pyrazol-3-yl)(4-fluoro-4-(hydroxymethyl)piperidin-1-yl)methanone (8)

To a mixture of 1-(2-(1-(4-fluoro-2,3-dimethylphenyl)piperidin-4-yl)ethyl)-1,4,5,6-tetrahydrocyclopenta[c]pyrazole-3-carboxylic acid (8-5) (30 mg, 0.078 mmol) in DMF (389 µl) at ambient temperature were added (4-fluoropiperidin-4-yl)methanol (20.73 mg, 0.156 mmol), DIPEA (27.2 µl, 0.156 mmol), and HATU (44.4 mg, 0.117 mmol). The mixture was stirred for 2 h before acidifying with a few drops of TFA. The mixture was purified directly by column chromatography on a C18 column (5-95% ACN/water with 0.05% TFA modifier) to afford the title compound. MS: 501.2 (M+1). $^1$H NMR (500 MHz, DMSO-d6) δ 7.06-6.92 (m, 2H), 4.64-4.54 (m, 2H), 4.29-4.23 (m, 2H), 4.07 (t, J=6.9 Hz, 2H), 3.43 (d, J=19.8 Hz, 2H), 3.39-3.32 (m, 2H), 3.07-2.93 (m, 3H), 2.71 (t, J=7.1 Hz, 2H), 2.64-2.57 (m, 2H), 2.47 (t, J=7.0 Hz, 2H), 2.20 (s, 3H), 2.12 (s, 3H), 1.86-1.70 (m, 6H), 1.69-1.52 (m, 2H), 1.48-1.32 (s, 3H).

The examples in the following table were prepared in an analogous manner to Example 8 using appropriate starting materials described previously or commercially available.

| Ex. # | Structure | Chemical Name | Mass [M + H]$^+$ |
|---|---|---|---|
| 9 | 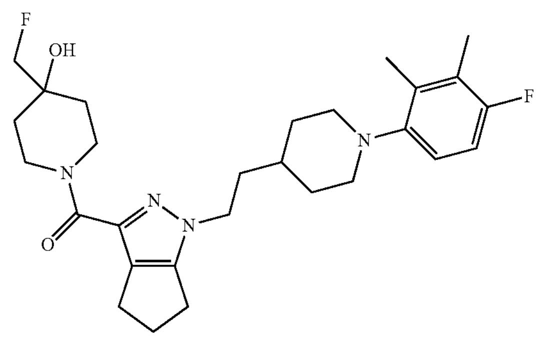 [SMILES: Cc1c(F)ccc(N2CCC(CCn3nc(C(=O)N4CCC(O)(CF)CC4)c4c3CCC4)CC2)c1C] | [1-[2-[1-(4-fluoro-2,3-dimethyl-phenyl)piperidin-1-ium-4-yl]ethyl]-5,6-dihydro-4H-cyclopenta[c]pyrazol-3-yl]-[4-(fluoromethyl)-4-hydroxy-1-piperidyl]methanone | 501.2 |
| 10 | 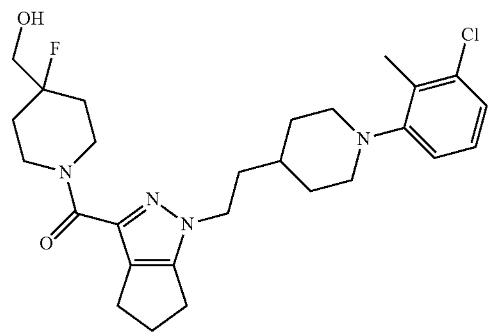 [SMILES: Cc1c(Cl)cccc1N1CCC(CCn2nc(C(=O)N3CCC(F)(CO)CC3)c3c2CCC3)CC1] | [1-[2-[1-(3-chloro-2-methyl-phenyl)piperidin-1-ium-4-yl]ethyl]-5,6-dihydro-4H-cyclopenta[c]pyrazol-3-yl]-[4-fluoro-4-(hydroxymethyl)-1-piperidyl]methanone | 503.2 |
| 11 | 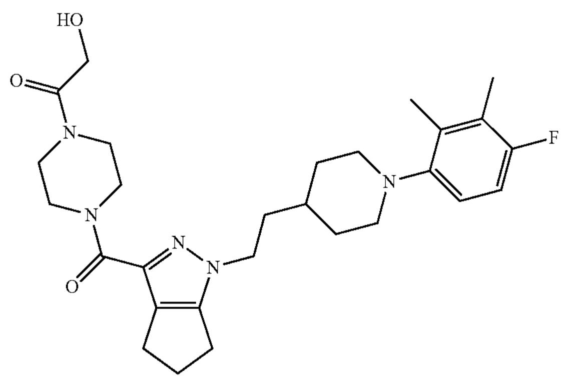 [SMILES: Cc1c(F)ccc(N2CCC(CCn3nc(C(=O)N4CCN(C(=O)CO)CC4)c4c3CCC4)CC2)c1C] | 1-[4-[1-[2-[1-(4-fluoro-2,3-dimethyl-phenyl)piperidin-1-ium-4-yl]ethyl]-5,6-dihydro-4H-cyclopenta[c]pyrazole-3-carbonyl]piperazin-1-yl]-2-hydroxy-ethanone | 512.2 |

| Ex. # | Structure | Chemical Name | Mass [M + H]⁺ |
|---|---|---|---|
| 12 | 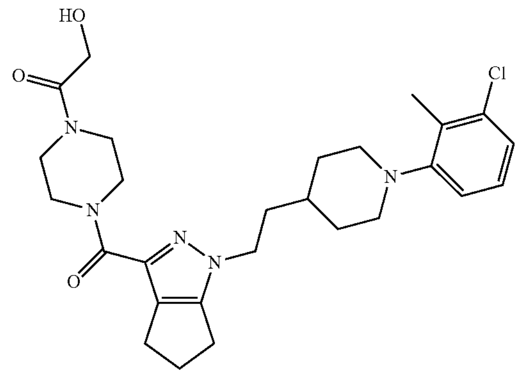 [SMILES: Cc1c(Cl)cccc1N1CCC(CCn2nc(C(=O)N3CCN(C(=O)CO)CC3)c3c2CCC3)CC1] | 1-[4-[1-[2-[1-(3-chloro-2-methyl-phenyl)piperidin-1-ium-4-yl]ethyl]-5,6-dihydro-4H-cyclopenta[c]pyrazole-3-carbonyl]piperazin-1-yl]-2-hydroxy-ethanone | 514.2 |
| 13 | Chiral, cis | [1-[2-[1-(4-fluoro-2,3-dimethyl-phenyl)piperidin-1-ium-4-yl]ethyl]-5,6-dihydro-4H-cyclopenta[c]pyrazol-3-yl]-(3-fluoro-4-hydroxy-1-piperidyl)methanone | 487.2 |
| 14 | Chiral, cis | [1-[2-[1-(3-chloro-2-methyl-phenyl)piperidin-1-ium-4-yl]ethyl]-5,6-dihydro-4H-cyclopenta[c]pyrazol-3-yl]-(3-fluoro-4-hydroxy-1-piperidyl)methanone | 489.1 |
| 15 | 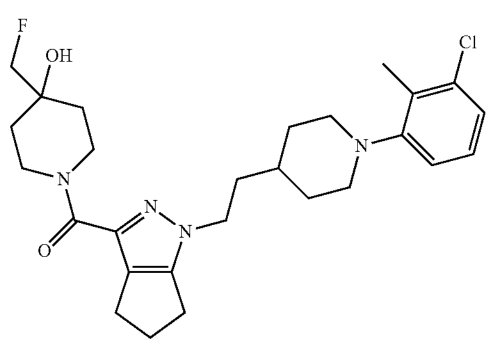 [SMILES: Cc1c(Cl)cccc1N1CCC(CCn2nc(C(=O)N3CCC(O)(CF)CC3)c3c2CCC3)CC1] | [1-[2-[1-(3-chloro-2-methyl-phenyl)piperidin-1-ium-4-yl]ethyl]-5,6-dihydro-4H-cyclopenta[c]pyrazol-3-yl]-(3-fluoro-4-hydroxy-1-piperidyl)methanone | 503.2 |

Example 16: N-(1-(1-(2-(1-(2-(trifluoromethyl)phenyl)piperidin-4-yl)ethyl)-4,5,6,7-tetrahydro-1H-indazole-3-carbonyl)piperidin-4-yl)acetamide

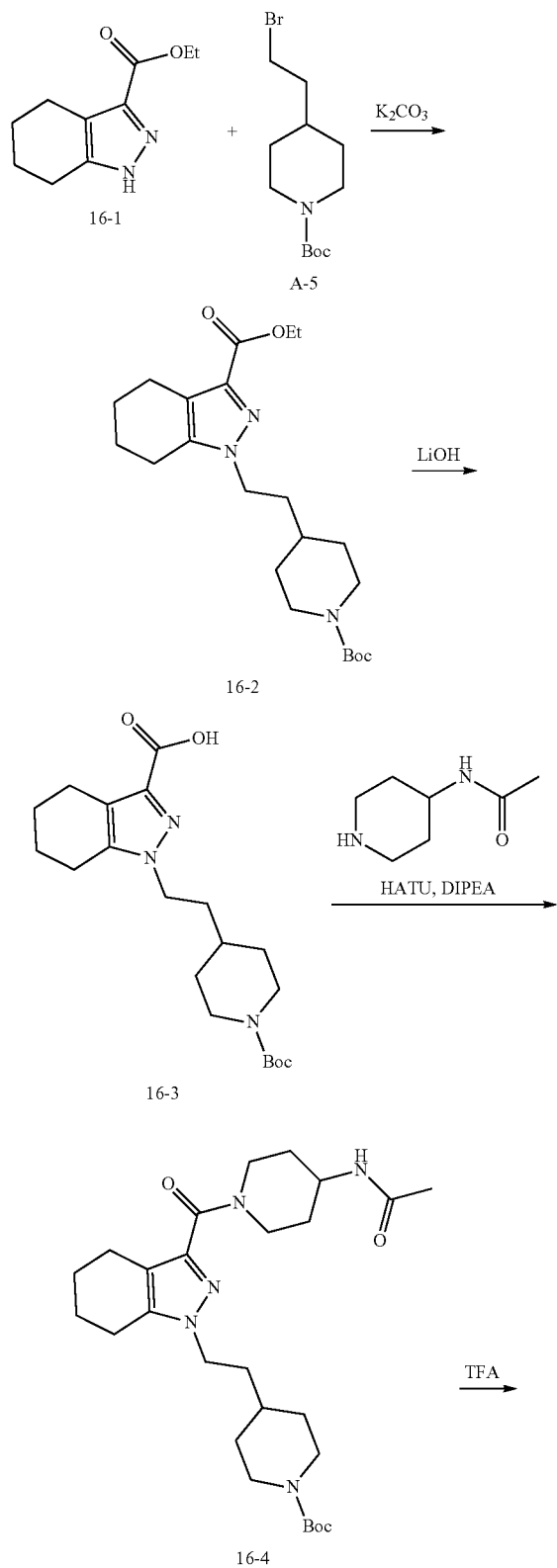

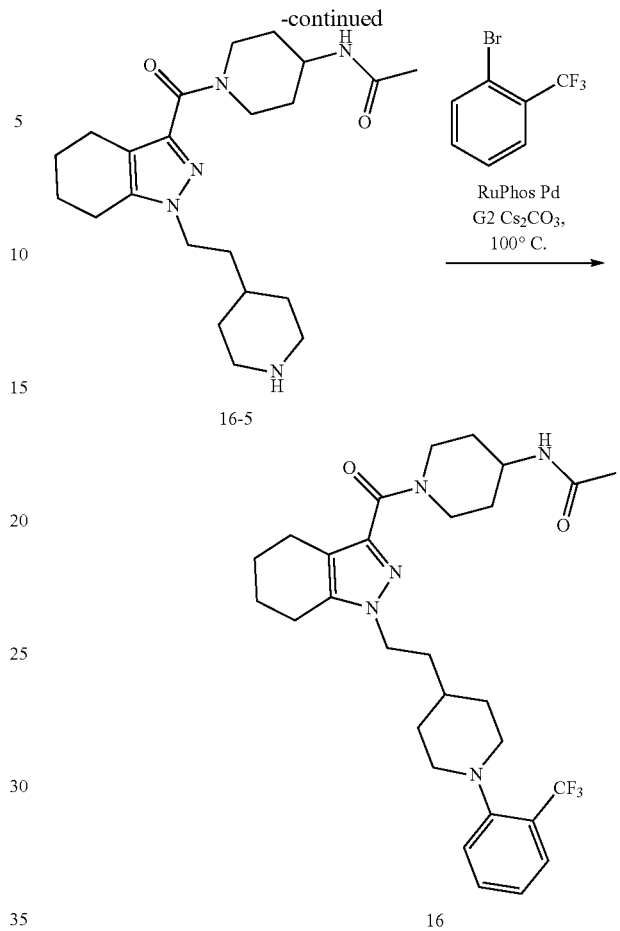

Step 1: 1-(2-(1-(tert-butoxycarbonyl)piperidin-4-yl)ethyl)-4,5,6,7-tetrahydro-1H-indazole-3-carboxylate (16-2)

To a mixture of ethyl 4,5,6,7-tetrahydro-1H-indazole-3-carboxylate (1.50 g, 7.72 mmol) in dioxane (23.40 ml) at ambient temperature were added tert-butyl 4-(2-bromoethyl)piperidine-1-carboxylate (2.482 g, 8.50 mmol) and $Cs_2CO_3$ (3.02 g, 9.27 mmol). The mixture was heated to 80° C. and stirred overnight. The mixture was cooled and the insolubles were filtered off before concentrating. The resulting residue was purified using an ISCO (120 g, silica) with a solvent system of 2% to 70% 3:1 EtOAc:EtOH/hexane to obtain the title compound. MS: 406.2 (M+H).

Step 2: 1-(2-(1-(tert-butoxycarbonyl)piperidin-4-yl)ethyl)-4,5,6,7-tetrahydro-1H-indazole-3-carboxylic Acid (16-3)

To a solution of ethyl 1-(2-(1-(tert-butoxycarbonyl)piperidin-4-yl)ethyl)-4,5,6,7-tetrahydro-1H-indazole-3-carboxylate (2.0 g, 4.93 mmol) in THF (20 ml)/MeOH (10 ml)/water (10 ml) was added lithium hydroxide monohydrate (828 mg, 19.73 mmol). The reaction was stirred at RT. After 5 h, a clean reaction was neutralized with HCl (2.025 ml, 24.66 mmol) and concentrated under reduced pressure to afford the title compound which was used in the next step without purification. MS: 400.3 (M+Na).

Step 3: tert-butyl 4-(2-(3-(4-acetamidopiperidine-1-carbonyl)-4,5,6,7-tetrahydro-1H-indazol-1-yl)ethyl)piperidine-1-carboxylate (16-4)

To a solution of 1-(2-(1-(tert-butoxycarbonyl)piperidin-4-yl)ethyl)-4,5,6,7-tetrahydro-1H-indazole-3-carboxylic acid (1.86 g, 4.93 mmol) in DMF (40 ml) were added 2-(3H-[1,2,3]triazolo[4,5-b]pyridin-3-yl)-1,1,3,3-tetramethylisouronium hexafluorophosphate (V) (2.248 g, 5.91 mmol), N-(piperidin-4-yl)acetamide (0.841 g, 5.91 mmol) followed by DIPEA (2.58 ml, 14.78 mmol). The reaction mixture was stirred at RT for 2 h. The reaction was concentrated to remove most of DMF and to the residue was added water (300 mL) and 50 ml of brine. The mixture was then extracted with EtOAc (3×150 mL). The combined organic fractions were washed with sat. brine (100 mL), dried over $Na_2SO_4$, filtered and the solvent was evaporated under reduced pressure. The residue was purified by column chromatography on silica gel Isolute Flash Si; 100 g prepacked, eluting with 0-10% MeOH in DCM to isolate the title compound. MS: 502.4 (M+H).

Step 4: N-(1-(1-(2-(piperidin-4-yl)ethyl)-4,5,6,7-tetrahydro-1H-indazole-3-carbonyl)piperidin-4-yl)acetamide (16-5)

Tert-butyl 4-(2-(3-(4-acetamidopiperidine-1-carbonyl)-4,5,6,7-tetrahydro-1H-indazol-1-yl)ethyl)piperidine-1-carboxylate (1.52 g, 3.03 mmol) was stirred in DCM (20 ml) and TFA (11.67 ml, 151 mmol) at RT. After 3 h, the starting material was well consumed. The reaction was concentrated under reduced pressure and neutralized with $NH_3$/MeOH. The mixture was concentrated to remove solvents and the residue was purified by preparative HPLC reverse phase (C-18 column), eluting with 0-100% ACN/water to afford the title compound. MS: 402.4 (M+H).

Step 5: N-(1-(1-(2-(1-(2-(trifluoromethyl)phenyl)piperidin-4-yl)ethyl)-4,5,6,7-tetrahydro-1H-indazole-3-carbonyl)piperidin-4-yl)acetamide (Example 16)

To a solution of 1-bromo-2-(trifluoromethyl)benzene (36.0 mg, 0.160 mmol) in dioxane (700 μl) in a 10 ml of microwave vial were added N-(1-(1-(2-(piperidin-4-yl)ethyl)-4,5,6,7-tetrahydro-1H-indazole-3-carbonyl)piperidin-4-yl)acetamide (30 mg, 0.075 mmol), RuPhos G2 (5.80 mg, 7.47 μmol) and $Cs_2CO_3$ (73.0 mg, 0.224 mmol) under nitrogen. The vial was capped and heated to 100° C. under nitrogen overnight. The reaction mixture was concentrated and the residue was purified by preparative HPLC reversed phase (C-18 column), eluting with 0-100% ACN/water to afford the title compound. MS: 546.5 (M+1).

$^1$H NMR (400 MHz, Methanol-$d_4$) δ 7.66-7.51 (m, 2H), 7.43 (d, J=8.0 Hz, 1H), 7.24 (t, J=7.6 Hz, 1H), 4.52 (d, J=14.0 Hz, 1H), 4.32 (d, J=12.8 Hz, 1H), 4.11 (t, J=7.1 Hz, 2H), 4.02-3.80 (m, 2H), 3.25 (d, J=11.6 Hz, 1H), 3.00 (d, J=11.3 Hz, 3H), 2.77-2.59 (m, 4H), 2.55 (t, J=6.0 Hz, 2H), 2.01-1.71 (m, 13H), 1.51-1.38 (in, 5H).

The examples in the following table were prepared in an analogous manner to Example 16 using appropriate starting materials described previously or commercially available.

| Ex. # | Structure | Chemical Name | Mass [M + H]$^+$ |
| --- | --- | --- | --- |
| 17 | 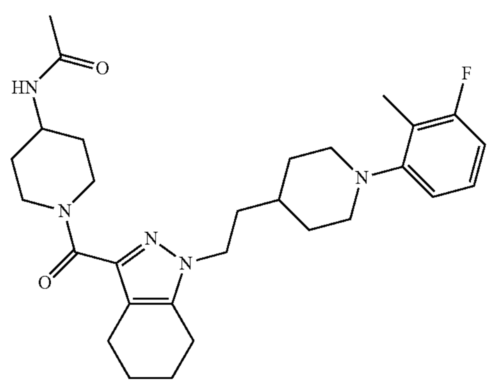 [SMILES: CC(=O)NC1CCN(C(=O)c2nn(CCC3CCN(c4cccc(F)c4C)CC3)c3c2CCCC3)CC1] | N-[1-[1-[2-[1-(3-fluoro-2-methyl-phenyl)-4-piperidyl]ethyl]-4,5,6,7-tetrahydroindazole-3-carbonyl]-4-piperidyl]acetamide | 510.3 |
| 18 | 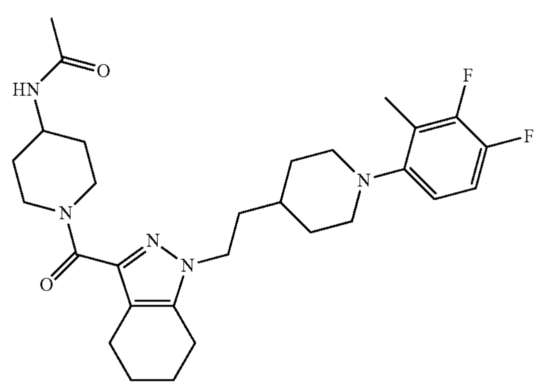 [SMILES: CC(=O)NC1CCN(C(=O)c2nn(CCC3CCN(c4ccc(F)c(F)c4C)CC3)c3c2CCCC3)CC1] | N-[1-[1-[2-[1-(3,4-difluoro-2-methyl-phenyl)-4-piperidyl]ethyl]-4,5,6,7-tetrahydroindazole-3-carbonyl]-4-piperidyl]acetamide | 528.3 |

-continued

| Ex. # | Structure | Chemical Name | Mass [M + H]+ |
|---|---|---|---|
| 19 | 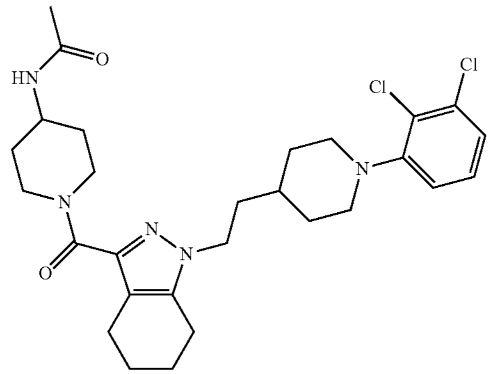 [SMILES: CC(=O)NC1CCN(C(=O)c2nn(CCC3CCN(c4cccc(Cl)c4Cl)CC3)c3c2CCCC3)CC1] | N-[1-[1-[2-[1-(2,3-dichlorophenyl)-4-piperidyl]ethyl]-4,5,6,7-tetrahydroindazole-3-carbonyl]-4-piperidyl]acetamide | 546.3 |
| 20 | 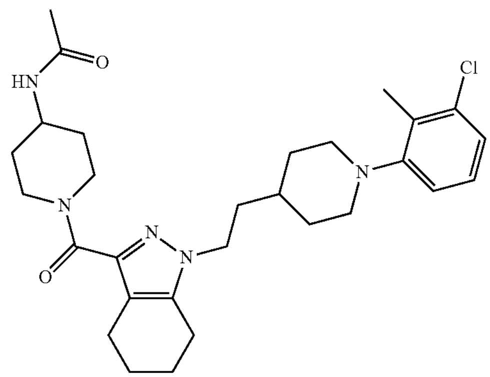 [SMILES: CC(=O)NC1CCN(C(=O)c2nn(CCC3CCN(c4cccc(Cl)c4C)CC3)c3c2CCCC3)CC1] | N-[1-[1-[2-[1-(3-chloro-2-methyl-phenyl)-4-piperidyl]ethyl]-4,5,6,7-tetrahydroindazole-3-carbonyl]-4-piperidyl]acetamide | 526.3 |
| 21 | 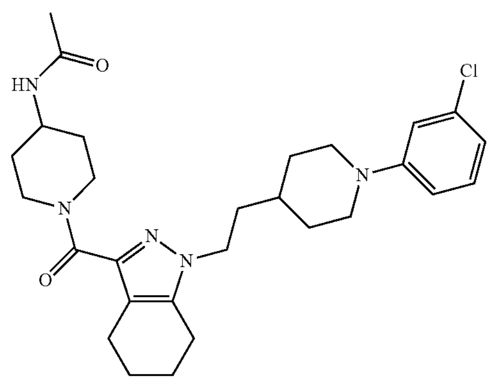 [SMILES: CC(=O)NC1CCN(C(=O)c2nn(CCC3CCN(c4cccc(Cl)c4)CC3)c3c2CCCC3)CC1] | N-[1-[1-[2-[1-(2-chlorophenyl)-4-piperidyl]ethyl]-4,5,6,7-tetrahydroindazole-3-carbonyl]-4-piperidyl]acetamide | 512.3 |
| 22 | 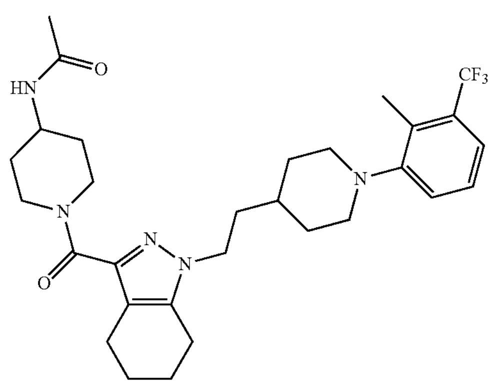 [SMILES: CC(=O)NC1CCN(C(=O)c2nn(CCC3CCN(c4cccc(C(F)(F)F)c4C)CC3)c3c2CCCC3)CC1] | N-[1-[1-[2-[1-[2-methyl-3-(trifluoromethyl)phenyl]-4-piperidyl]ethyl]-4,5,6,7-tetrahydroindazole-3-carbonyl]-4-piperidyl]acetamide | 560.4 |

| Ex. # | Structure | Chemical Name | Mass [M + H]+ |
|---|---|---|---|
| 23 | 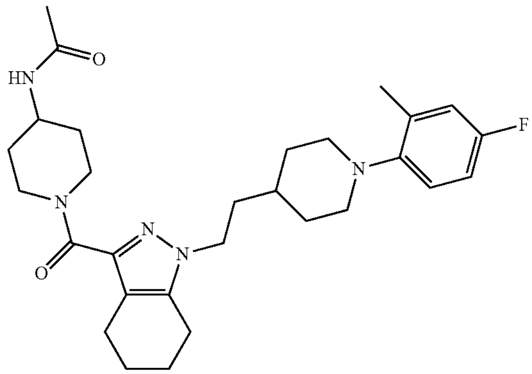 [SMILES: CC(=O)NC1CCN(C(=O)c2nn(CCC3CCN(c4ccc(F)cc4C)CC3)c3c2CCCC3)CC1] | N-[1-[1-[2-[1-(4-fluoro-2-methyl-phenyl)-4-piperidyl]ethyl]-4,5,6,7-tetrahydroindazole-3-carbonyl]-4-piperidyl]acetamide | 510.3 |
| 24 | 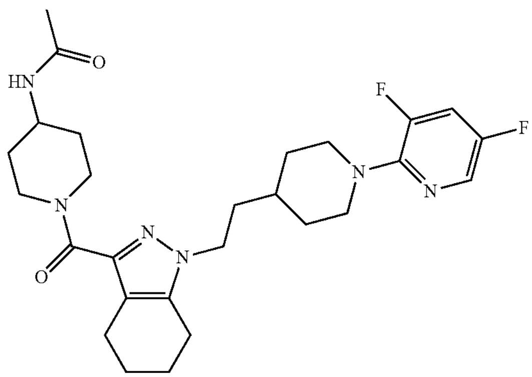 [SMILES: CC(=O)NC1CCN(C(=O)c2nn(CCC3CCN(c4ncc(F)cc4F)CC3)c3c2CCCC3)CC1] | N-[1-[1-[2-[1-(3,5-difluoro-2-pyridyl)-4-piperidyl]ethyl]-4,5,6,7-tetrahydroindazole-3-carbonyl]-4-piperidyl]acetamide | 514.2 |
| 25 | 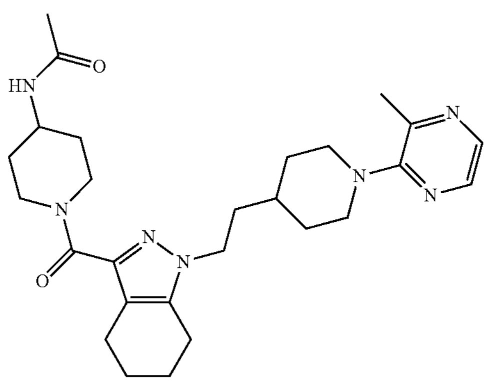 [SMILES: CC(=O)NC1CCN(C(=O)c2nn(CCC3CCN(c4nccnc4C)CC3)c3c2CCCC3)CC1] | N-[1-[1-[2-[1-(3-methylpyrazin-2-yl)-4-piperidyl]ethyl]-4,5,6,7-tetrahydroindazole-3-carbonyl]-4-piperidyl]acetamide | 494.2 |
| 26 | 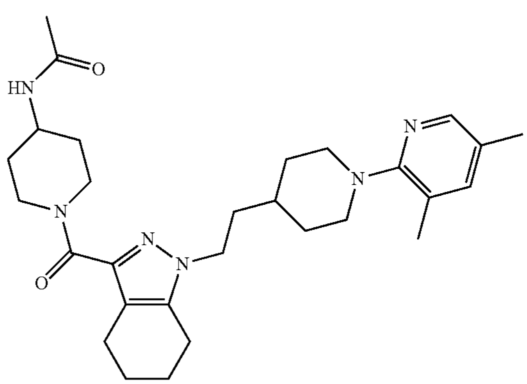 [SMILES: CC(=O)NC1CCN(C(=O)c2nn(CCC3CCN(c4ncc(C)cc4C)CC3)c3c2CCCC3)CC1] | N-[1-[1-[2-[1-(3,5-dimethyl-2-pyridyl)-4-piperidyl]ethyl]-4,5,6,7-tetrahydroindazole-3-carbonyl]-4-piperidyl]acetamide | 507.3 |

| Ex. # | Structure | Chemical Name | Mass [M + H]+ |
|---|---|---|---|
| 27 | 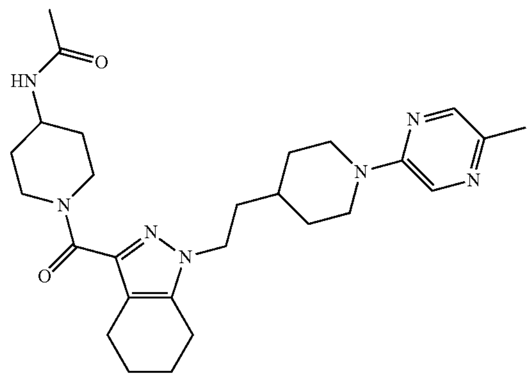 [SMILES: CC(=O)NC1CCN(C(=O)c2nn(CCC3CCN(c4cnc(C)cn4)CC3)c3c2CCCC3)CC1] | N-[1-[1-[2-[1-(5-methylpyrazin-2-yl)-4-piperidyl]ethyl]-4,5,6,7-tetrahydroindazole-3-carbonyl]-4-piperidyl]acetamide | 494.24 |
| 28 | 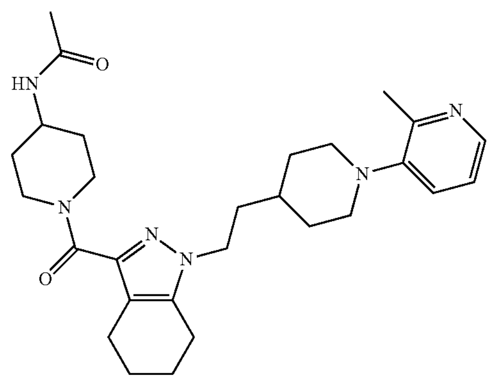 [SMILES: CC(=O)NC1CCN(C(=O)c2nn(CCC3CCN(c4cccnc4C)CC3)c3c2CCCC3)CC1] | N-[1-[1-[2-[1-(2-methyl-3-pyridyl)-4-piperidyl]ethyl]-4,5,6,7-tetrahydroindazole-3-carbonyl]-4-piperidyl]acetamide | 493.3 |
| 29 | 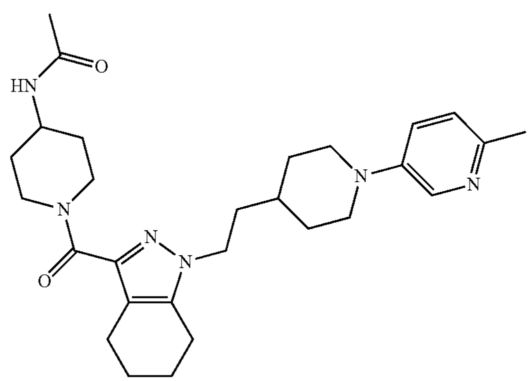 [SMILES: CC(=O)NC1CCN(C(=O)c2nn(CCC3CCN(c4ccc(C)nc4)CC3)c3c2CCCC3)CC1] | N-[1-[1-[2-[1-(6-methyl-3-pyridyl)-4-piperidyl]ethyl]-4,5,6,7-tetrahydroindazole-3-carbonyl]-4-piperidyl]acetamide | 493.3 |
| 30 | 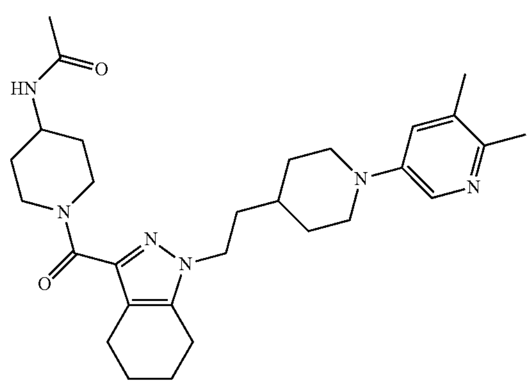 [SMILES: CC(=O)NC1CCN(C(=O)c2nn(CCC3CCN(c4cnc(C)c(C)c4)CC3)c3c2CCCC3)CC1] | N-[1-[1-[2-[1-(5,6-dimethyl-3-pyridyl)-4-piperidyl]ethyl]-4,5,6,7-tetrahydroindazole-3-carbonyl]-4-piperidyl]acetamide | 507.2 |

-continued

| Ex. # | Structure | Chemical Name | Mass [M + H]+ |
|---|---|---|---|
| 31 | 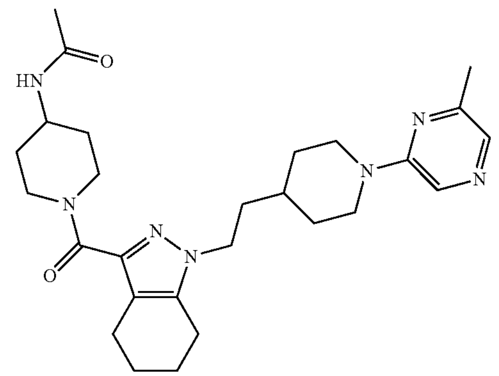 [SMILES: CC(=O)NC1CCN(C(=O)c2nn(CCC3CCN(c4cncc(C)n4)CC3)c3c2CCCC3)CC1] | N-[1-[1-[2-[1-(6-methylpyrazin-2-yl)-4-piperidyl]ethyl]-4,5,6,7-tetrahydroindazole-3-carbonyl]-4-piperidyl]acetamide | 494.2 |
| 32 | 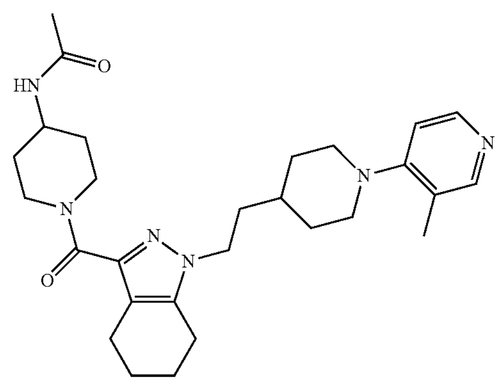 [SMILES: CC(=O)NC1CCN(C(=O)c2nn(CCC3CCN(c4ccncc4C)CC3)c3c2CCCC3)CC1] | N-[1-[1-[2-[1-(3-methyl-4-pyridyl)-4-piperidyl]ethyl]-4,5,6,7-tetrahydroindazole-3-carbonyl]-4-piperidyl]acetamide | 493.3 |
| 33 | 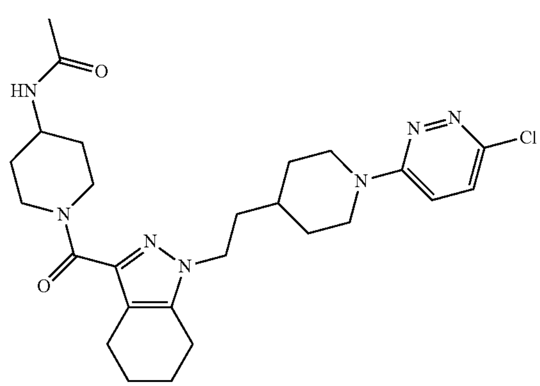 [SMILES: CC(=O)NC1CCN(C(=O)c2nn(CCC3CCN(c4ccc(Cl)nn4)CC3)c3c2CCCC3)CC1] | N-[1-[1-[2-[1-(6-chloropyridazin-3-yl)-4-piperidyl]ethyl]-4,5,6,7-tetrahydroindazole-3-carbonyl]-4-piperidyl]acetamide | 514.26 |

Example 34: N-[1-[1-[2-[1-[3-fluoro-4-(trifluoromethyl)-2-pyridyl]-4-piperidyl]ethyl]-4,5,6,7-tetrahydroindazole-3-carbonyl]-4-piperidyl]acetamide

Step 1: N-(1-(1-(2-(1-(3-(trifluoromethyl)pyridin-2-yl)piperidin-4-yl)ethyl)-4,5,6,7-tetrahydro-1H-indazole-3-carbonyl)piperidin-4-yl)acetamide (34)

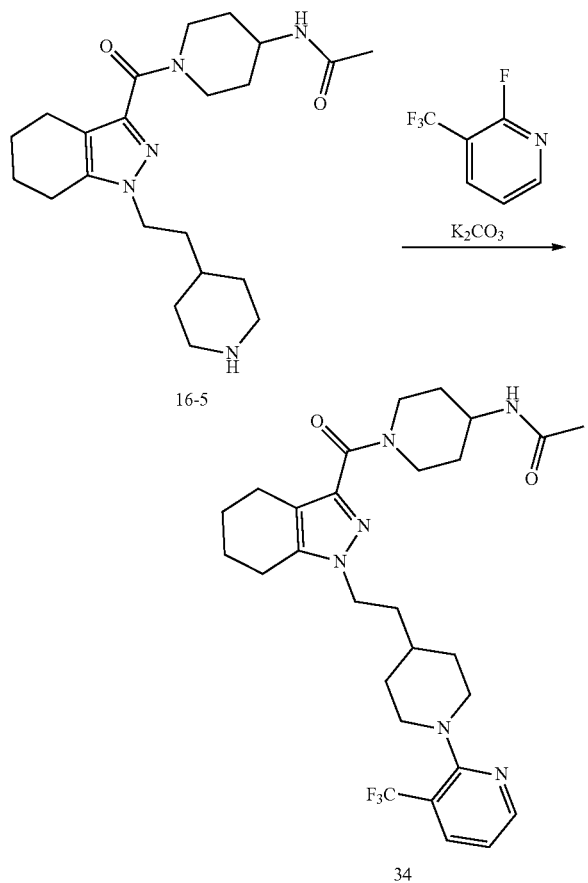

Bromo-2-(trifluoromethyl)benzene (33.8 mg, 0.150 mmol) was added to a mixture of N-(1-(1-(2-(piperidin-4-yl)ethyl)-4,5,6,7-tetrahydro-1H-indazole-3-carbonyl)piperidin-4-yl)acetamide (20 mg, 0.050 mmol) and K$_2$CO$_3$ (20.65 mg, 0.149 mmol) in ACN (700 µl) under nitrogen. The reaction was stirred at 75° C. After 2 h, the reaction went to completion. The mixture was filtered and washed with EtOAc. The filtrate was concentrated and the residue was purified by preparative HPLC reversed phase (C-18 column) eluting with 0-100% ACN/water to afford the title compound. MS: 547.3 (M+1). 1H NMR (500 MHz, DMSO-d6) δ 8.36 (s, 1H), 7.89 (d, J=7.7 Hz, 1H), 7.73 (dd, J=9.1, 2.3 Hz, 1H), 6.93 (d, J=9.1 Hz, 1H), 4.44-4.26 (m, 4H), 4.02 (t, J=7.0 Hz, 2H), 3.85-3.74 (m, 1H), 3.57-3.53 (m, 2H), 3.22-3.11 (m, 1H), 2.91-2.79 (m, 2H), 2.58 (t, J=5.9 Hz, 3H), 2.49-2.42 (m, 2H), 1.83-1.68 (m, 7H), 1.69-1.60 (m, 4H), 1.57-1.47 (m, 1H), 1.36-1.20 (m, 2H), 1.10 (q, J=11.7 Hz, 2H).

The examples in the following table were prepared in an analogous manner to Example 34 using appropriate starting materials described previously or commercially available.

| Ex. # | Structure | Chemical Name | Mass [M + H]$^+$ |
|---|---|---|---|
| 35 | 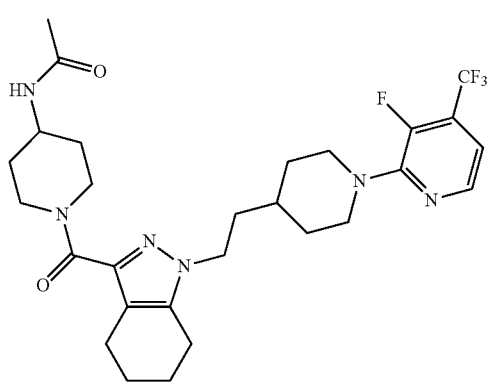 [SMILES: CC(=O)NC1CCN(C(=O)c2nn(CCC3CCN(c4nccc(C(F)(F)F)c4F)CC3)c3c2CCCC3)CC1] | N-[1-[1-[2-[1-[3-fluoro-4-(trifluoromethyl)-2-pyridyl]-4-piperidyl]ethyl]-4,5,6,7-tetrahydroindazole-3-carbonyl]-4-piperidyl]acetamide | 565.2 |

-continued

| Ex. # | Structure | Chemical Name | Mass [M + H]⁺ |
|---|---|---|---|
| 36 | 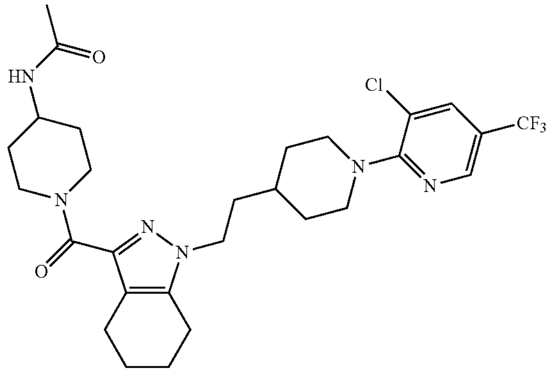 [SMILES: CC(=O)NC1CCN(C(=O)c2nn(CCC3CCN(c4ncc(C(F)(F)F)cc4Cl)CC3)c3c2CCCC3)CC1] | N-[1-[1-[2-[1-[3-chloro-5-(trifluoromethyl)-2-pyridyl]-4-piperidyl]ethyl]-4,5,6,7-tetrahydroindazole-3-carbonyl]-4-piperidyl]acetamide | 581.2 |
| 37 | 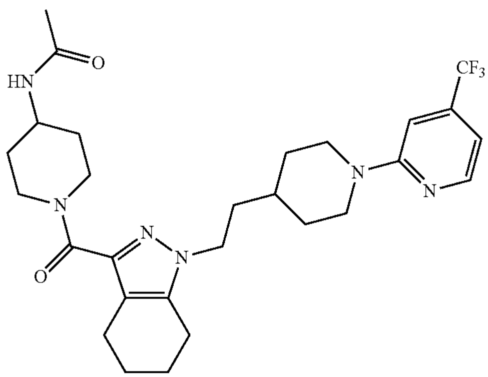 [SMILES: CC(=O)NC1CCN(C(=O)c2nn(CCC3CCN(c4cc(C(F)(F)F)ccn4)CC3)c3c2CCCC3)CC1] | N-[1-[1-[2-[1-[4-(trifluoromethyl)-2-pyridyl]-4-piperidyl]ethyl]-4,5,6,7-tetrahydroindazole-3-carbonyl]-4-piperidyl]acetamide | 547.2 |
| 38 | 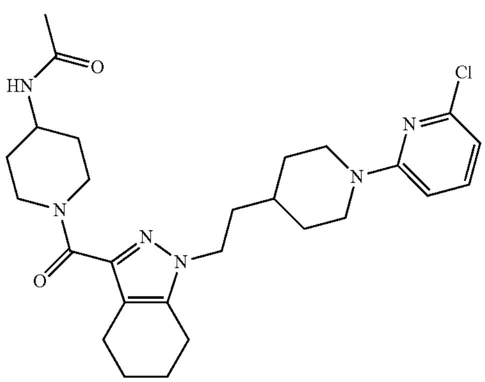 [SMILES: CC(=O)NC1CCN(C(=O)c2nn(CCC3CCN(c4cccc(Cl)n4)CC3)c3c2CCCC3)CC1] | N-[1-[1-[2-[1-(6-chloro-2-pyridyl)-4-piperidyl]ethyl]-4,5,6,7-tetrahydroindazole-3-carbonyl]-4-piperidyl]acetamide | 513.2 |
| 39 | 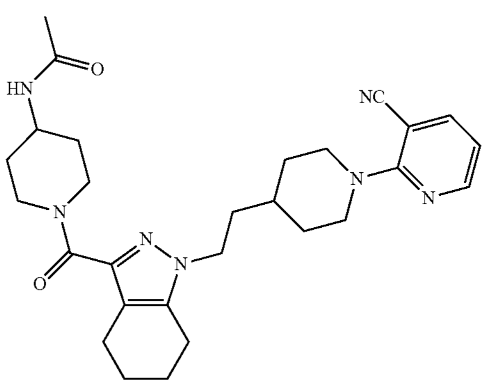 [SMILES: CC(=O)NC1CCN(C(=O)c2nn(CCC3CCN(c4ncccc4C#N)CC3)c3c2CCCC3)CC1] | N-[1-[1-[2-[1-(3-cyano-2-pyridyl)-4-piperidyl]ethyl]-4,5,6,7-tetrahydroindazole-3-carbonyl]-4-piperidyl]acetamide | 504.24 |

| Ex. # | Structure | Chemical Name | Mass [M + H]+ |
|---|---|---|---|
| 40 | 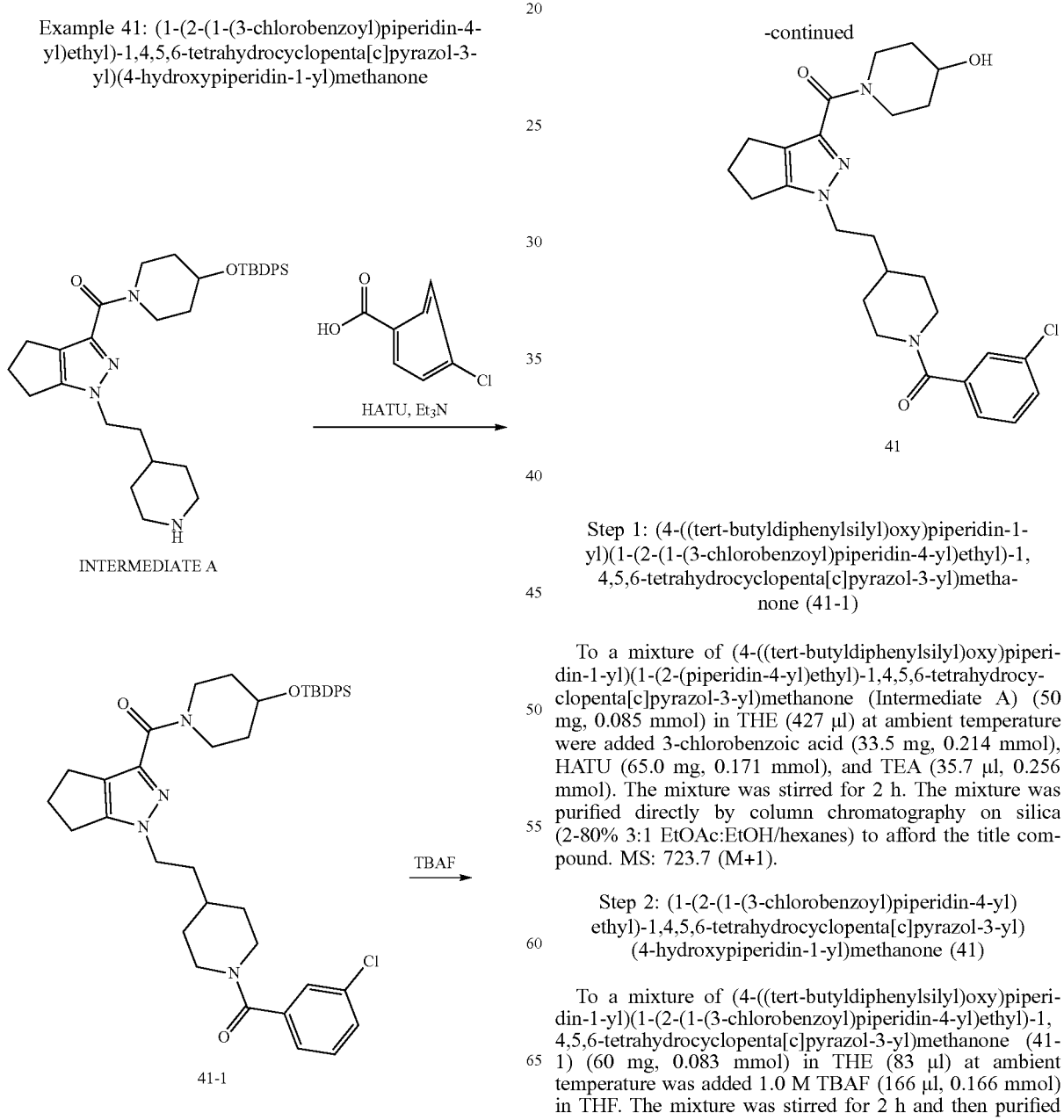 | N-[1-[1-[2-[1-(4-cyano-2-pyridyl)-4-piperidyl]ethyl]-4,5,6,7-tetrahydroindazole-3-carbonyl]-4-pipridyl]acetamide | 504.3 |

Example 41: (1-(2-(1-(3-chlorobenzoyl)piperidin-4-yl)ethyl)-1,4,5,6-tetrahydrocyclopenta[c]pyrazol-3-yl)(4-hydroxypiperidin-1-yl)methanone Step 1: (4-((tert-butyldiphenylsilyl)oxy)piperidin-1-yl)(1-(2-(1-(3-chlorobenzoyl)piperidin-4-yl)ethyl)-1,4,5,6-tetrahydrocyclopenta[c]pyrazol-3-yl)methanone (41-1)

To a mixture of (4-((tert-butyldiphenylsilyl)oxy)piperidin-1-yl)(1-(2-(piperidin-4-yl)ethyl)-1,4,5,6-tetrahydrocyclopenta[c]pyrazol-3-yl)methanone (Intermediate A) (50 mg, 0.085 mmol) in THF (427 µl) at ambient temperature were added 3-chlorobenzoic acid (33.5 mg, 0.214 mmol), HATU (65.0 mg, 0.171 mmol), and TEA (35.7 µl, 0.256 mmol). The mixture was stirred for 2 h. The mixture was purified directly by column chromatography on silica (2-80% 3:1 EtOAc:EtOH/hexanes) to afford the title compound. MS: 723.7 (M+1).

Step 2: (1-(2-(1-(3-chlorobenzoyl)piperidin-4-yl)ethyl)-1,4,5,6-tetrahydrocyclopenta[c]pyrazol-3-yl)(4-hydroxypiperidin-1-yl)methanone (41)

To a mixture of (4-((tert-butyldiphenylsilyl)oxy)piperidin-1-yl)(1-(2-(1-(3-chlorobenzoyl)piperidin-4-yl)ethyl)-1,4,5,6-tetrahydrocyclopenta[c]pyrazol-3-yl)methanone (41-1) (60 mg, 0.083 mmol) in THF (83 µl) at ambient temperature was added 1.0 M TBAF (166 µl, 0.166 mmol) in THF. The mixture was stirred for 2 h and then purified directly by reversed phase HPLC (5-95% ACN/water with 0.05% TFA modifier) to afford the title compound. MS: 485.5 (M+1). $^1$H NMR (500 MHz, DMSO-d6) δ 7.51 (dt, J=6.6, 1.6 Hz, 1H), 7.46 (t, J=7.7 Hz, 1H), 7.42 (t, J=1.7 Hz, 1H), 7.32 (d, J=7.5 Hz, 1H), 4.73 (d, J=4.3 Hz, 1H), 4.46-4.39 (m, 1H), 4.32-4.24 (m, 1H), 4.03 (t, J=7.0 Hz, 2H), 3.70 (dq, J=8.4, 4.3 Hz, 1H), 3.50-3.37 (m, 2H), 3.12-3.04 (m, 1H), 3.01-2.93 (m, 1H), 2.73-2.63 (m, 3H), 2.61-2.54 (m, 2H), 2.48-2.43 (m, 2H), 1.80-1.65 (m, 5H), 1.63-1.56 (m, 1H), 1.54-1.41 (m, 1H), 1.30 (ddt, J=13.3, 8.8, 4.8 Hz, 2H), 1.19-1.07 (m, 2H).

The example in the following table was prepared in an analogous manner to Example 41 using appropriate starting materials described previously or commercially available.

| Ex. # | Structure | Chemical Name | Mass [M + H]$^+$ |
|---|---|---|---|
| 42 | 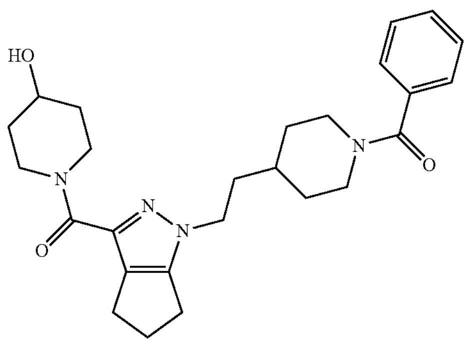 [SMILES: O=C(c1ccccc1)N1CCC(CCn2nc(C(=O)N3CCC(O)CC3)c3c2CCC3)CC1] | [4-[2-[3-(4-hydroxypiperidine-1-carbonyl)-5,6-dihydro-4H-cyclopenta[c]pyrazol-1-yl]ethyl]-1-piperidyl]-phenyl-methanone | 451.5 |

Examples 43 and 44: ((2R,6S)-2,6-dimethylmorpholino)(1-(2-(1-(2,3-dimethylphenyl)piperidin-4-yl)-2-hydroxyethyl)-1,4,5,6-tetrahydrocyclopenta[c]pyrazol-3-yl)methanone (Chiral, R or S) and ((2R,6S)-2,6-dimethylmorpholino)(1-(2-(1-(2,3-dimethylphenyl)piperidin-4-yl)-2-hydroxyethyl)-1,4,5,6-tetrahydrocyclopenta[c]pyrazol-3-yl)methanone (Chiral, S or R)

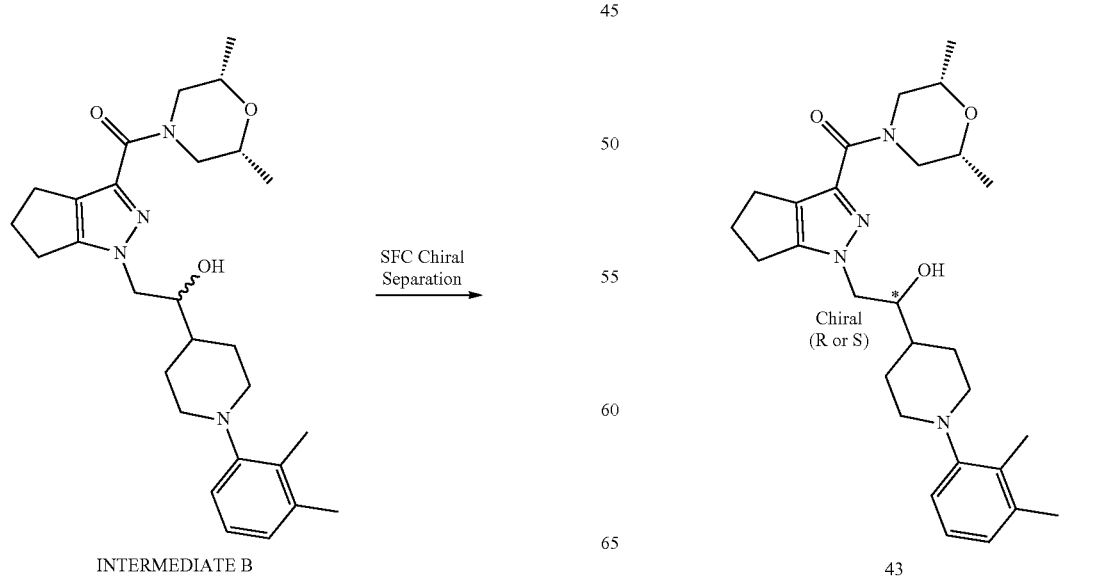

Step 1: ((2R,6S)-2,6-dimethylmorpholino)(1-(2-(1-(2,3-dimethylphenyl)piperidin-4-yl)-2-hydroxyethyl)-1,4,5,6-tetrahydrocyclopenta[c]pyrazol-3-yl)methanone (43, Chiral, R or S) and ((2R,6S)-2,6-dimethylmorpholino)(1-(2-(1-(2,3-dimethylphenyl)piperidin-4-yl)-2-hydroxyethyl)-1,4,5,6-tetrahydrocyclopenta[c]pyrazol-3-yl)methanone (44, Chiral, S or R)

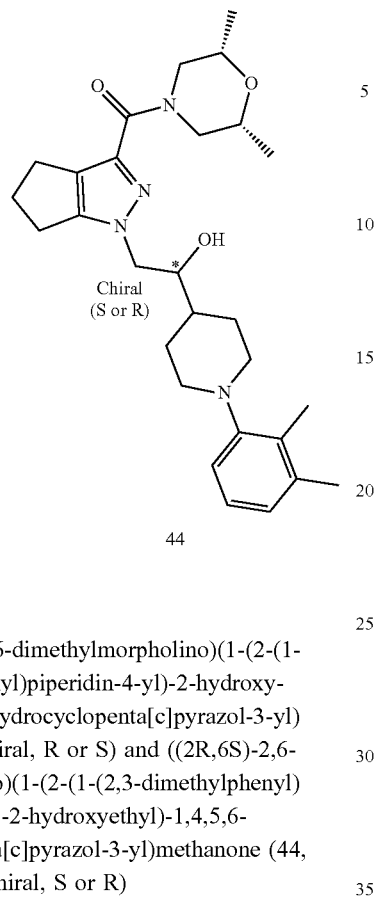

44

The racemic ((2R,6S)-2,6-dimethylmorpholino)(1-(2-(1-(2,3-dimethylphenyl)piperidin-4-yl)-2-hydroxyethyl)-1,4,5,6-tetrahydrocyclopenta[c]pyrazol-3-yl)methanone (Intermediate B) (100 mg, 0.208 mmol) was submitted for SFC purification to obtain two chiral isomers.

Example 43 (peak 1): MS: 481.6 (M+1). 1H NMR (500 MHz, DMSO-d6) δ 7.00 (t, J=7.6 Hz, 1H), 6.84 (t, J=6.2 Hz, 2H), 4.97 (d, J=5.6 Hz, 1H), 4.78 (t, J=12.6 Hz, 1H), 4.33 (d, J=11.8 Hz, 1H), 4.08 (d, J=12.6 Hz, 1H), 3.96 (dd, J=13.7, 6.8 Hz, 1H), 3.62 (s, 1H), 3.49 (s, 2H), 3.32 (s, 1H), 3.00 (d, J=10.2 Hz, 2H), 2.72 (t, J=7.0 Hz, 3H), 2.60 (t, J=6.7 Hz, 2H), 2.48-2.42 (m, 2H), 2.42-2.33 (m, 1H), 2.19 (s, 3H), 2.13 (s, 3H), 1.82 (d, J=11.7 Hz, 1H), 1.78-1.68 (m, 1H), 1.60-1.30 (m, 3H), 1.11 (s, 3H), 1.06 (s, 3H).

Example 44 (peak 2): MS: 481.6 (M+1). 1H NMR ((500 MHz, DMSO-d6) δ 7.00 (t, J=7.7 Hz, 1H), 6.88-6.79 (m, 2H), 4.97 (d, J=5.7 Hz, 1H), 4.77 (t, J=12.5 Hz, 1H), 4.33 (d, J=12.3 Hz, 1H), 4.08 (dd, J=13.9, 4.0 Hz, 1H), 3.96 (dd, J=13.9, 6.9 Hz, 1H), 3.62 (s, 1H), 3.54-3.42 (m, 2H), 3.32 (s, 2H), 3.00 (d, J=11.0 Hz, 2H), 2.72 (t, J=7.3 Hz, 3H), 2.64-2.56 (m, 2H), 2.45 (dd, J=14.1, 7.7 Hz, 2H), 2.42-2.34 (m, 1H), 2.19 (s, 3H), 2.13 (s, 3H), 1.82 (d, J=11.3 Hz, 1H), 1.79-1.68 (m, 1H), 1.62-1.32 (m, 3H), 1.13 (s, 3H), 1.06 (s, 3H).

Examples 45 and 46: ((2R,6S)-2,6-dimethylmorpholino)(1-(2-(1-(2,3-dimethylphenyl)piperidin-4-yl)-2-methoxyethyl)-1,4,5,6-tetrahydrocyclopenta[c]pyrazol-3-yl)methanone (Chiral, R or S) and ((2R,6S)-2,6-dimethylmorpholino)(1-(2-(1-(2,3-dimethylphenyl)piperidin-4-yl)-2-methoxyethyl)-1,4,5,6-tetrahydrocyclopenta[c]pyrazol-3-yl)methanone (Chiral, S or R)

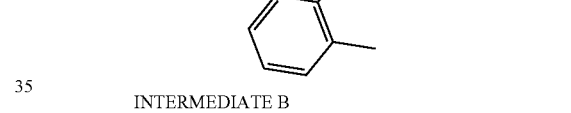

INTERMEDIATE B

NaH; MeI →

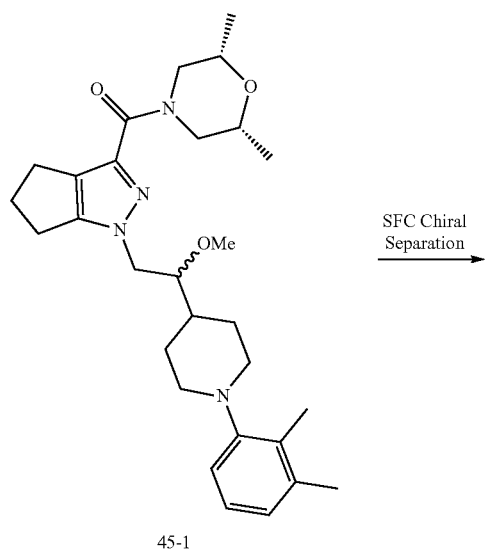

45-1

SFC Chiral Separation →

-continued

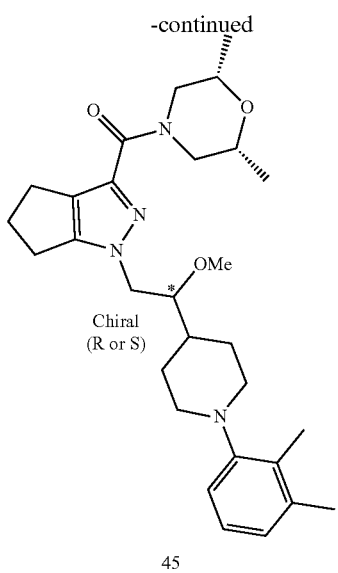

45

46

Step 1: ((2R,6S)-2,6-dimethylmorpholino)(1-(2-(1-(2,3-dimethylphenyl)piperidin-4-yl)-2-methoxy-ethyl)-1,4,5,6-tetrahydrocyclopenta[c]pyrazol-3-yl)methanone (45-1)

To a mixture of ((2R,6S)-2,6-dimethylmorpholino)(1-(2-(1-(2,3-dimethylphenyl)piperidin-4-yl)-2-hydroxyethyl)-1,4,5,6-tetrahydrocyclopenta[c]pyrazol-3-yl)methanone (Intermediate B) (100 mg, 0.208 mmol) in THF (1040 μl) at ambient temperature was added NaH (9.99 mg, 0.250 mmol). The mixture was stirred for 10 min before adding MeI (18.21 μl, 0.291 mmol). The mixture was stirred for 1 h before it was purified directly by column chromatography on silica (2-90% 3:1 EtOAc:EtOH/hexanes) to afford the title compound. MS: 495.5 (M+1).

Step 2: ((2R,6S)-2,6-dimethylmorpholino)(1-(2-(1-(2,3-dimethylphenyl)piperidin-4-yl)-2-methoxy-ethyl)-1,4,5,6-tetrahydrocyclopenta[c]pyrazol-3-yl)methanone (45, Chiral, R or S) and ((2R,6S)-2,6-dimethylmorpholino)(1-(2-(1-(2,3-dimethylphenyl)piperidin-4-yl)-2-methoxyethyl)-1,4,5,6-tetrahydrocyclopenta[c]pyrazol-3-yl)methanone (46, Chiral, S or R)

The racemic ((2R,6S)-2,6-dimethylmorpholino)(1-(2-(1-(2,3-dimethylphenyl)piperidin-4-yl)-2-methoxyethyl)-1,4,5,6-tetrahydrocyclopenta[c]pyrazol-3-yl)methanone (45-1) (100 mg, 0.202 mmol) was submitted for SFC purification to obtain two chiral isomers.

Example 45 (peak 1): MS: 495.6 (M+1). 1H NMR (500 MHz, DMSO-d6) δ 7.00 (t, J=7.7 Hz, 1H), 6.84 (d, J=7.6 Hz, 2H), 4.77 (dd, J=24.7, 12.9 Hz, 1H), 4.28 (dd, J=47.3, 13.1 Hz, 2H), 4.06 (dd, J=14.4, 5.7 Hz, 1H), 3.49 (dt, J=10.2, 5.0 Hz, 2H), 3.32 (s, 2H), 3.20 (s, 3H), 3.00 (d, J=10.8 Hz, 2H), 2.84-2.74 (m, 1H), 2.72 (t, J=7.2 Hz, 2H), 2.61 (t, J=7.1 Hz, 2H), 2.47 (t, J=7.0 Hz, 2H), 2.43-2.34 (m, 1H), 2.19 (s, 3H), 2.13 (s, 3H), 1.89-1.76 (m, 2H), 1.54-1.43 (m, 3H), 1.12 (s, 3H), 1.06 (s, 3H).

Example 46 (peak 2): MS: 495.6 (M+1). 1H NMR ((500 MHz, DMSO-d6) δ 7.00 (t, J=7.7 Hz, 1H), 6.84 (d, J=7.6 Hz, 2H), 4.77 (dd, J=24.7, 12.9 Hz, 1H), 4.33 (d, J=11.1 Hz, 1H), 4.24 (d, J=14.3 Hz, 1H), 4.06 (dd, J=14.4, 5.8 Hz, 1H), 3.49 (dt, J=10.2, 5.0 Hz, 2H), 3.32 (s, 2H), 3.20 (s, 3H), 3.00 (d, J=11.0 Hz, 2H), 2.85-2.76 (m, 1H), 2.72 (t, J=7.2 Hz, 2H), 2.61 (t, J=7.1 Hz, 2H), 2.47 (t, J=7.1 Hz, 2H), 2.43-2.34 (m, 1H), 2.19 (s, 3H), 2.13 (s, 3H), 1.90-1.76 (m, 2H), 1.56-1.40 (m, 3H), 1.11 (s, 3H), 1.05 (s, 3H).

Examples 47 and 48: ((2R,6S)-2,6-dimethylmorpholino)(1-(2-(1-(2,3-dimethylphenyl)piperidin-4-yl)-2-fluoroethyl)-1,4,5,6-tetrahydrocyclopenta[c]pyrazol-3-yl)methanone (Chiral, R or S) and ((2R,6S)-2,6-dimethylmorpholino)(1-(2-(1-(2,3-dimethylphenyl)piperidin-4-yl)-2-fluoroethyl)-1,4,5,6-tetrahydrocyclopenta[c]pyrazol-3-yl)methanone (Chiral, S or R)

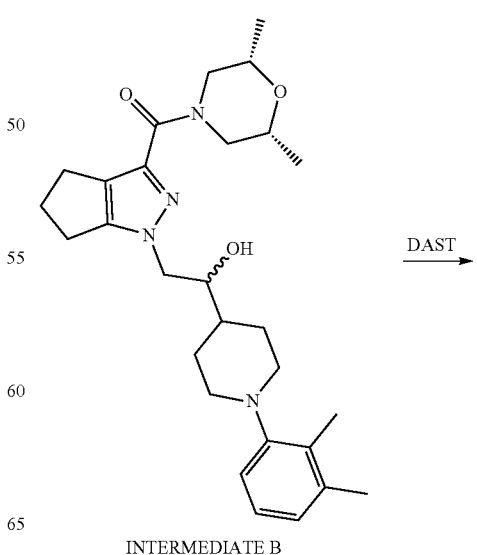

INTERMEDIATE B

-continued

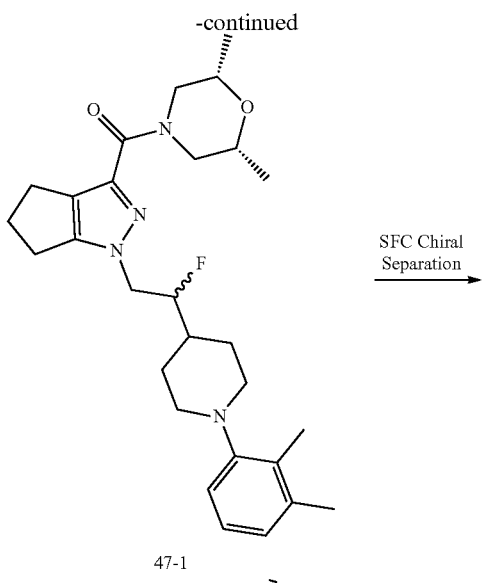

47-1

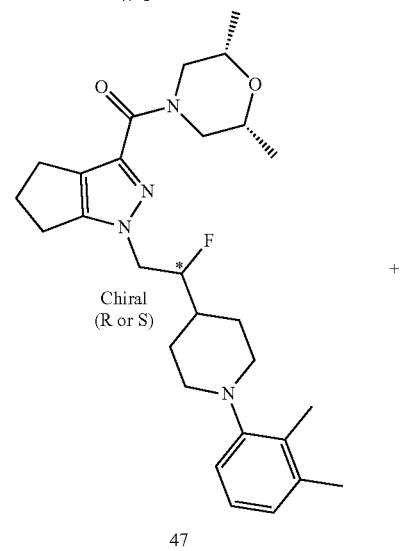

Chiral
(R or S)

47

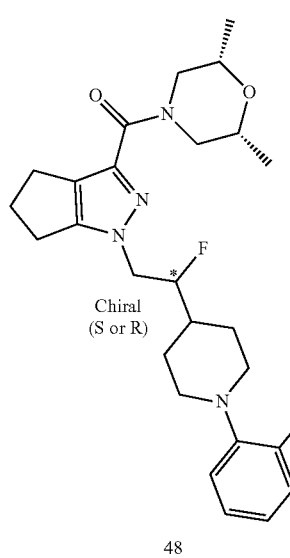

Chiral
(S or R)

48

SFC Chiral Separation →

+

Step 1: ((2R,6S)-2,6-dimethylmorpholino)(1-(2-(1-(2,3-dimethylphenyl)piperidin-4-yl)-2-fluoroethyl)-1,4,5,6-tetrahydrocyclopenta[c]pyrazol-3-yl)methanone (47-1)

To a mixture of ((2R,6S)-2,6-dimethylmorpholino)(1-(2-(1-(2,3-dimethylphenyl)piperidin-4-yl)-2-hydroxyethyl)-1,4,5,6-tetrahydrocyclopenta[c]pyrazol-3-yl)methanone (Intermediate B) (100 mg, 0.208 mmol) in DCM (1040 µl) at 0° C. was added DAST (41.2 µl, 0.312 mmol). The mixture was stirred for 2 h before quenching with MeOH (0.1 mL). The mixture was purified directly by column chromatography on silica (2-90% 3:1 EtOAc:EtOH/hexanes) to afford the title compound. MS: 483.5 (M+1).

Step 2: ((2R,6S)-2,6-dimethylmorpholino)(1-(2-(1-(2,3-dimethylphenyl)piperidin-4-yl)-2-fluoroethyl)-1,4,5,6-tetrahydrocyclopenta[c]pyrazol-3-yl)methanone (47, Chiral, R or S) and ((2R,6S)-2,6-dimethylmorpholino)(1-(2-(1-(2,3-dimethylphenyl)piperidin-4-yl)-2-fluoroethyl)-1,4,5,6-tetrahydrocyclopenta[c]pyrazol-3-yl)methanone (48, Chiral, S or R)

The racemic ((2R,6S)-2,6-dimethylmorpholino)(1-(2-(1-(2,3-dimethylphenyl)piperidin-4-yl)-2-fluoroethyl)-1,4,5,6-tetrahydrocyclopenta[c]pyrazol-3-yl)methanone (47-1) (40 mg, 0.083 mmol) was submitted for SFC purification to obtain two chiral isomers.

Example 47 (peak 1): MS: 483.5 (M+1). 1H NMR (500 MHz, DMSO-d6) δ 7.01 (t, J=7.6 Hz, 1H), 6.85 (d, J=7.0 Hz, 2H), 4.81-4.57 (m, 2H), 4.47-4.22 (m, 3H), 3.55-3.45 (m, 2H), 3.02 (d, J=11.0 Hz, 2H), 2.77 (q, J=12.2 Hz, 1H), 2.70 (t, J=6.3 Hz, 2H), 2.64-2.54 (m, 4H), 2.48-2.33 (m, 3H), 2.19 (s, 3H), 2.14 (s, 3H), 1.84 (d, J=11.2 Hz, 2H), 1.68 (s, 1H), 1.60-1.46 (m, 2H), 1.11 (s, 3H), 1.06 (s, 3H).

Example 48 (peak 2): MS: 483.5 (M+1). 1H NMR ((500 MHz, DMSO-d6) δ 7.01 (t, J=7.6 Hz, 1H), 6.89-6.78 (m, 2H), 4.81-4.57 (m, 2H), 4.47-4.21 (m, 3H), 3.59-3.43 (m, 2H), 3.02 (d, J=11.0 Hz, 2H), 2.77 (q, J=12.0 Hz, 1H), 2.70 (d, J=6.5 Hz, 2H), 2.63-2.58 (m, 4H), 2.54-2.33 (m, 3H), 2.19 (s, 3H), 2.14 (s, 3H), 1.84 (d, J=11.1 Hz, 2H), 1.68 (s, 1H), 1.59-1.48 (m, 2H), 1.11 (s, 3H), 1.06 (s, 3H).

Examples 49 and 50: 1-(4-(1-(2-(4-(4-fluoro-2,3-dimethylphenyl)cyclohexyl)ethyl)-1,4,5,6-tetrahydrocyclopenta[c]pyrazole-3-carbonyl)piperazin-1-yl)-2-hydroxyethan-1-one (Chiral, cis or trans) and 1-(4-(1-(2-(4-(4-fluoro-2,3-dimethylphenyl)cyclohexyl)ethyl)-1,4,5,6-tetrahydrocyclopenta[c]pyrazole-3-carbonyl)piperazin-1-yl)-2-hydroxyethan-1-one (Chiral, trans or cis)

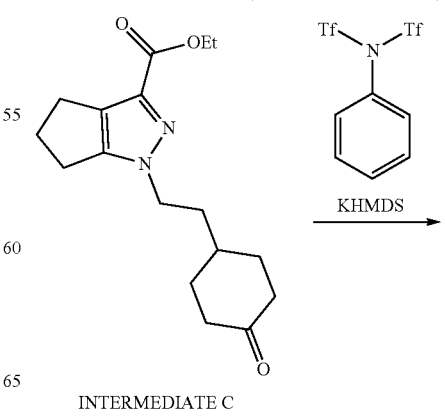

INTERMEDIATE C

KHMDS →

-continued
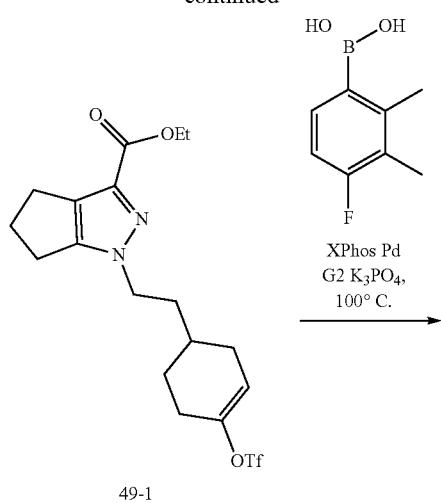
49-1
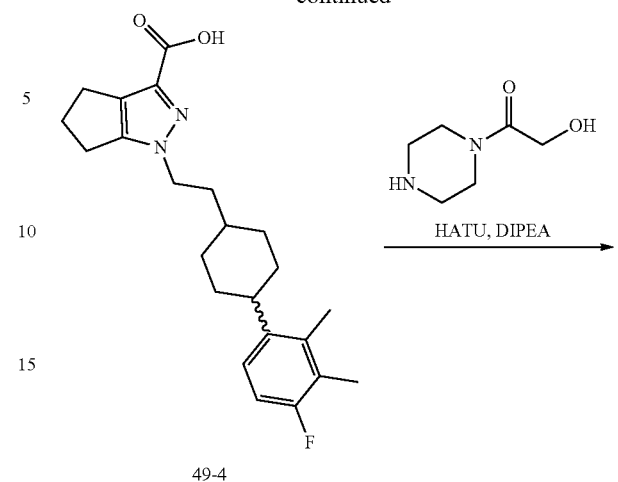
49-4
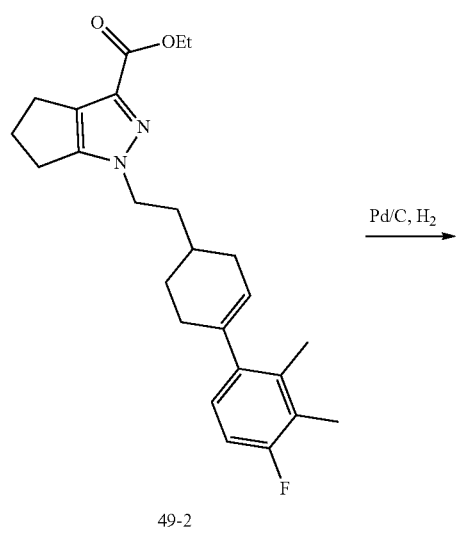
49-2
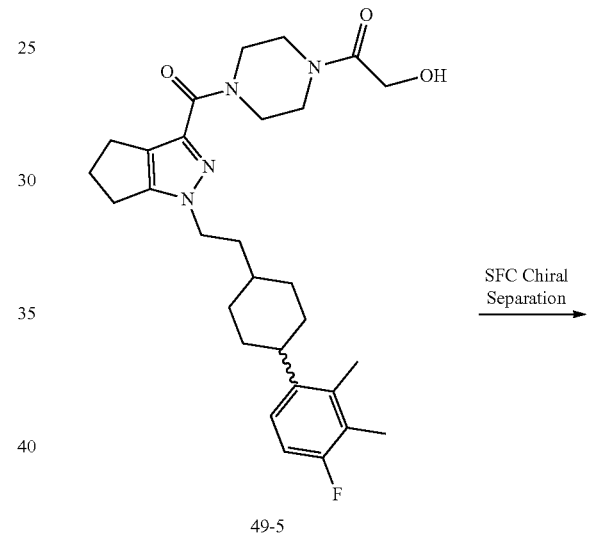
49-5
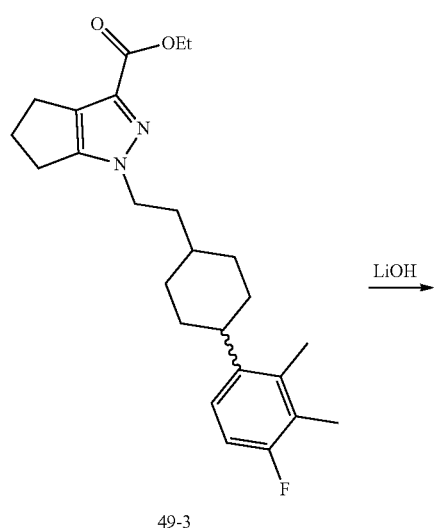
49-3
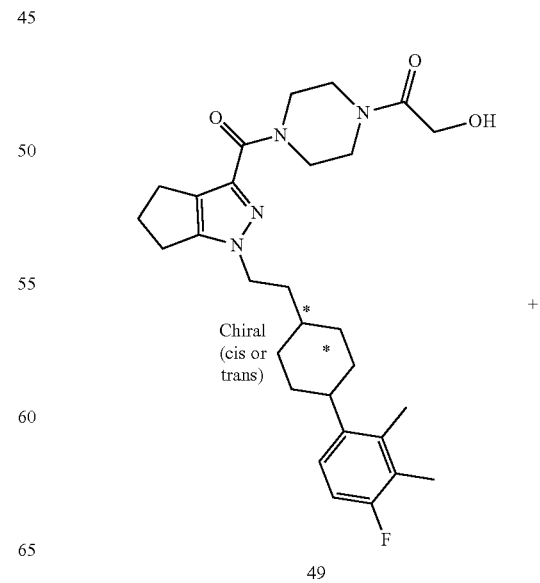
49

-continued

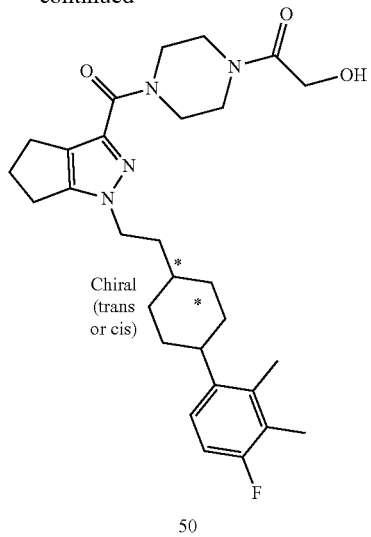

50

Step 1: ethyl 1-(2-(4-(((trifluoromethyl)sulfonyl)oxy)cyclohex-3-en-1-yl)ethyl)-1,4,5,6-tetrahydrocyclopenta[c]pyrazole-3-carboxylate (49-1)

To a mixture of ethyl 1-(2-(4-oxocyclohexyl)ethyl)-1,4,5,6-tetrahydrocyclopenta[c]pyrazole-3-carboxylate (Intermediate C) (500 mg, 1.643 mmol) in THF (4978 µl) at −78° C. was added 1,1,1-trifluoro-N-phenyl-N-(((trifluoromethyl)sulfonyl)methanesulfonamide (646 mg, 1.807 mmol) followed by 1.0 M KHMDS (2135 µl, 2.135 mmol) in THF dropwise over 5 min. The mixture was stirred at this temperature for 2 h before quenching with a sat. solution of NaHCO₃ (10 mL) and warming to RT. The mixture was extracted with EtOAc (20 mL×3), dried over Na₂SO₄, and concentrated. The residue was purified by column chromatography on silica (2-60% 3:1 EtOAc:EtOH/hexanes) to afford the title compound. MS: 437.1 (M+1).

Step 2: ethyl 1-(2-(4'-fluoro-2',3'-dimethyl-2,3,4,5-tetrahydro-[1,1'-biphenyl]-4-yl)ethyl)-1,4,5,6-tetrahydrocyclopenta[c]pyrazole-3-carboxylate (49-2)

To a mixture of ethyl 1-(2-(4-(((trifluoromethyl)sulfonyl)oxy)cyclohex-3-en-1-yl)ethyl)-1,4,5,6-tetrahydrocyclopenta[c]pyrazole-3-carboxylate (49-1) (500 mg, 1.146 mmol) in dioxane (4582 µl) at ambient temperature were added K₃PO₄ (608 mg, 2.86 mmol) dissolved in water (1146 µl) and (4-fluoro-2,3-dimethylphenyl)boronic acid (385 mg, 2.291 mmol). Xphos Pd G2 (45.1 mg, 0.057 mmol) was added and the mixture was heated to 100° C. for 1 h. The mixture was cooled, water (10 mL) and EtOAc (10 mL) were added, and the mixture was extracted with EtOAc (10 mL×2), dried over Na₂SO₄, and concentrated. The residue was purified by column chromatography on silica (2-60% 3:1 EtOAc:EtOH/hexanes) to afford the title compound. MS: 411.1 (M+1).

Step 3: ethyl 1-(2-(4-(4-fluoro-2,3-dimethylphenyl)cyclohexyl)ethyl)-1,4,5,6-tetrahydrocyclopenta[c]pyrazole-3-carboxylate (49-3)

To a mixture of ethyl 1-(2-(4'-fluoro-2',3'-dimethyl-2,3,4,5-tetrahydro-[1,1'-biphenyl]-4-yl)ethyl)-1,4,5,6-tetrahydrocyclopenta[c]pyrazole-3-carboxylate (49-2) (275 mg, 0.670 mmol) in MeOH (3349 µl)/THF (3349 µl) at ambient temperature were added Pd/C (71.3 mg, 0.067 mmol) and a balloon of H₂ (vacuum purge three times). The mixture was stirred for 18 h before filtering through a pad of Celite and the filtrated was concentrated to afford the title compound. MS: 413.1 (M+1).

Step 4: 1-(2-(4-(4-fluoro-2,3-dimethylphenyl)cyclohexyl)ethyl)-1,4,5,6-tetrahydrocyclopenta[c]pyrazole-3-carboxylic Acid (49-4)

To a mixture of ethyl 1-(2-(4-(4-fluoro-2,3-dimethylphenyl)cyclohexyl)ethyl)-1,4,5,6-tetrahydrocyclopenta[c]pyrazole-3-carboxylate (49-3) (254 mg, 0.616 mmol) in THF (1539 µl)/MeOH (1539 µl) at ambient temperature was added LiOH (924 µl, 1.847 mmol). The mixture was heated to 50° C. and stirred for 2 h before cooling and then acidifying with TFA. The mixture was purified directly by column chromatography on C18 (5-95% ACN/water with 0.05% TFA modifier) to afford the title compound. MS: 385.1 (M+1).

Step 5: 1-(4-(1-(2-(4-(4-fluoro-2,3-dimethylphenyl)cyclohexyl)ethyl)-1,4,5,6-tetrahydrocyclopenta[c]pyrazole-3-carbonyl)piperazin-1-yl)-2-hydroxyethanone (49-5)

To a mixture of 1-(2-(4-(4-fluoro-2,3-dimethylphenyl)cyclohexyl)ethyl)-1,4,5,6-tetrahydrocyclopenta[c]pyrazole-3-carboxylic acid (49-4) (50 mg, 0.130 mmol) in DMF (650 µl) at ambient temperature were added 2-hydroxy-1-(piperazin-1-yl)ethanone (37.5 mg, 0.260 mmol), DIPEA (45.4 µl, 0.260 mmol), and HATU (74.2 mg, 0.195 mmol). The mixture was stirred for 2 h before acidifying with a few drops of TFA. The mixture was purified directly by column chromatography on C18 (5-95% ACN/water with 0.05% TFA modifier) to afford the title compound. MS: 511.2 (M+1).

Step 6: 1-(4-(1-(2-(4-(4-fluoro-2,3-dimethylphenyl)cyclohexyl)ethyl)-1,4,5,6-tetrahydrocyclopenta[c]pyrazole-3-carbonyl)piperazin-1-yl)-2-hydroxyethan-1-one (49, Chiral, cis) and 1-(4-(1-(2-(4-(4-fluoro-2,3-dimethylphenyl)cyclohexyl)ethyl)-1,4,5,6-tetrahydrocyclopenta[c]pyrazole-3-carbonyl)piperazin-1-yl)-2-hydroxyethan-1-one (50, Chiral, trans)

The diastereomeric ((2R,6S)-2,6-dimethylmorpholino)(1-(2-(1-(2,3-dimethylphenyl)piperidin-4-yl)-2-fluoroethyl)-1,4,5,6-tetrahydrocyclopenta[c]pyrazol-3-yl)methanone (49-5) was submitted for SFC purification to obtain two chiral isomers.

Example 49 (peak 1): MS: 511.2 (M+1). 1H NMR (500 MHz, Chloroform-d) δ 7.01 (dd, J=8.6, 5.8 Hz, 1H), 6.85 (t, J=8.9 Hz, 1H), 4.21 (s, 3H), 4.05 (t, J=7.1 Hz, 2H), 3.83-3.69 (m, 4H), 3.35 (s, 2H), 2.78 (dt, J=15.3, 7.0 Hz, 2H), 2.75-2.67 (m, 3H), 2.59 (p, J=7.4 Hz, 2H), 2.23 (s, 3H), 2.20 (d, J=1.7 Hz, 3H), 1.98 (q, J=7.2 Hz, 2H), 1.81-1.73 (m, 1H), 1.73-1.65 (m, 4H), 1.57 (dtd, J=18.5, 13.2, 5.6 Hz, 4H).

Example 50 (peak 2): MS: 511.2 (M+1). 1H NMR (500 MHz, Chloroform-d) δ 6.99 (dd, J=8.5, 6.0 Hz, 1H), 6.85 (t, J=8.9 Hz, 1H), 4.21 (s, 3H), 4.06 (t, J=7.3 Hz, 2H), 3.83-3.71 (m, 4H), 3.35 (s, 2H), 2.80 (t, J=6.9 Hz, 2H), 2.74-2.66 (m, 3H), 2.59 (p, J=7.4 Hz, 2H), 2.23 (s, 3H), 2.20 (d, J=1.6 Hz, 3H), 1.91 (d, J=10.8 Hz, 2H), 1.83 (d, J=12.0 Hz, 2H), 1.78 (q, J=7.2 Hz, 2H), 1.46-1.29 (m, 3H), 1.23-1.10 (m, 2H).

The examples in the following table were prepared in an analogous manner to Example 50 using appropriate starting materials described previously or commercially available.

| Ex. # | Structure | Chemical Name | Mass [M + H]+ |
|---|---|---|---|
| 51 | 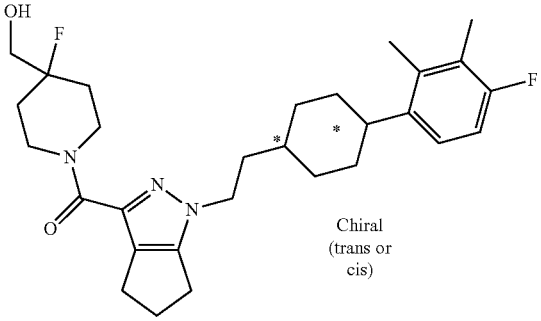 [SMILES: Cc1c(F)ccc(C2CCC(CCn3nc(C(=O)N4CCC(F)(CO)CC4)c4c3CCC4)CC2)c1C] Chiral (trans or cis) | (1-(2-(4-(4-fluoro-2,3-dimethylphenyl)cyclohexyl)ethyl)-1,4,5,6-tetrahydrocyclopenta[c]pyrazol-3-yl)(4-fluoro-4-(hydroxymethyl)piperidin-1-yl)methanone | 500.2 |
| 52 | 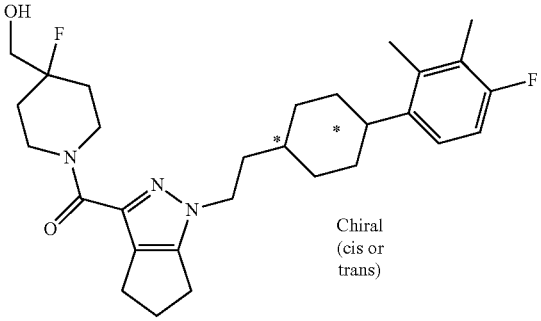 [SMILES: Cc1c(F)ccc(C2CCC(CCn3nc(C(=O)N4CCC(F)(CO)CC4)c4c3CCC4)CC2)c1C] Chiral (cis or trans) | (1-(2-(4-(4-fluoro-2,3-dimethylphenyl)cyclohexyl)ethyl)-1,4,5,6-tetrahydrocyclopenta[c]pyrazol-3-yl)(4-fluoro-4-(hydroxymethyl)piperidin-1-yl)methanone | 500.1 |

Examples 53 and 54: (1-(2-((1s,4S)-4-(3-chloro-2-methylphenoxy)cyclohexyl)ethyl)-1,4,5,6-tetrahydrocyclopenta[c]pyrazol-3-yl)((2R,6S)-2,6-dimethylmorpholino)methanone (Chiral, cis) and (1-(2-((1r,4R)-4-(3-chloro-2-methylphenoxy)cyclohexyl)ethyl)-1,4,5,6-tetrahydrocyclopenta[c]pyrazol-3-yl)((2R,6S)-2,6-dimethylmorpholino)methanone (Chiral, trans)

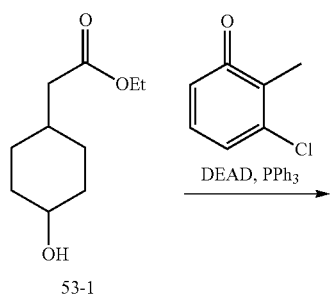

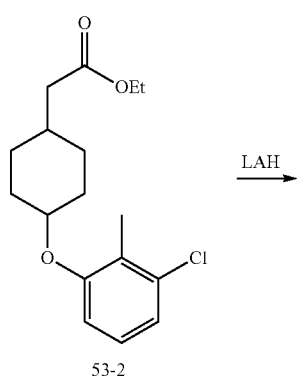

-continued

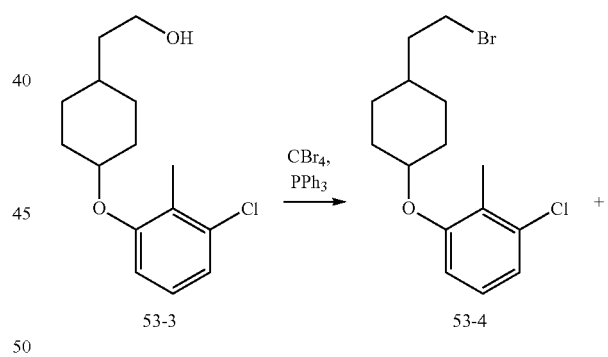

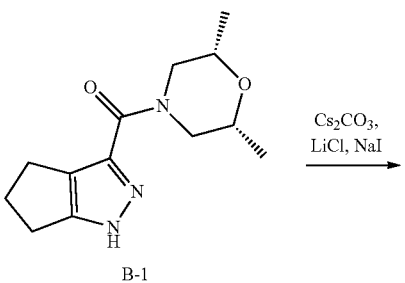

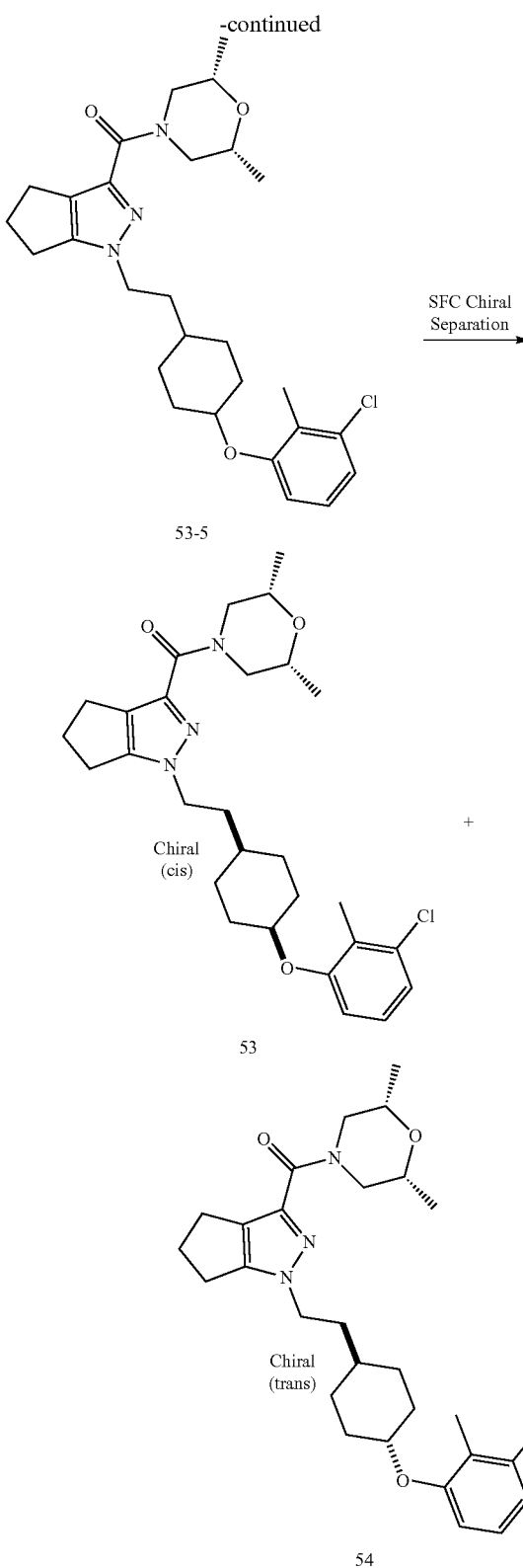

added 3-chloro-2-methylphenol (621 mg, 4.35 mmol) and triphenylphosphine (1142 mg, 4.35 mmol). DEAD (1983 µl, 4.35 mmol) in toluene was added to the mixture dropwise and the mixture was allowed to warm to RT. The mixture was stirred for 16 h before concentrating. The residue was purified by column chromatography on silica (2-40% 3:1 EtOAc:EtOH/hexane) to afford the title compound. MS: 297.2 (M+1).

Step 2: 2-(4-(3-chloro-2-methylphenoxy)cyclohexyl)ethanol (53-3)

To a mixture of methyl 2-(4-(3-chloro-2-methylphenoxy)cyclohexyl)acetate (53-2) (862 mg, 2.90 mmol) in THF (2904 µl) at 0° C. was added 1.0 M LAH (2904 µl, 2.90 mmol) in THF dropwise. The mixture was stirred for 2 h before quenching carefully with $Na_2SO_4$ and water. After stirring for another 20 min, the solution was filtered through a pad of Celite and washed with EtOAc (25 mL). The filtrate was concentrated. The residue was purified by column chromatography on silica (2-50% 3:1 EtOAc:EtOH/hexane) to afford the title compound. MS: 269.1 (M+1).

Step 3: 1-((4-(2-bromoethyl)cyclohexyl)oxy)-3-chloro-2-methylbenzene (53-4)

To a mixture of 2-(4-(3-chloro-2-methylphenoxy)cyclohexyl)ethanol (53-3) (355 mg, 1.321 mmol) in DCM (8805 µl) at 0° C. was added $CBr_4$ (657 mg, 1.981 mmol) followed by triphenylphosphine (520 mg, 1.981 mmol). The mixture was slowly warmed to ambient temperature and allowed to stir overnight. The mixture was concentrated, taken up in EtOAc (a precipitate formed), filtered, and the filtrate was concentrated to afford the title compound. MS: 331.2 (M+1).

Step 4: 1-(2-(4-(4-fluoro-2,3-dimethylphenyl)cyclohexyl)ethyl)-1,4,5,6-tetrahydrocyclopenta[c]pyrazole-3-carboxylic Acid (53-5)

To a mixture of ((2R,6S)-2,6-dimethylmorpholino)(1,4,5,6-tetrahydrocyclopenta[c]pyrazol-3-yl)methanone (B-1) (428 mg, 1.717 mmol) in NMP (2641 µl) at ambient temperature were added 1-((4-(2-bromoethyl)cyclohexyl)oxy)-3-chloro-2-methylbenzene (53-4) (438 mg, 1.321 mmol), $Cs_2CO_3$ (861 mg, 2.64 mmol), lithium chloride (112 mg, 2.64 mmol), and sodium iodide (198 mg, 1.321 mmol). The mixture was warmed to 80° C. and stirred overnight. The mixture was cooled and taken up in $Et_2O$ (30 mL) and water (30 mL). The mixtures were separated, dried over $Na_2SO_4$, and concentrated. The residue was purified by column chromatography on silica (2-60% 3:1 EtOAc:EtOH/hexanes) to afford the title compound. MS: 500.4 (M+1).

Step 5: 1-(2-((1s,4S)-4-(3-chloro-2-methylphenoxy)cyclohexyl)ethyl)-1,4,5,6-tetrahydrocyclopenta[c]pyrazol-3-yl)((2R,6S)-2,6-dimethylmorpholino)methanone (53, Chiral, cis) and (1-(2-((1r,4R)-4-(3-chloro-2-methylphenoxy)cyclohexyl)ethyl)-1,4,5,6-tetrahydrocyclopenta[c]pyrazol-3-yl)((2R,6S)-2,6-dimethylmorpholino)methanone (54, Chiral, trans)

The diastereomeric 1-(2-(4-(4-fluoro-2,3-dimethylphenyl)cyclohexyl)ethyl)-1,4,5,6-tetrahydrocyclopenta[c]pyrazole-3-carboxylic acid (53-5) was submitted for SFC purification to obtain two chiral isomers.

Example 53 (peak 1): MS: 500.4 (M+1). 1H NMR (500 MHz, Chloroform-d) δ 7.12-7.00 (m, 1H), 6.95 (d, J=7.9 Hz, Step 1: methyl 2-(4-(3-chloro-2-methylphenoxy)cyclohexyl)acetate (53-2)

To a mixture of methyl 2-(4-hydroxycyclohexyl)acetate (53-1) (500 mg, 2.90 mmol) in THF (5806 µl) at 0° C. were 1H), 6.73 (d, J=8.4 Hz, 1H), 4.80-4.74 (m, 1H), 4.55 (s, 2H), 4.10-4.03 (m, 1H), 3.65 (s, 2H), 2.94-2.47 (m, 6H), 2.04 (d, J=10.9 Hz, 2H), 1.79 (d, J=7.0 Hz, 3H), 1.54-1.32 (m, 7H), 1.32-1.10 (m, 8H), 0.95-0.69 (m, 3H).

Example 54 (peak 2): MS: 500.4 (M+1). 1H NMR (500 MHz, Chloroform-d) δ 7.04 (t, J=8.0 Hz, 1H), 7.00-6.91 (m, 1H), 6.76 (d, J=8.0 Hz, 1H), 4.74 (d, J=12.7 Hz, 1H), 4.56 (d, J=12.6 Hz, 1H), 4.17-3.99 (m, 2H), 3.64 (s, 2H), 3.43 (s, 1H), 2.94-2.41 (m, 6H), 2.20-1.72 (m, 6H), 1.55-1.00 (m, 16H).

The examples in the following table were prepared in an analogous manner to Example 54 using appropriate starting materials described previously or commercially available.

| Ex. # | Structure | Chemical Name | Mass [M + H]+ |
|---|---|---|---|
| 55 | Chiral (cis or trans) | (1-((4-(3-chloro-2-methylphenoxy)cyclohexyl)methyl)-1,4,5,6-tetrahydrocyclopenta[c]pyrazol-3-yl)((2R,6S)-2,6-dimethylmorpholino)methanone | 486.3 |
| 56 | Chiral (trans or cis) | (1-((4-(3-chloro-2-methylphenoxy)cyclohexyl)methyl)-1,4,5,6-tetrahydrocyclopenta[c]pyrazol-3-yl)((2R,6S)-2,6-dimethylmorpholino)methanone | 486.3 |

Example 57: 1-(4-(1-(2-((1s,4s)-4-(2-chloro-5-methylphenoxy)cyclohexyl)ethyl)-1,4,5,6-tetrahydrocyclopenta[c]pyrazole-3-carbonyl)piperazin-1-yl)-2-hydroxyethan-1-one

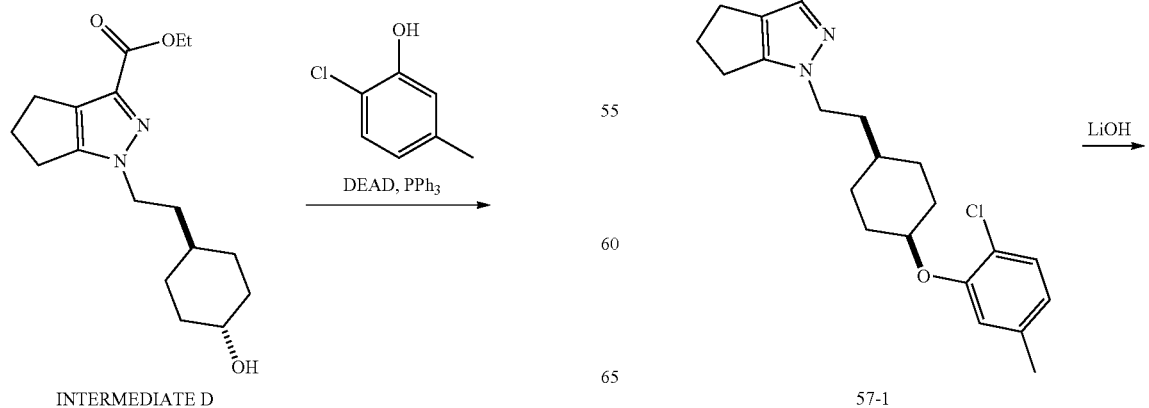

INTERMEDIATE D 57-1

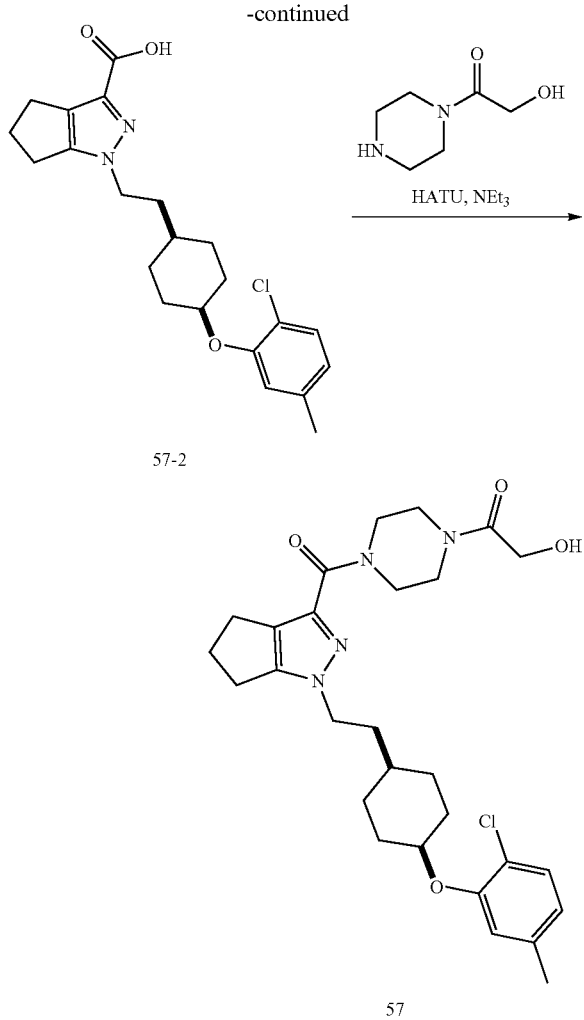

Step 1: ethyl 1-(2-(4-(2-chloro-5-methylphenoxy)cyclohexyl)ethyl)-1,4,5,6-tetrahydrocyclopenta[c]pyrazole-3-carboxylate (57-1)

To a mixture of ethyl 1-(2-(4-hydroxycyclohexyl)ethyl)-1,4,5,6-tetrahydrocyclopenta[c]pyrazole-3-carboxylate (Intermediate D) (150 mg, 0.490 mmol) in THF (1958 µl) at 0° C. were added 2-chloro-5-methylphenol (140 mg, 0.979 mmol) and triphenylphosphine (257 mg, 0.979 mmol). DEAD (446 µl, 0.979 mmol) in toluene was added dropwise and the reaction was allowed to warm to ambient temperature while stirring overnight. The mixture was purified directly by column chromatography on C18 (5-95% ACN/water with 0.05% TFA modifier) to afford the title compound. MS: 431.1 (M+1).

Step 2: 1-(2-(4-(2-chloro-5-methylphenoxy)cyclohexyl)ethyl)-1,4,5,6-tetrahydrocyclopenta[c]pyrazole-3-carboxylic Acid (57-2)

To a solution of ethyl 1-(2-(4-(2-chloro-5-methylphenoxy)cyclohexyl)ethyl)-1,4,5,6-tetrahydrocyclopenta[c]pyrazole-3-carboxylate (57-1) (40 mg, 0.093 mmol) in MeOH (232 µl)/THF (232 µl) at ambient temperature was added LiOH (139 µl, 0.278 mmol). The reaction was stirred for 4 h before the mixture was concentrated to afford the title compound. MS: 403.1 (M+1).

Step 3: 1-(4-(1-(2-((1s,4s)-4-(2-chloro-5-methylphenoxy)cyclohexyl)ethyl)-1,4,5,6-tetrahydrocyclopenta[c]pyrazole-3-carbonyl)piperazin-1-yl)-2-hydroxyethan-1-one (57)

To a mixture of 1-(2-(4-(2-chloro-5-methylphenoxy)cyclohexyl)ethyl)-1,4,5,6-tetrahydrocyclopenta[c]pyrazole-3-carboxylic acid (57-2) (18 mg, 0.045 mmol) in DMF (447 µl) at ambient temperature were added 2-hydroxy-1-(piperazin-1-yl)ethanone (19.32 mg, 0.134 mmol), TEA (18.68 µl, 0.134 mmol), and HATU (34.0 mg, 0.089 mmol). The mixture was stirred for 2 h before acidifying with a few drops of TFA. The mixture was purified directly by column chromatography on C18 (5-95% ACN/water with 0.05% TFA modifier) to afford the title compound. MS: 529.2 (M+1). $^1$H NMR (500 MHz, Chloroform-d) δ 7.23 (d, J=8.0 Hz, 1H), 6.75 (s, 1H), 6.70 (d, J=7.8 Hz, 1H), 5.64 (s, 2H), 4.59 (s, 1H), 4.25 (s, 2H), 4.17-4.04 (m, 4H), 3.78-3.72 (m, 4H), 3.39 (s, 2H), 2.74 (dt, J=15.3, 6.9 Hz, 4H), 2.60 (q, J=6.7 Hz, 2H), 2.31 (s, 3H), 2.06 (d, J=11.0 Hz, 2H), 1.81 (q, J=7.1 Hz, 2H), 1.61-1.49 (m, 5H), 1.37 (s, 1H).

The examples in the following table were prepared in an analogous manner to Example 57 using appropriate starting materials described previously or commercially available.

| Ex. # | Structure | Chemical Name | Mass [M + H]$^+$ |
|---|---|---|---|
| 58 | 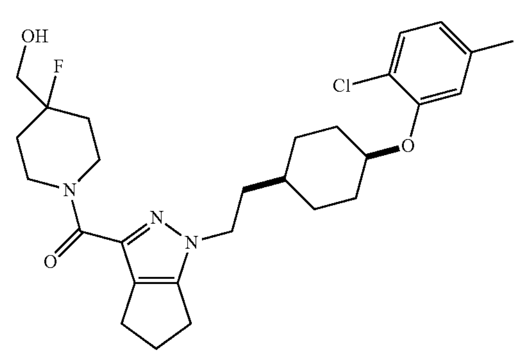 | (1-(2-((1s,4s)-4-(2-chloro-5-methylphenoxy)cyclohexyl)ethyl)-1,4,5,6-tetrahydrocyclopenta[c]pyrazol-3-yl)(4-fluoro-4-(hydroxymethyl)piperidin-1-yl)methanone | 518.1 |

| Ex. # | Structure | Chemical Name | Mass [M + H]⁺ |
|---|---|---|---|
| 59 | 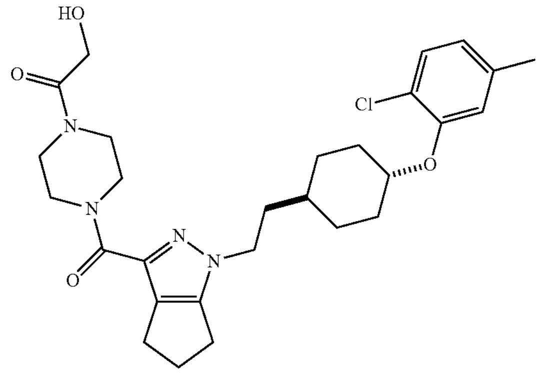 | 1-(4-(1-(2-((1r,4r)-4-(2-chloro-5-methylphenoxy)cyclohexyl)ethyl)-1,4,5,6-tetrahydrocyclopenta[c]pyrazole-3-carbonyl)piperazin-1-yl)-2-hydroxyethan-1-one | 529.2 |
| 60 | 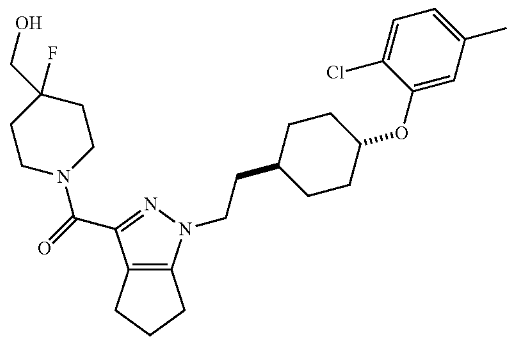 | (1-(2-((1r,4r)-4-(2-chloro-5-methylphenoxy)cyclohexyl)ethyl)-1,4,5,6-tetrahydrocyclopenta[c]pyrazol-3-yl)(4-fluoro-4-(hydroxymethyl)piperidin-1-yl)methanone | 518.1 |

Example 61: N-(1-(1-(2-((1s,4s)-4-(2-methylphenoxy)cyclohexyl)ethyl)-1,4,5,6-tetrahydrocyclopenta[c]pyrazole-3-carbonyl)piperidin-4-yl)acetamide

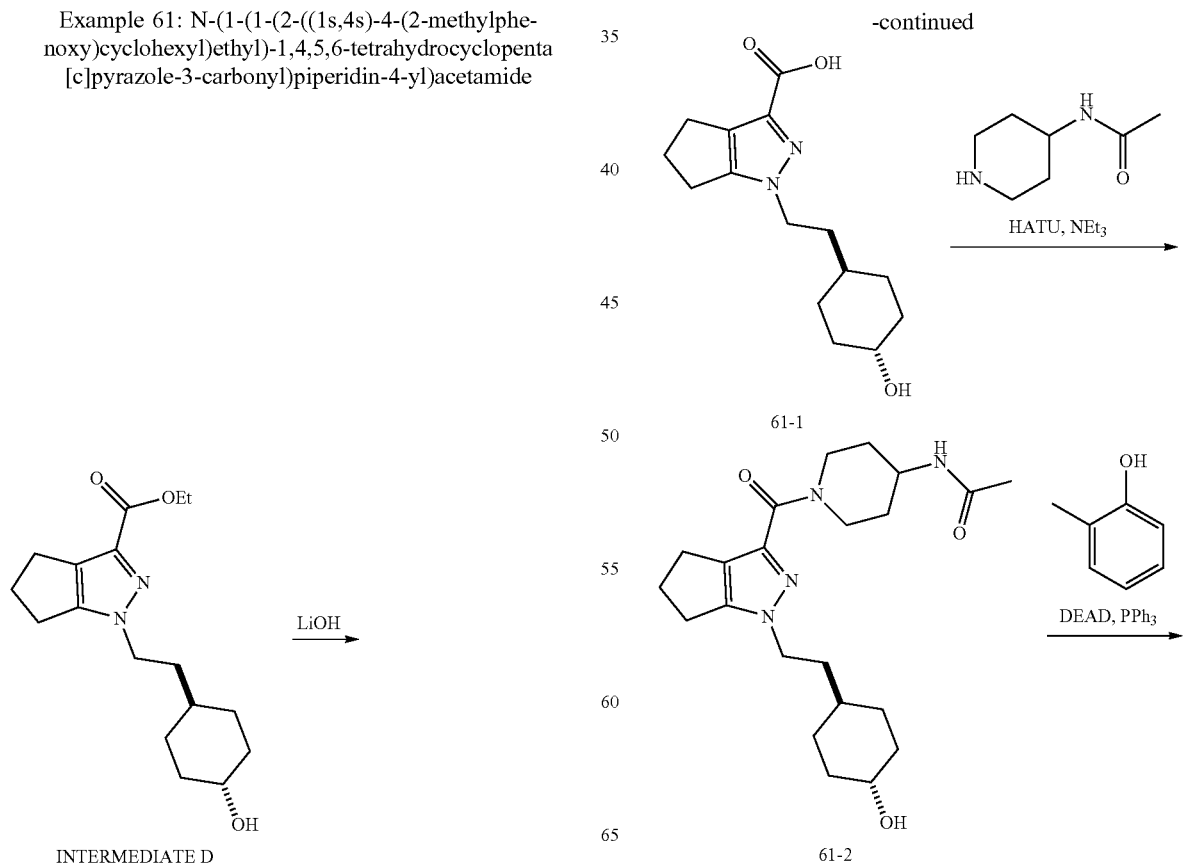

-continued

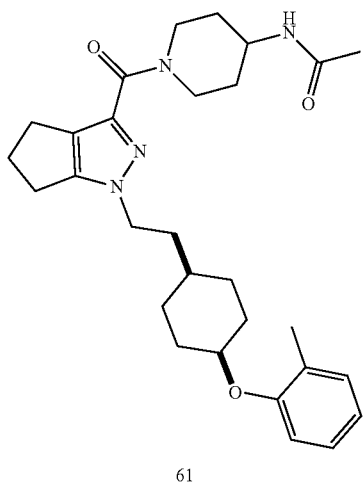

61

Step 1: 1-(2-(4-hydroxycyclohexyl)ethyl)-1,4,5,6-tetrahydrocyclopenta[c]pyrazole-3-carboxylic Acid (61-1)

To a solution of ethyl 1-(2-(4-hydroxycyclohexyl)ethyl)-1,4,5,6-tetrahydrocyclopenta[c]pyrazole-3-carboxylate (431 mg, 1.407 mmol) in THF (6 ml)/MeOH (3 ml)/water (3 ml) in a 40 ml of vial was added LiOH (135 mg, 5.63 mmol). The reaction mixture was stirred at RT. After overnight stirring, the reaction was neutralized with HCl (0.578 ml, 7.03 mmol) and concentrated under reduced pressure to give the title compound, which was used for next step without purification. MS: 279.2 (M+1)$^+$ Step 2: N-(1-(1-(2-(4-hydroxycyclohexyl)ethyl)-1,4,5,6-tetrahydrocyclopenta[c]pyrazole-3-carbonyl)piperidin-4-yl)acetamide (62-2)

To a solution of 1-(2-(4-hydroxycyclohexyl)ethyl)-1,4,5,6-tetrahydrocyclopenta[c]pyrazole-3-carboxylic acid (0029-all crude) (392 mg, 1.408 mmol) in DMF (14 ml) were added N-(piperidin-4-yl)acetamide (240 mg, 1.690 mmol), HATU (643 mg, 1.690 mmol) followed by DIPEA (0.492 ml, 2.82 mmol). The reaction solution was stirred at RT for 1.5 h. The mixture was then concentrated under reduced pressure. The residue was purified by ISCO preparative reversed phase HPLC (150 g C18 column), eluting with 10-100% water in ACN to afford the title compound. MS: 403.6 (M+1)$^+$.

Step 3: N-(1-(1-(2-(4-(o-tolyloxy)cyclohexyl)ethyl)-1,4,5,6-tetrahydrocyclopenta[c]pyrazole-3-carbonyl)piperidin-4-yl)acetamide (61)

A 2-dram vial containing a stir bar was charged with triphenylphosphine polymer-bound (58.4 mg, 0.224 mmol) and THF (1.0 mL). The polymer was allowed to swelled for 15 min. Diethylazoldicarboxylate as a solution in toluene (0.102 ml, 0.224 mmol, 40% wt) was added to the vial. The mixture was then stirred for 15 min before the addition of o-cresol (24.18 mg, 0.224 mmol). The mixture was stirred for another 15 min, then N-(1-(1-(2-(4-hydroxycyclohexyl)ethyl)-1,4,5,6-tetrahydrocyclopenta[c]pyrazole-3-carbonyl)piperidin-4-yl)acetamide (30 mg, 0.075 mmol) in THF (0.6 ml) was added dropwise. The resulting suspension was stirred at RT overnight. The mixture was then filtered and concentrated under reduced pressure. The crude material was purified by ISCO preparative reversed phase HPLC (C18 column), eluting with 10-100% water in ACN to afford the title compound. MS: 493.3 (M+1)$^+$. $^1$H NMR (500 MHz, DMSO-$d_6$) δ 7.84-7.59 (m, 1H), 7.05-6.89 (m, 1H), 6.79-6.72 (m, 1H), 6.68-6.61 (m, 1H), 4.58-4.53 (m, 2H), 4.19-4.09 (m, 1H), 4.04-4.02 (m, 2H), 3.81-3.80 (m, 1H), 3.31-3.22 (m, 4H), 3.26-3.16 (m, 1H), 2.96-2.79 (m, 1H), 2.70-2.67 (m, 2H), 2.59-2.55 (m, 4H), 2.48-2.45 (m, 1H), 1.96 (s, 3H), 1.89-1.86 (m, 2H), 1.79 (s, 3H), 1.68-1.65 (m, 2H), 1.52-1.47 (m, 2H), 1.30-1.23 (s, −4H).

The examples in the following table were prepared in an analogous manner to Example 61 using appropriate starting materials described previously or commercially available.

| Ex. # | Structure | Chemical Name | Mass [M + H]$^+$ |
|---|---|---|---|
| 62 | 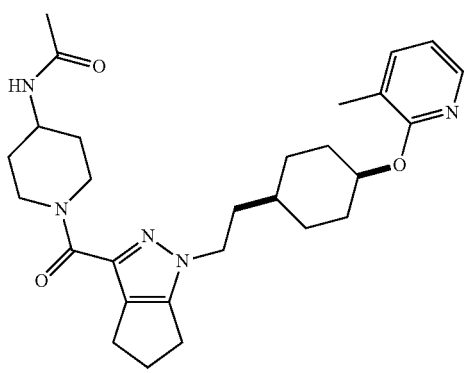 | N-(1-(1-(2-((1s,4s)-4-((3-methylpyridin-2-yl)oxy)cyclohexyl)ethyl)-1,4,5,6-tetrahydrocyclopenta[c]pyrazole-3-carbonyl)piperidin-4-yl)acetamide | 494.1 |

| Ex. # | Structure | Chemical Name | Mass [M + H]+ |
|---|---|---|---|
| 63 | 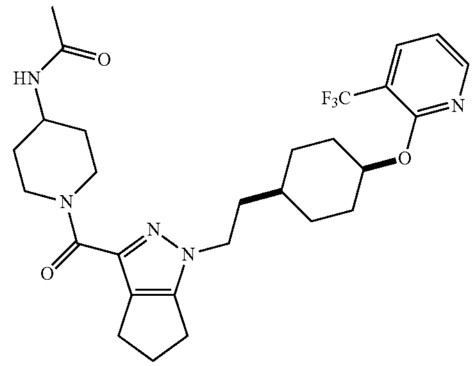 | N-(1-(1-(2-((1s,4s)-4-((3-(trifluoromethyl)pyridin-2-yl)oxy)cyclohexyl)ethyl)-1,4,5,6-tetrahydrocyclopenta[c]pyrazole-3-carbonyl)piperidin-4-yl)acetamide | 548.0 |
| 64 | 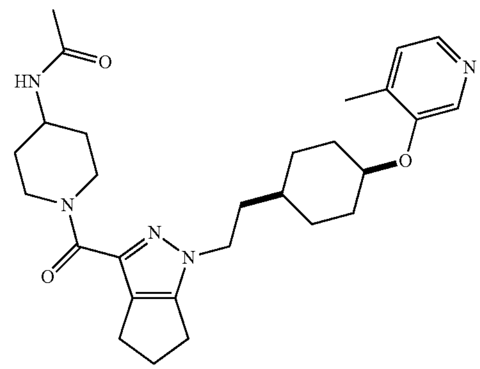 | N-(1-(1-(2-((1s,4s)-4-((4-methylpyridin-3-yl)oxy)cyclohexyl)ethyl)-1,4,5,6-tetrahydrocyclopenta[c]pyrazole-3-carbonyl)piperidin-4-yl)acetamide | 494.1 |
| 65 | 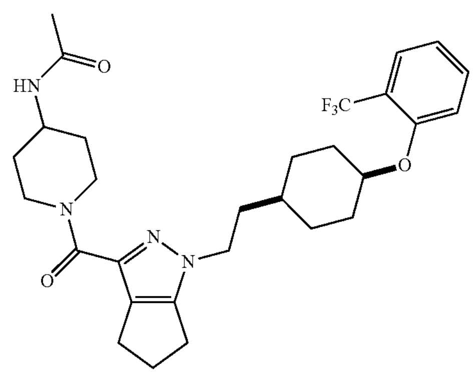 | N-(1-(1-(2-((1s,4s)-4-(2-(trifluoromethyl)phenoxy)cyclohexyl)ethyl)-1,4,5,6-tetrahydrocyclopenta[c]pyrazole-3-carbonyl)piperidin-4-yl)acetamide | 547.1 |
| 66 | 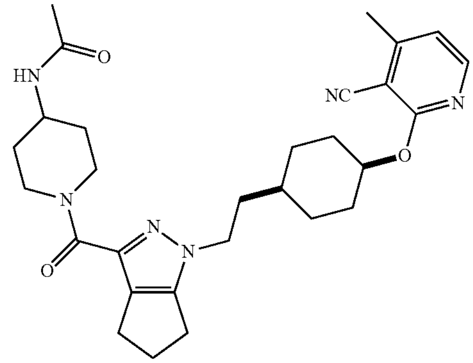 | N-(1-(1-(2-((1s,4s)-4-((3-cyano-4-methylpyridin-2-yl)oxy)cyclohexyl)ethyl)-1,4,5,6-tetrahydrocyclopenta[c]pyrazole-3-carbonyl)piperidin-4-yl)acetamide | 519.1 |

-continued

| Ex. # | Structure | Chemical Name | Mass [M + H]+ |
|---|---|---|---|
| 67 | 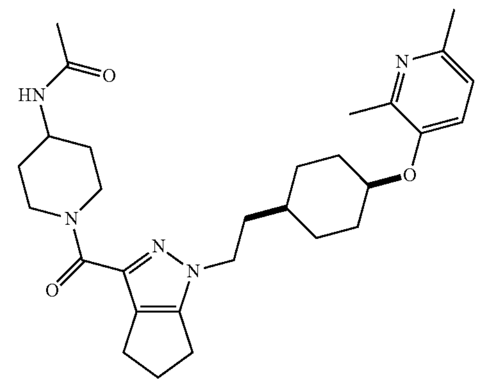 | N-(1-(1-(2-((1s,4s)-4-((2,6-dimethylpyridin-3-yl)oxy)cyclohexyl)ethyl)-1,4,5,6-tetrahydrocyclopenta[c]pyrazole-3-carbonyl)piperidin-4-yl)acetamide | 508.4 |
| 68 | 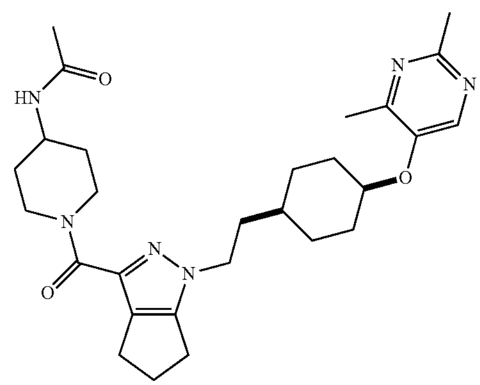 | N-(1-(1-(2-((1s,4s)-4-((2,4-dimethylpyrimidin-5-yl)oxy)cyclohexyl)ethyl)-1,4,5,6-tetrahydrocyclopenta[c]pyrazole-3-carbonyl)piperidin-4-yl)acetamide | 509.1 |
| 69 | 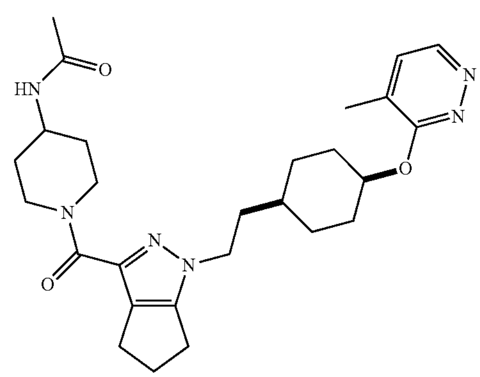 | N-(1-(1-(2-((1s,4s)-4-((4-methylpyridazin-3-yl)oxy)cyclohexyl)ethyl)-1,4,5,6-tetrahydrocyclopenta[c]pyrazole-3-carbonyl)piperidin-4-yl)acetamide | 495.1 |
| 70 | 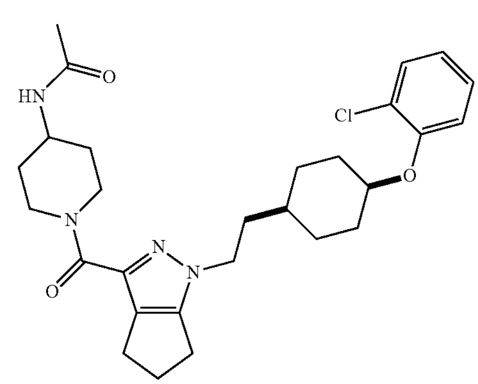 | N-[1-[1-[2-[4-(2-chlorophenoxy)cyclohexyl]ethyl]-5,6-dihydro-4H-cyclopenta[c]pyrazole-3-carbonyl]-4-piperidyl]acetamide | 513.0 |

103

Example 71: N-(1-(4-bromo-1-(2-((1s,4s)-4-((3-methylpyridin-2-yl)oxy)cyclohexyl)ethyl)-1H-pyrazole-3-carbonyl)-piperidin-4-yl)acetamide

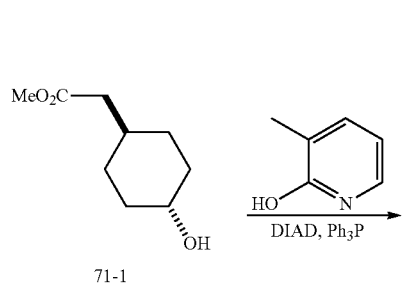

71-1

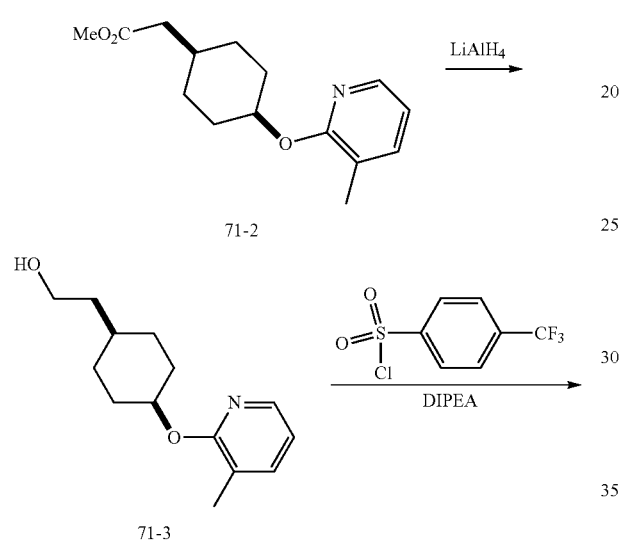

71-2

71-3

71-4

71-5

104

-continued

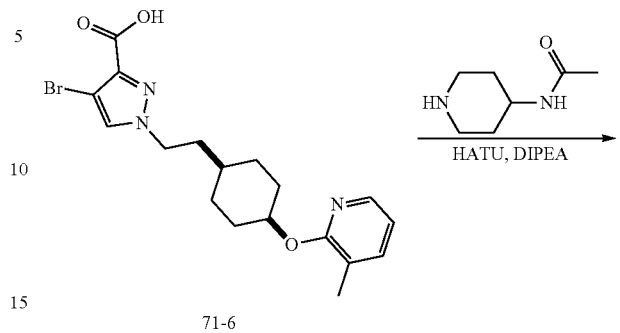

71-6

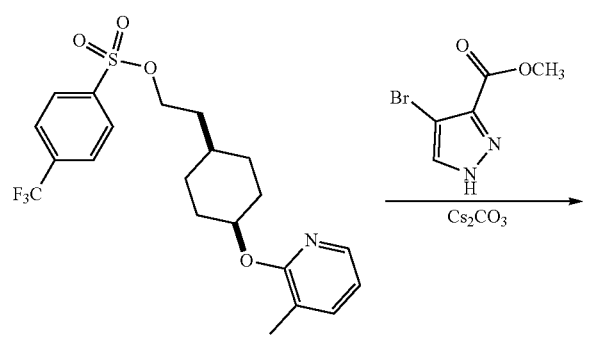

71

Step 1: methyl 2-((1s,4s)-4-((3-methylpyridin-2-yl)oxy)cyclohexyl)acetate (71-2)

To a solution of methyl 2-trans-4-hydroxycyclohexyl)acetate (0.5 g, 2.90 mmol) in THE (1.0 ml) at 0 C were added 2-hydroxy-3-methylpyridine (0.475 g, 4.35 mmol), triphenylphosphine (1.523 g, 5.81 mmol), and diisopropylazodicarboxylate (1.129 ml, 5.81 mmol). The mixture was stirred at 50° C. overnight. The reaction was diluted with 200 ml EtOAc and 100 ml of water. The layers were separated and the aq. was extracted with 200 ml of EtOAc. The combined organic layer was concentrated under reduced pressure. The residue was purified by column chromatography on silica gel Isolute Flash Si; 100 g prepacked, eluting with 0-30% EtOAc/isohexane to afford the title compound. MS: 264.4 (M+H)$^+$.

Step 2: 2-((1s,4s)-4-((3-methylpyridin-2-yl)oxy)cyclohexyl)ethanol (71-3)

To a solution of methyl 2-((1s,4s)-4-((3-methylpyridin-2-yl)oxy)cyclohexyl)acetate in THE (3 ml) at 0° C. was added LiAlH$_4$ (1.495 ml, 1.495 mmol). The reaction was stirred at RT for 2 h. The reaction was then cooled in an ice bath and quenched with HCl (0.153 ml, 1.868 mmol). To the resulting mixture was added water (30 mL) and extracted with EtOAc

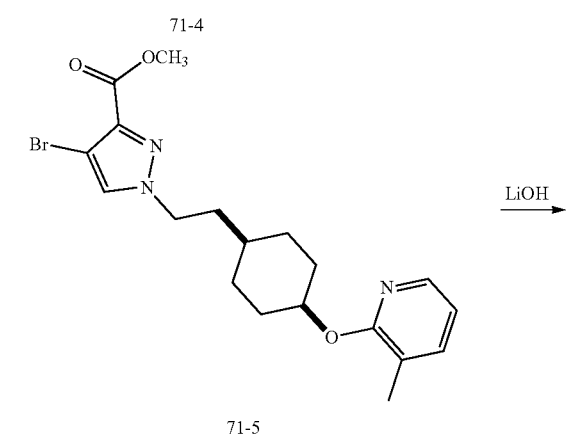

(3×75 mL). The combined organic fractions were washed with brine, dried over Na₂SO₄, filtered and the solvent was evaporated under reduced pressure to afford the title compound, which was used in the next step without further purification. MS: 236.2 (M+H)⁺.

Step 3: 2-((1s,4s)-4-((3-methylpyridin-2-yl)oxy)cyclohexyl)ethyl 4-(trifluoromethyl)benzenesulfonate (71-4)

To a solution of 2-((1s,4s)-4-((3-methylpyridin-2-yl)oxy)cyclohexyl)ethanol (438 mg, 1.861 mmol) in DCM (7 ml) at 0° C. was added DIPEA (0.975 ml, 5.58 mmol) followed by 4-(trifluoromethyl)benzene-1-sulfonyl chloride (510 mg, 2.085 mmol). After stirring at RT for 18 h, the reaction mixture was directly purified by column chromatography on silica gel Isolute Flash Si; 100 g prepacked, eluting with 0-20% EtOAc/isohexane to afford the title compound. MS: 444.2 (M+H)⁺.

Step 4: methyl 4-bromo-1-(2-((1s,4s)-4-((3-methylpyridin-2-yl)oxy)cyclohexyl)ethyl)-1H-pyrazole-3-carboxylate (71-5)

To a solution of methyl 4-bromo-1H-pyrazole-3-carboxylate (422 mg, 2.056 mmol) in dioxane (5 ml) was added 2-((1s,4s)-4-((3-methylpyridin-2-yl)oxy)cyclohexyl)ethyl 4-(trifluoromethyl)benzene-sulfonate (760 mg, 1.714 mmol) followed by Cs₂CO₃ (1117 mg, 3.43 mmol). The reaction was stirred at 50° C. overnight. To the mixture was added water (100 mL) and then extracted with EtOAc (3×100 mL). The combined organic fractions were washed with brine, dried over Na₂SO₄, filtered and the solvent was evaporated under reduced pressure. The residue was purified by column chromatography on silica gel Isolute Flash Si; 100 g prepacked, eluting with 0-50% EtOAc/isohexane to afford the title compound. MS: 424.2 (M+H)⁺.

Step 5: 4-bromo-1-(2-((1s,4s)-4-((3-methylpyridin-2-yl)oxy)cyclohexyl)ethyl)-1H-pyrazole-3-carboxylic Acid (71-6)

The title compound was prepared in an analogous manner of that described above in the preparation of compound 61-1. MS: 408.2 (M+H)⁺.

Step 6: N-(1-(4-bromo-1-(2-((1s,4s)-4-((3-methylpyridin-2-yl)oxy)cyclohexyl)ethyl)-1H-pyrazole-3-carbonyl)piperidin-4-yl)acetamide (71)

The title compound was prepared in an analogous manner of that described above in the preparation of compound 61-2. MS: 532.2 (M+H)⁺. ¹H NMR (400 MHz, Methanol-d₄) δ 7.88 (d, J=8.1 Hz, 2H), 7.46 (d, J=7.1 Hz, 1H), 6.79 (dd, J=7.1, 5.1 Hz, 1H), 5.23 (s, 1H), 4.53 (d, J=13.3 Hz, 1H), 4.23 (t, J=7.2 Hz, 2H), 3.94 (ddd, J=14.8, 10.6, 4.0 Hz, 1H), 3.82 (d, J=14.0 Hz, 1H), 3.65 (s, 1H), 3.28-3.18 (m, 1H), 3.08-2.98 (m, 1H), 2.19 (s, 3H), 1.99 (d, J=9.8 Hz, 3H), 1.92 (s, 2H), 1.90-1.78 (m, 3H), 1.59 (t, J=12.9 Hz, 4H), 1.53-1.29 (m, 5H).

Example 72: N-(1-(1-(2-((1s,4s)-4-((3-methylpyridin-2-yl)oxy)cyclohexyl)ethyl)-1H-pyrazole-3-carbonyl)piperidin-4-yl)acetamide

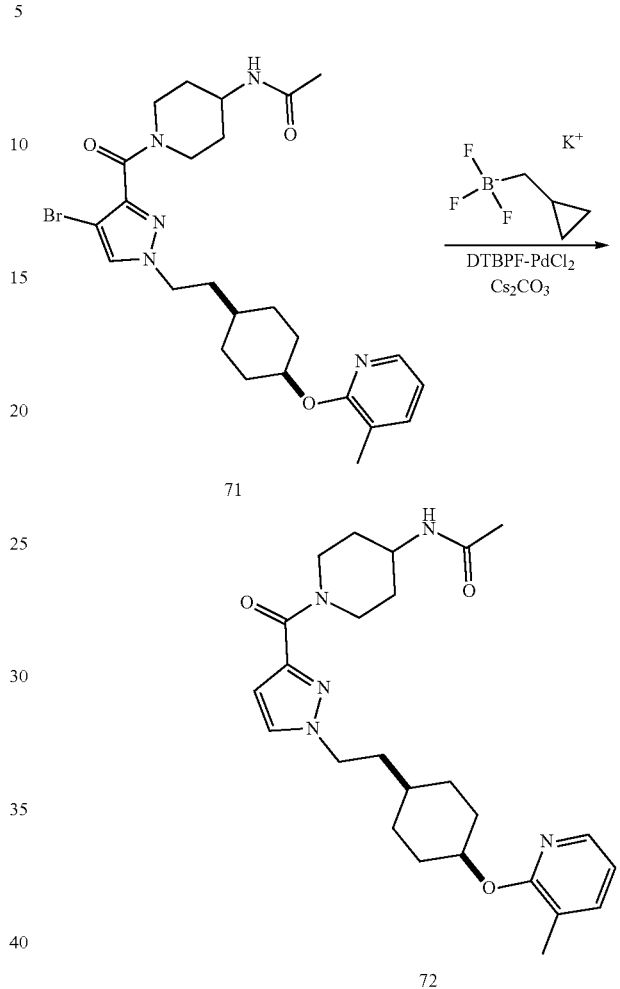

Step 1: N-(1-(1-(2-((1s,4s)-4-((3-methylpyridin-2-yl)oxy)cyclohexyl)ethyl)-1H-pyrazole-3-carbonyl)piperidin-4-yl)acetamide (72)

Under nitrogen atmosphere, to a solution of N-(1-(4-bromo-1-(2-((1s,4s)-4-((3-methylpyridin-2-yl)oxy)cyclohexyl)ethyl)-1H-pyrazole-3-carbonyl)piperidin-4-yl)acetamide (20 mg, 0.038 mmol) in MeOH (1 ml) in a 10 ml of microwave vial were added potassium(cyclopropylmethyl)trifluoro-boranuide (9.13 mg, 0.056 mmol), DTBPF-PdCl₂ (2.45 mg, 3.76 μmol) and Cs₂CO₃ (36.7 mg, 0.113 mmol). The vial was capped and heated at 100° C. for 5 h. The mixture was filtered and concentrated. The residue was purified by Gilson preparative HPLC (C18 column), eluting with 10-90% water in ACN+0.05% TFA to afford the title compound. MS 454.3 (M+H)⁺. ¹H NMR (400 MHz, Methanol-d₄) δ 7.91 (d, J=5.2 Hz, 1H), 7.69 (s, 1H), 7.62 (d, J=7.2 Hz, 1H), 6.91 (dd, J=7.2, 5.4 Hz, 1H), 6.57 (s, 1H), 5.22 (s, 2H), 4.57 (d, J=15.0 Hz, 2H), 4.25 (t, J=7.0 Hz, 3H), 3.94 (t, J=10.8 Hz, 2H), 3.01 (d, J=11.1 Hz, 1H), 2.22 (s, 3H), 2.01 (d, J=14.6 Hz, 2H), 1.92 (s, 3H), 1.83 (q, J=6.9 Hz, 2H), 1.61 (t, J=12.3 Hz, 4H), 1.44 (ddd, J=22.3, 14.3, 4.8 Hz, 5H), 1.28 (s, 1H).

Example 73: N-(1-(1-(2-((1s,4s)-4-((3-methylpyridin-2-yl)oxy)cyclohexyl)ethyl)-4-(3,3,3-trifluoropropyl)-1H-pyrazole-3-carbonyl)piperidin-4-yl)acetamide

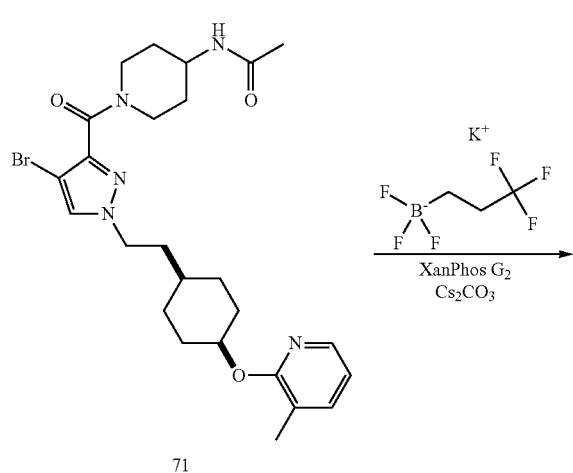

Step 1: N-(1-(1-(2-((1s,4s)-4-((3-methylpyridin-2-yl)oxy)cyclohexyl)ethyl)-4-(3,3,3-trifluoropropyl)-1H-pyrazole-3-carbonyl)piperidin-4-yl)acetamide (73)

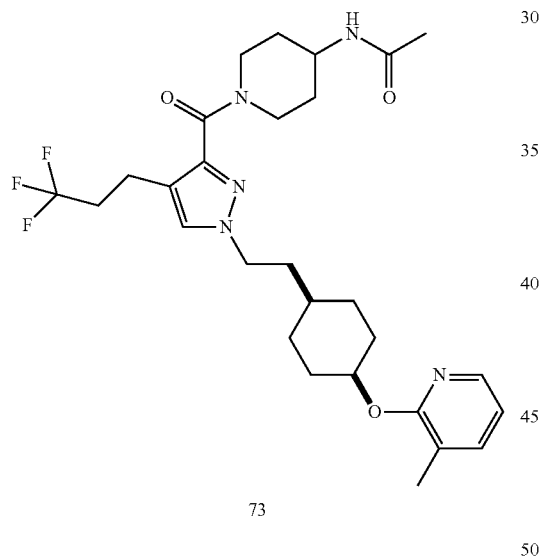

The title compound was prepared in an analogous manner to example 72 using appropriate starting materials and XanPhos G2 catalyst. MS: 550.4 (M+H)$^+$. $^1$H NMR (400 MHz, Methanol-d$_4$) δ 8.04-7.79 (m, 1H), 7.63 (s, 1H), 7.57 (d, J=7.1 Hz, 1H), 6.88 (dd, J=7.1, 5.2 Hz, 1H), 5.21 (s, 2H), 4.54 (d, J=7.1 Hz, 1H), 4.20 (t, J=7.1 Hz, 3H), 4.07-3.83 (m, 2H), 3.28-3.19 (m, 1H), 3.07-2.96 (m, 1H), 2.80 (dd, J=9.3, 6.7 Hz, 2H), 2.60-2.35 (m, 2H), 2.22 (s, 3H), 2.01 (d, J=16.2 Hz, 3H), 1.93 (s, 3H), 1.82 (q, J=6.9 Hz, 3H), 1.60 (t, J=13.1 Hz, 3H), 1.53-1.31 (m, 4H).

Example 74: N-(1-(4-cyclopropyl-1-(2-((1s,4s)-4-((3-methylpyridin-2-yl)oxy)cyclohexyl)ethyl)-1H-pyrazole-3-carbonyl)piperidin-4-yl)acetamide

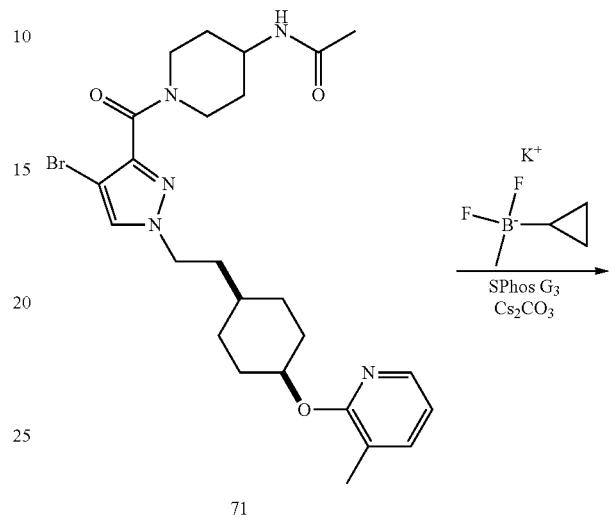

Step 1: N-(1-(1-(2-((1s,4s)-4-((3-methylpyridin-2-yl)oxy)cyclohexyl)ethyl)-4-(3,3,3-trifluoropropyl)-1H-pyrazole-3-carbonyl)piperidin-4-yl)acetamide (74)

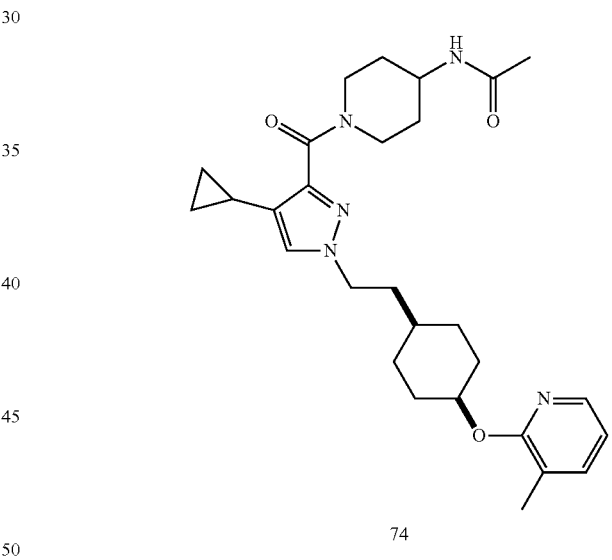

The title compound was prepared in an analogous manner to Example 72 using appropriate starting materials and Phos G2 catalyst. MS: 494.4 (M+H)$^+$. $^1$H NMR (400 MHz, Methanol-d$_4$) δ 7.91 (d, J=4.9 Hz, 1H), 7.63 (d, J=7.1 Hz, 1H), 7.37 (s, 1H), 6.92 (dd, J=7.1, 5.5 Hz, 1H), 5.20 (s, 1H), 4.54 (d, J=13.2 Hz, 1H), 4.13 (t, J=7.1 Hz, 2H), 3.93 (dd, J=9.6, 5.1 Hz, 2H), 3.28-3.17 (m, 1H), 3.07-2.90 (m, 1H), 2.22 (s, 3H), 2.08-1.91 (m, J=30.5 Hz, 6H), 1.89-1.68 (m, 4H), 1.60-1.54 (m, J=9.2 Hz, 4H), 1.53-1.25 (m, 5H), 0.87-0.77 (m, 2H), 0.50 (q, J=5.8, 5.0 Hz, 2H).

Example 75: (1-(2-(4-(2,3-dimethylphenyl)piperazin-1-yl)ethyl)-1H-indazol-3-yl)(pyrrolidin-1-yl)methanone

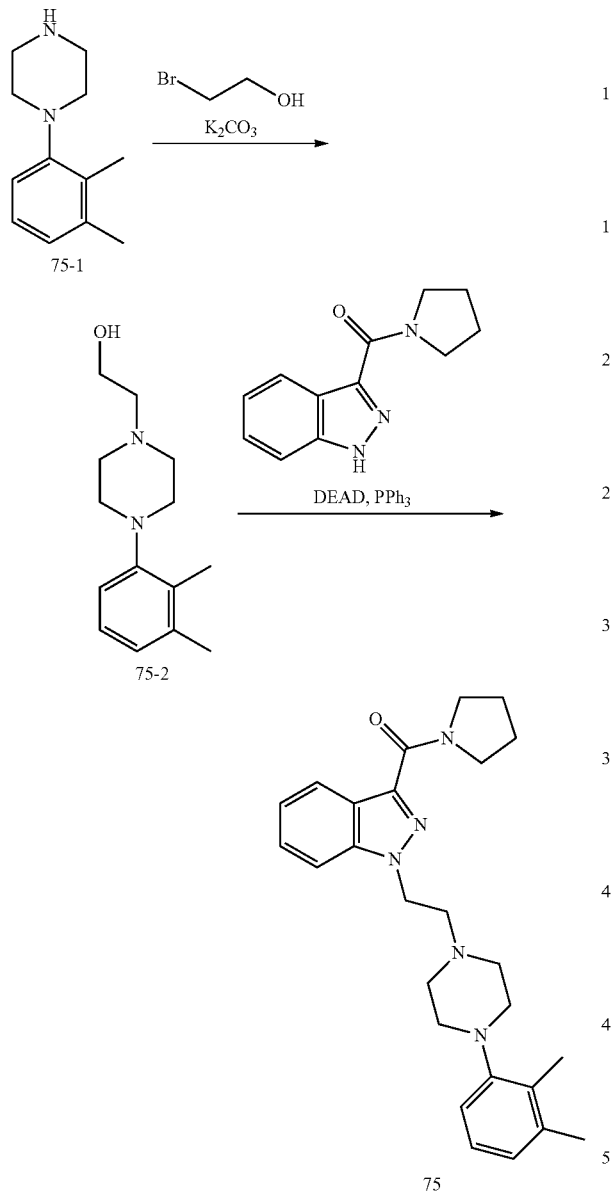

Step 1: 2-(4-(2,3-dimethylphenyl)piperazin-1-yl)ethanol (75-2)

To a mixture of 1-(2,3-dimethylphenyl)piperazine (75-1) (500 mg, 2.63 mmol) in DMF (5255 µl) at ambient temperature were added 2-bromoethanol (373 µl, 5.26 mmol) and $K_2CO_3$ (726 mg, 5.26 mmol). The mixture was stirred for 16 h before quenching with water (25 mL). The mixture was extracted with EtOAc (3×25 mL), dried over $Na_2SO_4$, and concentrated. The residue was purified by column chromatography on silica (15-100% 3:1 EtOAc:EtOH/hexanes) to afford the title compound. MS: 235.2 (M+1).

Step 2: (1-(2-(4-(2,3-dimethylphenyl)piperazin-1-yl)ethyl)-1H-indazol-3-yl)(pyrrolidin-1-yl)methanone (75)

To a mixture of (1H-indazol-3-yl)(pyrrolidin-1-yl)methanone (100 mg, 0.465 mmol) in THF (929 µl) at ambient temperature were added 2-(4-(2,3-dimethylphenyl)piperazin-1-yl)ethanol (75-2) (218 mg, 0.929 mmol) and triphenylphosphine (244 mg, 0.929 mmol). DEAD (317 µl, 0.697 mmol) was added dropwise. The mixture was stirred for 4 h before acidifying with a few drops of TFA. The mixture was purified directly by column chromatography on C18 (5-95% ACN/water with 0.05% TFA modifier) to afford the title compound. MS: 432.4 (M+1). $^1$H NMR (500 MHz, DMSO-d6) δ 8.19 (d, J=8.2 Hz, 1H), 7.86 (d, J=8.5 Hz, 1H), 7.56-7.48 (m, 1H), 7.34-7.27 (m, 1H), 7.07 (t, J=7.7 Hz, 1H), 6.93 (d, J=7.4 Hz, 1H), 6.90 (d, J=7.9 Hz, 1H), 4.97 (t, J=6.4 Hz, 2H), 3.96 (t, J=6.7 Hz, 2H), 3.80 (t, J=5.9 Hz, 2H), 3.74-3.67 (m, 2H), 3.58 (t, J=6.8 Hz, 2H), 3.41-3.32 (m, 2H), 3.20-3.11 (m, 2H), 2.98-2.88 (m, 2H), 2.21 (s, 3H), 2.17 (s, 3H), 1.93 (p, J=6.7, 6.0 Hz, 2H), 1.87 (p, J=6.5 Hz, 2H).

Example 76: N-(1-(1-(((2S,4S)-4-((5-chloropyridin-2-yl)oxy)tetrahydro-2H-pyran-2-yl)methyl)-5,5-difluoro-4,5,6,7-tetrahydro-1H-indazole-3-carbonyl)piperidin-4-yl)acetamide

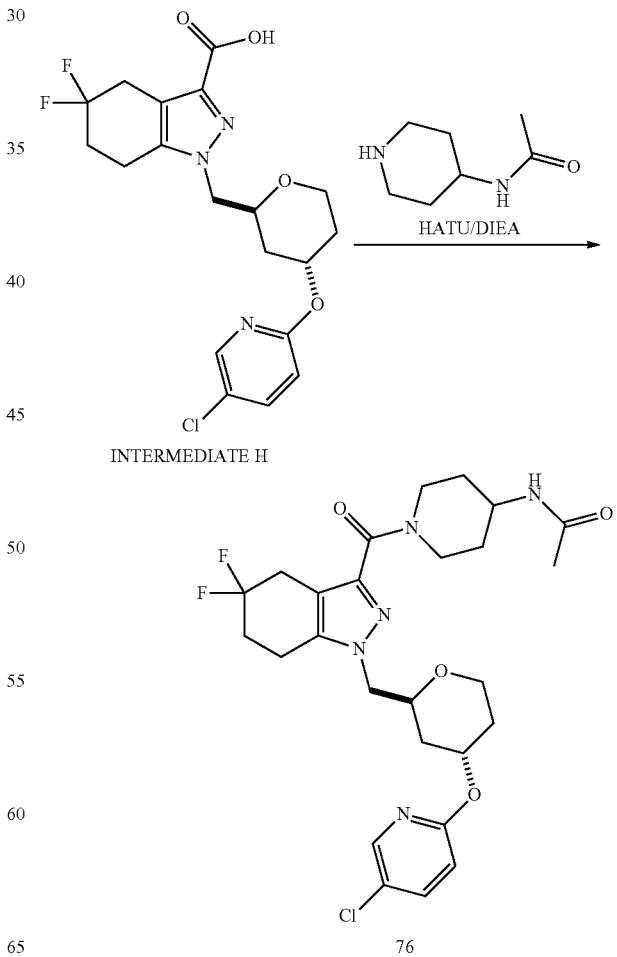

To a stirring solution of 1-(((2S,4S)-4-((5-chloropyridin-2-yl)oxy)tetrahydro-2H-pyran-2-yl)methyl)-5,5-difluoro-4,5,6,7-tetrahydro-1H-indazole-3-carboxylic acid (83 mg, 0.194 mmol) and HATU (111 mg, 0.291 mmol) in DMF (1 ml) were added 4-acetamidopiperidine (33.1 mg, 0.233 mmol) and DIEA (0.068 ml, 0.388 mmol). The mixture was stirred at RT for 10 min, quenched with drops of water, and directly purified on C18 reversed chromatography with 0 to 100% ACN in water with 0.05% TFA. The title compound was collected and lyophilized as a solid. The product was also proceeded for chiral separation. MS: 552.22 (M+1). 1H NMR (500 MHz, Methanol-d4) δ 8.09 (s, 1H), 7.67 (d, J=6.4 Hz, 1H), 6.82 (d, J=8.7 Hz, 1H), 5.42 (s, 1H), 4.49 (s, 2H), 4.11 (d, J=17.5 Hz, 3H), 3.97 (s, 1H), 3.81 (d, J=5.4 Hz, 2H), 3.17-3.03 (m, 3H), 2.95 (s, 2H), 2.28 (s, 2H), 2.06-1.75 (m, 7H), 1.65 (s, 2H), 1.48 (s, 2H).

The examples in the following table were prepared in an analogous manner to Example 76 using appropriate starting materials described previously or commercially available.

| Ex. # | Structure | Chemical Name | Mass [M + H]+ |
|---|---|---|---|
| 77 | 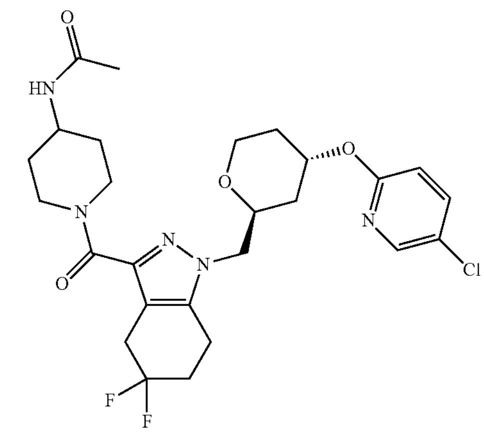 [SMILES: CC(=O)NC1CCN(C(=O)c2nn(C[C@@H]3C[C@@H](Oc4ccc(Cl)cn4)CCO3)c3c2CC(F)(F)CC3)CC1] | 6-{3-[4-(acetylamino)piperidine-1-carbonyl]-5,5-difluoro-4,5,6,7-tetrahydro-1H-indazol-1-yl}-1,5-anhydro-3-O-(5-chloropyridin-2-yl)-2,4,6-trideoxy-D-erythro-hexitol | 552.2 |
| 78 | 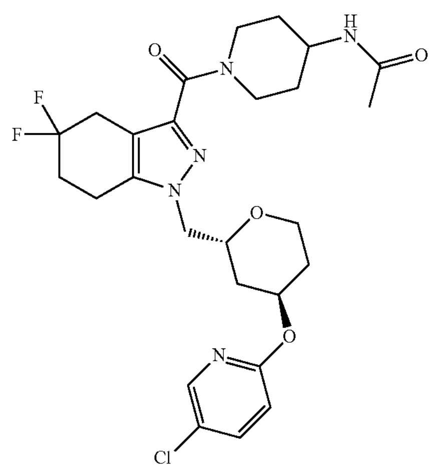 [SMILES: CC(=O)NC1CCN(C(=O)c2nn(C[C@H]3C[C@H](Oc4ccc(Cl)cn4)CCO3)c3c2CC(F)(F)CC3)CC1] | 1-{3-[4-(acetylamino)piperidine-1-carbonyl]-5,5-difluoro-4,5,6,7-tetrahydro-1H-indazol-1-yl}-2,6-anhydro-4-O-(5-chloropyridin-2-yl)-1,3,5-trideoxy-D-erythro-hexitol | 552.2 |
| 79 | 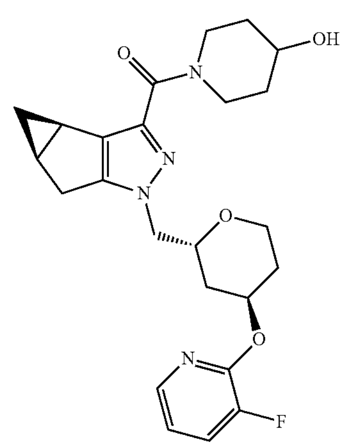 [SMILES: O=C(c1nn(C[C@H]2C[C@H](Oc3ncccc3F)CCO2)c2c1[C@@H]1C[C@@H]1C2)N1CCC(O)CC1] | 2,6-anhydro-1,3,5-trideoxy-4-O-(3-fluoropyridin-2-yl)-1-[(3bR,4aR)-3-(4-hydroxypiperidine-1-carbonyl)-3b,4,4a,5-tetrahydro-1H-cyclopropa[3,4]cyclopenta[1,2-c]pyrazol-1-yl]-D-erythro-hexitol | 457.3 |

-continued
| Ex. # | Structure | Chemical Name | Mass [M + H]+ |
|---|---|---|---|
| 80 | 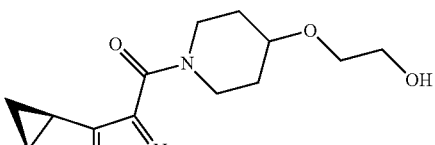 | 2,6-anhydro-1,3,5-trideoxy-4-O-(3-fluoropyridin-2-yl)-1-{(3bR,4aR)-3-[4-(2-hydroxyethoxy)piperidine-1-carbonyl]-3b,4,4a,5-tetrahydro-1H-cyclopropa[3,4]cyclopenta[1,2-c]pyrazol-1-yl}-D-erythro-hexitol | 501.3 |
Example 81: (4-hydroxypiperidin-1-yl)((3bR,4aR)-1-(2-((1s,4S)-4-((3-methylpyridin-2-yl)oxy)cyclohexyl)ethyl)-3b,4,4a,5-tetrahydro-1H-cyclopropa[3,4]cyclopenta[1,2-c]pyrazol-3-yl)methanone
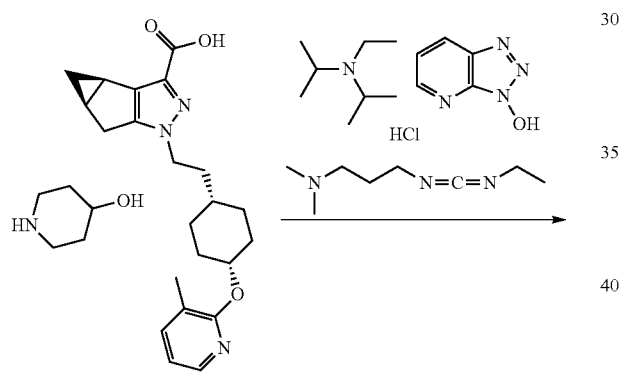
INTERMEDIATE K
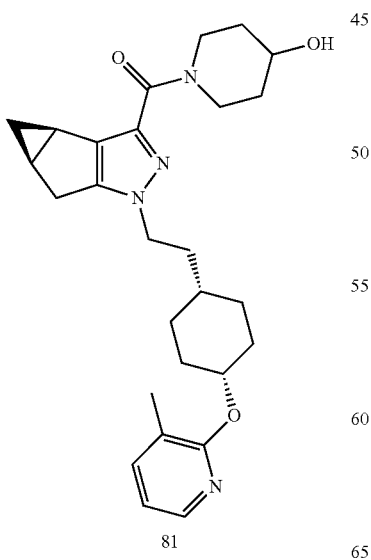
81

To a stirred solution of (3bR,4aR)-1-(2-((1s,4R)-4-((3-methylpyridin-2-yl)oxy)cyclohexyl)ethyl)-3b,4,4a,5-tetrahydro-1H-cyclopropa[3,4]cyclopenta[1,2-c]pyrazole-3-carboxylic acid (40 mg, 0.105 mmol), 1-hydroxy-7-azabenzotriazole (17.13 mg, 0.126 mmol) and EDC (24.12 mg, 0.126 mmol) in DCM (4 ml) and DMF (1.000 ml), were added piperidin-4-ol (10.61 mg, 0.105 mmol) and DIEA (0.037 ml, 0.210 mmol). The mixture was stirred at RT for 2 h. The mixture was purified on reversed phase chromatography with 10 to 100% ACN in water with 0.1% TFA. The title compound was isolated and lyophilized to get a solid. MS: 465.39 (M+1). 1H NMR (500 MHz, Methanol-d4) δ 7.94 (d, J=5.1 Hz, 1H), 7.61 (d, J=7.1 Hz, 1H), 6.91 (dd, J=7.0, 5.4 Hz, 1H), 5.25 (s, 1H), 4.24 (d, J=13.4 Hz, 2H), 4.12-3.82 (m, 4H), 3.61-3.41 (m, 1H), 2.97 (dd, J=16.4, 6.2 Hz, 1H), 2.84 (d, J=16.4 Hz, 1H), 2.25 (s, 3H), 2.14 (d, J=5.9 Hz, 2H), 2.08-1.85 (m, 5H), 1.78 (q, J=6.9 Hz, 2H), 1.71-1.28 (m, 9H), 1.23-1.04 (m, 1H), 0.33-0.14 (m, 1H).

The examples in the following table were prepared in an analogous manner to Example 81 using appropriate starting materials described previously or commercially available.

| Ex. # | Structure | Chemical Name | Mass [M + H]+ |
|---|---|---|---|
| 82 | 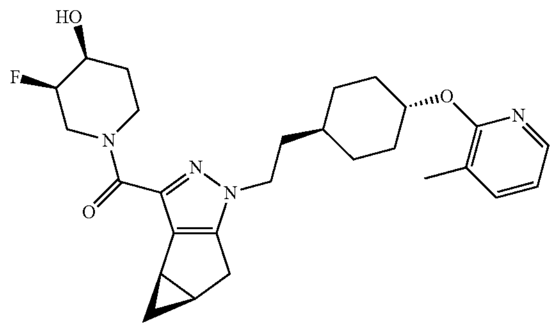 [SMILES: Cc1cccnc1O[C@H]1CC[C@H](CCn2nc(C(=O)N3CC[C@H](O)[C@H](F)C3)c3c2C[C@H]2C[C@@H]32)CC1] | [(3R,4S)-3-fluoro-4-hydroxypiperidin-1-yl][(3bR,4aR)-1-(2-{trans-4-[(3-methylpyridin-2-yl)oxy]cyclohexyl}ethyl)-3b,4,4a,5-tetrahydro-1H-cyclopropa[3,4]cyclopenta[1,2-c]pyrazol-3-yl]methanone | 483.4 |
| 83 | 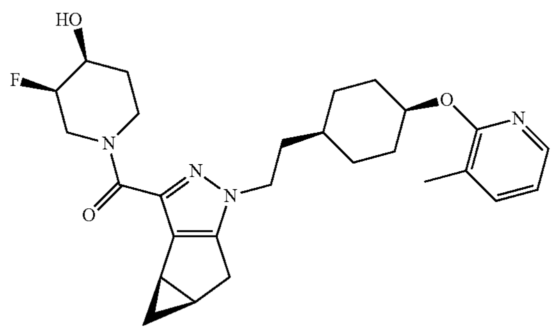 [SMILES: Cc1cccnc1O[C@H]1CC[C@@H](CCn2nc(C(=O)N3CC[C@H](O)[C@H](F)C3)c3c2C[C@H]2C[C@@H]32)CC1] | [(3R,4S)-3-fluoro-4-hydroxypiperidin-1-yl][(3bR,4aR)-1-(2-{cis-4-[(3-methylpyridin-2-yl)oxy]cyclohexyl}ethyl)-3b,4,4a,5-tetrahydro-1H-cyclopropa[3,4]cyclopenta[1,2-c]pyrazol-3-yl]methanone | 483.4 |
| 84 | 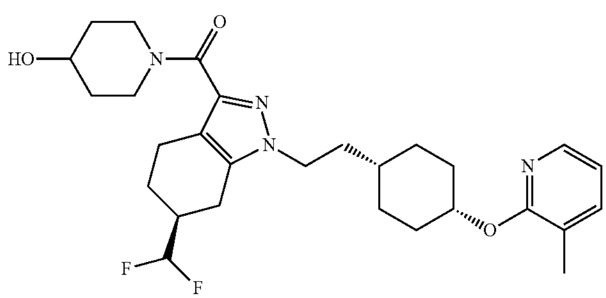 | [(6S)-6-(difluoromethyl)-1-(2-{cis-4-[(3-methylpyridin-2-yl)oxy]cyclohexyl}ethyl)-4,5,6,7-tetrahydro-1H-indazol-3-yl](4-hydroxypiperidin-1-yl)methanone | 517.4 |
| 85 | 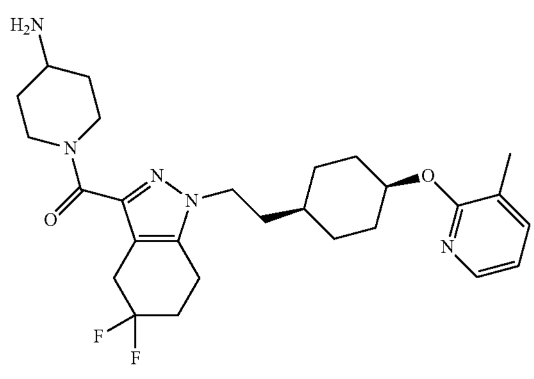 [SMILES: Cc1cccnc1O[C@H]1CC[C@@H](CCn2nc(C(=O)N3CCC(N)CC3)c3c2CCC(F)(F)C3)CC1] | (4-aminopiperidin-1-yl)[5,5-difluoro-1-(2-{cis-4-[(3-methylpyridin-2-yl)oxy]cyclohexyl}ethyl)-4,5,6,7-tetrahydro-1H-indazol-3-yl]methanone | 502.4 |

| Ex. # | Structure | Chemical Name | Mass [M + H]+ |
|---|---|---|---|
| 86 | 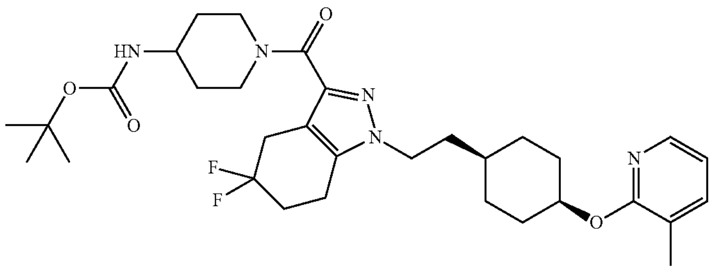 [SMILES: Cc1cccnc1O[C@H]1CC[C@@H](CCn2nc(C(=O)N3CCC(NC(=O)OC(C)(C)C)CC3)c3c2CCC(F)(F)C3)CC1] | tert-butyl {1-[5,5-difluoro-1-(2-{cis-4-[(3-methylpyridin-2-yl)oxy]cyclohexyl}ethyl)-4,5,6,7-tetrahydro-1H-indazole-3-carbonyl]piperidin-4-yl}carbamate | 602.4 |
| 87 | 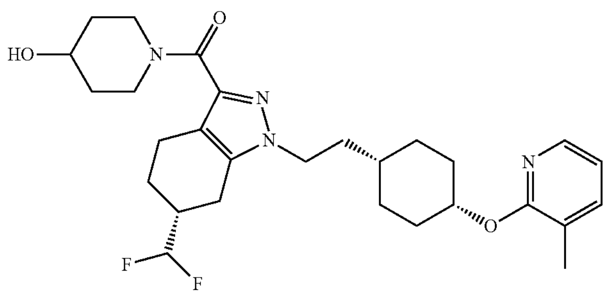 [SMILES: Cc1cccnc1O[C@H]1CC[C@@H](CCn2nc(C(=O)N3CCC(O)CC3)c3c2C[C@H](C(F)F)CC3)CC1] | [(6R)-6-(difluoromethyl)-1-(2-{cis-4-[(3-methylpyridin-2-yl)oxy]cyclohexyl}ethyl)-4,5,6,7-tetrahydro-1H-indazol-3-yl](4-hydroxypiperidin-1-yl)methanone | 517.4 |
| 88 | 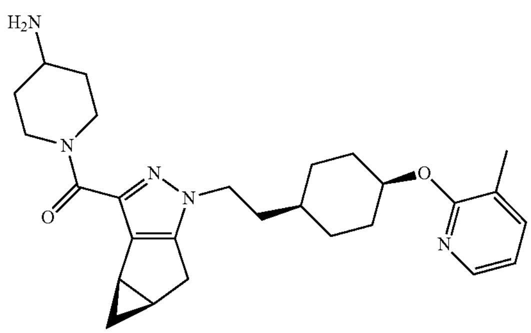 [SMILES: Cc1cccnc1O[C@H]1CC[C@@H](CCn2nc(C(=O)N3CCC(N)CC3)c3c2C[C@H]2C[C@@H]32)CC1] | (4-aminopiperidin-1-yl)[(3bR,4aR)-1-(2-{cis-4-[(3-methylpyridin-2-yl)oxy]cyclohexyl}ethyl)-3b,4,4a,5-tetrahydro-1H-cyclopropa[3,4]cyclopenta[1,2-c]pyrazol-3-yl]methanone | 464.4 |
| 89 | 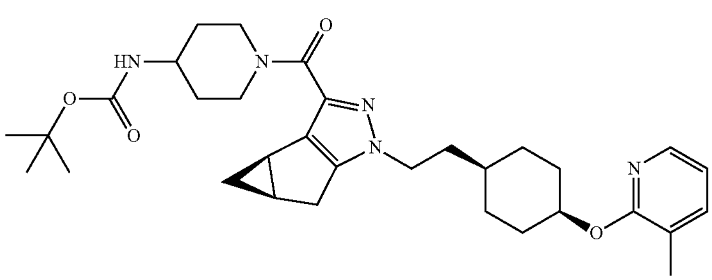 [SMILES: Cc1cccnc1O[C@H]1CC[C@@H](CCn2nc(C(=O)N3CCC(NC(=O)OC(C)(C)C)CC3)c3c2C[C@H]2C[C@@H]32)CC1] | tert-butyl {1-[(3bR,4aR)-1-(2-{cis-4-[(3-methylpyridin-2-yl)oxy]cyclohexyl}ethyl)-3b,4,4a,5-tetrahydro-1H-cyclopropa[3,4]cyclopenta[1,2-c]pyrazole-3-carbonyl]piperidin-4-yl}carbamate | 564.4 |

| Ex. # | Structure | Chemical Name | Mass [M + H]+ |
|---|---|---|---|
| 90 | 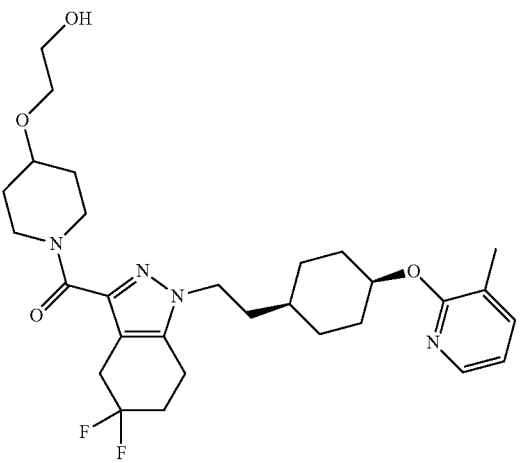 [SMILES: Cc1cccnc1O[C@H]1CC[C@@H](CCn2nc(C(=O)N3CCC(OCCO)CC3)c3c2CCC(F)(F)C3)CC1] | [5,5-difluoro-1-(2-{cis-4-[(3-methylpyridin-2-yl)oxy]cyclohexyl}ethyl)-4,5,6,7-tetrahydro-1H-indazol-3-yl][4-(2-hydroxyethoxy)piperidin-1-yl]methanone | 547.3 |
| 91 | 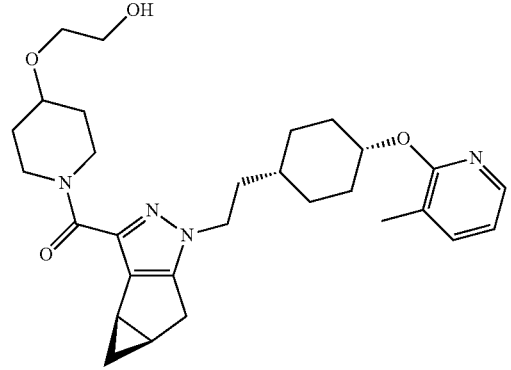 [SMILES: Cc1cccnc1O[C@H]1CC[C@@H](CCn2nc(C(=O)N3CCC(OCCO)CC3)c3c2C[C@H]2C[C@@H]32)CC1] | [4-(2-hydroxyethoxy)piperidin-1-yl][(3bR,4aR)-1-(2-{cis-4-[(3-methylpyridin-2-yl)oxy]cyclohexyl}ethyl)-3b,4,4a,5-tetrahydro-1H-cyclopropa[3,4]cyclopenta[1,2-c]pyrazol-3-yl]methanone | 509.4 |
| 92 | 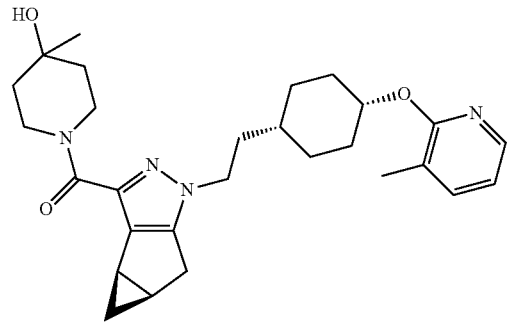 [SMILES: Cc1cccnc1O[C@H]1CC[C@@H](CCn2nc(C(=O)N3CCC(C)(O)CC3)c3c2C[C@H]2C[C@@H]32)CC1] | (4-hydroxy-4-methylpiperidin-1-yl)[(3bR,4aR)-1-(2-{cis-4-[(3-methylpyridin-2-yl)oxy]cyclohexyl}ethyl)-3b,4,4a,5-tetrahydro-1H-cyclopropa[3,4]cyclopenta[1,2-c]pyrazol-3-yl]methanone | 479.4 |
| 93 | 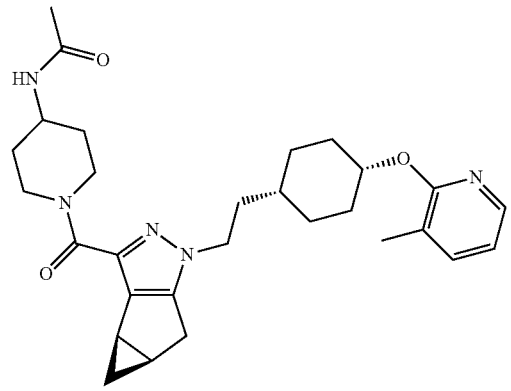 [SMILES: CC(=O)NC1CCN(C(=O)c2nn(CC[C@H]3CC[C@@H](Oc4ncccc4C)CC3)c3c2[C@@H]2C[C@@H]2C3)CC1] | N-{1-[(3bR,4aR)-1-(2-{cis-4-[(3-methylpyridin-2-yl)oxy]cyclohexyl}ethyl)-3b,4,4a,5-tetrahydro-1H-cyclopropa[3,4]cyclopenta[1,2-c]pyrazole-3-carbonyl]piperidin-4-yl}acetamide | 506.4 |

-continued
| Ex. # | Structure | Chemical Name | Mass [M + H]+ |
|---|---|---|---|
| 94 | 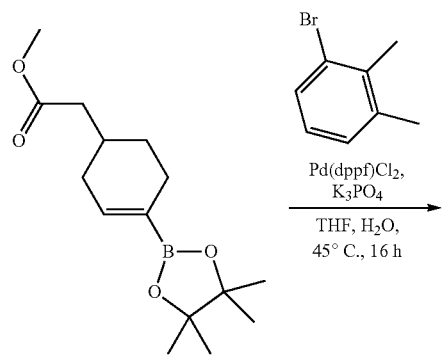 | 2-hydroxy-1-(4-((3bR,4aR)-1-(2-((1s,4S)-4-((3-methylpyridin-2-yl)oxy)cyclohexyl)ethyl)-3b,4,4a,5-tetrahydro-1H-cyclopropa[3,4]cyclopenta[1,2-c]pyrazole-3-carbonyl)piperazin-1-yl)ethan-1-one | 508.4 |
Example 95: (1-(2-(4-(2,3-dimethylphenyl)cyclohexyl)ethyl)-1,4,5,6-tetrahydrocyclopenta[c]pyrazol-3-yl)(4-hydroxypiperidin-1-yl)methanone (chiral. cis or trans)
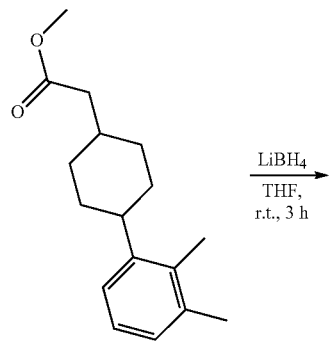
-continued
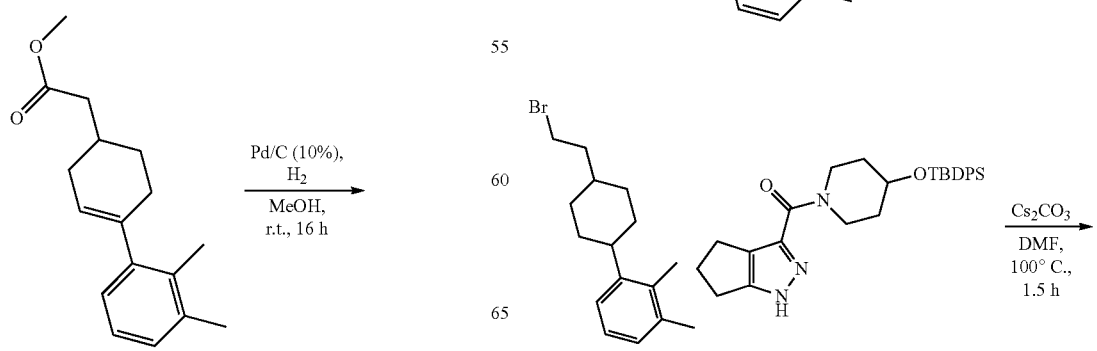

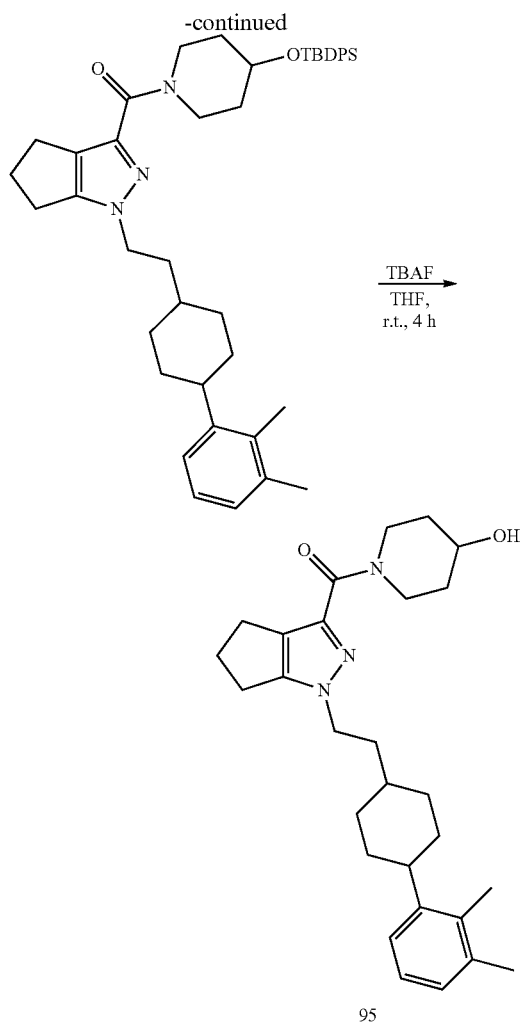

95

Step 1: methyl 2-(2',3'-dimethyl-2,3,4,5-tetrahydro-[1,1'-biphenyl]-4-yl)acetate To a stirred mixture of methyl 2-(4-(4,4,5,5-tetramethyl-1,3,2-dioxaborolan-2-yl)cyclohex-3-en-1-yl)acetate (300 mg, 1.071 mmol) in THF (10 mL) were added 1-bromo-2,3-dimethylbenzene (218 mg, 1.178 mmol), Pd(dppf)Cl$_2$ (70 mg, 0.107 mmol), K$_3$PO$_4$ (455 mg, 2.142 mmol) and water (1 mL) under nitrogen. After the addition was finished, the reaction was stirred at 45° C. The reaction was monitored by TLC (petroleum ether/EtOAc=2/1), after stirring at 45° C. for 16 h, the reaction was finished. Then the solvent was removed in vacuo. The residue was purified by column chromatography on silica gel (eluting with petroleum ether/EtOAc=10/0 to 8/2) to give methyl 2-(2',3'-dimethyl-2,3,4,5-tetrahydro-[1,1'-biphenyl]-4-yl)acetate as an oil.

Step 2: methyl 2-(4-(2,3-dimethylphenyl)cyclohexyl)acetate

To a stirred solution of methyl 2-(2',3'-dimethyl-2,3,4,5-tetrahydro-[1,1'-biphenyl]-4-yl)acetate (600 mg, 2.322 mmol) in MeOH (20 mL) was added 10% Pd—C (300 mg, 0.282 mmol) at RT. After the addition was finished, the reaction was stirred at RT under nitrogen. The reaction was monitored by $^1$H NMR, after stirring at RT for 16 h, the reaction was finished. The catalyst was removed by filtration and the filtrate was concentrated in vacuo to give the crude product methyl 2-(4-(2,3-dimethylphenyl)cyclohexyl)acetate as an oil which was used in the next step without further purification.

Step 3: 2-(4-(2,3-dimethylphenyl)cyclohexyl)ethan-1-ol

To a stirred mixture of methyl 2-(4-(2,3-dimethylphenyl)cyclohexyl)acetate (440 mg, 1.690 mmol) in THF (5 mL) was added LiBH$_4$ (74 mg, 3.38 mmol) at 0° C. After the addition was finished, the reaction was slowly warmed to RT. The reaction was monitored by TLC (petroleum ether/EtOAc=10/1). After stirring at RT for 3 h, the reaction was finished. The reaction was quenched with water (10 mL), then extracted with EtOAc (10 mL×3). The combined organic layers were dried over anhydrous Na$_2$SO$_4$, filtered and concentrated in vacuo. The residue was purified by column chromatography on silica gel (SiO$_2$, 12 g) (eluting with petroleum ether/EtOAc=10/0 to 7/3) to afford the title compound as an oil.

Step 4: 1-(4-(2-bromoethyl)cyclohexyl)-2,3-dimethylbenzene

To a stirred mixture of 2-(4-(2,3-dimethylphenyl)cyclohexyl)ethanol (300 mg, 1.291 mmol) and CBr$_4$ (642 mg, 1.937 mmol) in CH$_2$Cl$_2$ (5 mL) was added PPh$_3$ (508 mg, 1.937 mmol) at RT. After the addition was finished, the reaction was stirred at 20° C. The reaction was monitored by TLC (petroleum ether). After stirring at RT for 0.5 h, the reaction was finished. Then the solvent was removed in vacuo and the residue was purified by column chromatography on silica gel (12 g, petroleum ether/EtOAc=10/0 to 7/3) to afford the title compound as an oil.

Step 5: (4-((tert-butyldiphenylsilyl)oxy)piperidin-1-yl)(1-(2-(4-(2,3-dimethylphenyl)cyclohexyl)ethyl)-1,4,5,6-tetrahydrocyclopenta[c]pyrazol-3-yl)methanone To a stirred mixture of (4-((tert-butyldiphenylsilyl)oxy)piperidin-1-yl)(1,4,5,6-tetrahydrocyclopenta[c]pyrazol-3-yl)methanone (110 mg, 0.232 mmol) and 1-(4-(2-bromoethyl)cyclohexyl)-2,3-dimethylbenzene (72 mg, 0.244 mmol) in DMF (4 mL) was added Cs$_2$CO$_3$ (113 mg, 0.348 mmol) at RT. After the addition was finished, the reaction was stirred at 100° C. The reaction was monitored by LCMS. After stirring at 100° C. for 1.5 h, the reaction was finished. After cooled to RT, the salt was removed by filtration, and the filtrate was concentrated in vacuo. The residue was purified by reverse phase HPLC on a GILSON 281 instrument fitted with a Phenomenex Synergi C18 (150×30 mm×4 μm) using water (0.225% formic acid) and ACN as eluents (mobile phase A water (0.225% formic acid), Mobile phase B ACN, Detective wavelength: 220 nm) to give two isomers, (4-((tert-butyldiphenylsilyl)oxy)piperidin-1-yl)(1-(2-(4-(2,3-dimethylphenyl)cyclohexyl)ethyl)-1,4,5,6-tetrahydrocyclopenta[c]pyrazol-3-yl)methanone as an oil and (4-((tert-butyldiphenylsilyl)oxy)piperidin-1-yl)(1-(2-(4-(2,3-dimethylphenyl)cyclohexyl)ethyl)-1,4,5,6-tetrahydrocyclopenta[c]pyrazol-3-yl)methanone as an oil. MS (ESI) m/z: 688.4 [M+H$^+$].

Step 6: (1-(2-(4-(2,3-dimethylphenyl)cyclohexyl)ethyl)-1,4,5,6-tetrahydrocyclopenta[c]pyrazol-3-yl)(4-hydroxypiperidin-1-yl)methanone To a stirred mixture of (4-((tert-butyldiphenylsilyl)oxy)piperidin-1-yl)(1-(2-(4-(2,3-dimethylphenyl)cyclohexyl)

ethyl)-1,4,5,6-tetrahydrocyclopenta[c]pyrazol-3-yl)methanone (70 mg, 0.102 mmol) in THF (5 mL) was added 1 M TBAF (0.15 mL, 0.150 mmol) RT. After the addition was finished, the reaction was stirred at RT. The reaction was monitored by LCMS, after stirring at RT for 4 h, the reaction was finished. The reaction was concentrated in vacuo. The residue was purified by reverse phase HPLC on a GILSON 281 instrument fitted with an Agela ASB C18 (150×25 mm×5 μm) using water (0.1% TFA) and ACN as eluents (Mobile phase A water (0.1% TFA), Mobile phase B ACN, Detective wavelength: 220 nm) to afford the title compound as a solid. $^1$H NMR (400 MHz, CDCl3) δ 7.12-7.06 (m, 2H), 7.05-6.99 (m, 1H), 4.46 (br s, 1H), 4.26 (br s, 1H), 4.05 (t, 2H), 4.01-3.91 (m, 1H), 3.54 (br s, 1H), 3.28 (br s, 1H), 2.85-2.68 (m, 5H), 2.64-2.53 (m, 2H), 2.30 (s, 3H), 2.23 (s, 3H), 2.06-1.88 (m, 4H), 1.83-1.66 (m, 5H), 1.65-1.61 (m, 4H), 1.60-1.57 (m, 2H); MS (ESI) m/z: 450.1 [M+H$^+$];
Example 96: (1-(2-(4-(2,3-dimethylphenyl)cyclohexyl)ethyl)-1,4,5,6-tetrahydrocyclopenta[c]pyrazol-3-yl)(4-hydroxypiperidin-1-yl)methanone (chiral, cis or trans)

Example 96 was prepared using the same de-TBDPS method from the other isomer. $^1$H NMR (400 MHz, CDCl3) δ 7.12-7.05 (m, 2H), 7.05-6.99 (m, 1H), 4.45-4.19 (m, 2H), 4.06 (br t, J=7.2 Hz, 1H), 4.11-4.03 (m, 1H), 3.99 (td, J=4.2, 7.9 Hz, 1H), 3.65-3.49 (m, 1H), 3.35 (br s, 1H), 2.85-2.69 (m, 5H), 2.59 (q, J=6.9 Hz, 2H), 2.30 (s, 3H), 2.22 (s, 3H), 2.06-1.91 (m, 4H), 1.83-1.66 (m, 5H), 1.66-1.52 (m, 6H); MS (ESI) m/z: 450.1 [M+H$^+$];

Example 97: ((3bR,4aR)-1-(2-(1-(3-chloro-2-methylphenyl)-4-hydroxypiperidin-4-yl)ethyl)-3b,4,4a,5-tetrahydro-1H-cyclopropa[3,4]cyclopenta[1,2-c]pyrazol-3-yl)((3R,4S)-3-fluoro-4-hydroxypiperidin-1-yl)methanone

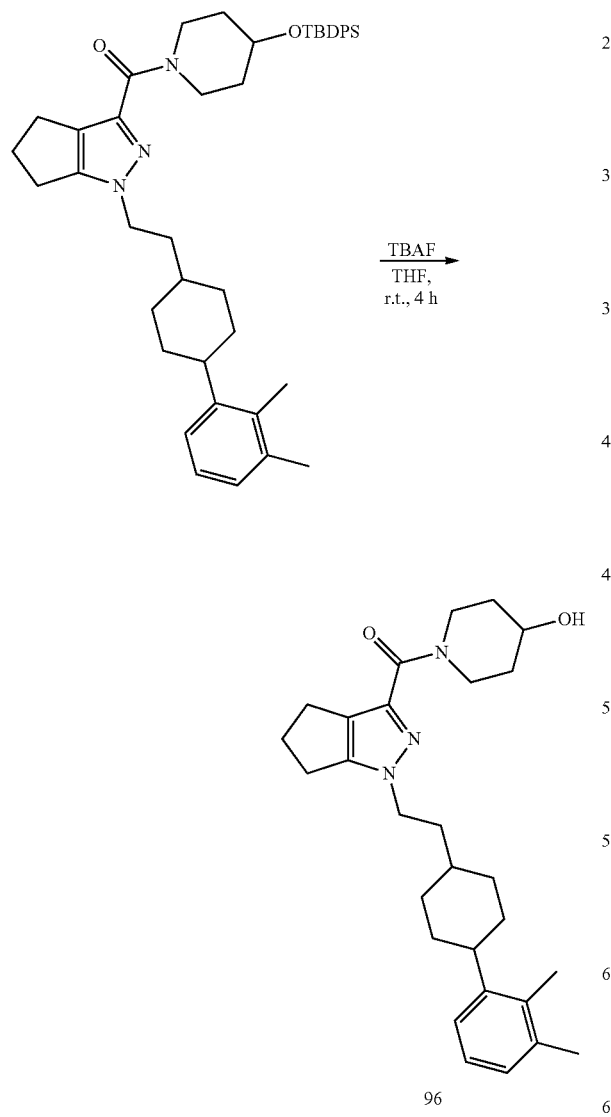
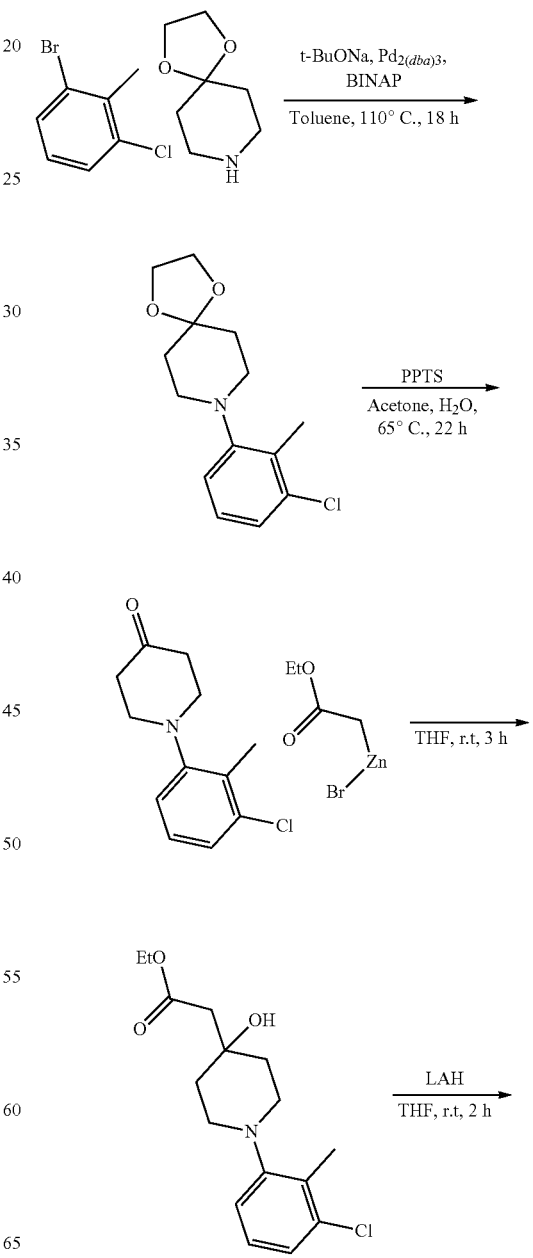

-continued

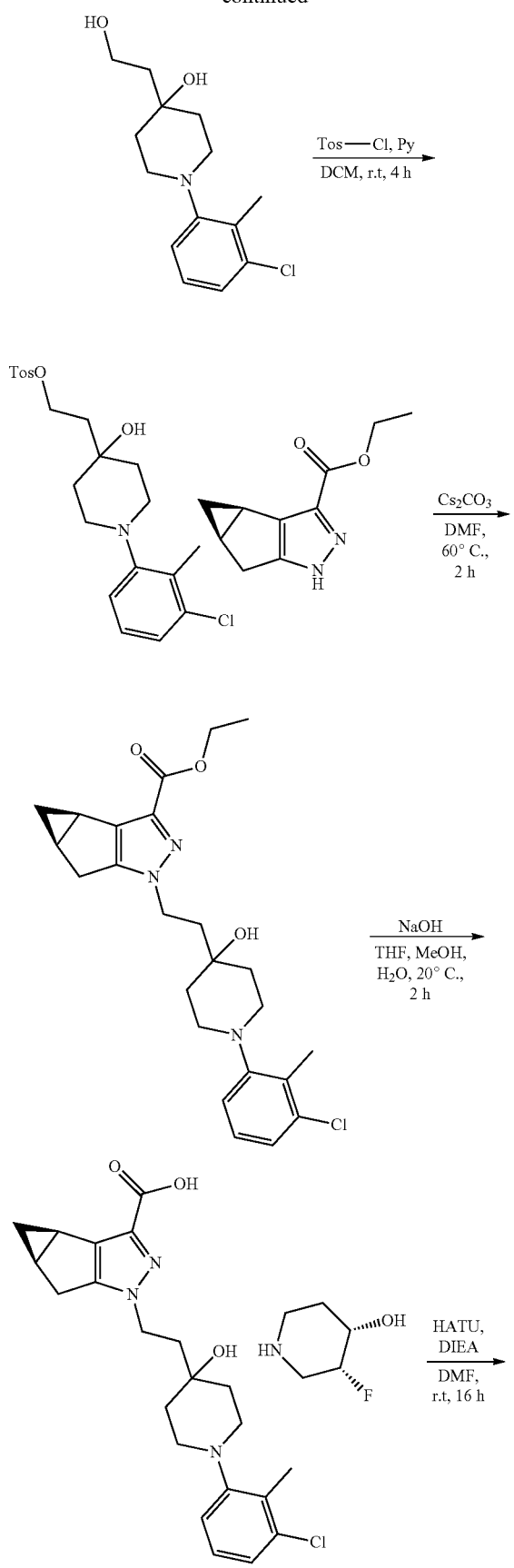

-continued

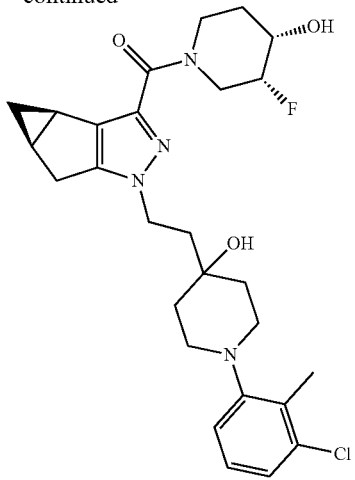

97

Step 1: 8-(3-chloro-2-methylphenyl)-1,4-dioxa-8-azaspiro[4.5]decane

To a solution of 1-bromo-3-chloro-2-methylbenzene (2 g, 9.73 mmol) in toluene (30 mL) were added 1,4-dioxa-8-azaspiro[4.5]decane (1.672 g, 11.68 mmol), t-BuONa (1.871 g, 19.47 mmol), BINAP (0.606 g, 0.973 mmol) and $Pd_2(dba)_3$ (0.446 g, 0.487 mmol) at RT. After the addition was finished, the reaction was stirred at 110° C. under nitrogen. The reaction was monitored by LCMS, after stirring at 110° C. for 16 h, the reaction was finished. After removing the solvent, the reaction was diluted with water (200 mL), the mixture was extracted by EtOAc (100 mL×2), the organic layers were collected, washed with brine (ca. 30 mL), dried over $Na_2SO_4$, and after filtration, the filtrate was concentrated in vacuo. The residue was purified by flash silica gel chromatography (Bio®; Agela© Flash Column Silica-CS (12 g), Eluent of 0~6% EtOAc/petroleum ether gradient @ 30 mL/min) to afford the title compound as a solid. MS (ESI) m/z: 268.1 [M+H⁺].

Step 2: 1-(3-chloro-2-methylphenyl)piperidin-4-one

To a solution of 8-(3-chloro-2-methylphenyl)-1,4-dioxa-8-azaspiro[4.5]decane (1.6 g, 5.98 mmol) in acetone (15 mL) and water (15 mL) was added PPTS (3.00 g, 11.95 mmol) at RT. After the addition was finished, the mixture was stirred at 65° C. The reaction was monitored by LCMS, after stirring at 65° C. for 22 h, the reaction was finished. The reaction was cooled to RT and diluted with water (200 mL), extracted with EtOAc (50 mL×2), the organic was collected and washed with brine, dried over anhydrous $Na_2SO_4$, then concentrated under reduced pressure. The residue was purified by silica column chromatography (petroleum ether:EtOAc=10:1 to 5:1) to give the title compound as an oil. MS (ESI) m/z: 224.1 [M+H⁺].

Step 3: ethyl 2-(1-(3-chloro-2-methylphenyl)-4-hydroxypiperidin-4-yl)acetate

To a solution of 1-(3-chloro-2-methylphenyl)piperidin-4-one (900 mg, 4.02 mmol) in THF (10 mL) were added (2-ethoxy-2-oxoethyl)zinc(II) bromide (10.06 mL, 10.06 mmol) (1 M in THF) at RT. After the addition was finished, the mixture was stirred at the same temperature. The reaction was monitored by TLC (petroleum ether:EtOAc=5:1), after stirring at RT for 3 h, the reaction was finished. The reaction was diluted with water (200 mL), extracted with EtOAc (50 mL×2), the organic was collected and washed with brine, dried over anhydrous $Na_2SO_4$, then concentrated under reduced pressure. The residue was purified by flash silica gel chromatography (ISCO©; Agela© Flash Column Silica-CS (4 g), Eluent of 0~6% EtOAc/petroleum ether gradient @ 30 mL/min) to give the title compound as an oil. MS (ESI) m/z: 312.1 [M+H$^+$].

Step 4: 1-(3-chloro-2-methylphenyl)-4-(2-hydroxyethyl)piperidin-4-ol

To a solution of ethyl 2-(1-(3-chloro-2-methylphenyl)-4-hydroxypiperidin-4-yl)acetate (600 mg, 1.924 mmol) in THF (1 mL) was added $LiAlH_4$ (146 mg, 3.85 mmol) at 0° C. After the addition was finished, the reaction mixture was stirred at RT. The reaction was monitored by LC-MS, after stirring at RT for 2 h, the reaction was finished. After cooled to 0° C., sodium sulfate decahydrate (1488 mg, 4.62 mmol) was added into the mixture, and after filtration, the filtrate was concentrated in vacuo to afford the title compound as a solid which was used directly in next step without further purification. MS (ESI) m/z: 270.1 [M+H$^+$]

Step 5: 2-(1-(3-chloro-2-methylphenyl)-4-hydroxypiperidin-4-yl)ethyl 4-methylbenzenesulfonate To a stirred solution of 1-(3-chloro-2-methylphenyl)-4-(2-hydroxyethyl)piperidin-4-ol (469 mg, 1.739 mmol) in DCM (5 mL) were added pyridine (187 mg, 2.364 mmol) and 4-methylbenzene-1-sulfonyl chloride (902 mg, 4.73 mmol) at 0° C. After the addition was finished, the reaction was stirred at RT. The reaction was monitored by LC-MS, after stirred at RT for 3 h, the reaction was finished. The reaction was diluted with water (20 mL), the mixture was extracted by EtOAc (10 mL×2), the organic layers were collected, washed with brine (ca. 10 mL), dried over $Na_2SO_4$, and after filtration, the filtrate was concentrated in vacuo. The residue was purified by reversed phase HPLC on a GILSON 281 instrument fitted with a Phenomenex Synergi C18 150*30 mm*4 um using water (0.1% TFA)-ACN as eluents, followed by lyophilization to give to afford the title compound as an oil. MS (ESI) m/z: 424.2 [M+H$^+$]

Step 6: ethyl (3bR,4aR)-1-(2-(1-(3-chloro-2-methylphenyl)-4-hydroxypiperidin-4-yl)ethyl)-3b,4,4a,5-tetrahydro-1H-cyclopropa[3,4]cyclopenta[1,2-c]pyrazole-3-carboxylate To a stirred solution of 2-(1-(3-chloro-2-methylphenyl)-4-hydroxypiperidin-4-yl)ethyl 4-methylbenzenesulfonate (100 mg, 0.236 mmol) in DMF (3 mL) were added cesium carbonate (154 mg, 0.472 mmol) and (3bR,4aR)-ethyl 3b,4,4a,5-tetrahydro-1H-cyclopropa[3,4]cyclopenta[1,2-c]pyrazole-3-carboxylate (50 mg, 0.260 mmol) at 0° C. After the addition was finished, the reaction was stirred at 60° C. The reaction was monitored by LCMS, after stirring at 60° C. for 2 h, the reaction was finished. The reaction was diluted with water (50 mL), the mixture was extracted by EtOAc (30 mL×2), the organic layers were collected, washed with brine (ca. 10 mL), dried over $Na_2SO_4$, and after filtration, the filtrate was concentrated in vacuo. The residue was purified by reversed phase HPLC on a GILSON 281 instrument fitted with a Phenomenex Synergy C18 150×30 mm×4 um using water (0.1% TFA)-ACN as eluents, followed by lyophilization to afford the title compound as a solid. MS (ESI) m/z: 444.3 [M+H$^+$]

Step 7: (3bR,4aR)-1-(2-(1-(3-chloro-2-methylphenyl)-4-hydroxypiperidin-4-yl)ethyl)-3b,4,4a,5-tetrahydro-1H-cyclopropa[3,4]cyclopenta[1,2-c]pyrazole-3-carboxylic acid To a solution of (3bR,4aR)-ethyl 1-(2-(1-(3-chloro-2-methylphenyl)-4-hydroxypiperidin-4-yl)ethyl)-3b,4,4a,5-tetrahydro-1H-cyclopropa[3,4]cyclopenta[1,2-c]pyrazole-3-carboxylate (50 mg, 0.113 mmol) in THF (4 mL), water (2 mL) and MeOH (1 mL) was added sodium hydroxide (0.2 mL, 0.400 mmol) (2 M in water) at RT. After the addition was finished, the reaction was stirred at the RT. The reaction was monitored by LC-MS, after stirred at RT for 4 h, the reaction was finished. The mixture was acidified to pH~5 by using 1 M HCl, then diluted with water (10 mL), and extracted with EtOAc (10 mL×2). The organic layers were collected, washed with brine (ca. 10 mL), dried over $Na_2SO_4$, and after filtration, the filtrate was concentrated in vacuo to afford the title compound as a solid, which was used directly in next step without further purification. MS (ESI) m/z: 416.3 [M+H$^+$]

Step 8: ((3bR,4aR)-1-(2-(1-(3-chloro-2-methylphenyl)-4-hydroxypiperidin-4-yl)ethyl)-3b,4,4a,5-tetrahydro-1H-cyclopropa[3,4]cyclopenta[1,2-c]pyrazol-3-yl)((3R,4S)-3-fluoro-4-hydroxypiperidin-1-yl)methanone To a stirred solution of (3bR,4aR)-1-(2-(1-(3-chloro-2-methylphenyl)-4-hydroxypiperidin-4-yl)ethyl)-3b,4,4a,5-tetrahydro-1H-cyclopropa[3,4]cyclopenta[1,2-c]pyrazole-3-carboxylic acid (20 mg, 0.048 mmol) in DMF (1 mL) were added HATU (40 mg, 0.105 mmol), DIEA (0.05 mL, 0.286 mmol) and followed by (3R,4S)-3-fluoropiperidin-4-ol (10 mg, 0.084 mmol) at RT. After the addition was complete, the mixture was stirred at RT. The reaction was monitored by LCMS, after stirred at RT for 16 h, the reaction was finished to afford a solution. The residue was purified by reversed phase HPLC on a GILSON 281 instrument fitted with a Phenomenex Synergi C18 150×30 mm×4 um using water (0.1% TFA)-ACN as eluents, followed by lyophilization to afford the title compound as a solid. $^1$H NMR (400 MHz, $CD_3OD$) δ 7.1-7.2 (m, 3H), 4.7 (br s, 1H), 4.3 (br d, J=13.6 Hz, 1H), 4.1-4.2 (m, 2H), 3.9 (br s, 1H), 3.7-3.7 (m, 1H), 3.2-3.2 (m, 1H), 3.0-3.1 (m, 2H), 2.8-3.0 (m, 4H), 2.3 (s, 3H), 2.1 (br s, 2H), 2.0 (br t, J=7.2 Hz, 2H), 1.8-1.9 (m, 5H), 1.7 (br s, 2H), 1.5 (br s, 1H), 1.1 (br s, 1H), 0.2 (br s, 1H); MS (ESI) m/z: 517.4 [M+H$^+$]

Example 98: ((3bR,4aR)-1-(2-(1-(3-chloro-2-methylphenyl)-4-hydroxypiperidin-4-yl)ethyl)-3b,4,4a,5-tetrahydro-1H-cyclopropa[3,4]cyclopenta[1,2-c]pyrazol-3-yl)((3S,4R)-3-fluoro-4-hydroxypiperidin-1-yl)methanone

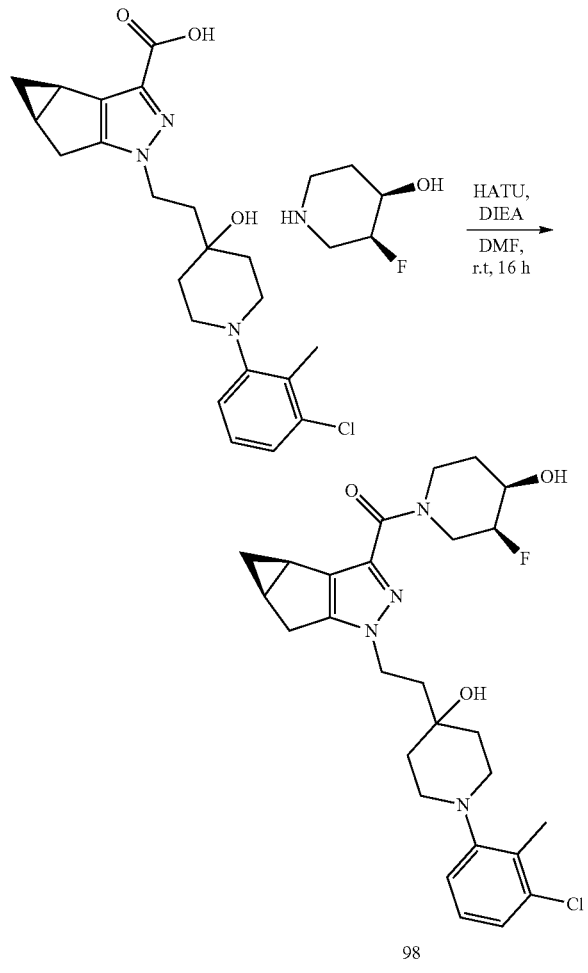 [SMILES: Cc1c(Cl)cccc1N1CCC(O)(CCn2nc(C(=O)O)c3c2C[C@H]2C[C@@H]32)CC1 ; O[C@@H]1CCNC[C@@H]1F ; Cc1c(Cl)cccc1N1CCC(O)(CCn2nc(C(=O)N3CC[C@@H](O)[C@@H](F)C3)c3c2C[C@H]2C[C@@H]32)CC1]

Example 99: ((3bR,4aR)-1-(2-(4-(2,3-dimethylphenyl)piperazin-1-yl)ethyl)-3b,4,4a,5-tetrahydro-1H-cyclopropa[3,4]cyclopenta[1,2-c]pyrazol-3-yl)(4-hydroxypiperidin-1-yl)methanone

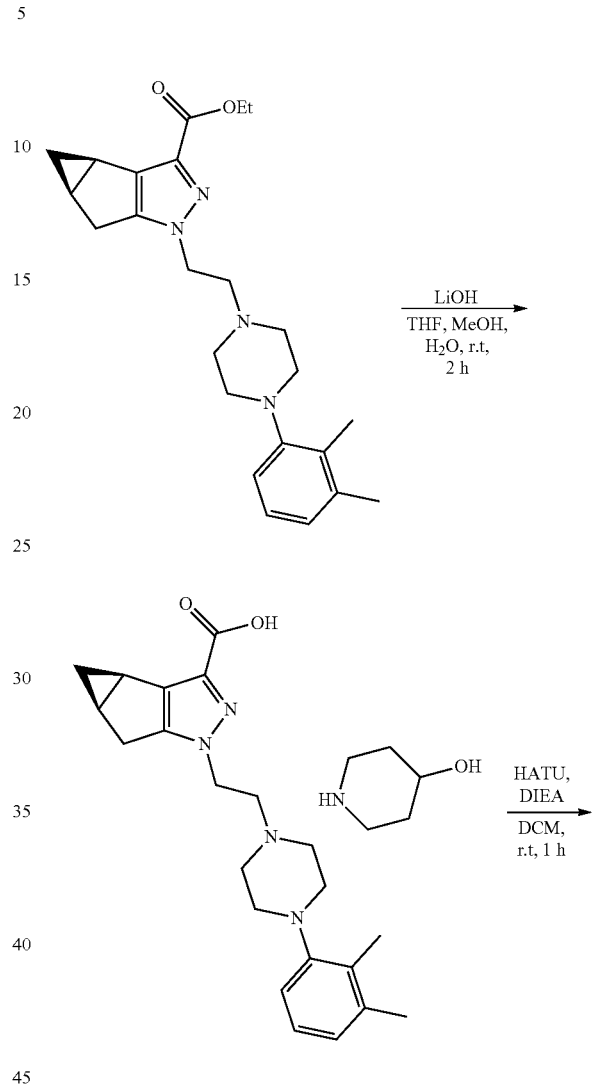

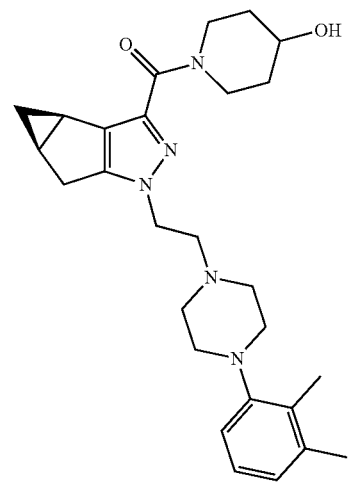

To a stirred solution of (3bR,4aR)-1-(2-(1-(3-chloro-2-methylphenyl)-4-hydroxypiperidin-4-yl)ethyl)-3b,4,4a,5-tetrahydro-1H-cyclopropa[3,4]cyclopenta[1,2-c]pyrazole-3-carboxylic acid (20 mg, 0.048 mmol) in DMF (1 mL) were added HATU (40 mg, 0.105 mmol), DIEA (0.05 mL, 0.286 mmol) and followed by (3S,4R)-3-fluoropiperidin-4-ol (10 mg, 0.084 mmol) at RT. After the addition was complete, the mixture was stirred at RT. The reaction was monitored by LCMS, after stirred at RT for 16 h, the reaction was finished to afford a solution. The residue was purified by reversed phase HPLC on a GILSON 281 instrument fitted with a Phenomenex Synergi C18 150×30 mm×4 um using water (0.1% TFA)-ACN as eluents, followed by lyophilization to afford the title compound as a solid. $^1$H NMR (400 MHz, CD$_3$OD) δ 7.2 (s, 3H), 4.6 (br s, 1H), 4.3 (br d, J=11.8 Hz, 1H), 4.2 (br t, J=7.5 Hz, 2H), 3.9 (br s, 1H), 3.5 (br d, J=14.9 Hz, 1H), 3.1-3.2 (m, 3H), 2.9-3.0 (m, 3H), 2.9 (d, J=16.7 Hz, 1H), 2.4 (s, 3H), 2.1 (br d, J=6.6 Hz, 2H), 2.0-2.1 (m, 2H), 1.8-2.0 (m, 4H), 1.7-1.8 (m, 2H), 1.3 (t, J=7.5 Hz, 1H), 1.1-1.2 (m, 1H), 0.3 (q, J=4.2 Hz, 1H); MS (ESI) m/z: 517.4 [M+H$^+$]

Step 1: (3bR,4aR)-1-(2-(4-(2,3-dimethylphenyl)piperazin-1-yl)ethyl)-3b,4,4a,5-tetrahydro-1H-cyclopropa[3,4]cyclopenta[1,2-c]pyrazole-3-carboxylic acid To a stirred solution of (3bR,4aR)-ethyl 1-(2-(4-(2,3-dimethylphenyl)piperazin-1-yl)ethyl)-3b,4,4a,5-tetrahydro-1H-cyclopropa[3,4]cyclopenta[1,2-c]pyrazole-3-carboxylate (25 mg, 0.061 mmol) in THF (2 mL) and water (1 mL) were added LiOH (5 mg, 0.209 mmol) and MeOH (0.3 mL). After the addition was complete, the mixture was stirred at RT. The reaction was monitored by TLC (petroleum ether/EtOAc=1:1), after stirring at RT for 2 h, the reaction was finished. The reaction was diluted with water (10 mL), acidified with 1N HCl to pH=6 and extracted by EtOAc (15 mL×4). The organic layers were collected, washed with brine (10 mL), dried over Na$_2$SO$_4$, and after filtration, the filtrate was concentrated in vacuo to afford the title compound as a gum which was used in the next step directly without further purification. MS (ESI) m/z: 381.2[M+H$^+$].

Step 2: ((3bR,4aR)-1-(2-(4-(2,3-dimethylphenyl)piperazin-1-yl)ethyl)-3b,4,4a,5-tetrahydro-1H-cyclopropa[3,4]cyclopenta[1,2-c]pyrazol-3-yl)(4-hydroxypiperidin-1-yl)methanone To a stirred solution of (3bR,4aR)-1-(2-(4-(2,3-dimethylphenyl)piperazin-1-yl)ethyl)-3b,4,4a,5-tetrahydro-1H-cyclopropa[3,4]cyclopenta[1,2-c]pyrazole-3-carboxylic acid (10 mg, 0.026 mmol) in DCM (3 mL) were added HATU (15 mg, 0.039 mmol), DIEA (0.02 mL, 0.115 mmol) and followed by piperidin-4-ol (3 mg, 0.030 mmol) at RT. After the addition was complete, the mixture was stirred at RT. The reaction was monitored by LCMS, after stirred at RT for 1 h. The reaction was finished to afford a solution. After concentrated in vacuo, the residue was purified by reversed phase HPLC on a GILSON 281 instrument fitted with Phenomenex Synergi C18 150×30 mm×4 um using water (0.1% TFA)-ACN as eluents (Mobile phase A water (0.1% TFA), Mobile phase B ACN, Detective wavelength 220 nm) and lyophilized to afford the title compound as a gum. $^1$HNMR (400 MHz, CD$_3$OD) δ 7.05-7.11 (m, 1H), 6.97 (br d, J=8.4 Hz, 2H), 4.45-4.51 (m, 2H), 4.05-4.30 (m, 2H), 3.78-3.99 (m, 2H), 3.73 (br t, J=5.2 Hz, 3H), 3.34-3.61 (m, 4H), 3.08-3.28 (m, 4H), 3.03 (dd, J=16.6, 6.6 Hz, 1H), 2.86-2.94 (m, 1H), 2.27 (d, J=4.8 Hz, 6H), 2.09-2.24 (m, 2H), 1.94 (br s, 2H), 1.56 (br s, 2H), 1.18 (td, J=7.6, 4.8 Hz, 1H), 0.29 (br d, J=4.0 Hz, 1H); MS (ESI) m/z: 464.1[M+H$^+$].

Example 100: N-(1-((3bR,4aR)-1-(2-(4-(2,3-dimethylphenyl)piperazin-1-yl)ethyl)-3b,4,4a,5-tetrahydro-1H-cyclopropa[3.4]cyclopenta[1,2-c]pyrazole-3-carbonyl)piperidin-4-yl)acetamide

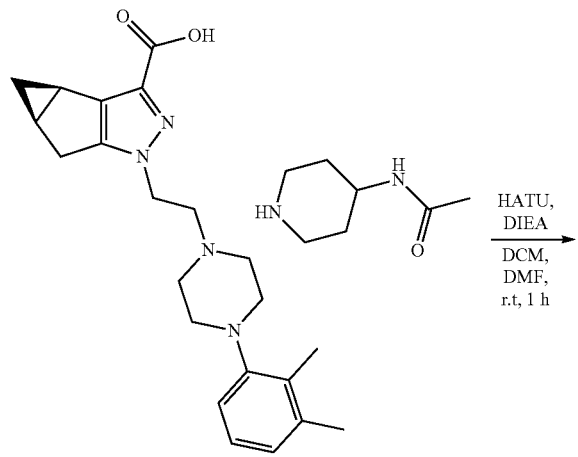

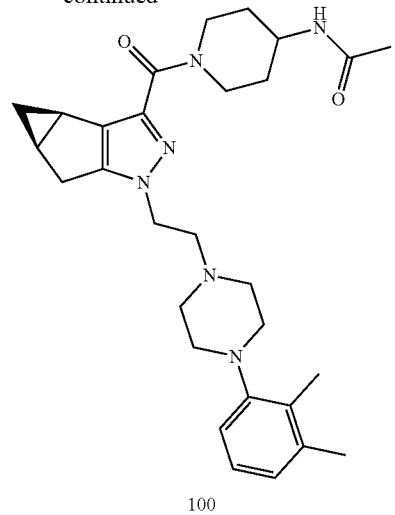

100

To a stirred solution of (3bR,4aR)-1-(2-(4-(2,3-dimethylphenyl)piperazin-1-yl)ethyl)-3b,4,4a,5-tetrahydro-1H-cyclopropa[3,4]cyclopenta[1,2-c]pyrazole-3-carboxylic acid (10 mg, 0.026 mmol) in DCM (3 mL) and DMF (1 mL) were added HATU (15 mg, 0.039 mmol), DIEA (0.02 mL, 0.115 mmol) and followed by N-(piperidin-4-yl)acetamide (4 mg, 0.028 mmol) at RT. After the addition was complete, the mixture was stirred at RT. The reaction was monitored by LCMS, after stirred at RT for 1 h, the reaction was finished to afford a solution. After concentrated in vacuo, the residue was purified by reversed phase HPLC on a GILSON 281 instrument fitted with Phenomenex Synergi C18 150×30 mm×4 um using water (0.1% TFA)-ACN as eluents (Mobile phase A water (0.1% TFA), Mobile phase B ACN, Detective wavelength 220 nm) and lyophilized to afford the title compound as a gum. $^1$HNMR (400 MHz, CD$_3$OD) δ 7.05-7.12 (m, 1H), 6.97 (d, J=8.0 Hz, 2H), 4.43-4.60 (m, 3H), 4.32 (br d, J=13.2 Hz, 1H) 3.95 (br t, J=11.2 Hz, 1H), 3.64-3.87 (m, 4H), 3.35-3.47 (m, 2H), 2.97-3.28 (m, 7H), 2.85-2.94 (m, 1H), 2.27 (d, J=5.2 Hz, 6H), 2.10-2.24 (m, 2H), 1.98 (br d, J=10.0 Hz, 2H), 1.93 (s, 3H), 1.37-1.58 (m, 2H), 1.17 (br d, J=4.6 Hz, 1H), 0.29 (br d, J=4.2 Hz, 1H), MS (ESI) m/z: 505.1[M+H$^+$].

Example 101: ((3bR,4aR)-1-(2-(4-(3-chloro-2-methylphenyl)piperazin-1-yl)ethyl)-3b,4,4a,5-tetrahydro-1H-cyclopropa[3,4]cyclopenta[1,2-c]pyrazol-3-yl)(4-hydroxypiperidin-1-yl)methanone

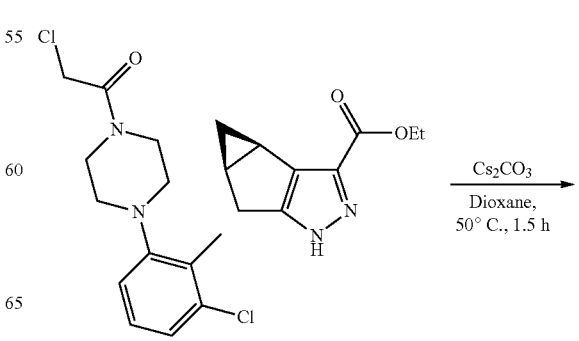

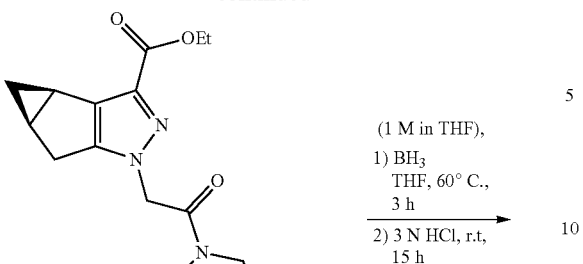

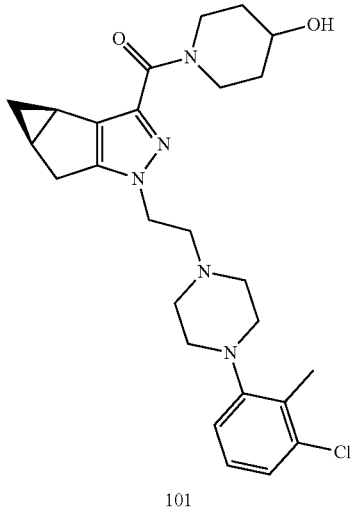 [SMILES: Cc1c(Cl)cccc1N1CCN(CCn2nc(C(=O)N3CCC(O)CC3)c3c2C[C@H]2C[C@@H]32)CC1]

101

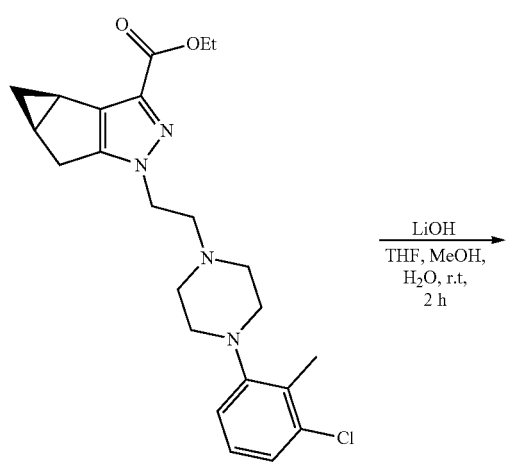

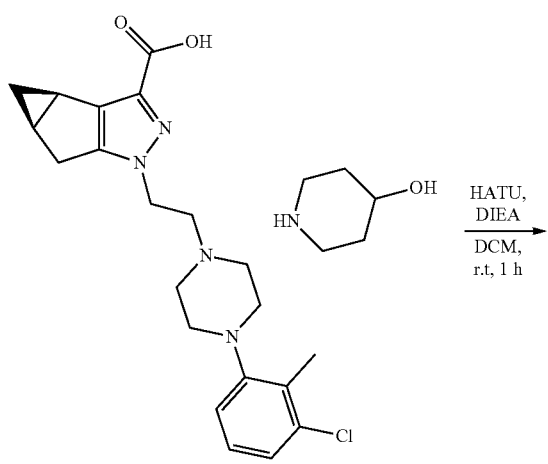

Step 1: (3bR,4aR)-ethyl 1-(2-(4-(3-chloro-2-methylphenyl)piperazin-1-yl)-2-oxoethyl)-3b,4,4a,5-tetrahydro-1H-cyclopropa[3,4]cyclopenta[1,2-c]pyrazole-3-carboxylate To a stirred solution of (3bR,4aR)-ethyl 3b,4,4a,5-tetrahydro-1H-cyclopropa[3,4]cyclopenta[1,2-c]pyrazole-3-carboxylate (500 mg, 2.60 mmol) in dioxane (15 mL) were added Cs₂CO₃ (1017 mg, 3.12 mmol) and 2-chloro-1-(4-(3-chloro-2-methylphenyl)piperazin-1-yl)ethanone (747 mg, 2.60 mmol) at RT. After the addition was complete, the mixture was stirred at 50° C. The reaction was monitored by TLC (petroleum ether/EtOAc=2:1), after stirred at 50° C. for 1.5 h, the reaction was finished to afford a suspension. After cooled to RT, the reaction was diluted with water (30 mL) and extracted by EtOAc (30 mL×3). The organic layers were collected, washed with brine (20 mL), dried over anhydrous Na₂SO₄, and after filtration, the filtrate was concentrated in vacuo. The residue was purified by flash silica gel chromatography (ISCO®; Agela® Flash Column Silica-CS (20 g), Eluent of 21~40% EtOAc/petroleum ether gradient @ 30 mL/min) to afford the title compound. MS (ESI) m/z: 443.2 [M+H⁺].

Step 2: (3bR,4aR)-ethyl 1-(2-(4-(3-chloro-2-methylphenyl)piperazin-1-yl)ethyl)-3b,4,4a,5-tetrahydro-1H-cyclopropa[3,4]cyclopenta[1,2-c]pyrazole-3-carboxylate A solution of 1M BH₃ (1.36 mL, 1.360 mmol, in THF) was added to a solution of (3bR,4aR)-ethyl 1-(2-(4-(3-chloro-2-methylphenyl)piperazin-1-yl)-2-oxoethyl)-3b,4,4a,5-tetrahydro-1H-cyclopropa[3,4]cyclopenta[1,2-c]pyrazole-3-carboxylate (200 mg, 0.452 mmol) in THF (5 mL) at RT under nitrogen. After the addition was complete, the mixture was stirred at 60° C. for 3 h, an aq. 3N solution of HCl (5 mL) was added and the mixture was stirred at 25° C. The reaction was monitored by TLC (petroleum ether/EtOAc=1:1) and LCMS, after stirring at 25° C. for 15 h, the reaction was finished. The solvent was removed under reduced pressure, then diluted with water (20 mL) and extracted by EtOAc (30 mL×3). The organic layers were collected, washed with brine (20 mL), dried over anhydrous Na$_2$SO$_4$, and after filtration, the filtrate was concentrated in vacuo. The residue was purified by column chromatography on silica gel (eluting with petroleum ether/EtOAc=2:1) to afford the title compound as a gum. MS (ESI) m/z: 429.2 [M+H$^+$]

Step 3: (3bR,4aR)-1-(2-(4-(3-chloro-2-methylphenyl)piperazin-1-yl)ethyl)-3b,4,4a,5-tetrahydro-1H-cyclopropa[3,4]cyclopenta[1,2-c]pyrazole-3-carboxylic acid To a stirred solution of (3bR,4aR)-ethyl 1-(2-(4-(3-chloro-2-methylphenyl)piperazin-1-yl)ethyl)-3b,4,4a,5-tetrahydro-1H-cyclopropa[3,4]cyclopenta[1,2-c]pyrazole-3-carboxylate (100 mg, 0.233 mmol) in THF (4 mL) and water (2 mL) were added LiOH (17 mg, 0.710 mmol) and MeOH (0.3 mL). After the addition was complete, the mixture was stirred at RT. The reaction was monitored by TLC (petroleum ether/EtOAc=1:2), after stirred at RT for 2 h, the reaction was finished. The reaction was diluted with water (10 mL), acidified with 1N HCl to pH=6 and extracted by EtOAc (15 mL×4). The organic layers were collected, washed with brine (10 mL), dried over Na$_2$SO$_4$, and after filtration, the filtrate was concentrated in vacuo to afford the title compound as a solid which was used into the next step directly without further purification. MS (ESI) m/z: 401.1 [M+H$^+$]

Step 4: ((3bR,4aR)-1-(2-(4-(3-chloro-2-methylphenyl)piperazin-1-yl)ethyl)-3b,4,4a,5-tetrahydro-1H-cyclopropa[3,4]cyclopenta[1,2-c]pyrazol-3-yl)(4-hydroxypiperidin-1-yl)methanone To a stirred solution of (3bR,4aR)-1-(2-(4-(3-chloro-2-methylphenyl)piperazin-1-yl)ethyl)-3b,4,4a,5-tetrahydro-1H-cyclopropa[3,4]cyclopenta[1,2-c]pyrazole-3-carboxylic acid (20 mg, 0.050 mmol) in DCM (3 mL) were added HATU (29 mg, 0.076 mmol), DIEA (0.03 mL, 0.172 mmol), followed by piperidin-4-ol (6 mg, 0.059 mmol) at RT. After the addition was complete, the mixture was stirred at the same temperature. The reaction was monitored by LCMS, after stirred at RT for 1 h, the reaction was finished to afford a solution. After concentration in vacuo, the residue was purified by reversed phase HPLC on a GILSON 281 instrument fitted with Phenomenex Synergi C18 150×30 mm×4 um using water (0.1% TFA)-ACN as eluents (Mobile phase A water (0.1% TFA), Mobile phase B ACN, Detective wavelength 220 nm) and lyophilized to afford the title compound as a gum. $^1$HNMR (400 MHz, CD$_3$OD) δ 7.16-7.22 (m, 2H), 7.06-7.12 (m, 1H), 4.48 (br t, J=5.2 Hz, 2H), 4.04-4.29 (m, 2H), 3.87-3.99 (m, 1H), 3.63-3.87 (m, 4H), 3.34-3.61 (m, 4H), 3.08-3.28 (m, 4H), 2.99-3.07 (m, 1H), 2.86-2.94 (m, 1H), 2.39 (s, 3H), 2.22 (br d, J=6.2 Hz, 1H), 2.13 (br s, 1H), 1.94 (br s, 2H), 1.46-1.63 (m, 2H), 1.18 (td, J=7.6, 5.0 Hz, 1H), 0.29 (q, J=4.2 Hz, 1H), MS (ESI) m/z: 484.1[M+H$^+$].

Example 102: N-(1-((3bR,4aR)-1-(2-(4-(3-chloro-2-methylphenyl)piperazin-1-yl)ethyl)-3b,4,4a,5-tetrahydro-1H-cyclopropa[3,4]cyclopenta[1,2-c]pyrazole-3-carbonyl)piperidin-4-yl)acetamide

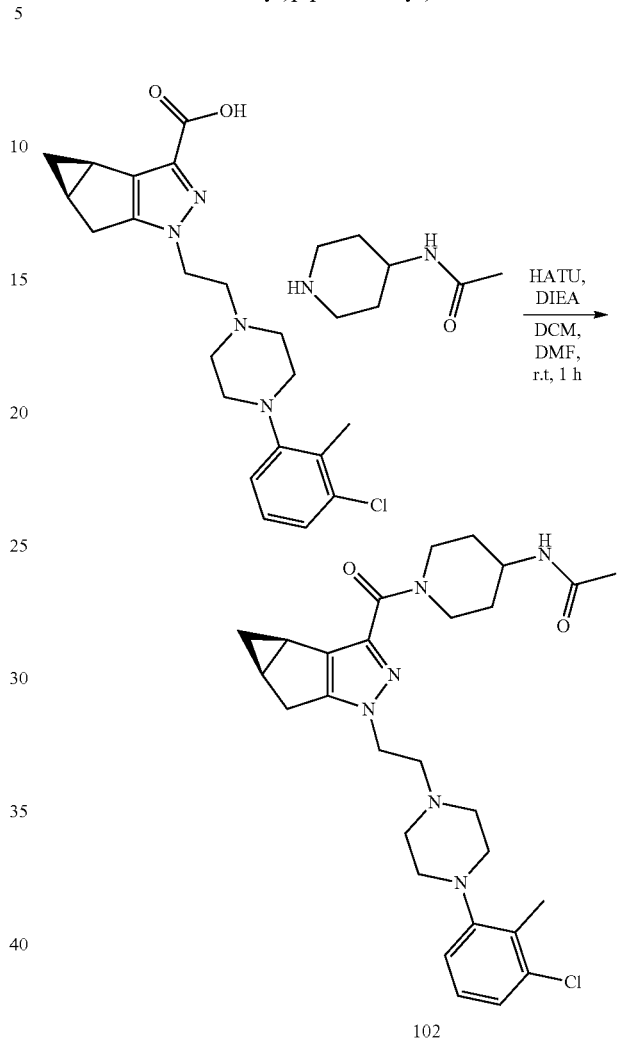

102

To a stirred solution of (3bR,4aR)-1-(2-(4-(3-chloro-2-methylphenyl)piperazin-1-yl)ethyl)-3b,4,4a,5-tetrahydro-1H-cyclopropa[3,4]cyclopenta[1,2-c]pyrazole-3-carboxylic acid (20 mg, 0.050 mmol) in DCM (3 mL) and DMF (1 mL) were added HATU (29 mg, 0.076 mmol), DIEA (0.03 mL, 0.172 mmol), followed by N-(piperidin-4-yl)acetamide (8 mg, 0.056 mmol) at RT. After the addition was complete, the mixture was stirred at RT. The reaction was monitored by LCMS. After stirring at RT for 1 h, the reaction was finished. After concentrating in vacuo, the residue was purified by reversed phase HPLC on a GILSON 281 instrument fitted with Phenomenex Synergi C18 150×30 mm×4 um using water (0.1% TFA)-ACN as eluents (Mobile phase A water (0.1% TFA), Mobile phase B ACN, Detective wavelength 220 nm) and lyophilized to give the title compound as a gum. $^1$HNMR (400 MHz, CD$_3$OD) δ 7.16-7.22 (m, 2H), 7.06-7.12 (m, 1H), 4.45-4.60 (m, 3H), 4.31 (br d, J=12.6 Hz, 1H), 3.95 (br t, J=10.8 Hz, 1H), 3.73 (br t, J=5.4 Hz, 4H), 3.33-3.50 (m, 3H), 2.96-3.28 (m, 6H), 2.86-2.93 (m, 1H), 2.39 (s, 3H), 2.08-2.26 (m, 2H), 1.97 (br d, J=10.4 Hz, 2H), 1.93 (s, 3H), 1.36-1.58 (m, 2H), 1.17 (br d, J=3.6 Hz, 1H), 0.29 (br d, J=3.8 Hz, 1H); MS (ESI) m/z: 525.1[M+H$^+$].

Example 103: 1-(2-(1-(2,3-dimethylphenyl)piperidin-4-yl)ethyl)-1H-indazol-3-yl)(pyrrolidin-1-yl)methanone

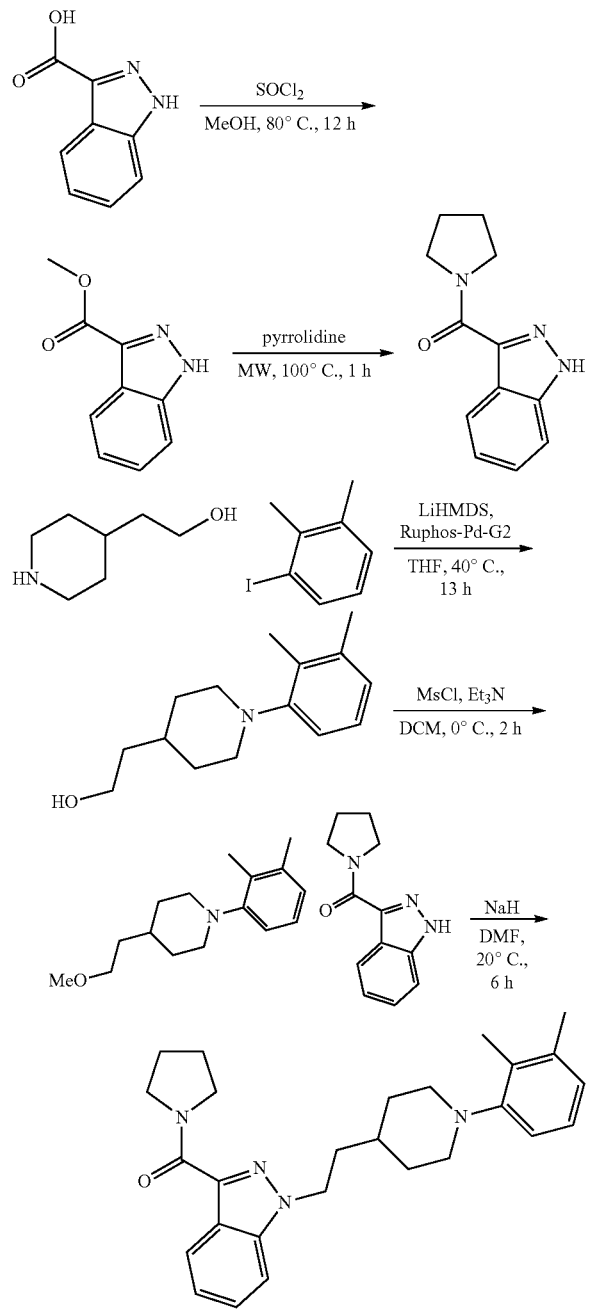

103

Step 1: methyl 1H-indazole-3-carboxylate

To a stirred solution of 1H-indazole-3-carboxylic acid (4 g, 24.67 mmol) in MeOH (50 mL) was added thionyl chloride (13.6 mL, 186 mmol) at 0° C. After the addition was finished, the reaction was stirred at 80° C. The reaction was monitored by TLC (CH$_2$Cl$_2$/MeOH=6:1 Rf=0.8). After stirring at 80° C. for 12 h, the reaction was finished. Then the mixture was concentrated under reduced pressure. To the residue was added sat. sodium bicarbonate (200 mL), then extracted with EtOAc (200 mL×3). The organic phase was combined and dried over anhydrous sodium sulfate, the mixture was filtered and the filtrate was concentrated under reduced pressure to afford the title compound as a solid.

Step 2: (1H-indazol-3-yl)(pyrrolidin-1-yl)methanone

A solution of methyl 1H-indazole-3-carboxylate (1 g, 5.68 mmol) in pyrrolidine (4 mL, 47.8 mmol) at 20° C. was stirred and heated to 100° C. The reaction was monitored by TLC (petroleum ether/EtOAc=1:1), after stirred at 100° C. for 1 h, the reaction was finished. The mixture was concentrated to give a crude product, then purified by silica gel chromatography (petroleum ether:EtOAc=10:1~1:1) to afford the title compound as a solid.

Step 3: 2-(1-(2,3-dimethylphenyl)piperidin-4-yl)ethanol

A mixture of 1-iodo-2,3-dimethylbenzene (1 g, 4.31 mmol), 2-(piperidin-4-yl)ethanol (0.668 g, 5.17 mmol) and Ruphos precatalyst G2 (0.067 g, 0.086 mmol) in THF (20 mL) was stirred at RT for 5 min under nitrogen. Then LiHMDS (8.6 mL, 8.60 mmol) (1 M in THF) was added, and the resulting mixture was stirred 40° C. The reaction was monitored by LCMS, after stirred at 40° C. for 13 h, the reaction was finished. The reaction mixture was cooled and diluted with EtOAc (20 mL), and a sat. solution of brine (20 mL) was slowly added under stirring, diluted with water (10 mL), extracted with EtOAc (20 mL×3). The organic layer was dried over Na$_2$SO$_4$, filtered and concentrated in vacuo, then it was purified by silica column chromatography (petroleum ether:EtOAc=100:1~5:1) to afford the title compound as an oil. MS (ESI) m/z: 234.2 [M+H$^+$]

Step 4: 2-(1-(2,3-dimethylphenyl)piperidin-4-yl)ethyl methanesulfonate

To a stirred solution of 2-(1-(2,3-dimethylphenyl)piperidin-4-yl)ethanol (100 mg, 0.429 mmol) in DCM (2 mL) were added Et$_3$N (0.2 mL, 1.435 mmol), MsCl (0.5 mL, 6.42 mmol) at 0° C. After the addition was finished, the reaction was stirred at 0° C. The reaction was monitored by TLC (petroleum ether/EtOAc=1:1, Rf=0.7), after stirred at 0° C. for 2 h, the reaction was finished. The mixture was diluted with water (10 mL), and extracted with EtOAc (20 mL×2). The organic phase was washed with brine (ca. 20 mL), dried over Na$_2$SO$_4$, and concentrated under reduced pressure to afford the title compound as an oil, which was used in the next step without further purification. MS (ESI) m/z: 312.1 [M+H$^+$].

Step 5: (1-(2-(1-(2,3-dimethylphenyl)piperidin-4-yl)ethyl)-1H-indazol-3-yl)(pyrrolidin-1-yl)methanone To a stirred solution of (1H-indazol-3-yl)(pyrrolidin-1-yl)methanone (104 mg, 0.482 mmol) in DMF (2 mL) was added NaH (38 mg, 0.950 mmol) at 0° C. After the addition was finished, the reaction was stirred at 0° C. for 15 min; then to the mixture was added 2-(1-(2,3-dimethylphenyl)piperidin-4-yl)ethyl methanesulfonate (100 mg, 0.321 mmol) at 0° C. After the addition was finished, the reaction was stirred at RT. The reaction was monitored by LCMS, after stirred at RT for 6 h, the reaction was finished. The mixture was quenched with NH₄Cl (3 mL), diluted with water (20 mL), and extracted with EtOAc (30 mL×3). The organic layer was concentrated under reduced pressure, the residue was purified by reversed phase HPLC on a GILSON 281 instrument fitted with Agela ASB 150×25 mm×5 um using water (0.1% TFA)-ACN as eluents (Mobile phase A water (0.1% TFA), Mobile phase B ACN, Detective wavelength 220 nm) and concentration to afford the title compound as a solid. $^1$H NMR (400 MHz, CDCl₃) δ 8.34 (d, J=8.2 Hz, 1H), 7.41-7.47 (m, 2H), 7.28-7.31 (m, 1H), 7.14-7.19 (m, 2H), 7.06-7.11 (m, 1H), 4.53 (t, J=6.6 Hz, 2H), 4.01 (t, J=6.4 Hz, 2H), 3.78 (t, J=6.6 Hz, 2H), 3.57 (br d, J=11.7 Hz, 2H), 3.02 (br t, J=11.7 Hz, 2H), 2.37 (s, 3H), 2.30 (s, 3H), 2.10-2.20 (m, 2H), 1.92-2.10 (m, 8H); MS (ESI) m/z: 431.1 [M+H⁺].

Example 104: (1-(2-(4-(2,3-dimethylphenyl)piperidin-1-yl)ethyl)-1H-indazol-3-yl)(pyrrolidin-1-yl)methanone

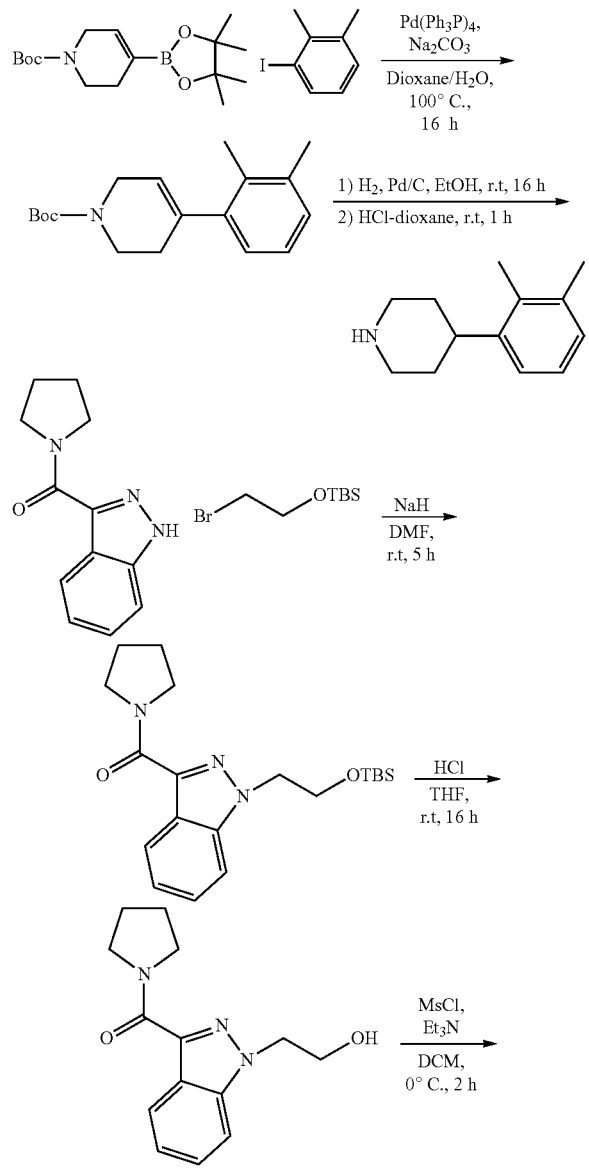

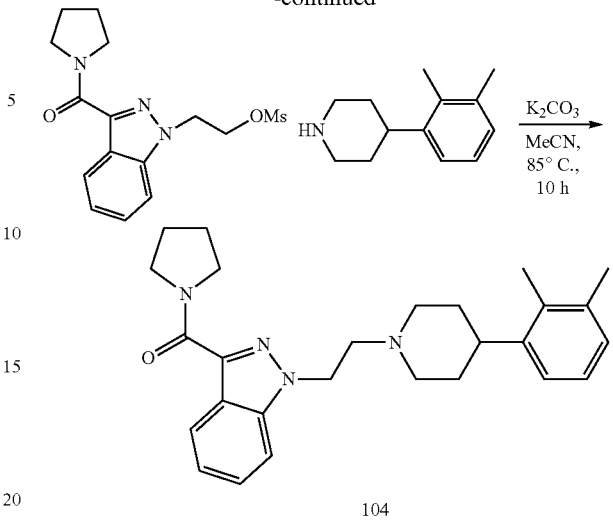

Step 1: tert-butyl 4-(2,3-dimethylphenyl)-5,6-dihydropyridine-1(2H)-carboxylate

To a stirred solution of 1-iodo-2,3-dimethylbenzene (200 mg, 0.862 mmol) in dioxane (5 mL) and water (1 mL) were added Na₂CO₃ (274 mg, 2.59 mmol), Pd(Ph₃P)₄ (199 mg, 0.172 mmol) and tert-butyl 4-(4,4,5,5-tetramethyl-1,3,2-dioxaborolan-2-yl)-5,6-dihydropyridine-1(2H)-carboxylate (320 mg, 1.034 mmol) at RT under nitrogen. After the addition was finished, the reaction was stirred at 100° C. under nitrogen. The reaction was monitored by LCMS. After stirring at 100° C. for 16 h, the reaction was finished. Then the mixture was concentrated under reduced pressure. To the residue was added water (20 mL), and extracted with EtOAc (20 mL×2). The organic layer was washed with brine (20 mL), dried over Na₂SO₄, filtered, and the filtrate was concentrated under reduced pressure. The residue was purified by silica gel column chromatography using (petroleum ether/EtOAc=100:1-20:1 as eluent) to afford the title compound as a solid, which was used directly in next step without further purification. MS (ESI) m/z: 232.1[M-56]

Step 2: tert-butyl 4-(2,3-dimethylphenyl)piperidine-1-carboxylate

To a stirred solution of tert-butyl 4-(2,3-dimethylphenyl)-5,6-dihydropyridine-1(2H)-carboxylate (160 mg, 0.557 mmol) in EtOH (5 mL) was added Pd—C (200 mg, 1.879 mmol) 10%) at RT. After the addition was finished, the reaction was stirred at the same temperature under nitrogen. The reaction was monitored by LCMS after stirred at RT for 16 h, the reaction was finished. The mixture was filtered, and the filtrate was concentrated under reduced pressure to afford the title compound as an oil, which was used directly in next step without further purification. MS (ESI) m/z: 234.1[M-56]

Step 3: 4-(2,3-dimethylphenyl)piperidine hydrochloride

To a stirred solution of tert-butyl 4-(2,3-dimethylphenyl)piperidine-1-carboxylate (161 mg, 0.556 mmol) in dioxane (5 mL) was added HCl (2 mL, 8.00 mmol) (4M in dioxane) at RT. After the addition was finished, the reaction was stirred at RT. The reaction was monitored by LCMS after stirred at RT for 1 h, the reaction was finished. Then the mixture was concentrated under reduced pressure to afford the title compound as a solid which was used directly in next step without further purification. MS (ESI) m/z: 190.2 [M+H]$^+$ Step 4: (1-(2-((tert-butyldimethylsilyl)oxy)ethyl)-1H-indazol-3-yl)(pyrrolidin-1-yl)methanone To a stirred solution of (1H-indazol-3-yl)(pyrrolidin-1-yl) methanone (216 mg, 1.003 mmol) in DMF (5 mL) was added sodium hydride (60 mg, 2.500 mmol) (60%) at 0° C. After the addition was finished, the reaction was stirred at 0° C. for 15 min; then to the mixture was added (2-bromoethoxy)(tert-butyl)dimethylsilane (200 mg, 0.836 mmol) at 0° C. After the addition was finished, the reaction was stirred at RT. The reaction was monitored by TLC (petroleum ether/EtOAc=1:1, Rf=0.8), after stirred at RT for 5 h, the reaction was finished. The mixture was quenched with sat. solution of NH$_4$Cl (2 mL), then diluted with water (40 mL), and extracted with EtOAc (50 mL×2). The organic layer was washed with brine (ca. 20 mL), dried over Na$_2$SO$_4$, and filtered, the filtrate was concentrated under reduced pressure. The residue was purified by silica gel column chromatography using (petroleum ether/EtOAc=100:1-10:1 as eluent) to afford the title compound as a solid. MS (ESI) m/z: 374.2 [M+H]$^+$.

Step 5: (1-(2-hydroxyethyl)-1H-indazol-3-yl)(pyrrolidin-1-yl)methanone

To a stirred solution of (1-(2-((tert-butyldimethylsilyl) oxy)ethyl)-1H-indazol-3-yl)(pyrrolidin-1-yl)methanone (50 mg, 0.134 mmol) in THF (1.5 mL) was added HCl (0.5 mL, 1.500 mmol) at RT. After the addition was finished, the reaction was stirred at RT. The reaction was monitored by LCMS, and after stirred at RT for 16 h, the reaction was finished. Sat. NaHCO$_3$ was added to adjust the pH=7-8, diluted with water (10 mL), extracted with EtOAc (20 mL×2). The organic layer was washed with brine (ca. 15 mL), dried over Na$_2$SO$_4$ and filtered. The filtrate was concentrated under reduced pressure to afford the title compound as a solid, which was used directly in next step without further purification. MS (ESI) m/z: 260.1[M+H]$^+$ Step 6: 2-(3-(pyrrolidine-1-carbonyl)-1H-indazol-1-yl)ethyl methanesulfonate To a stirred solution of (1-(2-hydroxyethyl)-1H-indazol-3-yl)(pyrrolidin-1-yl)methanone (94 mg, 0.363 mmol) in DCM (2 mL) were added Et$_3$N (0.15 mL, 1.076 mmol) and Ms-Cl (0.05 mL, 0.642 mmol) at 0° C. After the addition was finished, the reaction was stirred at 0° C. The reaction was monitored by TLC (CH$_2$Cl$_2$/MeOH=10:1 Rf=0.7). After stirring at 0° C. for 2 h, the reaction was finished. The mixture was diluted with water (15 mL), and extracted with DCM (20 mL×2). The organic layer was washed with brine (10 mL), dried over Na$_2$SO$_4$, and filtered. The filtrate was concentrated under reduced pressure to afford the title compound as an oil, which was used in the next step without further purification. MS (ESI) m/z: 338.1 [M+H]$^+$.

Step 7: (1-(2-(4-(2,3-dimethylphenyl)piperidin-1-yl) ethyl)-1H-indazol-3-yl)(pyrrolidin-1-yl)methanone To a stirred solution of 2-(3-(pyrrolidine-1-carbonyl)-1H-indazol-1-yl)ethyl methanesulfonate (122 mg, 0.362 mmol) in MeCN (5 mL) were added 4-(2,3-dimethylphenyl)piperidine hydrochloride (80 mg, 0.354 mmol), K$_2$CO$_3$ (80 mg, 0.579 mmol) at RT. After the addition was finished, the reaction was stirred at 85° C. The reaction was monitored by LC-MS. After stirring at 85° C. for 10 h, the reaction was finished. The mixture was diluted with water (20 mL), and extracted with EtOAc (20 mL×2). The organic layer was washed with brine (ca. 10 mL), dried over Na$_2$SO$_4$, and filtered, the filtrate was concentrated under reduced pressure. The residue was purified by reversed phase HPLC on a GILSON 281 instrument fitted with Agela ASB 150×25 mm×5 um using water (0.1% TFA)-ACN as eluents (Mobile phase A water (0.1% TFA), Mobile phase B ACN, Detective wavelength 220 nm) and concentration to afford the title compound as a solid. $^1$H NMR (400 MHz, CDCl$_3$) δ 8.30 (d, J=8.3 Hz, 1H) 7.57-7.62 (m, 1H) 7.50-7.55 (m, 1H) 7.32 (t, J=7.2 Hz, 1H) 7.10-7.16 (m, 1H) 7.03-7.09 (m, 2H) 4.98 (t, J=6.4 Hz, 2H) 3.93-4.01 (m, 2H) 3.64-3.81 (m, 6H) 2.93 (br d, J=12.3 Hz, 1H) 2.79 (br t, J=12.5 Hz, 2H) 2.28 (s, 3H) 2.23 (br s, 1H) 2.18 (s, 3H) 1.89-2.06 (m, 7H); MS (ESI) m/z: 431.1 [M+H]$^+$.

Biological Assays

IDO1 Cellular Assay in HeLa Cells Stimulated with IFNγ

HeLa cells were cultured in complete HeLa culture medium (90% EMEM, 10% heat-inactivated fetal bovine serum) and expanded to about 1×10$^9$ cells. The cells were then collected and frozen down at 1×10$^7$ cells/vial in 1 mL frozen medium (90% complete HeLa culture medium, 10% DMSO).

Compounds to be tested were serially diluted in ten 3-fold steps in DMSO starting from 10 mM DMSO stocks in Echo low volume plate(s). Compound dilutions or DMSO alone were then dispensed from the dilution plate(s) into Greiner black 384-well assay plate(s) (catalog #781086, 50 nL/well) using an Echo 550 acoustic liquid handler (Labcyte).

Frozen HeLa cells were thawed and transferred into HeLa assay medium (99% complete HeLa culture medium, 1% Pen/Strep) with 20 mL medium/vial of cells. The cells were spun down at 250 g in a table top centrifuge for 5 min and suspended in same volume of HeLa assay medium. The cells were then counted and adjusted to a density of 2×10$^5$ cells/mL in HeLa assay medium. Sterile L-tryptophan were added to the cells with final concentration of 300 uM L-tryptophan. A small aliquot (2 mL/plate) of HeLa cells were set aside and were not treated with IFNγ, to serve as the Max-E control. The rest of HeLa cells were added with sterile IFNγ (Cat #285-IF, R & D systems) with a final concentration of 100 ng/mL.

HeLa cells with and without IFNγ were dispensed to the respective wells of 384-well assay plates containing the compounds. The plates were incubated for about 48 hours at a 37° C., 5% CO$_2$ incubator. Afterwards, 12 μL of 0.5 M methyl isonipecotate in dimethyl sulfoxide were added into each well and the plates were sealed and incubated at 37° C. without CO$_2$ overnight. The plates were centrifuged for 1 min at 200×g. The resulting fluorescence was measured in a Spectramax plate reader (Molecular Devices) with a 400 nm excitation filter and a 510 nm emission filter.

The fluorescence intensity of each well was corrected for the background observed in wells with non-IFNγ-treated cells and was expressed as a fraction of the intensity observed in wells of IFNγ-treated cells and DMSO only. Potencies were calculated by linear least squares fit to the four parameter logistic IC$_{50}$ equation.

The biological activity data using the IDO1 cellular assay described above are summarized in the table below. Compounds disclosed herein generally have IC$_{50}$ of about 0.1 nM to about 20,000 nM, or more specifically, about 1 nM to about 10,000 nM, or more specifically, about 5 nM to about 5,000 nM, or more specifically, about 10 nM to about 1,000 nM, or still more specifically, about 10 nM to about 500 nM. Specific $IC_{50}$ activity data for the exemplified compounds disclosed herein is provided in the following table.

IDO1 Human Whole Blood Assay

Compounds to be tested were serially diluted in ten 3-fold steps in DMSO starting from 10 mM. 3 µL of compound dilutions or DMSO alone were then dispensed from the dilution plate into a polypropylene 96-well assay plate containing 97 µL of RPMI using an Echo 555 acoustic liquid handler (Labcyte). LPS and IFNγ was prepared in in RPMI to a 10× of final conc. (1000 ng/mL), final concentration is 100 ng/mL.

Human whole blood was drawn in sodium heparin coated tubes from healthy internal donors. 240 µL of blood was transferred to each of the wells of a v-bottom 96 well plate. 30 µL of compound was transferred from intermediate dilution plate, and incubated for 15 min. 30 µL from stimulants was then transferred to blood and mixed thoroughly. Plate was covered with breathable membrane and incubated at 37° C. for overnight (18 h).

On day 2 isotope labeled standard of kynurenine and tryptophan was made in water at 10× concentration and 30 µL was added to the blood at 3 µM final concentration. The assay plates were centrifuged at 300×G for 10 min with no brake to separate plasma from red blood cells. 60 µL of plasma samples was removed without disturbing red blood cells. Plasma was diluted with RPMI in 1:1 ratio and proteins were precipitated out with two volume of Acetonitrile. The plates were centrifuged at 4000×G for 60 min. 20 µL of supernatant was carefully transferred to a 384 well plate contain 40 µL of 0.1% formic acid in water and analyzed by LC/MS/MS.

LC/MS/MS analyses were performed using Thermo Fisher's LX4-TSQ Quantum Ultra system. This system consists of four Agilent binary high-performance liquid chromatography (HPLC) pumps and a TSQ Quantum Ultra triple quadrupole MS/MS instrument. For each sample, 5 µL were injected onto an Atlantis T3 column (2.1 mm×150 mm, 3 µm particle size) from Waters. The mobile phase gradient pumped at 0.8 mL/min was used to elute the analytes from the column at 25° C. The elution started at 0% B increasing linearly to 25% B at 6.5 min, holding at 25% for 1 min, re-equilibrating to 10 min. Mobile phase A consisted of 0.1% formic acid in water. Mobile phase B consisted of 0.1% of formic acid in acetonitrile. Data was acquired in positive mode using a HESI interface. The operational parameters for the TSQ Quantum Ultra instrument were a spray voltage of 4000 V, capillary temperature of 380° C., vaporizer temperature 400° C., shealth gas 60 arbitrary units, Aux gas 20 arbitrary units, tube lens 85 and collision gas 1.2 mTorr. SRM chromatograms of kynurenine (Q1: 209.2>Q3:94.0) and internal standard (Q1: 215.3>Q3:98.2) were collected for 90 sec. The peak area was integrated by Xcalibur Quan software. The ratios between the kynurenine generated in the reaction and 2D6-Kynurenine spiked-in internal standard were used to generate percentage inhibition and $IC_{50}$ values. Compounds were titrated and $IC_{50}$'s were calculated by 4 parameter sigmoidal curve fitting formula.

The biological activity data of selective compounds using HeLa Cells assay and the IDO1 human whole blood assay described above are summarized in the table below.

| Ex. # | HeLa Cell Potency, $IC_{50}$ (nM) | Human Whole Blood Potency, $IC_{50}$ (nM) |
|---|---|---|
| 1 | 12.19 | 340.6 |
| 2 | 32.67 | |
| 3 | 37.73 | |
| 4 | 67.25 | |
| 5 | 93.83 | |
| 6 | 111 | |
| 7 | 125.4 | |
| 8 | 4.352 | 250.8 |
| 9 | 8.388 | |
| 10 | 8.655 | |
| 11 | 11.99 | 799.9 |
| 12 | 16.66 | |
| 13 | 24.56 | |
| 14 | 29.68 | |
| 15 | 31.57 | |
| 16 | 2.329 | |
| 17 | 1.439 | |
| 18 | 1.522 | 437.3 |
| 19 | 1.727 | |
| 20 | 1.308 | 285.6 |
| 21 | 1.875 | |
| 22 | 1.811 | |
| 23 | 1.793 | |
| 24 | 2.558 | |
| 25 | 3.659 | |
| 26 | 6.232 | |
| 27 | 7.74 | |
| 28 | 9.466 | |
| 29 | 22.66 | |
| 30 | 39.82 | |
| 31 | 41.52 | |
| 32 | 42.44 | |
| 33 | 68.53 | |
| 34 | 2.833 | 887.6 |
| 35 | 1.658 | 934.5 |
| 36 | 4.142 | |
| 37 | 5.024 | |
| 38 | 20.86 | |
| 39 | 21.95 | |
| 40 | 22.91 | |
| 41 | 233.2 | |
| 42 | 443.5 | |
| 43 | 102.9 | |
| 44 | 13.49 | |
| 45 | 1190 | |
| 46 | 66.7 | |
| 47 | 73.55 | |
| 48 | 8.126 | 963.8 |
| 49 | 3.572 | 177.2 |
| 50 | 42.26 | |
| 51 | 93.83 | |
| 52 | 2.987 | 448.5 |
| 53 | 3.27 | 822.1 |
| 54 | 47.74 | |
| 55 | 68.29 | |
| 56 | 21.16 | |
| 57 | 2.609 | 516.6 |
| 58 | 1.601 | 538.2 |
| 59 | 45.14 | |
| 60 | 47.34 | |
| 61 | 0.5771 | 30.58 |
| 62 | 0.688 | |
| 63 | 0.7266 | |
| 64 | 0.6186 | 214.7 |
| 65 | <0.5081 | 130.1 |
| 66 | 0.6422 | 153.4 |
| 67 | 2.327 | 208.9 |
| 68 | 1.518 | 517 |
| 69 | 97.65 | |
| 70 | 0.5505 | 160.6 |
| 71 | 13.31 | |
| 72 | 15.49 | |
| 73 | 14.3 | |
| 74 | 2.756 | 177.8 |
| 75 | 202.7 | |
| 76 | 2.183 | |
| 77 | 4.997 | 136 |
| 78 | 314.6 | |

-continued

| Ex. # | HeLa Cell Potency, IC$_{50}$ (nM) | Human Whole Blood Potency, IC$_{50}$ (nM) |
|---|---|---|
| 79 | 9.78 | |
| 80 | 12.03 | |
| 81 | 1.431 | |
| 82 | 143.3 | |
| 83 | 0.8831 | 110.4 |
| 84 | 22.58 | |
| 85 | 27.33 | |
| 86 | 26.78 | |
| 87 | 12.04 | 736.5 |
| 88 | 4.473 | |
| 89 | 3.367 | |
| 90 | 1.771 | |
| 91 | 1.972 | |
| 92 | 1.409 | |
| 93 | 1.533 | |
| 94 | 1.835 | |
| 95 | 2.125 | 165.5 |
| 96 | 2.617 | 327.7 |
| 97 | 21.35 | |
| 98 | 7.892 | |
| 99 | 33.79 | |
| 100 | 2.323 | 247.4 |
| 101 | 41.82 | |
| 102 | 2.059 | 261.4 |
| 103 | 15.37 | 1034 |
| 104 | 215.9 | |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of formula (I), or a pharmaceutically acceptable salt thereof:

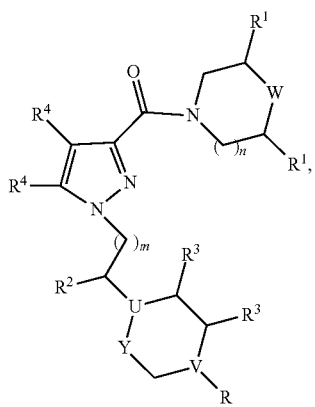

(I)

wherein:
m is 0 or 1; n is 0 or 1;
U is selected from (1) N and (2) $CR^a$, wherein Ra is selected from: (a) H and (b) —OH;
V is selected from (1) N and (2) $CR^b$, wherein $R^b$ is selected from: (1) H and (2) $C_{1-6}$ alkyl;
W is selected from (1) —O—, (2) —$NR^c$—, and (3) —$CR^dR^d$—;
wherein $R^c$ is selected from:
 (a) H,
 (b) —OH, and
 (c) —C(O)—$C_{1-6}$ alkyl, optionally substituted with —OH;
each occurrence of $R^d$ is independently selected from:
 (a) H,
 (b) halogen,
 (c) —OH,
 (d) —$NH_2$,
 (e) —NH—C(O)—$C_{1-6}$ alkyl, optionally substituted with —OH,
 (f) —NH—C(O)—O—$C_{1-6}$ alkyl,
 (g) $C_{1-6}$ alkyl, optionally substituted 1-3 substituents independently selected from —OH and halogen, and
 (h) —O—$C_{1-6}$ alkyl, optionally substituted with —OH;
Y is selected from (1) —O— and (2) —$CH_2$—;
R is selected from:
 (1) H,
 (2) aryl,
 (3) —O-aryl,
 (4) —C(O)-aryl,
 (5) heteroaryl, and
 (6) —O-heteroaryl,
 wherein each of the aryl of (2), (3), and (4) and each of the heteroaryl of (5) and (6) is optionally substituted with 1-3 substituents independently selected from:
  (a) —OH,
  (b) halogen,
  (c) —CN, and
  (d) $C_{1-6}$ alkyl, optionally substituted with 1-3 halogens;
each occurrence of $R^1$ is independently selected from: (1) H, (2) halogen, and (3) $C_{1-6}$ alkyl, optionally substituted with —OH;
$R^2$ is selected from: (1) H, (2) halogen, (3) —OH, (4) —O—$C_{1-6}$ alkyl, and (5) $C_{1-6}$ alkyl, optionally substituted with —OH;
each occurrence of $R^3$ is independently selected from: (1) H, (2) halogen, (3) —OH, (4) $C_{1-6}$ alkyl, optionally substituted with —OH, and (5) —O-heteroaryl, optionally substituted with 1-3 halogens; and
each occurrence of $R^4$ is independently selected from: (1) H, (2) halogen, (3) $C_{1-6}$ alkyl, optionally substituted with 1-3 halogens, and (4) $C_{3-6}$ cycloalkyl;
or alternatively, the two $R^4$ groups together with the two carbon atoms to which they are attached form a 5-7 membered monocyclic or bicyclic carbocyclyl, optionally substituted with 1-3 substituents independently selected from (a) halogen and (b) $C_{1-6}$ alkyl, wherein the $C_{1-6}$alkyl is optionally substituted with halogen.

2. The compound of claim 1, or a pharmaceutically acceptable salt thereof, wherein U is selected from (1) N, (2) CH, and (3) C(OH).

3. The compound of claim 1, or a pharmaceutically acceptable salt thereof, wherein V is selected from (1) N and (2) CH.

4. The compound of claim 1, or a pharmaceutically acceptable salt thereof, wherein W is selected from:
 (1) —O—,
 (2) —N(C(O)—$C_{1-4}$ alkyl)-, optionally substituted with —OH—, and
 (3) —$CR^dR^d$—, wherein each occurrence of $R^d$ is independently selected from:
  (a) H,
  (b) halogen,
  (c) —OH,
  (d) —$NH_2$, (e) —NH—C(O)—CH$_3$, optionally substituted with —OH,
(f) —NH—C(O)—O—C$_{1-4}$ alkyl,
(g) C$_{1-4}$ alkyl, optionally substituted with 1-3 substituents independently selected from —OH and halogen, and
(h) —O—C$_{1-4}$ alkyl, optionally substituted with —OH.

5. The compound of claim 1, or a pharmaceutically acceptable salt thereof, wherein W is selected from:
(1) —O—,
(2) —N(C(O)—CH$_2$—OH)—,
(3) —CR$^d$R$^d$—, wherein each occurrence of R$^d$ is independently selected from:
(a) H,
(b) halogen,
(c) —OH,
(d) —NH$_2$,
(e) —NH—C(O)—CH$_3$, optionally substituted with —OH,
(f) —NH—C(O)—O—CH$_3$,
(g) C$_{1-4}$ alkyl, optionally substituted with 1-3 substituents independently selected from —OH and halogen, and
(h) —O—C$_{1-4}$ alkyl, optionally substituted with —OH.

6. The compound of claim 1, or a pharmaceutically acceptable salt thereof, wherein:
R is selected from:
(1) H,
(2) phenyl,
(3) —O-phenyl,
(4) —C(O)-phenyl,
(5) a 5-6 membered monocyclic heteroaryl,
(6) a 9-12 membered bicyclic fused heteroaryl, and
(7) —O-heteroaryl, wherein the heteroaryl is a 5-6 membered monocyclic heteroaryl,
wherein each of the phenyl of (2), (3), and (4) and each of the heteroaryl of (5), (6), and (7) is optionally substituted with 1-3 substituents independently selected from:
(a) —OH,
(b) halogen,
(c) —CN, and
(d) C$_{1-4}$ alkyl, optionally substituted with 1-3 halogens.

7. The compound of claim 1, or a pharmaceutically acceptable salt thereof, wherein:
R is selected from:
(1) H,
(2) phenyl,
(3) —O-phenyl,
(4) —C(O)-phenyl,
(5) a heteroaryl selected from quinolinyl, pyrazinyl, pyrazolyl, pyridazinyl, pyridinyl, and pyrimidinyl, and
(6) —O-heteroaryl, wherein the heteroaryl is selected from pyrazinyl, pyrazolyl, pyridazinyl, pyridinyl, and pyrimidinyl,
wherein each of the phenyl of (2), (3), and (4) and each of the heteroaryl of (5) and (6) is optionally substituted with 1-3 substituents independently selected from:
(a) —OH,
(b) halogen,
(c) —CN, and
(d) C$_{1-4}$ alkyl, optionally substituted with 1-3 halogens.

8. The compound of claim 1, or a pharmaceutically acceptable salt thereof, wherein each occurrence of R$^1$ is independently selected from: (1) H, (2) halogen, and (3) methyl.

9. The compound of claim 1, or a pharmaceutically acceptable salt thereof, wherein R$^2$ is selected from: (1) H, (2) halogen, (3) —OH, and (4) —O—C$_{1-4}$ alkyl.

10. The compound of claim 1, or a pharmaceutically acceptable salt thereof, wherein each occurrence of R$^3$ is independently selected from: (1) H and (2) —O-pyridinyl, optionally substituted with halogen.

11. The compound of claim 1, or a pharmaceutically acceptable salt thereof, wherein:
each occurrence of R$^4$ is independently selected from: (1) H, (2) halogen, (3) C$_{1-4}$ alkyl, optionally substituted with 1-3 halogens, and (4) cyclopropyl;
or alternatively, the two R$^4$ groups together with the two carbon atoms to which they are attached form a 5-6 membered carbocyclyl selected from:
(1) monocyclic saturated or partially unsaturated carbocyclyl,
(2) bicyclic fused saturated or partially unsaturated carbocyclyl, and
(3) monocyclic aromatic carbocyclyl;
wherein each of the carbocyclyl of (1), (2), and (3) is optionally substituted with 1-3 substituents independently selected from (a) halogen and (b) C$_{1-6}$ alkyl, optionally substituted with halogen.

12. The compound of claim 1, or a pharmaceutically acceptable salt thereof, of formula (Ia):

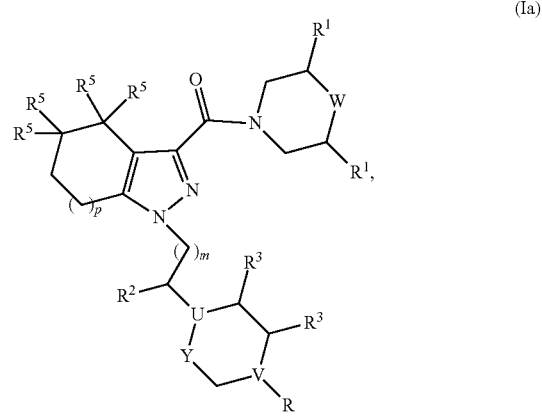

(Ia)

wherein:
m is 0 or 1; p is 0 or 1;
U is selected from (1) N, (2) CH, and (3) C(OH);
V is selected from (1) N and (2) CH;
W is selected from:
(1) —O—,
(2) —N(C(O)—CH$_2$—OH)—,
(3) —CR$^d$R$^d$—, wherein each occurrence of R$^d$ is independently selected from:
(a) H,
(b) halogen,
(c) —OH,
(d) —NH$_2$,
(e) —NH—C(O)—CH$_3$, optionally substituted with —OH,
(f) —NH—C(O)—O—CH$_3$, (g) $C_{1-4}$ alkyl, optionally substituted with 1-3 substituents independently selected from —OH and halogen, and
(h) —O—$C_{1-4}$ alkyl, optionally substituted with —OH;
Y is selected from (1) —O— and (2) —$CH_2$—;
R is selected from:
(1) H,
(2) aryl,
(3) —O-aryl,
(4) —C(O)-aryl,
(5) heteroaryl, and
(6) —O-heteroaryl,
wherein each of the aryl of (2), (3) and (4) and each of the heteroaryl of (5) and (6) is optionally substituted with 1-3 substituents independently selected from:
(a) —OH,
(b) halogen,
(c) —CN, and
(d) $C_{1-6}$ alkyl, optionally substituted with 1-3 halogens;
each occurrence of $R^1$ is independently selected from: (1) H, (2) halogen, and (3) $C_{1-6}$ alkyl, optionally substituted with —OH;
$R^2$ is selected from: (1) H, (2) halogen, (3) —OH, (4) —O—$C_{1-6}$ alkyl, and (5) $C_{1-6}$ alkyl, optionally substituted with —OH;
each occurrence of $R^3$ is independently selected from: (1) H, (2) halogen, (3) —OH, (4) $C_{1-6}$ alkyl, optionally substituted with —OH, and (5) —O-heteroaryl, optionally substituted with 1-3 halogens; and
each occurrence of $R^5$ is independently selected from: (1) H, (2) halogen, and (3) $C_{1-4}$ alkyl, optionally substituted with 1-3 halogens;
or alternatively, two $R^5$ groups on two adjacent ring carbons together with the two ring carbons form a 3-4 membered new carbocyclic ring.

13. The compound of claim 12, or a pharmaceutically acceptable salt thereof:
wherein:
R is selected from:
(1) phenyl,
(2) —O-phenyl,
(3) —C(O)-phenyl,
(4) a heteroaryl selected from quinolinyl, pyrazinyl, pyrazolyl, pyridazinyl, pyridinyl, and pyrimidinyl, and
(5) —O-heteroaryl, wherein the heteroaryl is selected from pyrazinyl, pyrazolyl, pyridazinyl, pyridinyl, and pyrimidinyl,
wherein each of the phenyl of (1), (2), and (3) and each of the heteroaryl of (4) and (5) is optionally substituted with 1-3 substituents independently selected from:
(a) —OH,
(b) halogen,
(c) —CN, and
(d) $C_{1-4}$ alkyl, optionally substituted with 1-3 halogens;
each occurrence of $R^1$ is independently selected from: (1) H, (2) halogen, and (3) methyl;
$R^2$ is selected from: (1) H, (2) halogen, (3) —OH, and (4) —O—$C_{1-4}$ alkyl;
each occurrence of $R^3$ is H; and
each occurrence of $R^5$ is independently selected from: (1) H, (2) halogen, and (3) $C_{1-4}$ alkyl, optionally substituted with 1-3 halogens.

14. The compound of claim 1, or a pharmaceutically acceptable salt thereof, of formula (Ib):

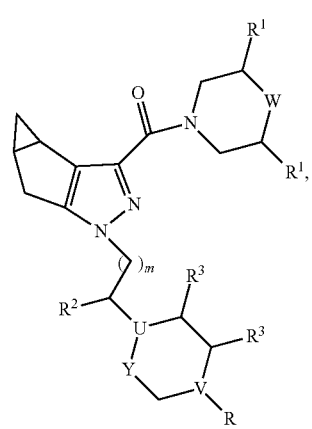

(Ib)

wherein:
m is 0 or 1;
U is selected from (1) N, (2) CH, and (3) C(OH);
V is selected from (1) N and (2) CH;
W is selected from:
(1) —O—,
(2) —N(C(O)—$CH_2$—OH)—,
(3) —$CR^dR^d$—, wherein each occurrence of $R^d$ is independently selected from:
(a) H,
(b) halogen,
(c) —OH,
(d) —$NH_2$,
(e) —NH—C(O)—$CH_3$, optionally substituted with —OH,
(f) —NH—C(O)—O—$CH_3$,
(g) $C_{1-4}$ alkyl, optionally substituted with 1-3 substituents independently selected from —OH and halogen, and
(h) —O—$C_{1-4}$ alkyl, optionally substituted with —OH;
Y is selected from (1) —O— and (2) —$CH_2$—;
R is selected from:
(1) H,
(2) aryl,
(3) —O-aryl,
(4) —C(O)-aryl,
(5) heteroaryl, and
(6) —O-heteroaryl,
wherein each of the aryl of (2), (3) and (4) and each of the heteroaryl of (5) and (6) is optionally substituted with 1-3 substituents independently selected from:
(a) —OH,
(b) halogen,
(c) —CN, and
(d) $C_{1-6}$ alkyl, optionally substituted with 1-3 halogens;
each occurrence of $R^1$ is independently selected from: (1) H, (2) halogen, and (3) $C_{1-6}$ alkyl, optionally substituted with —OH;
$R^2$ is selected from: (1) H, (2) halogen, (3) —OH, (4) —O—$C_{1-6}$ alkyl, and (5) $C_{1-6}$ alkyl, optionally substituted with —OH; and
each occurrence of $R^3$ is independently selected from: (1) H, (2) halogen, (3) —OH, (4) $C_{1-6}$ alkyl, optionally substituted with —OH, and (5) —O-heteroaryl, optionally substituted with 1-3 halogens.

15. The compound of claim 14, or a pharmaceutically acceptable salt thereof:
wherein:
R is selected from:
(1) phenyl,
(2) —O-phenyl,
(3) —C(O)-phenyl,
(4) a heteroaryl selected from quinolinyl, pyrazinyl, pyrazolyl, pyridazinyl, pyridinyl, and pyrimidinyl, and
(5) —O-heteroaryl, wherein the heteroaryl is selected from pyrazinyl, pyrazolyl, pyridazinyl, pyridinyl, and pyrimidinyl,
wherein each of the phenyl of (1), (2), and (3) and each of the heteroaryl of (4) and (5) is optionally substituted with 1-3 substituents independently selected from:
(a) —OH,
(b) halogen,
(c) —CN, and
(d) $C_{1-4}$ alkyl, optionally substituted with 1-3 halogens;
each occurrence of $R^1$ is independently selected from: (1) H, (2) halogen, and (3) methyl;
$R^2$ is selected from: (1) H, (2) halogen, (3) —OH, and (4) —O—$C_{1-4}$ alkyl; and
each occurrence of $R^3$ is H.

16. The compound of claim 1, or a pharmaceutically acceptable salt thereof, of formula (Ic):

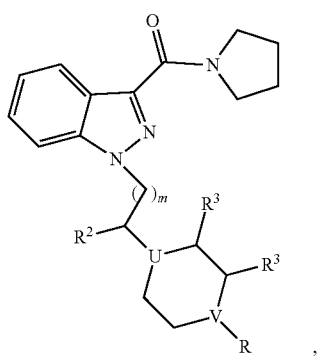

(Ic)

wherein:
m is 0 or 1;
U is selected from (1) N, (2) CH, and (3) C(OH);
V is selected from (1) N and (2) CH;
R is selected from:
(1) aryl,
(2) —O-aryl,
(3) —C(O)-aryl,
(4) heteroaryl, and
(5) —O-heteroaryl,
wherein each of the aryl of (1), (2) and (3) and each of the heteroaryl of (4) and (5) is optionally substituted with 1-3 substituents independently selected from:
(a) —OH,
(b) halogen,
(c) —CN, and
(d) $C_{1-6}$ alkyl, optionally substituted with 1-3 halogens;

$R^2$ is selected from: (1) H, (2) halogen, (3) —OH, (4) —O—$C_{1-6}$ alkyl, and (5) $C_{1-6}$ alkyl, optionally substituted with —OH; and
each occurrence of $R^3$ is independently selected from: (1) H, (2) halogen, (3) —OH, and (4) $C_{1-6}$ alkyl, optionally substituted with —OH.

17. The compound of claim 16, or a pharmaceutically acceptable salt thereof:
wherein:
m is 1;
R is phenyl, optionally substituted with 1-3 substituents independently selected from:
(a) —OH,
(b) halogen, and
(c) $C_{1-4}$ alkyl, optionally substituted with 1-3 halogens;
$R^2$ is H; and
each occurrence of $R^3$ is H.

18. The compound of claim 1, or a pharmaceutically acceptable salt thereof, of formula (Id):

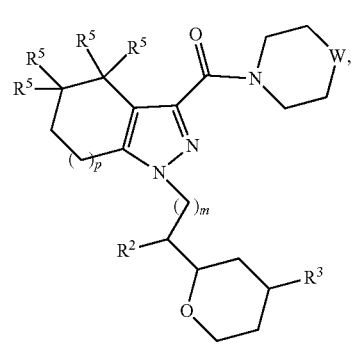

(Id)

wherein:
m is 0 or 1; p is 0 or 1;
W is —$CR^dR^d$—, wherein each occurrence of $R^d$ is independently selected from:
(a) H,
(b) —OH,
(c) —NH—C(O)—$CH_3$, optionally substituted with —OH, and
(d) —O—$C_{1-4}$ alkyl, optionally substituted with —OH;
$R^3$ is —O-heteroaryl, optionally substituted with 1-3 halogens; and
each occurrence of $R^5$ is independently selected from: (1) H, (2) halogen, and (3) $C_{1-4}$ alkyl, optionally substituted with 1-3 halogens;
or alternatively, two $R^5$ groups on two adjacent ring carbons together with the two ring carbons form a 3-4 membered new carbocyclic ring.

19. The compound of claim 18, or a pharmaceutically acceptable salt thereof:
wherein:
m is 0 or 1; p is 0 or 1;
W is —$CR^dR^d$—, wherein each occurrence of $R^d$ is independently selected from:
(a) H,
(b) —OH,
(c) —NH—C(O)—$CH_3$, and
(d) —O—$C_{1-4}$ alkyl, optionally substituted with —OH;
$R^3$ is —O-pyridinyl, optionally substituted with halogen; and
each occurrence of $R^5$ is independently selected from: (1) H and (2) halogen;

or alternatively, two R⁵ groups on two adjacent ring carbons together with the two ring carbons form a new cyclopropyl ring.

20. The compound of claim 1 selected from the group consisting of:
(1-(2-(1-(2,3-dimethylphenyl)piperidin-4-yl)ethyl)-1,4,5,6-tetrahydrocyclopenta[c]pyrazol-3-yl)(4-hydroxypiperidin-1-yl)methanone,
[1-[2-[1-(3-fluorophenyl)piperidin-1-ium-4-yl]ethyl]-5,6-dihydro-4H-cyclopenta[c]pyrazol-3-yl]-(4-hydroxy-1-piperidyl)methanone,
[1-[2-[1-(3-chloro-2-methyl-phenyl)piperidin-1-ium-4-yl]ethyl]-5,6-dihydro-4H-cyclopenta[c]pyrazol-3-yl]-(4-hydroxy-1-piperidyl)methanone,
(4-hydroxy-1-piperidyl)-[1-[2-[1-[3-(trifluoromethyl)phenyl]-4-piperidyl]ethyl]-5,6-dihydro-4H-cyclopenta[c]pyrazol-3-yl]methanone,
[1-[2-[1-(2,3-difluorophenyl)piperidin-1-ium-4-yl]ethyl]-5,6-dihydro-4H-cyclopenta[c]pyrazol-3-yl]-(4-hydroxy-1-piperidyl)methanone,
[1-[2-[1-(6-fluoroquinolin-1-ium-4-yl)-4-piperidyl]ethyl]-5,6-dihydro-4H-cyclopenta[c]pyrazol-3-yl]-(4-hydroxy-1-piperidyl)methanone,
(4-hydroxy-1-piperidyl)-[1-[2-[1-[3-(trifluoromethyl)pyridin-1-ium-4-yl]-4-piperidyl]ethyl]-5,6-dihydro-4H-cyclopenta[c]pyrazol-3-yl]methanone,
(1-(2-(1-(4-fluoro-2,3-dimethylphenyl)piperidin-4-yl)ethyl)-1,4,5,6-tetrahydrocyclopenta[c]pyrazol-3-yl)(4-fluoro-4-(hydroxymethyl)piperidin-1-yl)methanone,
[1-[2-[1-(4-fluoro-2,3-dimethyl-phenyl)piperidin-1-ium-4-yl]ethyl]-5,6-dihydro-4H-cyclopenta[c]pyrazol-3-yl]-[4-(fluoromethyl)-4-hydroxy-1-piperidyl]methanone,
[1-[2-[1-(3-chloro-2-methyl-phenyl)piperidin-1-ium-4-yl]ethyl]-5,6-dihydro-4H-cyclopenta[c]pyrazol-3-yl]-[4-fluoro-4-(hydroxymethyl)-1-piperidyl]methanone,
1-[4-[1-[2-[1-(4-fluoro-2,3-dimethyl-phenyl)piperidin-1-ium-4-yl]ethyl]-5,6-dihydro-4H-cyclopenta[c]pyrazole-3-carbonyl]piperazin-1-yl]-2-hydroxy-ethanone,
1-[4-[1-[2-[1-(3-chloro-2-methyl-phenyl)piperidin-1-ium-4-yl]ethyl]-5,6-dihydro-4H-cyclopenta[c]pyrazole-3-carbonyl]piperazin-1-yl]-2-hydroxy-ethanone,
[1-[2-[1-(4-fluoro-2,3-dimethyl-phenyl)piperidin-1-ium-4-yl]ethyl]-5,6-dihydro-4H-cyclopenta[c]pyrazol-3-yl]-(3-fluoro-4-hydroxy-1-piperidyl)methanone,
[1-[2-[1-(3-chloro-2-methyl-phenyl)piperidin-1-ium-4-yl]ethyl]-5,6-dihydro-4H-cyclopenta[c]pyrazol-3-yl]-(3-fluoro-4-hydroxy-1-piperidyl)methanone,
[1-[2-[1-(3-chloro-2-methyl-phenyl)piperidin-1-ium-4-yl]ethyl]-5,6-dihydro-4H-cyclopenta[c]pyrazol-3-yl]-(3-fluoro-4-hydroxy-1-piperidyl)methanone,
N-(1-(1-(2-(1-(2-(trifluoromethyl)phenyl)piperidin-4-yl)ethyl)-4,5,6,7-tetrahydro-1H-indazole-3-carbonyl)piperidin-4-yl)acetamide,
N-[1-[1-[2-[1-(3-fluoro-2-methyl-phenyl)-4-piperidyl]ethyl]-4,5,6,7-tetrahydroindazole-3-carbonyl]-4-piperidyl]acetamide,
N-[1-[1-[2-[1-(3,4-difluoro-2-methyl-phenyl)-4-piperidyl]ethyl]-4,5,6,7-tetrahydroindazole-3-carbonyl]-4-piperidyl]acetamide,
N-[1-[1-[2-[1-(2,3-dichlorophenyl)-4-piperidyl]ethyl]-4,5,6,7-tetrahydroindazole-3-carbonyl]-4-piperidyl]acetamide,
N-[1-[1-[2-[1-(3-chloro-2-methyl-phenyl)-4-piperidyl]ethyl]-4,5,6,7-tetrahydroindazole-3-carbonyl]-4-piperidyl]acetamide,
N-[1-[1-[2-[1-(2-chlorophenyl)-4-piperidyl]ethyl]-4,5,6,7-tetrahydroindazole-3-carbonyl]-4-piperidyl]acetamide,
N-[1-[1-[2-[1-[2-methyl-3-(trifluoromethyl)phenyl]-4-piperidyl]ethyl]-4,5,6,7-tetrahydroindazole-3-carbonyl]-4-piperidyl]acetamide,
N-[1-[1-[2-[1-(4-fluoro-2-methyl-phenyl)-4-piperidyl]ethyl]-4,5,6,7-tetrahydroindazole-3-carbonyl]-4-piperidyl]acetamide,
N-[1-[1-[2-[1-(3,5-difluoro-2-pyridyl)-4-piperidyl]ethyl]-4,5,6,7-tetrahydroindazole-3-carbonyl]-4-piperidyl]acetamide,
N-[1-[1-[2-[1-(3-methylpyrazin-2-yl)-4-piperidyl]ethyl]-4,5,6,7-tetrahydroindazole-3-carbonyl]-4-piperidyl]acetamide,
N-[1-[1-[2-[1-(3,5-dimethyl-2-pyridyl)-4-piperidyl]ethyl]-4,5,6,7-tetrahydroindazole-3-carbonyl]-4-piperidyl]acetamide,
N-[1-[1-[2-[1-(5-methylpyrazin-2-yl)-4-piperidyl]ethyl]-4,5,6,7-tetrahydroindazole-3-carbonyl]-4-piperidyl]acetamide,
N-[1-[1-[2-[1-(2-methyl-3-pyridyl)-4-piperidyl]ethyl]-4,5,6,7-tetrahydroindazole-3-carbonyl]-4-piperidyl]acetamide,
N-[1-[1-[2-[1-(6-methyl-3-pyridyl)-4-piperidyl]ethyl]-4,5,6,7-tetrahydroindazole-3-carbonyl]-4-piperidyl]acetamide,
N-[1-[1-[2-[1-(5,6-dimethyl-3-pyridyl)-4-piperidyl]ethyl]-4,5,6,7-tetrahydroindazole-3-carbonyl]-4-piperidyl]acetamide,
N-[1-[1-[2-[1-(6-methylpyrazin-2-yl)-4-piperidyl]ethyl]-4,5,6,7-tetrahydroindazole-3-carbonyl]-4-piperidyl]acetamide,
N-[1-[1-[2-[1-(3-methyl-4-pyridyl)-4-piperidyl]ethyl]-4,5,6,7-tetrahydroindazole-3-carbonyl]-4-piperidyl]acetamide,
N-[1-[1-[2-[1-(6-chloropyridazin-3-yl)-4-piperidyl]ethyl]-4,5,6,7-tetrahydroindazole-3-carbonyl]-4-piperidyl]acetamide,
N-[1-[1-[2-[1-[3-fluoro-4-(trifluoromethyl)-2-pyridyl]-4-piperidyl]ethyl]-4,5,6,7-tetrahydroindazole-3-carbonyl]-4-piperidyl]acetamide,
N-[1-[1-[2-[1-[3-fluoro-4-(trifluoromethyl)-2-pyridyl]-4-piperidyl]ethyl]-4,5,6,7-tetrahydroindazole-3-carbonyl]-4-piperidyl]acetamide,
N-[1-[1-[2-[1-[3-chloro-5-(trifluoromethyl)-2-pyridyl]-4-piperidyl]ethyl]-4,5,6,7-tetrahydroindazole-3-carbonyl]-4-piperidyl]acetamide,
N-[1-[1-[2-[1-[4-(trifluoromethyl)-2-pyridyl]-4-piperidyl]ethyl]-4,5,6,7-tetrahydroindazole-3-carbonyl]-4-piperidyl]acetamide,
N-[1-[1-[2-[1-(6-chloro-2-pyridyl)-4-piperidyl]ethyl]-4,5,6,7-tetrahydroindazole-3-carbonyl]-4-piperidyl]acetamide,
N-[1-[1-[2-[1-(3-cyano-2-pyridyl)-4-piperidyl]ethyl]-4,5,6,7-tetrahydroindazole-3-carbonyl]-4-piperidyl]acetamide,
N-[1-[1-[2-[1-(4-cyano-2-pyridyl)-4-piperidyl]ethyl]-4,5,6,7-tetrahydroindazole-3-carbonyl]-4-piperidyl]acetamide,
(1-(2-(1-(3-chlorobenzoyl)piperidin-4-yl)ethyl)-1,4,5,6-tetrahydrocyclopenta[c]pyrazol-3-yl)(4-hydroxypiperidin-1-yl)methanone,
[4-[2-[3-(4-hydroxypiperidine-1-carbonyl)-5,6-dihydro-4H-cyclopenta[c]pyrazol-1-yl]ethyl]-1-piperidyl]-phenyl-methanone, ((2R,6S)-2,6-dimethylmorpholino)(1-(2-(1-(2,3-dimethylphenyl)piperidin-4-yl)-2-hydroxyethyl)-1,4,5,6-tetrahydrocyclopenta[c]pyrazol-3-yl)methanone, ((2R,6S)-2,6-dimethylmorpholino)(1-(2-(1-(2,3-dimethylphenyl)piperidin-4-yl)-2-methoxyethyl)-1,4,5,6-tetrahydrocyclopenta[c]pyrazol-3-yl)methanone, ((2R,6S)-2,6-dimethylmorpholino)(1-(2-(1-(2,3-dimethylphenyl)piperidin-4-yl)-2-fluoroethyl)-1,4,5,6-tetrahydrocyclopenta[c]pyrazol-3-yl)methanone, 1-(4-(1-(2-(4-(4-fluoro-2,3-dimethylphenyl)cyclohexyl)ethyl)-1,4,5,6-tetrahydrocyclopenta[c]pyrazole-3-carbonyl)piperazin-1-yl)-2-hydroxyethan-1-one, (1-(2-(4-(4-fluoro-2,3-dimethylphenyl)cyclohexyl)ethyl)-1,4,5,6-tetrahydrocyclopenta[c]pyrazol-3-yl)(4-fluoro-4-(hydroxymethyl)piperidin-1-yl)methanone, (1-(2-(4-(4-fluoro-2,3-dimethylphenyl)cyclohexyl)ethyl)-1,4,5,6-tetrahydrocyclopenta[c]pyrazol-3-yl)(4-fluoro-4-(hydroxymethyl)piperidin-1-yl)methanone, (1-(2-((1s,4S)-4-(3-chloro-2-methylphenoxy)cyclohexyl)ethyl)-1,4,5,6-tetrahydrocyclopenta[c]pyrazol-3-yl)((2R,6S)-2,6-dimethylmorpholino)methanone, (1-((4-(3-chloro-2-methylphenoxy)cyclohexyl)methyl)-1,4,5,6-tetrahydrocyclopenta[c]pyrazol-3-yl)((2R,6S)-2,6-dimethylmorpholino)methanone, (1-((4-(3-chloro-2-methylphenoxy)cyclohexyl)methyl)-1,4,5,6-tetrahydrocyclopenta[c]pyrazol-3-yl)((2R,6S)-2,6-dimethylmorpholino)methanone, 1-(4-(1-(2-((1s,4s)-4-(2-chloro-5-methylphenoxy)cyclohexyl)ethyl)-1,4,5,6-tetrahydrocyclopenta[c]pyrazole-3-carbonyl)piperazin-1-yl)-2-hydroxyethan-1-one, (1-(2-((1s,4s)-4-(2-chloro-5-methylphenoxy)cyclohexyl)ethyl)-1,4,5,6-tetrahydrocyclopenta[c]pyrazol-3-yl)(4-fluoro-4-(hydroxymethyl)piperidin-1-yl)methanone, 1-(4-(1-(2-((1r,4r)-4-(2-chloro-5-methylphenoxy)cyclohexyl)ethyl)-1,4,5,6-tetrahydrocyclopenta[c]pyrazole-3-carbonyl)piperazin-1-yl)-2-hydroxyethan-1-one, (1-(2-((1r,4r)-4-(2-chloro-5-methylphenoxy)cyclohexyl)ethyl)-1,4,5,6-tetrahydrocyclopenta[c]pyrazol-3-yl)(4-fluoro-4-(hydroxymethyl)piperidin-1-yl)methanone, N-(1-(1-(2-((1s,4s)-4-(2-methylphenoxy)cyclohexyl)ethyl)-1,4,5,6-tetrahydrocyclopenta[c]pyrazole-3-carbonyl)piperidin-4-yl)acetamide, N-(1-(1-(2-((1s,4s)-4-((3-methylpyridin-2-yl)oxy)cyclohexyl)ethyl)-1,4,5,6-tetrahydrocyclopenta[c]pyrazole-3-carbonyl)piperidin-4-yl)acetamide, N-(1-(1-(2-((1s,4s)-4-((3-(trifluoromethyl)pyridin-2-yl)oxy)cyclohexyl)ethyl)-1,4,5,6-tetrahydrocyclopenta[c]pyrazole-3-carbonyl)piperidin-4-yl)acetamide, N-(1-(1-(2-((1s,4s)-4-((4-methylpyridin-3-yl)oxy)cyclohexyl)ethyl)-1,4,5,6-tetrahydrocyclopenta[c]pyrazole-3-carbonyl)piperidin-4-yl)acetamide, N-(1-(1-(2-((1s,4s)-4-(2-(trifluoromethyl)phenoxy)cyclohexyl)ethyl)-1,4,5,6-tetrahydrocyclopenta[c]pyrazole-3-carbonyl)piperidin-4-yl)acetamide, N-(1-(1-(2-((1s,4s)-4-((3-cyano-4-methylpyridin-2-yl)oxy)cyclohexyl)ethyl)-1,4,5,6-tetrahydrocyclopenta[c]pyrazole-3-carbonyl)piperidin-4-yl)acetamide, N-(1-(1-(2-((1s,4s)-4-((2,6-dimethylpyridin-3-yl)oxy)cyclohexyl)ethyl)-1,4,5,6-tetrahydrocyclopenta[c]pyrazole-3-carbonyl)piperidin-4-yl)acetamide, N-(1-(1-(2-((1s,4s)-4-((2,4-dimethylpyrimidin-5-yl)oxy)cyclohexyl)ethyl)-1,4,5,6-tetrahydrocyclopenta[c]pyrazole-3-carbonyl)piperidin-4-yl)acetamide, N-(1-(1-(2-((1s,4s)-4-((4-methylpyridazin-3-yl)oxy)cyclohexyl)ethyl)-1,4,5,6-tetrahydrocyclopenta[c]pyrazole-3-carbonyl)piperidin-4-yl)acetamide, N-[1-[1-[2-[4-(2-chlorophenoxy)cyclohexyl]ethyl]-5,6-dihydro-4H-cyclopenta[c]pyrazole-3-carbonyl]-4-piperidyl]acetamide, N-(1-(4-bromo-1-(2-((1s,4s)-4-((3-methylpyridin-2-yl)oxy)cyclohexyl)ethyl)-1H-pyrazole-3-carbonyl)-piperidin-4-yl)acetamide, N-(1-(1-(2-((1s,4s)-4-((3-methylpyridin-2-yl)oxy)cyclohexyl)ethyl)-1H-pyrazole-3-carbonyl)piperidin-4-yl)acetamide, N-(1-(1-(2-((1s,4s)-4-((3-methylpyridin-2-yl)oxy)cyclohexyl)ethyl)-4-(3,3,3-trifluoropropyl)-1H-pyrazole-3-carbonyl)piperidin-4-yl)acetamide, N-(1-(4-cyclopropyl-1-(2-((1s,4s)-4-((3-methylpyridin-2-yl)oxy)cyclohexyl)ethyl)-1H-pyrazole-3-carbonyl)piperidin-4-yl)acetamide, (1-(2-(4-(2,3-dimethylphenyl)piperazin-1-yl)ethyl)-1H-indazol-3-yl)(pyrrolidin-1-yl)methanone, N-(1-(1-(((2S,4S)-4-((5-chloropyridin-2-yl)oxy)tetrahydro-2H-pyran-2-yl)methyl)-5,5-difluoro-4,5,6,7-tetrahydro-1H-indazole-3-carbonyl)piperidin-4-yl)acetamide, 6-{3-[4-(acetylamino)piperidine-1-carbonyl]-5,5-difluoro-4,5,6,7-tetrahydro-1H-indazol-1-yl}-1,5-anhydro-3-O-(5-chloropyridin-2-yl)-2,4,6-trideoxy-D-erythro-hexitol, 1-{3-[4-(acetylamino)piperidine-1-carbonyl]-5,5-difluoro-4,5,6,7-tetrahydro-1H-indazol-1-yl}-2,6-anhydro-4-O-(5-chloropyridin-2-yl)-1,3,5-trideoxy-D-erythro-hexitol, 2,6-anhydro-1,3,5-trideoxy-4-O-(3-fluoropyridin-2-yl)-1-[(3bR,4aR)-3-(4-hydroxypiperidine-1-carbonyl)-3b,4,4a,5-tetrahydro-1H-cyclopropa[3,4]cyclopenta[1,2-c]pyrazol-1-yl]-D-erythro-hexitol, 2,6-anhydro-1,3,5-trideoxy-4-O-(3-fluoropyridin-2-yl)-1-{(3bR,4aR)-3-[4-(2-hydroxyethoxy)piperidine-1-carbonyl]-3b,4,4a,5-tetrahydro-1H-cyclopropa[3,4]cyclopenta[1,2-c]pyrazol-1-yl}-D-erythro-hexitol, (4-hydroxypiperidin-1-yl)((3bR,4aR)-1-(2-((1s,4S)-4-((3-methylpyridin-2-yl)oxy)cyclohexyl)ethyl)-3b,4,4a,5-tetrahydro-1H-cyclopropa[3,4]cyclopenta[1,2-c]pyrazol-3-yl)methanone,

[(3R,4S)-3-fluoro-4-hydroxypiperidin-1-yl][(3bR,4aR)-1-(2-{trans-4-[(3-methylpyridin-2-yl)oxy]cyclohexyl}ethyl)-3b,4,4a,5-tetrahydro-1H-cyclopropa[3,4]cyclopenta[1,2-c]pyrazol-3-yl]methanone,

[(3R,4S)-3-fluoro-4-hydroxypiperidin-1-yl][(3bR,4aR)-1-(2-{cis-4-[(3-methylpyridin-2-yl)oxy]cyclohexyl}ethyl)-3b,4,4a,5-tetrahydro-1H-cyclopropa[3,4]cyclopenta[1,2-c]pyrazol-3-yl]methanone,

[(6S)-6-(difluoromethyl)-1-(2-{cis-4-[(3-methylpyridin-2-yl)oxy]cyclohexyl}ethyl)-4,5,6,7-tetrahydro-1H-indazol-3-yl](4-hydroxypiperidin-1-yl)methanone, (4-aminopiperidin-1-yl)[5,5-difluoro-1-(2-{cis-4-[(3-methylpyridin-2-yl)oxy]cyclohexyl}ethyl)-4,5,6,7-tetrahydro-1H-indazol-3-yl]methanone, tert-butyl {1-[5,5-difluoro-1-(2-{cis-4-[(3-methylpyridin-2-yl)oxy]cyclohexyl}ethyl)-4,5,6,7-tetrahydro-1H-indazole-3-carbonyl]piperidin-4-yl}carbamate,

[(6R)-6-(difluoromethyl)-1-(2-{cis-4-[(3-methylpyridin-2-yl)oxy]cyclohexyl}ethyl)-4,5,6,7-tetrahydro-1H-indazol-3-yl](4-hydroxypiperidin-1-yl)methanone, (4-aminopiperidin-1-yl)[(3bR,4aR)-1-(2-{cis-4-[(3-methylpyridin-2-yl)oxy]cyclohexyl}ethyl)-3b,4,4a,5-tetrahydro-1H-cyclopropa[3,4]cyclopenta[1,2-c]pyrazol-3-yl]methanone, tert-butyl {1-[(3bR,4aR)-1-(2-{cis-4-[(3-methylpyridin-2-yl)oxy]cyclohexyl}ethyl)-3b,4,4a,5-tetrahydro-1H-cyclopropa[3,4]cyclopenta[1,2-c]pyrazole-3-carbonyl]piperidin-4-yl}carbamate,

[5,5-difluoro-1-(2-{cis-4-[(3-methylpyridin-2-yl)oxy]cyclohexyl}ethyl)-4,5,6,7-tetrahydro-1H-indazol-3-yl][4-(2-hydroxyethoxy)piperidin-1-yl]methanone,

[4-(2-hydroxyethoxy)piperidin-1-yl][(3bR,4aR)-1-(2-{cis-4-[(3-methylpyridin-2-yl)oxy]cyclohexyl}ethyl)-3b,4,4a,5-tetrahydro-1H-cyclopropa[3,4]cyclopenta[1,2-c]pyrazol-3-yl]methanone, (4-hydroxy-4-methylpiperidin-1-yl)[(3bR,4aR)-1-(2-{cis-4-[(3-methylpyridin-2-yl)oxy]cyclohexyl}ethyl)-3b,4,4a,5-tetrahydro-1H-cyclopropa[3,4]cyclopenta[1,2-c]pyrazol-3-yl]methanone, N-{1-[(3bR,4aR)-1-(2-{cis-4-[(3-methylpyridin-2-yl)oxy]cyclohexyl}ethyl)-3b,4,4a,5-tetrahydro-1H-cyclopropa[3,4]cyclopenta[1,2-c]pyrazole-3-carbonyl]piperidin-4-yl}acetamide, 2-hydroxy-1-(4-((3bR,4aR)-1-(2-((1s,4S)-4-((3-methylpyridin-2-yl)oxy)cyclohexyl)ethyl)-3b,4,4a,5-tetrahydro-1H-cyclopropa[3,4]cyclopenta[1,2-c]pyrazole-3-carbonyl)piperazin-1-yl)ethan-1-one, (1-(2-(4-(2,3-dimethylphenyl)cyclohexyl)ethyl)-1,4,5,6-tetrahydrocyclopenta[c]pyrazol-3-yl)(4-hydroxypiperiin-1-yl)methanone, (1-(2-(4-(2,3-dimethylphenyl)cyclohexyl)ethyl)-1,4,5,6-tetrahydrocyclopenta[c]pyrazol-3-yl)(4-hydroxypiperiin-1-yl)methanone, ((3bR,4aR)-1-(2-(1-(3-chloro-2-methylphenyl)-4-hydroxypiperidin-4-yl)ethyl)-3b,4,4a,5-tetrahydro-1H-cyclopropa[3,4]cyclopenta[1,2-c]pyrazol-3-yl)((3R,4S)-3-fluoro-4-hydroxypiperidin-1-yl)methanone, ((3bR,4aR)-1-(2-(1-(3-chloro-2-methylphenyl)-4-hydroxypiperidin-4-yl)ethyl)-3b,4,4a,5-tetrahydro-1H-cyclopropa[3,4]cyclopenta[1,2-c]pyrazol-3-yl)((3S,4R)-3-fluoro-4-hydroxypiperidin-1-yl)methanone, ((3bR,4aR)-1-(2-(4-(2,3-dimethylphenyl)piperazin-1-yl)ethyl)-3b,4,4a,5-tetrahydro-1H-cyclopropa[3,4]cyclopenta[1,2-c]pyrazol-3-yl)(4-hydroxypiperidin-1-yl)methanone, N-(1-((3bR,4aR)-1-(2-(4-(2,3-dimethylphenyl)piperazin-1-yl)ethyl)-3b,4,4a,5-tetrahydro-1H-cyclopropa[3,4]cyclopenta[1,2-c]pyrazole-3-carbonyl)piperidin-4-yl)acetamide, ((3bR,4aR)-1-(2-(4-(3-chloro-2-methylphenyl)piperazin-1-yl)ethyl)-3b,4,4a,5-tetrahydro-1H-cyclopropa[3,4]cyclopenta[1,2-c]pyrazol-3-yl)(4-hydroxypiperidin-1-yl)methanone, N-(1-((3bR,4aR)-1-(2-(4-(3-chloro-2-methylphenyl)piperazin-1-yl)ethyl)-3b,4,4a,5-tetrahydro-1H-cyclopropa[3,4]cyclopenta[1,2-c]pyrazole-3-carbonyl)piperidin-4-yl)acetamide, 1-(2-(1-(2,3-dimethylphenyl)piperidin-4-yl)ethyl)-1H-indazol-3-yl)(pyrrolidin-1-yl)methanone, and (1-(2-(4-(2,3-dimethylphenyl)piperidin-1-yl)ethyl)-1H-indazol-3-yl)(pyrrolidin-1-yl)methanone;

or a pharmaceutically acceptable salt thereof.

* * * * *